US010934283B2

(12) United States Patent
Barrow et al.

(10) Patent No.: US 10,934,283 B2
(45) Date of Patent: Mar. 2, 2021

(54) COMT INHIBITING METHODS AND COMPOSITIONS

(71) Applicant: LIEBER INSTITUTE FOR BRAIN DEVELOPMENT, Baltimore, MD (US)

(72) Inventors: James Barrow, Arnold, MD (US); Glen Ernst, Bear, DE (US); Dominique Swinnen, Braine l'Alleud (BE); Florian Montel, Meitingen (DE); Sabine Defays, Tubize (BE); Yifang Huang, Lansdale, PA (US); Pablo de León, Baltimore, MD (US); Michael Steven Poslusney, Owings Mills, MD (US)

(73) Assignee: LIEBER INSTITUTE, INC., Baltimore, MD (US)

( * ) Notice: Subject to any disclaimer, the term of this patent is extended or adjusted under 35 U.S.C. 154(b) by 0 days.

(21) Appl. No.: 15/779,340

(22) PCT Filed: Nov. 25, 2016

(86) PCT No.: PCT/US2016/063779
§ 371 (c)(1),
(2) Date: May 25, 2018

(87) PCT Pub. No.: WO2017/091818
PCT Pub. Date: Jun. 1, 2017

(65) Prior Publication Data
US 2018/0305354 A1    Oct. 25, 2018

Related U.S. Application Data

(60) Provisional application No. 62/260,067, filed on Nov. 25, 2015.

(51) Int. Cl.
*C07D 471/04* (2006.01)
*A61P 25/00* (2006.01)
*A61K 31/165* (2006.01)
*A61K 31/197* (2006.01)
*A61K 31/4985* (2006.01)

(52) U.S. Cl.
CPC .......... *C07D 471/04* (2013.01); *A61K 31/165* (2013.01); *A61K 31/197* (2013.01); *A61K 31/4985* (2013.01); *A61P 25/00* (2018.01)

(58) Field of Classification Search
CPC .. C07D 471/04; A61K 31/165; A61K 31/197; A61K 31/4985; A61P 25/00
See application file for complete search history.

(56) References Cited

U.S. PATENT DOCUMENTS 5,834,485 A    11/1998  Dyke et al.
2005/0267152 A1  12/2005  Coulton et al.
2008/0161353 A1   7/2008  Barnham et al.
2010/0113529 A1   5/2010  Learmonth et al.
2011/0117192 A1   5/2011  Navon et al.
2013/0197219 A1   8/2013  Takahashi et al.
2014/0186280 A1   7/2014  Zurawski et al.
2016/0222001 A1   8/2016  Barrow et al.

FOREIGN PATENT DOCUMENTS

WO    WO 2005/016344    2/2005
WO    WO 2011/109254    9/2011
WO    WO 2011/114099    9/2011

OTHER PUBLICATIONS

STN Registry Database entry for CAS RN 1210687-36-7, Entered STN Mar. 17, 2010, Accessed Sep. 22, 2020.*
Ariyasu et al., "Design and Synthesis of 8-hydroxyquinoline-based Radioprotective Agents," Bioorganic & Medicinal Chemistry, vol. 22, No. 15, pp. 3891-3905, 2014.
Cheng et al., "Solution-processible Small Molecular Organic Light-Emitting Diode Material and Devices based on the Substituted Aluminum Quinolate," Chem. Mater., vol. 16, No. 15, pp. 2862-2868, 2004.
Eweas et al, Synthesis, anti-schistosomal activity and molecular modeling of two novel 8-hydroxyquinoline derivatives, Anti-Infective Agents, 2013, 11(1), p. 31-40, an abstract page (2013).
Eweas et al, Design, synthesis, anti-schistosomal activity and molecular docking of novel 8-hydroxyquinoline-5-sulfonyl 1,4-diazepine derivatives, Bioorganic Chemistry, 2013, 46, p. 17-25.
Hafez et al, Synthesis and biological activity of some new 8-hydroxyquinoline sulfonamide derivatives, Phosphorus, Sulfur and the Related Elements, 1988, 40(3-4), p. 219-225 ,an abstract page (1988).
Hafez et al, Nitriles in heterocyclic synthesis. Part II. synthesis and application of pyrano[3,2-h]quinoline sulfonamide derivatives, Journal of Chemical Technology and Biotechnology, 1992, 55(2), p. 95-101 ,an abstract page (1992).
Hafez et al., "Synthesis of Some Heterocyclic Sulfones Related to Quinolinol," Collect. Czech. Chem. Commun, vol. 58, pp. 2222-2226 (1993).
Hafez et al, Synthesis and application of some new 5-sulfonyl-N-heterocyclo-8- hydroxyquinoline derivatives as potential drugs, Phosphorus, Sulfur and Silicon and the Related Elements, 1991, 61 (3-4), p. 381-9, a copy of abstract (2 pages).
Hopkins et al., "Substituted Aluminum and Zinc Quinolates with Blue-Shifted Absorbance/luminescence Bands: Synthesis and Spectroscopic, Photoluminescence, and Electroluminescence Characterization," Chemistry of Materials, vol. 8, No. 2, pp. 344-351, (1996).
Kassem et al, Synthesis, antimicrobial, and antiviral activities of some new 5sulphonamido-8-hydroquinoline derivatives, Archives of Pharmacal Research, 35(6), p. 955-964. (2012).

(Continued)

*Primary Examiner* — Alicia L Otton
(74) *Attorney, Agent, or Firm* — Ballard Spahr LLP

(57) ABSTRACT

Compounds that inhibit COMT enzyme and pharmaceutical compositions comprising the same are provided herein. Methods of treating various psychiatric and neurological disorders with the compounds and pharmaceutical compositions described herein are also provided.

71 Claims, No Drawings

(56) References Cited

OTHER PUBLICATIONS

Kassem et al, Synthesis of some new derivatives of 8-hydroxyquinoline of possible biological activity, Bulletin of the National Research Centre (Egypt), 22(1), p. 97-106, an abstract page (Year: 1997).
Lieber Institute for Brain Development, Supplementary European Search Report for EP 16744242.5, 8 pages, dated Jan. 8, 2018.
Lieber Institute for Brain Development, Notification of Transmittal of the International Search Report and the Written Opinion of the International Search Authority, or the Declaration for PCT/US16/15832, 12 pages, dated Apr. 11, 2016.
Makhlouf et al., Effect of chelating 8-hydroxyquinoline derivatives on the corrosion of zinc in polybasic acids, Journal of the Electrochemical Society of India, 35(2), p. 89-92, an abstract page (Year: 1986).
Musiol et al, Investigating the activity spectrum for ring-substituted 8-hydroxyquinolines, Molecules, 2010, 15, p. 288-304, an abstract page (Year: 2010).
Patwa et al, Fries reaction. Part XIII: Preparation of 5- or 7-arylsulfonyl 8-hydroxyquinoline, Journal of the Institution of Chemists (india), 1976, 48, pt. 3, p. 116-18, a copy of abstract (1 page).
Tewari et al, 8-hydroxyquinolino-5-(p-tolyl)sulfonamide as a new gravimetric reagent for chromium (III), Science and Culture, 1980, 46(10), p. 357-358, an abstract page. (Year: 1980).
Thompson et al, 5- chloro-7-diethylaminomethyl-8-quinolinol and of other substituted 8-quinolinols in vitro and in experimental animals, American Journal of Tropical Medicine and hygiene, 1955, 4, p. 224-248. (Year: 1955).
Harrison et al., "Synthesis and Evaluation of Heterocyclic Catechol Mimics as Inhibitors of Catechol-O-methyltransferase {COMT)", ACS Medicinal Chemistry Letters, Jan. 26, 2015, pp. 318-323, vol. 6. No. 3.
Borchardt, "Catechol-O-methyltransferase 2. In Vitro Inhibition by Substituted 8-hydroxyquinolines", J Med. Chem., 1973, pp. 382-387, vol. 16 (4).
Pubchem-cid 145508910 Create date: Feb. 9, 2007, p. 3.
Lieber Institute for Brain Development, Extended European Search Report for EP 16869342.2, 8 pages, dated Apr. 12, 2019.

\* cited by examiner

COMT INHIBITING METHODS AND COMPOSITIONS

NIH GRANT

This invention was made with government support under R01MH107126 awarded by National Institutes of Health. The government has certain rights in the invention.

FIELD OF THE INVENTION

This invention relates to compounds, pharmaceutical compositions and their use for treating neuropsychiatric and neurodegenerative disorders. In particular, the invention relates to inhibitors of catechol-O-methyltransferase and their use as therapeutics for central nervous system disease.

BACKGROUND

Cognitive disorders are observed in many neurological and psychiatric disorders, be they neurodegenerative (e.g. Parkinson's disease, Alzheimer's disease), neurodevelopmental (e.g. schizophrenia, autism spectrum disorders) or the consequence of other etiology.

Parkinson's disease is a progressive neurodegenerative disorder (synucleopathy) diagnosed on the basis of characteristic motor disturbances, asymmetry of symptoms onset and response to levodopa (Litvan et al., 2003). Lewy bodies, neurofibrillary tangles and plaques are observed in nigral, limbic and neocortical regions. These degenerations are supposed to affect catecholaminergic (dopamine and norepinephrine) and cholinergic neurotransmission. In particular, an important part of cognitive deficits (executive function and working memory) have been related to a decreased prefrontal dopaminergic signaling in non-demented patients (Nandakumar et al., 2013).

Schizophrenia is the result of a complex series of neurodevelopmental or other changes that lead to impaired information processing in the brain (Marenco and Weinberger 2000). No single genetic change, aberrant protein function, or visible brain lesion has been demonstrated to lead to schizophrenia, and many different genetic and environmental changes are linked to increased disease risk (Fatemi and Folsom 2009). While many neurochemical signaling systems, such as the various monoamines, NMDA, and GABA, are likely to play a role in the etiology of schizophrenia (Pickard 2011), many pathways seem to converge on aberrant dopamine signaling as a final common pathway that leads to many of the observed symptoms (Howes and Kapur 2009).

With regard to the cognitive impairment, for which there is currently no treatment, patients with schizophrenia show significant deficits in specific cognitive domains, especially executive function, working memory, and episodic memory. Cognitive domains which are dysfunctioning in these two disorders are complex functions involving many neurotransmitters and brain regions; however, dopamine signaling in the dorsolateral prefrontal cortex (DLPFC) has been shown to play a critical role in these processes (Goldman-Rakic, Castner et al. 2004). One approach to rectifying cortical dopamine neurotransmission is to take advantage of the differential modes of clearance of dopamine from the different brain regions. In the midbrain, there is extensive expression of the dopamine transporter (DAT), which is thought to be primarily responsible for dopamine clearance from the synapse (Ciliax, Heilman et al. 1995). In contrast, cortical regions exhibit only low levels of DAT expression, and dopamine is cleared primarily by enzymatic catabolism of dopamine, with a contribution from the norepinephrine transporter (NET) (Yavich, Forsberg et al. 2007; Kaenmaki, Tammimaki et al. 2010). The primary enzymes responsible for dopamine catabolism in the prefrontal cortex ("PFC") are monoamine oxidase (MAO) and catechol-O-methyltransferase ("COMT").

Beyond Parkinson's and schizophrenia, inhibition of COMT may be useful in a number of neuro-psychiatric conditions, including ADHD, obsessive-compulsive disorder, alcoholism, depression, bipolar disorder (Lachman, Papolos et al. 1996), as well as age-associated cognitive symptoms, impulse control disorders, including compulsive gambling, sexual behavior, and other compulsive destructive behaviors. The role of COMT in dopamine metabolism in the brain make it an especially important target for improvement of cognition (Apud and Weinberger 2007).

Additionally, COMT inhibitors have shown utility in Parkinson's disease treatment, due to the role of COMT in metabolizing the dopamine precursor L-DOPA, which is given to Parkinson's disease patients to boost the levels of dopamine in the brain (Bonifacio, Palma et al. 2007). Since dopamine cannot cross the blood-brain barrier, L-DOPA is administered in its place and is transported into the brain and subsequently processed to dopamine. The percentage of exogenously administered L-DOPA that reaches the brain is ~1%, and this low brain availability necessitates a high dose, which leads to peripheral side effects (Nutt and Fellman 1984). The primary enzymes responsible for dopamine metabolism are aromatic amino acid decarboxylase (AAAD) and COMT. Therefore, extensive efforts have been undertaken to develop potent and selective inhibitors of both enzymes. Carbidopa is an AAAD inhibitor now routinely given with L-DOPA, reducing the efficacious L-DOPA dose by 60-80% (Nutt, Woodward et al. 1985). Addition of a COMT inhibitor further decreases the variability of L-DOPA exposure, and a brain-penetrating COMT inhibitor could also increase brain dopamine levels.

Inhibitors of COMT have been developed for treatment of Parkinson's disease (Learmonth, Kiss et al. 2010). Notably, the nitrocatechol scaffold has been exploited to provide the clinically used drugs tolcapone and entacapone (Bonifacio, Palma et al. 2007). While they are effective in blocking peripheral COMT activity, entacapone has negligible brain penetration, and tolcapone has low but measurable levels in the brain (Russ, et al. 1999). Compounds with improved brain penetration should have greater efficacy for Parkinson's disease, as well as have utility for other psychiatric and neurological conditions such as cognitive impairment in schizophrenia. Despite the early clinical success achieved with tolcapone, the drug has been associated with serious liver injury, including three deaths, and requires strict liver function monitoring (Olanow and Watkins 2007). Thus, the risk-benefit profile for tolcapone prevents its widespread deployment, and new, inhibitors of COMT are needed, especially those that are active in the brain. Borchardt disclosed a series of non-nitrocatechol quinoline COMT inhibitors, but these compounds had weak potency (Borchardt, Thakker et al. 1976).

Accordingly, there remains a need for potent inhibitors of COMT and methods of using the same to treat central nervous system disorders.

SUMMARY OF THE INVENTION

The present invention provides compounds, pharmaceutical compositions and methods of treating or preventing neurological or psychiatric disorders for which inhibiting COMT provides a therapeutic effect.

The present invention also provides methods of treating or preventing a neurological or psychiatric disorder, or treating symptoms associated with a neurological or psychiatric disorder, and in particular such disorders for which inhibiting COMT provides a therapeutic effect. In a particular embodiment, the invention provides a method of inhibiting COMT enzyme in a subject by administering compounds according to formula I, or a pharmaceutically acceptable salt thereof:

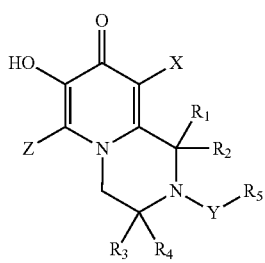

I wherein:

X is selected from hydrogen; chloro; bromo; iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_5$ is selected from aryl, heteroaryl, heterocycle, $C_1$-$C_{10}$ alkyl or $C_1$-$C_{10}$ cycloaklyl, optionally substituted with one or more groups selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and NHC(O)R, wherein R is $C_1$-$C_4$ alkyl; and Y is $(CR_6R_7)_n$, wherein n is from 0-3, and $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or when $R_5$ is phenyl, one of $R_6$ or $R_7$ comes together with $R_5$ to form a bicycle.

Also provided herein are COMT-inhibiting compounds in accordance with formula I, or pharmaceutically acceptable salts thereof:

Also provided herein are pharmaceutical compositions comprising the COMT-inhibiting compounds of the present invention.

DETAILED DESCRIPTION OF THE INVENTION

I. Definitions

The terms below, when used herein, have the following meanings unless indicated otherwise.

As used in this specification and the appended claims, the singular forms "a", "an" and "the" include plural references unless the content clearly dictates otherwise.

When any variable (e.g. aryl, heterocycle, $R^1$, etc.) occurs more than one time in any constituent, its definition on each occurrence is independent at every other occurrence.

"Alkyl" refers to a saturated hydrocarbon chain. Such hydrocarbon chains may be branched or linear. "Alkyl" groups may be substituted by one or more substituents selected from halogen, amido, aryl or alkoxy. Particular alkyl groups according to the present invention include methyl, trifluoromethyl, ethyl, propyl, butyl, pentyl, 1-methylbutyl, 1-ethylpropyl, 3-methylpentyl, octyl and the like.

The term "$C_1$-$C_6$" (for example), or "$C_{1-6}$", includes, for this example, alkyls containing 6, 5, 4, 3, 2, or 1 carbon atom(s).

"Cycloalkyl" refers to a saturated or unsaturated cyclic hydrocarbon radical, including bridged, fused, or spiro cyclic compounds, preferably having 3 to 8 carbon atoms. Nonlimiting examples of "$C_3$-$C_6$ cycloalkyl" groups according to the present invention are cyclopropyl, cyclopentyl, cyclohexyl and the like.

The compounds of the present invention may contain one or more asymmetric centers and may thus occur as racemates, racemic mixtures, single enantiomers, diastereomeric mixtures, and individual diastereomers.

It will be understood that, as used herein, references to the compounds of the present invention are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamme, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

A "pharmaceutically acceptable excipient" or "pharmaceutically acceptable carrier" refers to an excipient that can be included in the compositions of the invention and that causes no significant adverse toxicological effects to the subject or patient to which the composition is administered. "Pharmacologically effective amount," "physiologically effective amount," and "therapeutically effective amount"

are used interchangeably herein to mean the amount of an active agent present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "patient" refers to a living organism suffering from or prone to a condition that can be prevented or treated by administration of an active agent as described herein, and includes both humans and animals. In one embodiment, the patient is a human patient.

The term "mammal" "mammalian" or "mammals" includes humans, as well as animals, such as dogs, cats, horses, pigs and cattle.

Without being bound by theory, the administration of compounds according to the invention in an "effective amount" or "therapeutically effective amount" provides a concentration of the compound that functions as a COMT inhibitor sufficient to inhibit the effect of the COMT enzyme complex.

"Treating" or "treatment" of a disease state includes: 1) inhibiting the disease state, i.e., arresting the development of the disease state or its clinical symptoms; 2) attenuating the disease state, i.e. reducing the number or intensity of one or more symptoms associated with the disease state, such that one or more symptoms is reduced but may, or may not be completely eliminated; and/or 3) relieving the disease state, i.e., causing temporary or permanent regression of the disease state or its clinical symptoms.

"Prevent" or "preventing" a disease state includes: preventing the disease state, i.e. causing the clinical symptoms of the disease state not to develop in a subject that may be exposed to or predisposed to the disease state, but does not yet experience or display symptoms of the disease state.

All patents, patent applications and publications cited herein, whether supra or infra, are hereby incorporated by reference in their entirety.

II. Methods

One aspect of the invention is a method of treating or preventing a neurological or psychiatric disorder, or treating symptoms associated with a neurological or psychiatric disorder, and in particular such disorders for which inhibiting COMT provides a therapeutic effect. Without being bound by theory, the therapeutic effect provided according to the invention is achieved by inhibiting the metabolism of catecholamines by COMT. Accordingly, in an aspect of the invention, the invention provides methods of treating and/or preventing disease for which inhibiting degradation of catecholamines such as, for example, dopamine, norepinephrine or L-dihydroxyphenylalanine (L-DOPA) provides a beneficial therapeutic effect.

In another aspect, the invention provides a method of inhibiting COMT enzyme in a subject by administering compounds of formula I. These methods comprise administering to a subject in need thereof an effective amount of a COMT-inhibiting compound in accordance with formula I, or a pharmaceutically acceptable salt thereof:

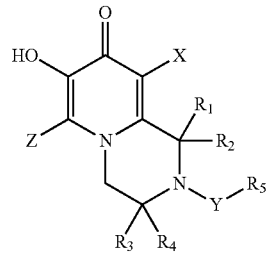

wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_5$ is selected from aryl, heteroaryl, heterocycle, $C_1$-$C_{10}$ alkyl or $C_1$-$C_{10}$ cycloaklyl, optionally substituted with one or more groups selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and NHC(O)R, wherein R is $C_1$-$C_4$ alkyl; and Y is $(CR_6R_7)_n$, wherein n is from 0-3, and $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or when $R_5$ is phenyl, one of $R_6$ or $R_7$ comes together with $R_5$ to form a bicycle.

In another aspect, the invention provides a method of inhibiting COMT enzyme in a subject by administering compounds of formula Ia. These methods comprise administering to a subject in need thereof an effective amount of a COMT-inhibiting compound in accordance with formula Ia, or a pharmaceutically acceptable salt thereof:

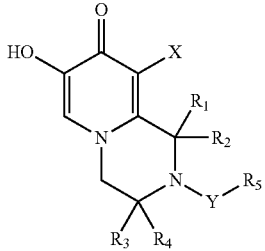

wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_5$ is selected from aryl, heteroaryl, heterocycle, $C_1$-$C_{10}$ alkyl or $C_1$-$C_{10}$ cycloaklyl, optionally substituted with one or more groups selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and NHC(O)R, wherein R is $C_1$-$C_4$ alkyl; and Y is $(CR_6R_7)_n$, wherein n is from 0-3, and $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; or when $R_5$ is phenyl, one of $R_6$ or $R_7$ comes together with $R_5$ to form a bicycle.

In another embodiment, the invention provides a method of inhibiting COMT enzyme in a subject by administering compounds of formula II. These methods comprise administering to a subject in need thereof an effective amount of a COMT-inhibiting compound in accordance with formula II, or a pharmaceutically acceptable salt thereof:

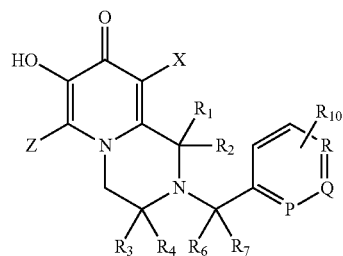

II wherein:

X is selected from hydrogen; chloro; bromo, iodo and cyclopropyl;

Z is selected from hydrogen and fluoro;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

P, Q and R are each independently selected from CH and N;

$R_{10}$ can be at one or more positions on the ring, and at each occurrence is independently selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P, Q or R to form a bicycle; and $R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or one of $R_6$ or $R_7$ comes together with P to form a bicycle.

In a particular embodiment, X is H. In another particular embodiment, $R_1$, $R_2$, $R_3$ and $R_4$ are hydrogen. In still another particular embodiment, three of $R_1$, $R_2$, $R_3$ and $R_4$ are hydrogen. In yet another particular embodiment, $R_1$, $R_2$, $R_3$, $R_4$, $R_6$ and $R_7$ are each hydrogen.

In a preferred embodiment, X is H; $R_1$, $R_2$, $R_3$, $R_4$, $R_6$ and $R_7$ are hydrogen, and P, Q and R are all CH. In another preferred embodiment, X is H; three of $R_1$, $R_2$, $R_3$ and $R_4$ are hydrogen; $R_6$ and $R_7$ are each hydrogen and P, Q and R are all CH. In still another preferred embodiment, X is H; three of $R_1$, $R_2$, $R_3$ and $R_4$ are hydrogen; one of $R_6$ or $R_7$ is hydrogen; and P, Q and R are all CH.

In another embodiment, the invention provides COMT-inhibiting compounds in accordance with formula IIa, or pharmaceutically acceptable salts thereof:

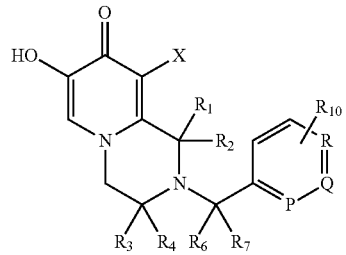

IIa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

P, Q and R are each independently selected from CH and N;

$R_{10}$ can be at one more positions on the ring, and at each occurrence is independently selected from hydrogen; mono-, di-, or trihalomethyl; $C_1$-$C_4$ alkyl, $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P, Q or R to form a bicycle; and $R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; or one of $R_6$ or $R_7$ comes together with P to form a bicycle.

In a particular embodiment, X is H. In another particular embodiment, $R_1$, $R_2$, $R_3$ and $R_4$ are hydrogen. In still another particular embodiment, three of $R_1$, $R_2$, $R_3$ and $R_4$ are hydrogen. In yet another particular embodiment, $R_1$, $R_2$, $R_3$, $R_4$, $R_6$ and $R_7$ are each hydrogen.

In a preferred embodiment, X is H; $R_1$, $R_2$, $R_3$, $R_4$, $R_6$ and $R_7$ are hydrogen, and P, Q and R are all CH. In another preferred embodiment, X is H; three of $R_1$, $R_2$, $R_3$, $R_4$, $R_6$ and $R_7$ are each hydrogen and P, Q and R are all CH. In still another preferred embodiment, X is H; three of $R_1$, $R_2$, $R_3$ and $R_4$ are hydrogen; one of $R_6$ or $R_7$ is hydrogen; and P, Q and R are all CH.

In another embodiment, the invention provides a method of inhibiting COMT enzyme in a subject by administering compounds of formula IIb. These methods comprise administering to a subject in need thereof an effective amount of a COMT-inhibiting compound in accordance with formula IIa, or a pharmaceutically acceptable salt thereof:

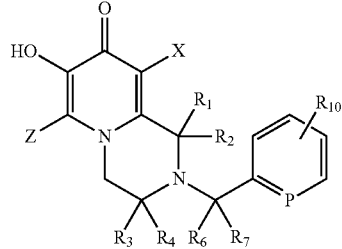

IIb wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

P is CH;

$R_{10}$ can be at one or more positions on the ring, and at each occurrence is independently selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P to form a bicycle; and $R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or one of $R_6$ or $R_7$ comes together with P to form a bicycle.

In a particular embodiment, Z is fluoro and X is H. In another particular embodiment, $R_1$, $R_2$, $R_3$ and $R_4$ are hydrogen. In yet another particular embodiment, $R_1$, $R_2$, $R_3$, $R_4$, $R_6$, $R_7$ are each hydrogen.

In a preferred embodiment, Z is fluoro and X is H and $R_1$, $R_2$, $R_3$, $R_4$, $R_6$ and $R_7$ are hydrogen. In yet another preferred embodiment, X is H; $R_1$, $R_2$, $R_3$, $R_4$, $R_6$, $R_7$ and $R_{10}$ is selected from optionally substituted phenyl or methyl.

In exemplary embodiments, a method of inhibiting COMT enzyme in a subject comprises administering one or more of the following compounds:

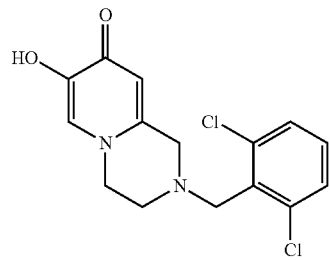
2

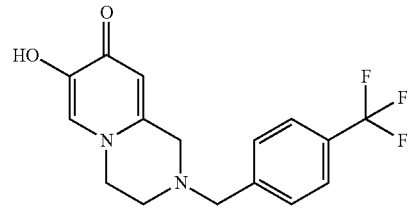
7

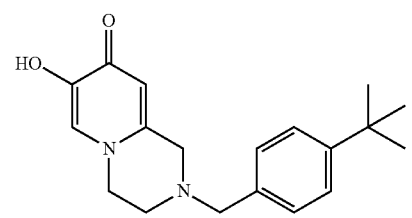
8

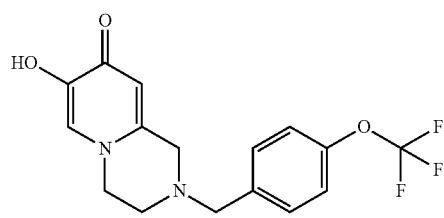

-continued

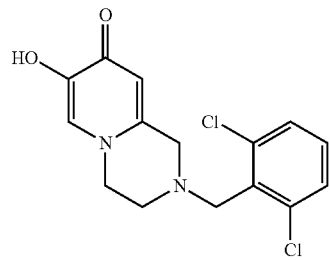
60

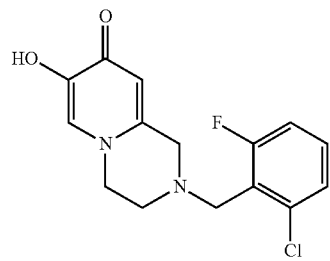
59

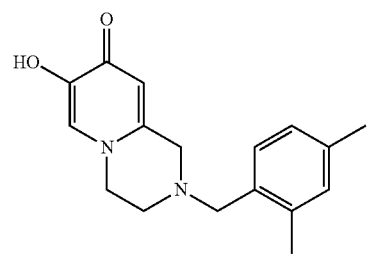
9

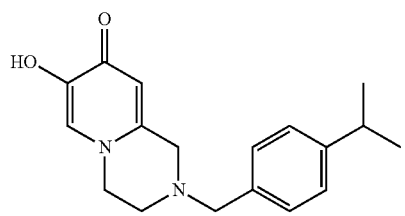
10

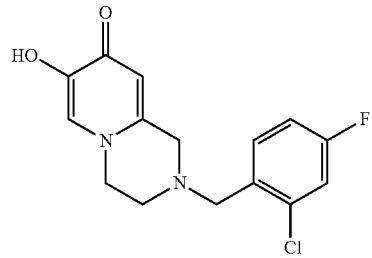
61

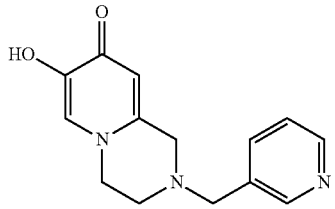
11

-continued
12
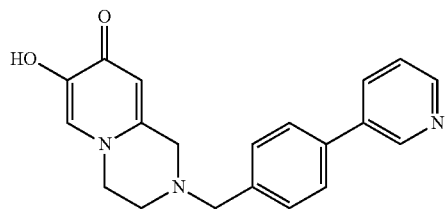
13
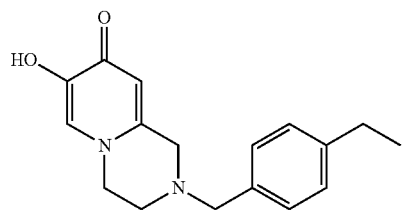
58
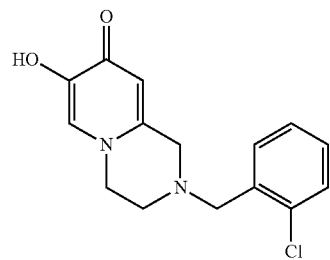
15
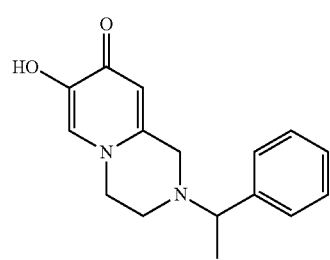
16
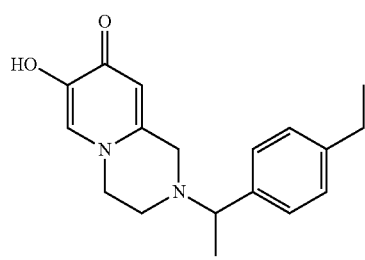
17
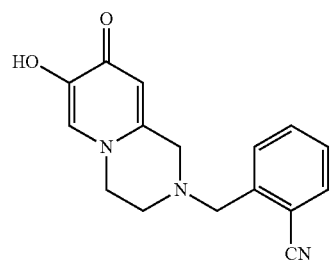
-continued
18
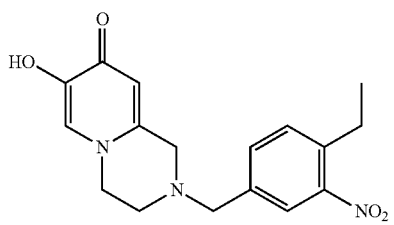
21
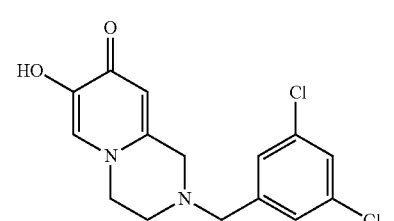
23
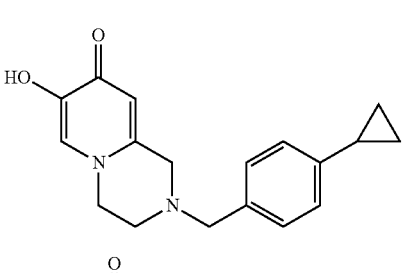
25
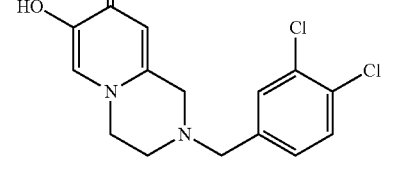
27
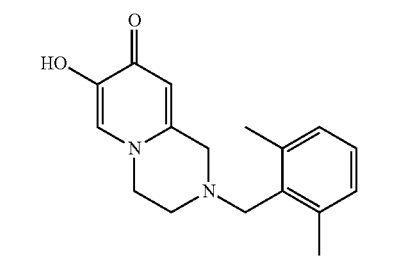
28
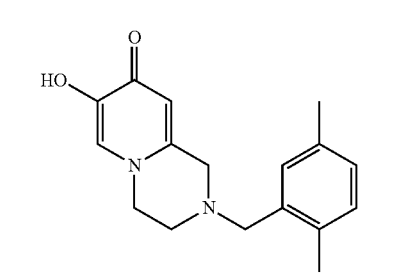
32
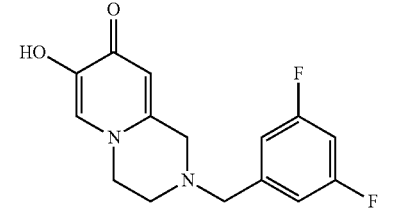

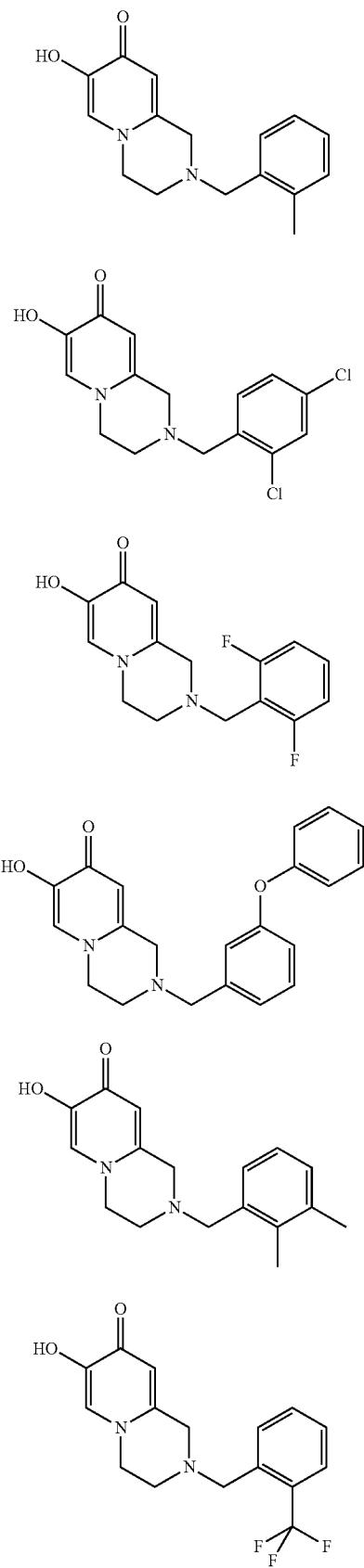

-continued
68
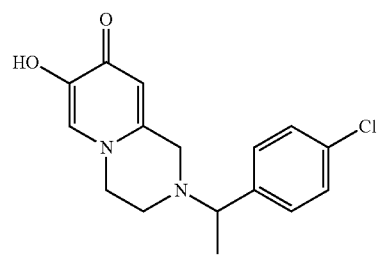
69
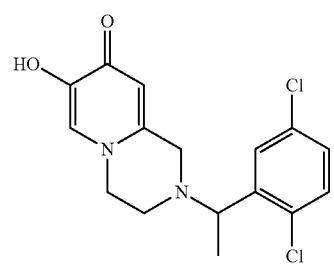
70
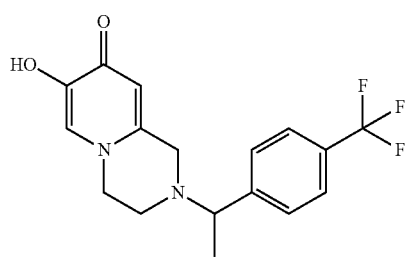
71
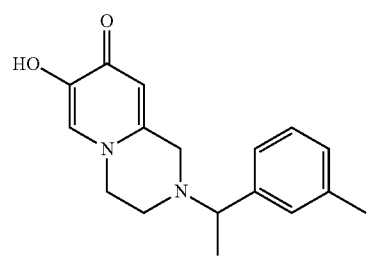
72
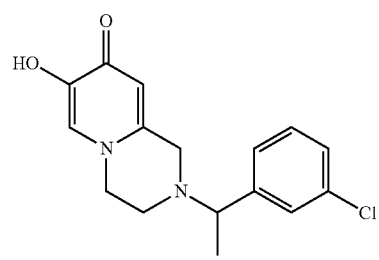
73
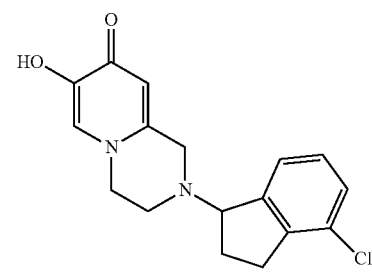
-continued
74
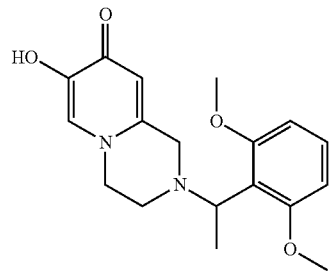
75
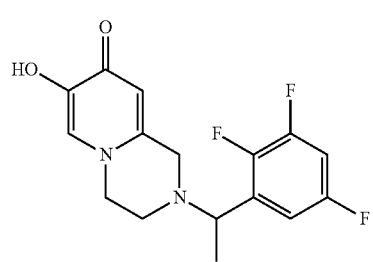
76
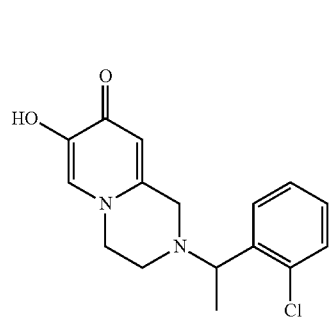
77
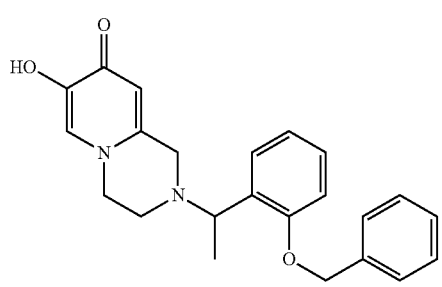
78
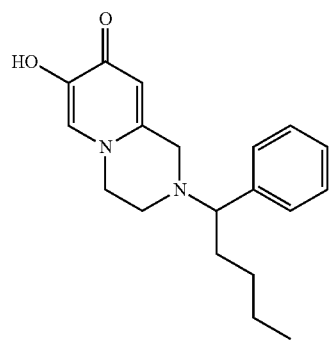

-continued
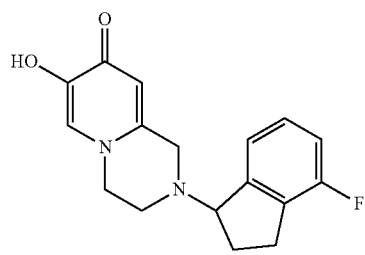
79
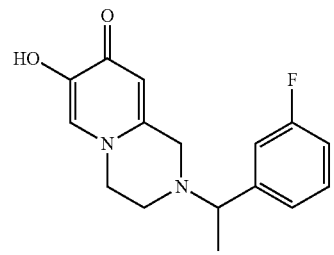
81
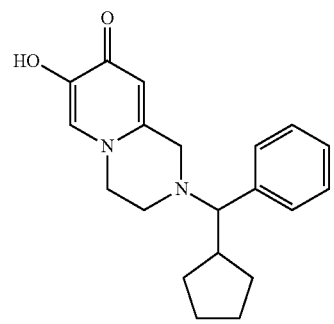
82
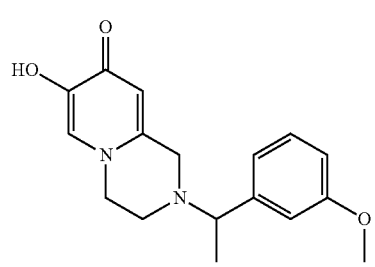
83
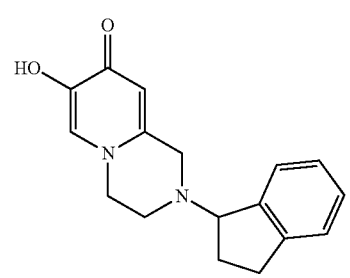
84
85
-continued
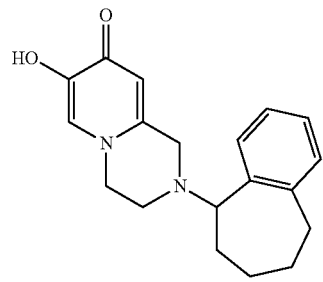
86
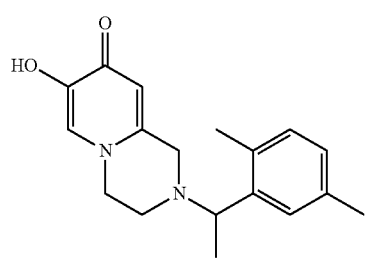
87
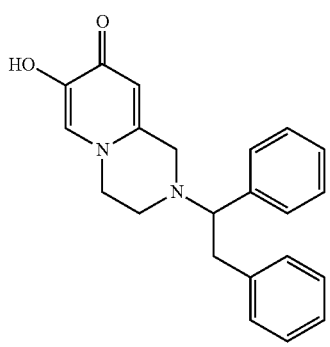
88
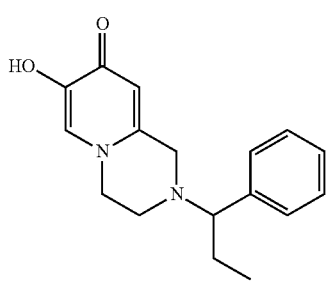
89
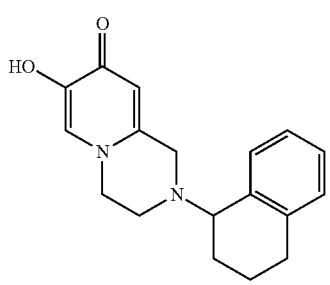
90

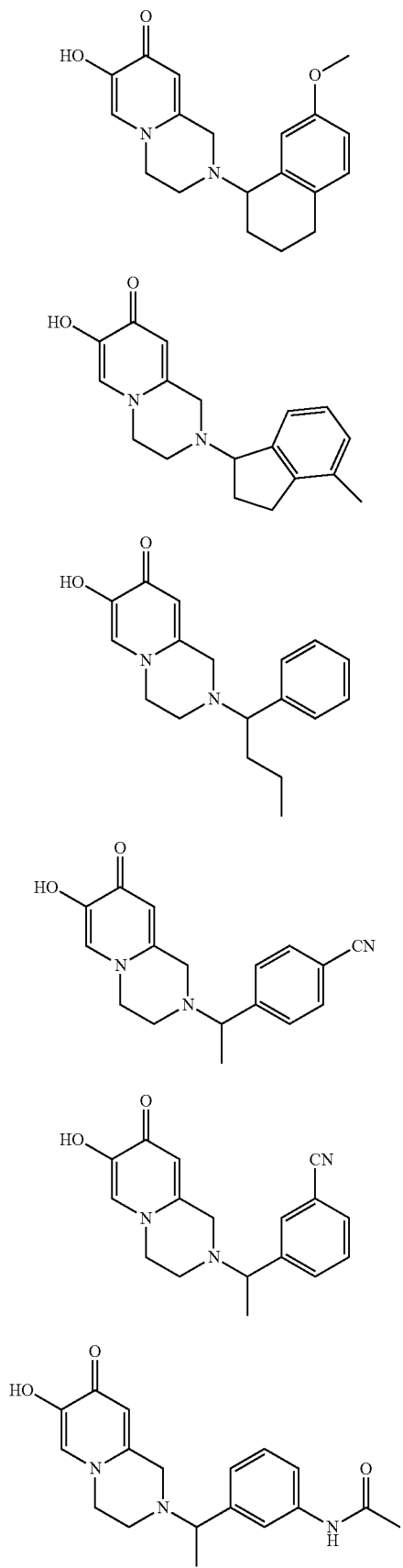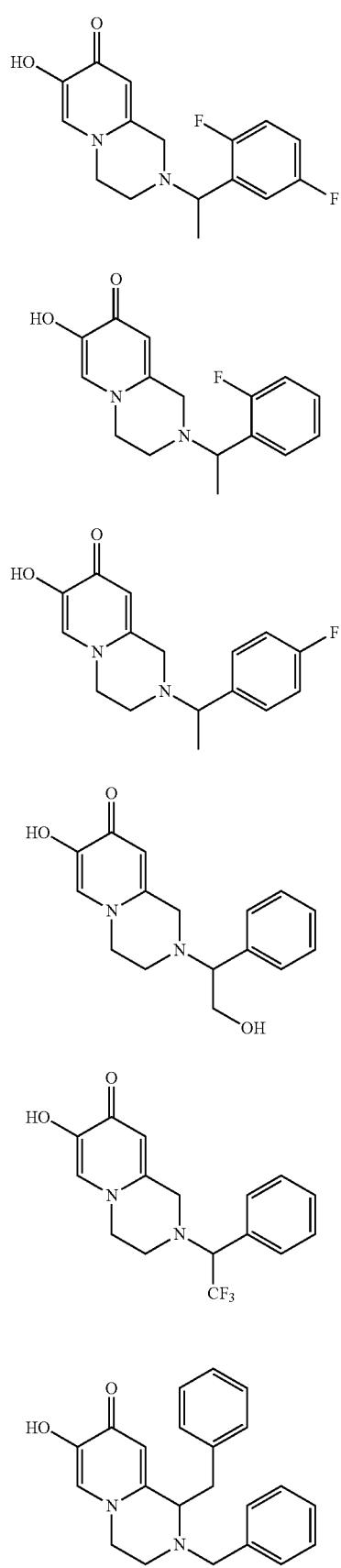

116
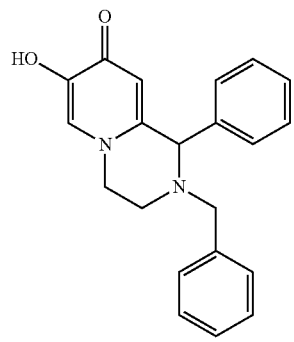
117
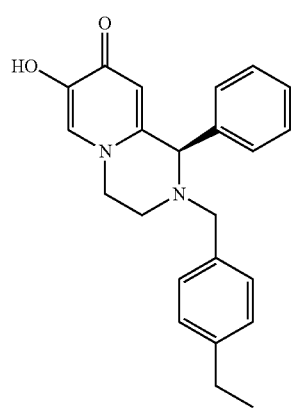
118
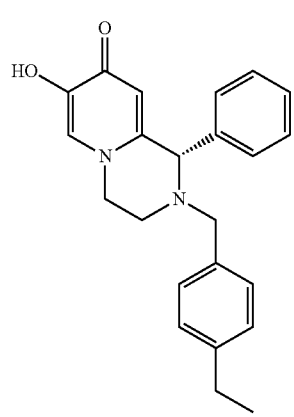
119
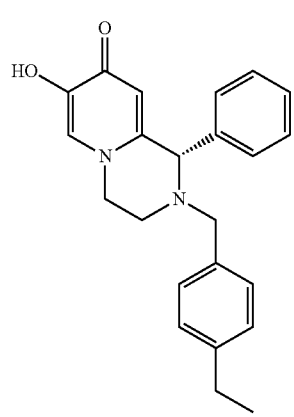
120
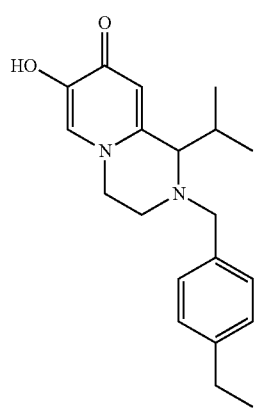
121
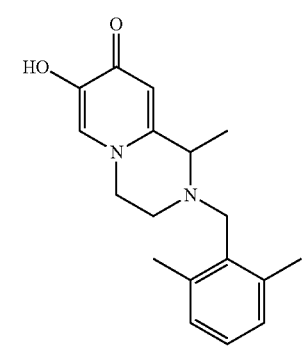
122
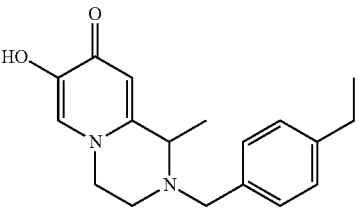
124
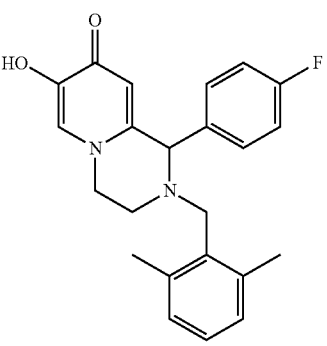

125 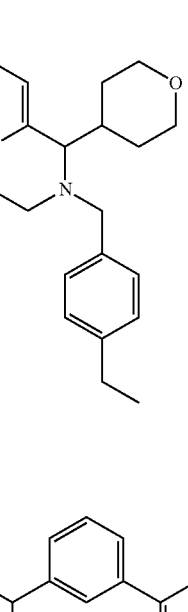
126 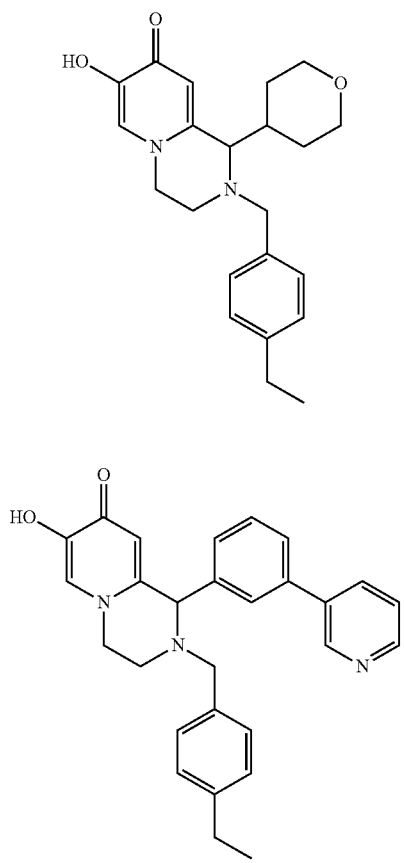
127 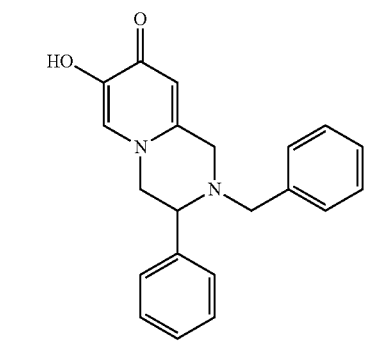
128 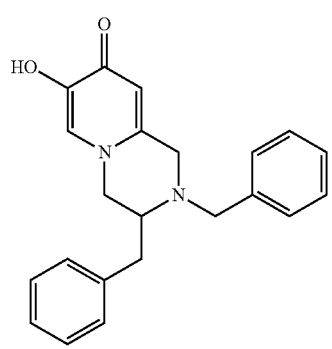
129 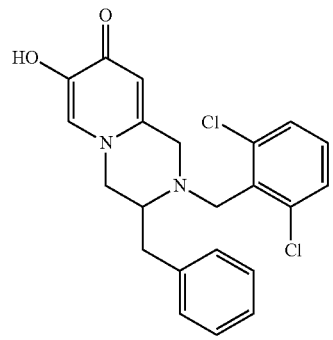
130 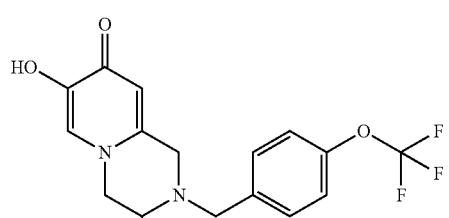
131 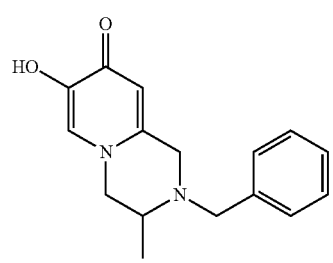
132 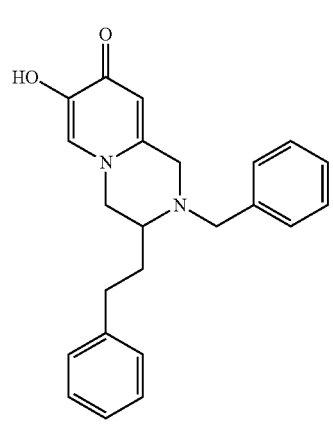
133 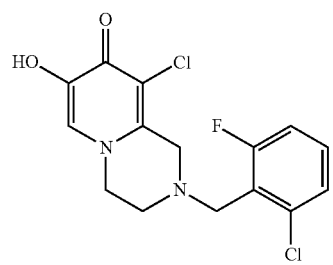

136
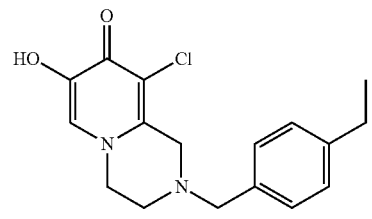
138
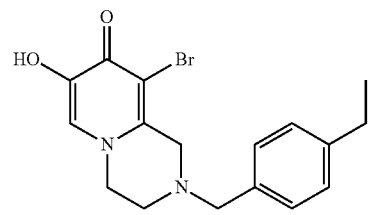
141
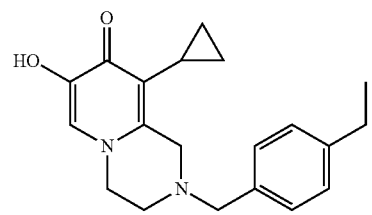
14
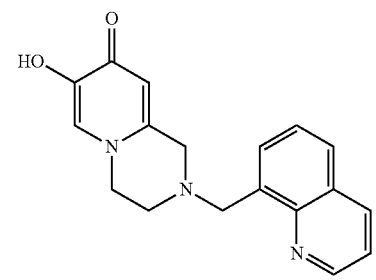
35
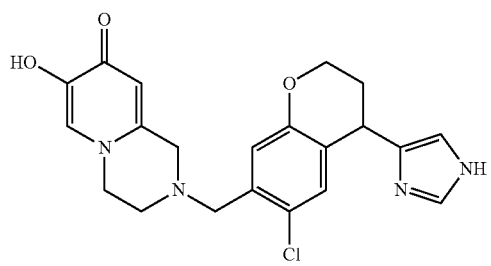
48
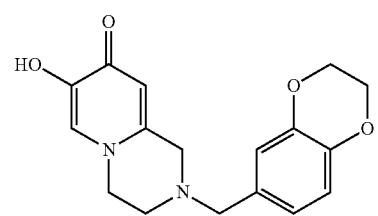
54
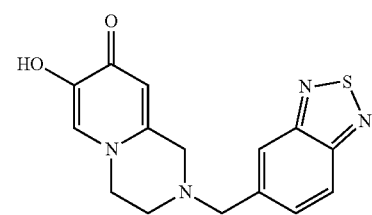
123
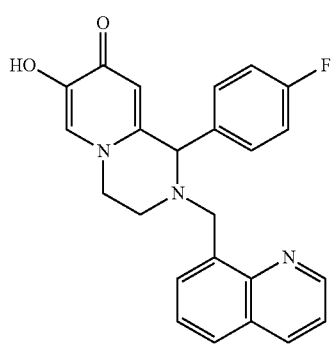
1
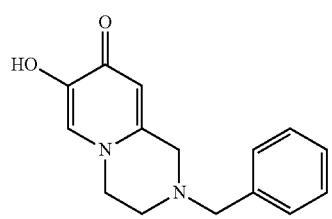
6
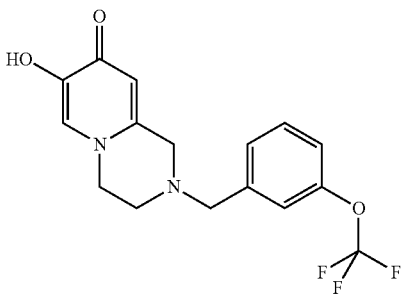
39
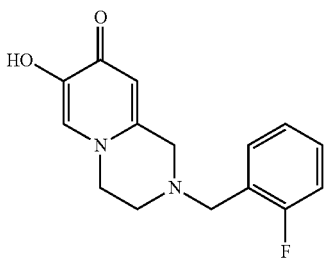
50
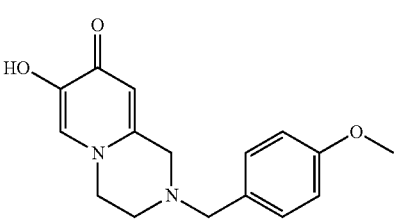
67
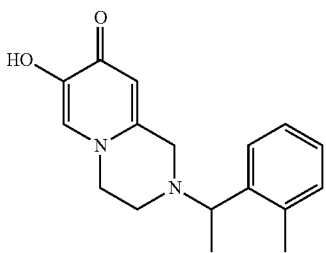

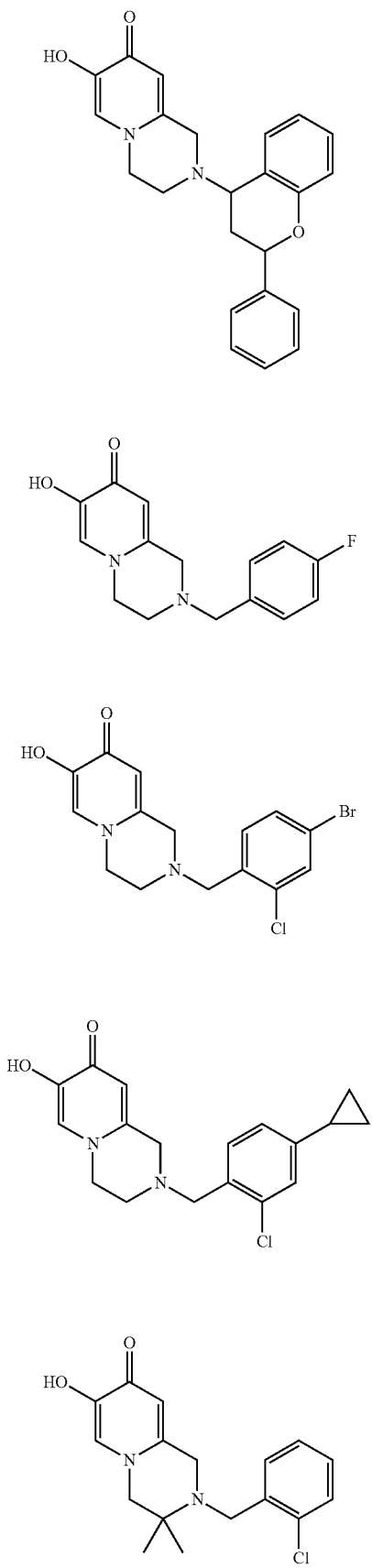
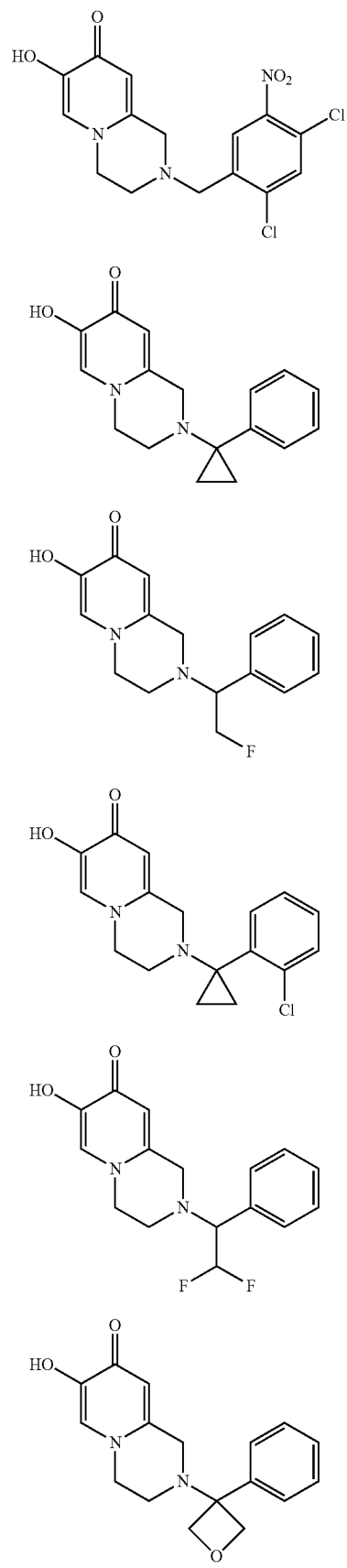

-continued

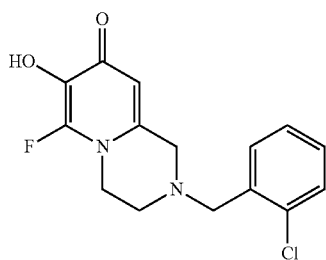

134

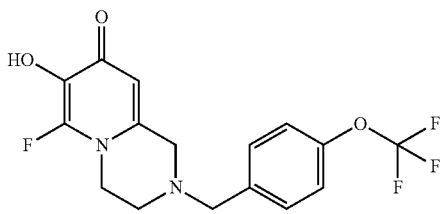

135

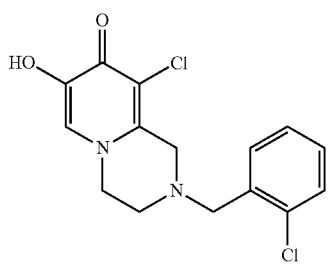

137

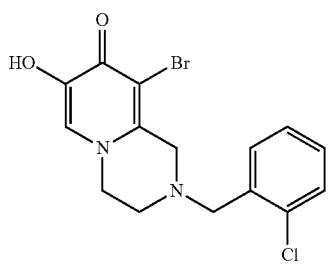

139

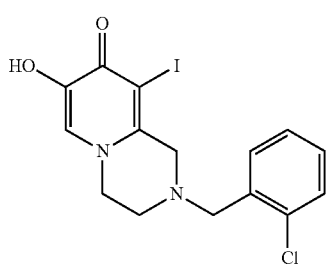

140

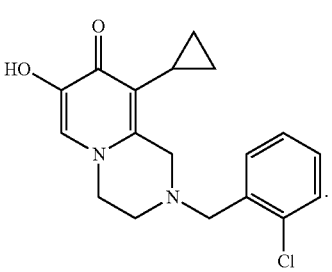

142

In another particular embodiment, the invention provides a method of inhibiting COMT enzyme in a subject by administering compounds of formula III. These methods comprise administering to a subject in need thereof an effective amount of a COMT-inhibiting compound in accordance with formula III, or a pharmaceutically acceptable salt thereof:

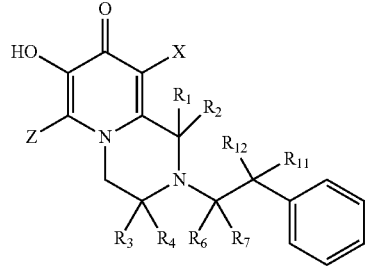

III wherein:
X is selected from hydrogen; chloro; bromo, iodo and cyclopropyl;
Z is selected from hydrogen and fluoro.
$R_1$ and $R_2$ are each independently selected from hydrogen; $C_{1-4}$ alkyl; aryl; substituted aryl; arylalkyl and heterocycle;
$R_3$ and $R_4$ are each independently selected from hydrogen; $C_1$-$C_4$ alkyl; aryl and arylalkyl; and
$R_6$, $R_7$, $R_{11}$ and $R_{12}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; $R_6$ and $R_7$, $R_{11}$ and $R_{12}$, $R_6$ or $R_7$ and $R_{11}$ or $R_{12}$ may also come together to form a $C_3$-$C_6$ cycloalkyl.

In a particular embodiment, X is H. In another particular embodiment, $R_1$, $R_2$, $R_3$ and $R_4$ are hydrogen. In yet another particular embodiment, $R_1$, $R_2$, $R_3$, $R_4$, $R_6$, $R_7$, $R_{11}$ and $R_{12}$ are each hydrogen.

In a preferred embodiment, X is H and $R_1$, $R_2$, $R_3$, $R_4$, $R_6$ and $R_7$ are hydrogen. In yet another preferred embodiment, X is H; $R_1$, $R_2$, $R_3$, $R_4$, $R_6$, $R_7$ and $R_{11}$ are hydrogen and $R_{12}$ is selected from phenyl or methyl.

In another particular embodiment, the invention provides a method of inhibiting COMT enzyme in a subject by administering compounds of formula IIIa. These methods comprise administering to a subject in need thereof an effective amount of a COMT-inhibiting compound in accordance with formula IIIa, or a pharmaceutically acceptable salt thereof:

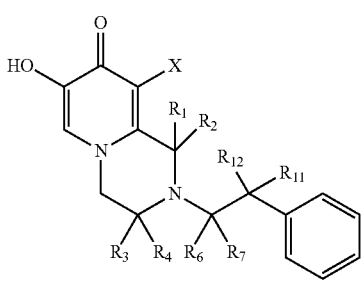

IIIa wherein:
X is selected from hydrogen; chloride; bromide and cyclopropyl;
$R_1$ and $R_2$ are each independently selected from hydrogen; $C_{1-4}$ alkyl; aryl; substituted aryl; arylalkyl and heterocycle;
$R_3$ and $R_4$ are each independently selected from hydrogen; $C_1$-$C_4$ alkyl; aryl and arylalkyl; and $R_6$, $R_7$, $R_{11}$ and $R_{12}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl.

In a particular embodiment, X is H. In another particular embodiment, $R_1$, $R_2$, $R_3$ and $R_4$ are hydrogen. In yet another particular embodiment, $R_1$, $R_2$, $R_3$, $R_4$, $R_6$, $R_7$, $R_{11}$ and $R_{12}$ are each hydrogen.

In a preferred embodiment, X is H and $R_1$, $R_2$, $R_3$, $R_4$, $R_6$ and $R_7$ are hydrogen. In yet another another preferred embodiment, X is H; $R_1$, $R_2$, $R_3$, $R_4$, $R_6$, $R_7$ and $R_{11}$ are hydrogen and $R_{12}$ is selected from phenyl or methyl. In exemplary embodiments, a method of inhibiting COMT enzyme in a subject comprises administering one or more of the following compounds:

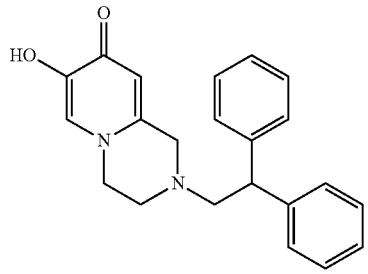

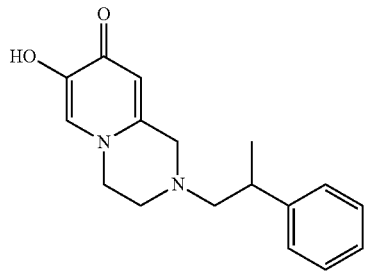

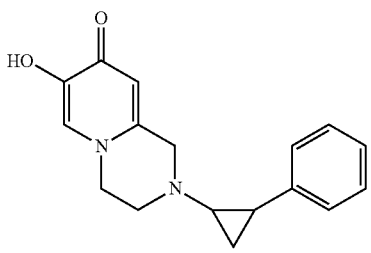

In another embodiment, the invention provides a method of inhibiting COMT enzyme in a subject by administering compounds of formula IV. These methods comprise administering to a subject in need thereof an effective amount of a COMT-inhibiting compound in accordance with formula IV, or a pharmaceutically acceptable salt thereof:

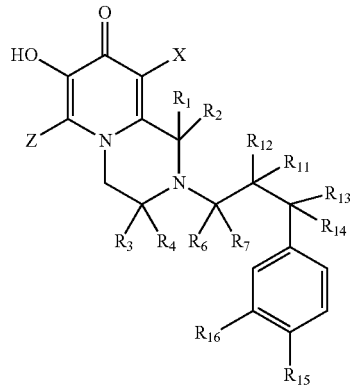

IV wherein:
X is selected from hydrogen; chloro; bromo, iodo and cyclopropyl;
Z is selected from hydrogen and fluoro.
$R_1$ and $R_2$ are each independently selected from hydrogen; $C_{1-4}$ alkyl; aryl; substituted aryl; arylakyl and heterocycle;
$R_3$ and $R_4$ are each independently selected from hydrogen; $C_1$-$C_4$ alkyl; aryl and arylalkyl;
$R_6$, $R_7$, $R_{11}$, $R_{12}$, $R_{13}$ and $R_{14}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl and aryl; $R_6$ and $R_7$, $R_{11}$ and $R_{12}$, $R_{13}$ and $R_{14}$, $R_6$ or $R_7$ and $R_{11}$ or $R_{12}$, $R_6$ or $R_7$ and $R_{13}$ or $R_{14}$, $R_{11}$ or $R_{12}$ and $R_{13}$ or $R_{14}$ may also come together to form a $C_3$-$C_6$ cycloalkyl; and
$R_{15}$ and $R_{16}$ are each hydrogen or come together to form a ring.

In a particular embodiment, X is H. In another particular embodiment, $R_1$, $R_2$, $R_3$ and $R_4$ are hydrogen. In still another particular embodiment, $R_1$, $R_2$, $R_3$, $R_4$, $R_6$, $R_7$, $R_{11}$, $R_{12}$, $R_{13}$ and $R_{14}$ are each hydrogen.

In a preferred embodiment, X is H; $R_1$, $R_2$, $R_3$, $R_4$, $R_6$, $R_7$, $R_{11}$, $R_{12}$, $R_{13}$, $R_{14}$, $R_{15}$ and $R_{16}$ are hydrogen. In yet another preferred embodiment, X is H; $R_1$, $R_2$, $R_3$, $R_4$, $R_6$, $R_7$, $R_{11}$, $R_{13}$ and $R_{14}$ are hydrogen; $R_{12}$ is methyl; and $R_{15}$-$R_{16}$ form a dioxolane.

In another embodiment, the invention provides a method of inhibiting COMT enzyme in a subject by administering compounds of formula IVa. These methods comprise administering to a subject in need thereof an effective amount of a COMT-inhibiting compound in accordance with formula IVa, or a pharmaceutically acceptable salt thereof:

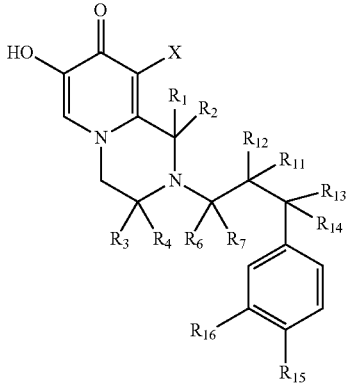

IVa wherein:

X is selected from hydrogen; chloride; bromide and cyclopropyl;

$R_1$ and $R_2$ are each independently selected from hydrogen; $C_{1-4}$ alkyl; aryl; substituted aryl; arylakyl and heterocycle;

$R_3$ and $R_4$ are each independently selected from hydrogen; $C_1$-$C_4$ alkyl; aryl and arylalkyl;

$R_6$, $R_7$, $R_{11}$, $R_{12}$, $R_{13}$ and $R_{14}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl and aryl; and $R_{15}$ and $R_{16}$ are each hydrogen or come together to form a ring.

In exemplary embodiments, a method of inhibiting COMT enzyme in a subject comprises administering one or more of the following compounds:

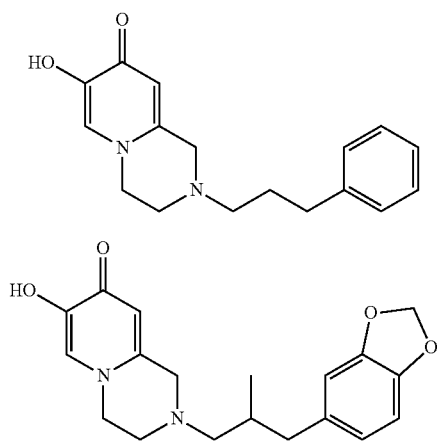

In another embodiment, the invention provides a method of inhibiting COMT enzyme in a subject by administering compounds of formula V. These methods comprise administering to a subject in need thereof an effective amount of a COMT-inhibiting compound in accordance with formula V, or a pharmaceutically acceptable salt thereof:

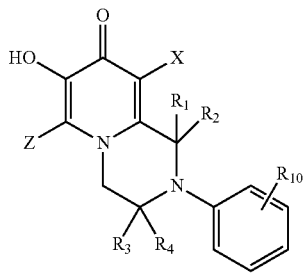

wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; and $R_{10}$ can be at one or more positions on the ring, and at each occurrence is independently selected from the group consisting of hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl.

In a preferred embodiment, X is H; $R_1$, $R_2$, $R_3$, and $R_4$ are hydrogen; and $R_{100}$ is selected from hydrogen, $C_1$-$C_4$ alkyl and mono-, di- or trihalomethyl. In a more specific embodiment, $R_{10}$ is hydrogen. In an alternative specific embodiment, $R_{10}$ is methyl. In yet another alternative specific embodiment, $R_{10}$ is trifluoromethyl.

In another embodiment, the invention provides a method of inhibiting COMT enzyme in a subject by administering compounds of formula Va. These methods comprise administering to a subject in need thereof an effective amount of a COMT-inhibiting compound in accordance with formula Va, or a pharmaceutically acceptable salt thereof:

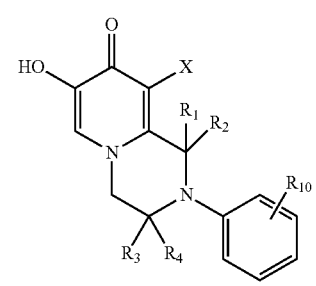

wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; and $R_{10}$ can be at one or more positions on the ring, and at each occurrence is independently selected from from the group consisting of hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl.

In a preferred embodiment, X is H; $R_1$, $R_2$, $R_3$, and $R_4$ are hydrogen; and $R_{10}$ is selected from hydrogen, $C_1$-$C_4$ alkyl and mono-, di- or trihalomethyl. In a more specific embodiment, $R_{10}$ is hydrogen. In an alternative specific embodiment, $R_{10}$ is methyl. In yet another alternative specific embodiment, $R_{10}$ is trifluoromethyl. In exemplary embodiments, a method of inhibiting COMT enzyme in a subject comprises administering one or more of the following compounds:

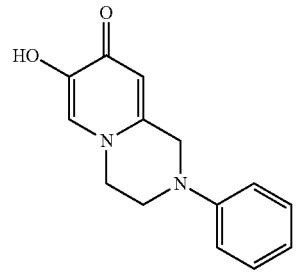

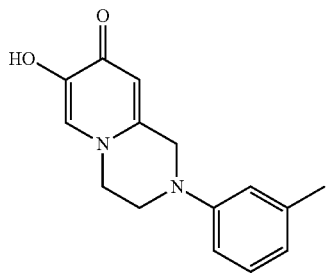

113

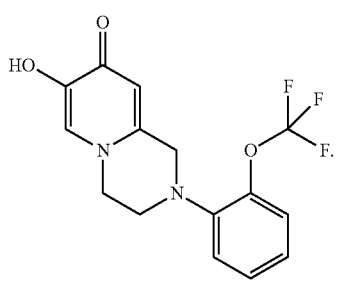

114

In another embodiment, the invention provides a method of inhibiting COMT enzyme in a subject by administering compounds of formula VI. These methods comprise administering to a subject in need thereof an effective amount of a COMT-inhibiting compound in accordance with formula VI or a pharmaceutically acceptable salt thereof:

VI wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; Y is $(CR_6R_7)_n$, wherein n is from 0-3, and $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl Het is a heterocycle. Het may be connected to the $R_6$/$R_7$ carbon at any position of the heterocycle, provided it provides proper valency. In particular embodiments, the heterocycle is aromatic. Examples of heteroaromatics include, but are not limited to indole; 1H-pyrazole; benzothiazole; benzotriazole; quinoline; isoquinoline; quinoxaline; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole; 2-phenylthiazole and 3,5-dimethyl-1-phenyl-1H-pyrazole.

In a preferred embodiment, X is H; $R_1$, $R_2$, $R_3$, $R_4$, $R_6$ and $R_7$, are hydrogen, and Het is selected from the group consisting of 1H-pyrazole; benzothiazole; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole; 2-phenylthiazole and 3,5-dimethyl-1-phenyl-1H-pyrazole.

In another embodiment, the invention provides a method of inhibiting COMT enzyme in a subject by administering compounds of formula VIa. These methods comprise administering to a subject in need thereof an effective amount of a COMT-inhibiting compound in accordance with formula VIa or a pharmaceutically acceptable salt thereof:

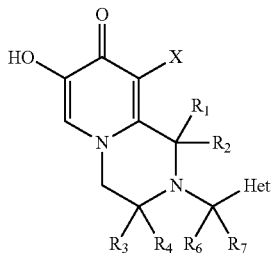

VIa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$ and $R_7$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; and Het is a heterocycle. Het may be connected to the $R_6$/$R_7$ carbon at any position of the heterocycle, provided it provides proper valency. In particular embodiments, the heterocycle is aromatic. Exemplary heteroaromatics include, but are not limited to indole; 1H-pyrazole; benzothiazole; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole; 2-phenylthiazole and 3,5-dimethyl-1-phenyl-1H-pyrazole.

In a preferred embodiment, X is H; $R_1$, $R_2$, $R_3$, $R_4$, $R_6$ and $R_7$, are hydrogen, and Het is selected from the group consisting of 1H-pyrazole; benzothiazole; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole; 2-phenylthiazole and 3,5-dimethyl-1-phenyl-1H-pyrazole.

In exemplary embodiments, a method of inhibiting COMT enzyme in a subject comprises administering one or more of the following compounds:
29
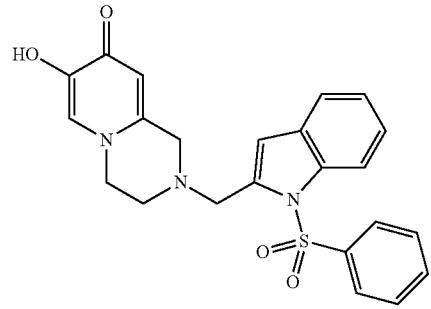
34
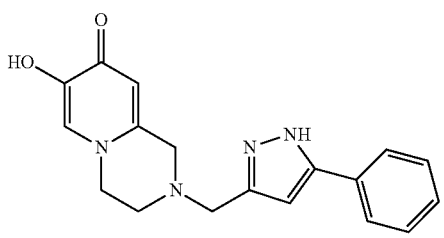
38
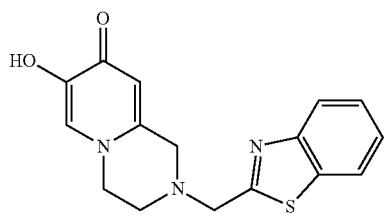
40
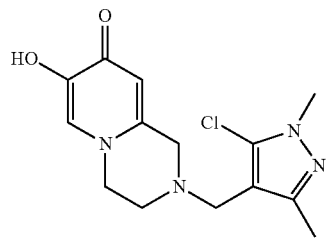
41
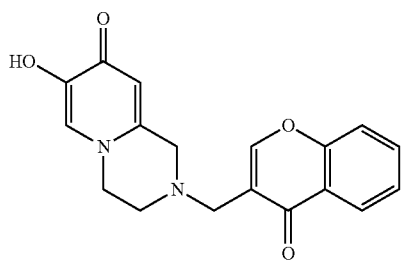
42
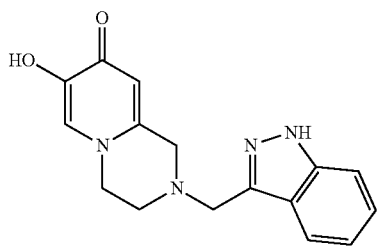
43
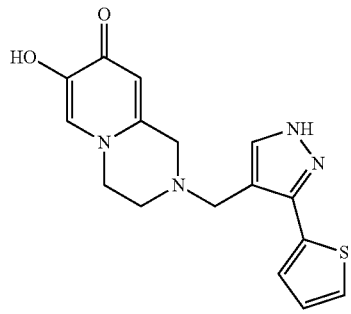
45
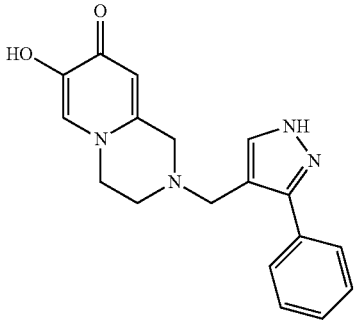
56
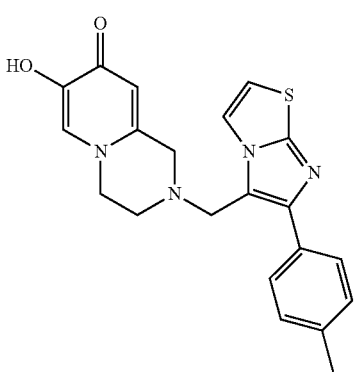
102
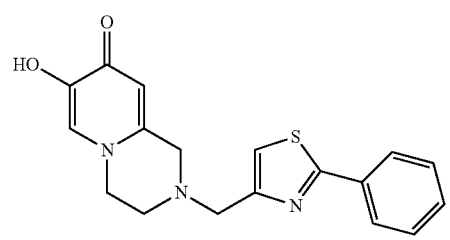
103
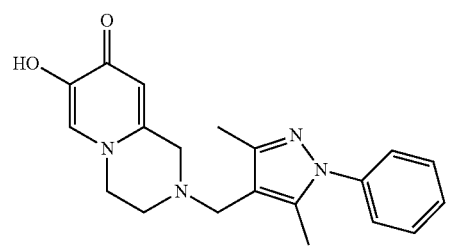

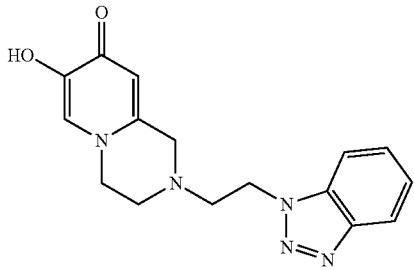

4

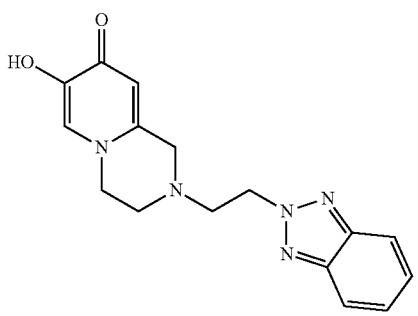

5

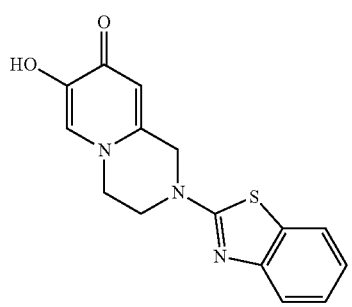

108

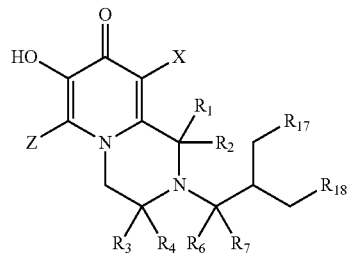

110

In another particular embodiment, the invention provides a method of inhibiting COMT enzyme in a subject by administering compounds of formula VII. These methods comprise administering to a subject in need thereof an effective amount of a COMT-inhibiting compound in accordance with formula VII, or a pharmaceutically acceptable salt thereof:

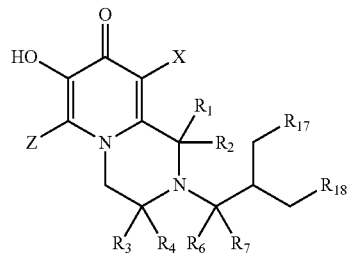

VII wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$ and $R_7$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; and $R_{17}$ and $R_{18}$ are selected from $C_1$-$C_4$ alkyl or come together to form a 5-10 membered cycloalkane, which can optionally be further substituted with $C_1$-$C_8$ alkyl or cycloalkyl.

In a preferred embodiment, X is H; $R_1$, $R_2$, $R_3$, $R_4$, $R_6$ and $R_7$, are hydrogen, and $R_{17}$ and $R_{18}$ are methyl. In another preferred embodiment, X is H; $R_1$, $R_2$, $R_3$, $R_4$, $R_6$ and $R_7$, are hydrogen, and $R_{17}$ and $R_{18}$ come together to form a 6, 7 or 8 membered cycloalkane, which is further substituted with $C_1$-$C_8$ alkyl or cycloalkyl.

In another particular embodiment, the invention provides a method of inhibiting COMT enzyme in a subject by administering compounds of formula VIIa. These methods comprise administering to a subject in need thereof an effective amount of a COMT-inhibiting compound in accordance with formula VIIa, or a pharmaceutically acceptable salt thereof:

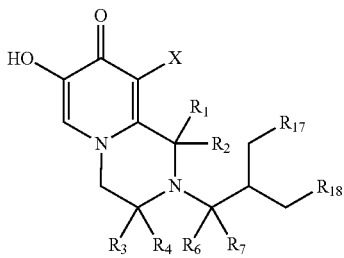

VIIa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$ and $R_7$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; and $R_{17}$ and $R_{18}$ are selected from $C_1$-$C_4$ alkyl or come together to form a 5-10 membered cycloalkane, which can optionally be further substituted with $C_1$-$C_8$ alkyl or cycloalkyl.

In a preferred embodiment, X is H; $R_1$, $R_2$, $R_3$, $R_4$, $R_6$ and $R_7$, are hydrogen, and $R_{17}$ and $R_{18}$ are methyl. In another preferred embodiment, X is H; $R_1$, $R_2$, $R_3$, $R_4$, $R_6$ and $R_7$, are hydrogen, and $R_{17}$ and $R_{18}$ come together to form a 6, 7 or 8 membered cycloalkane, which is further substituted with $C_1$-$C_8$ alkyl or cycloalkyl.

In exemplary embodiments, a method of inhibiting COMT enzyme in a subject comprises administering one or more of the following compounds:

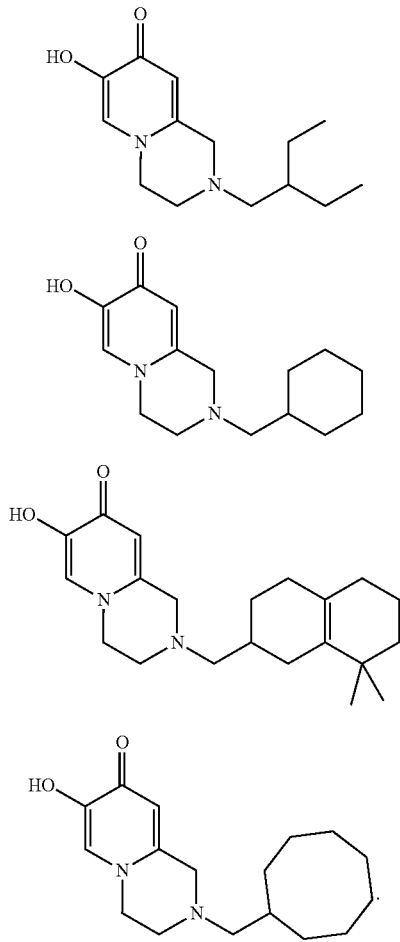

In another aspect, the invention provides a method of inhibiting COMT enzyme in a subject by administering to a subject in need thereof an effective amount of a compound selected from the following:

2-benzyl-7-hydroxy-1,2,3,4-tetrahydro-8H-pyrido[1,2-a]pyrazin-8-one
7-hydroxy-2-[4-(trifluoromethyl)benzyl]-1,2,3,4-tetrahydro-8H-pyrido[1,2-a]pyrazin-8-one
2-[(4-fluorophenyl)methyl]-7-hydroxy-3,4-dihydro-1H-pyrido[1,2-a]pyrazin-8-one
2-[2-(benzotriazol-1-yl)ethyl]-7-hydroxy-3,4-dihydro-1H-pyrido[1,2-a]pyrazin-8-one
2-[2-(benzotriazol-2-yl)ethyl]-7-hydroxy-3,4-dihydro-1H-pyrido[1,2-a]pyrazin-8-one
7-hydroxy-2-[3-(trifluoromethoxy)benzyl]-1,2,3,4-tetrahydro-8H-pyrido[1,2-a]pyrazin-8-one
2-(4-tert-butylbenzyl)-7-hydroxy-1,2,3,4-tetrahydro-8H-pyrido[1,2-a]pyrazin-8-one
7-hydroxy-2-[4-(trifluoromethoxy)benzyl]-1,2,3,4-tetrahydro-8H-pyrido[1,2-a]pyrazin-8-one
2-(2,4-dimethylbenzyl)-7-hydroxy-1,2,3,4-tetrahydro-8H-pyrido[1,2-a]pyrazin-8-one
7-hydroxy-2-[4-(propan-2-yl)benzyl]-1,2,3,4-tetrahydro-8H-pyrido[1,2-a]pyrazin-8-one
7-hydroxy-2-(pyridin-2-ylmethyl)-1,2,3,4-tetrahydro-8H-pyrido[1,2-a]pyrazin-8-one
7-hydroxy-2-[4-(pyridin-3-yl)benzyl]-1,2,3,4-tetrahydro-8H-pyrido[1,2-a]pyrazin-8-one
2-(4-ethylbenzyl)-7-hydroxy-1,2,3,4-tetrahydro-8H-pyrido[1,2-a]pyrazin-8-one
7-hydroxy-2-(quinolin-8-ylmethyl)-1,2,3,4-tetrahydro-8H-pyrido[1,2-a]pyrazin-8-one
7-hydroxy-2-(1-phenylethyl)-1,2,3,4-tetrahydro-8H-pyrido[1,2-a]pyrazin-8-one
2-[1-(4-ethylphenyl)ethyl]-7-hydroxy-1,2,3,4-tetrahydro-8H-pyrido[1,2-a]pyrazin-8-one
2-[(7-hydroxy-8-oxo-1,3,4,8-tetrahydro-2H-pyrido[1,2-a]pyrazin-2-yl)methyl]benzonitrile
2-(4-ethyl-3-nitrobenzyl)-7-hydroxy-1,2,3,4-tetrahydro-8H-pyrido[1,2-a]pyrazin-8-one
2-(2,2-di phenylethyl)-7-hydroxy-1,2,3,4-tetrahydro-8H-pyrido[1,2-a]pyrazin-8-one
2-(2-ethylbutyl)-7-hydroxy-1,2,3,4-tetrahydro-8H-pyrido[1,2-a]pyrazin-8-one
2-(3,5-dichlorobenzyl)-7-hydroxy-1,2,3,4-tetrahydro-8H-pyrido[1,2-a]pyrazin-8-one
2-(cyclohexylmethyl)-7-hydroxy-1,2,3,4-tetrahydro-8H-pyrido[1,2-a]pyrazin-8-one
2-(4-cyclopropyl benzyl)-7-hydroxy-1,2,3,4-tetrahydro-8H-pyrido[1,2-a]pyrazin-8-one
2-[(8,8-dimethyl-1,2,3,4,5,6,7,8-octahydronaphthalen-2-yl)methyl]-7-hydroxy-1,2,3,4-tetrahydro-8H-pyrido[1,2-a]pyrazin-8-one
2-(3,4-dichlorobenzyl)-7-hydroxy-1,2,3,4-tetrahydro-8H-pyrido[1,2-a]pyrazin-8-one
2-(cyclooctylmethyl)-7-hydroxy-1,2,3,4-tetrahydro-8H-pyrido[1,2-a]pyrazin-8-one
2-(2,6-dimethylbenzyl)-7-hydroxy-1,2,3,4-tetrahydro-8H-pyrido[1,2-a]pyrazin-8-one
2-(2,5-dimethylbenzyl)-7-hydroxy-1,2,3,4-tetrahydro-8H-pyrido[1,2-a]pyrazin-8-one
7-hydroxy-2-{[1-(phenylsulfonyl)-1H-indol-2-yl]methyl}-1,2,3,4-tetrahydro-8H-pyrido[1,2-a]pyrazin-8-one
7-hydroxy-2-(3-phenylpropyl)-1,2,3,4-tetrahydro-8H-pyrido[1,2-a]pyrazin-8-one
7-hydroxy-2-(2-phenylpropyl)-1,2,3,4-tetrahydro-8H-pyrido[1,2-a]pyrazin-8-one
2-(3,5-difluorobenzyl)-7-hydroxy-1,2,3,4-tetrahydro-8H-pyrido[1,2-a]pyrazin-8-one
7-hydroxy-2-(2-methylbenzyl)-1,2,3,4-tetrahydro-8H-pyrido[1,2-a]pyrazin-8-one
7-hydroxy-2-[(5-phenyl-1H-pyrazol-3-yl)methyl]-1,2,3,4-tetrahydro-8H-pyrido[1,2-a]pyrazin-8-one
2-{[6-chloro-4-(1H-imidazol-4-yl)-3,4-dihydro-2H-chromen-8-yl]methyl}-7-hydroxy-1,2,3,4-tetrahydro-8H-pyrido[1,2-a]pyrazin-8-one
7-hydroxy-2-(3-phenoxybenzyl)-1,2,3,4-tetrahydro-8H-pyrido[1,2-a]pyrazin-8-one
2-(2,3-dimethylbenzyl)-7-hydroxy-1,2,3,4-tetrahydro-8H-pyrido[1,2-a]pyrazin-8-one 2-(1,3-benzothiazol-2-ylmethyl)-7-hydroxy-1,2,3,4-tetrahydro-8H-pyrido[1,2-a]pyrazin-8-one
2-(2-fluorobenzyl)-7-hydroxy-1,2,3,4-tetrahydro-8H-pyrido[1,2-a]pyrazin-8-one
2-[(5-chloro-1,3-dimethyl-1H-pyrazol-4-yl)methyl]-7-hydroxy-1,2,3,4-tetrahydro-8H-pyrido[1,2-a]pyrazin-8-one
7-hydroxy-2-[(4-oxo-4H-chromen-3-yl)methyl]-1,2,3,4-tetrahydro-8H-pyrido[1,2-a]pyrazin-8-one
7-hydroxy-2-(1H-indazol-3-ylmethyl)-1,2,3,4-tetrahydro-8H-pyrido[1,2-a]pyrazin-8-one
7-hydroxy-2-{[3-(thiophen-2-yl)-1H-pyrazol-4-yl]methyl}-1,2,3,4-tetrahydro-8H-pyrido[1,2-a]pyrazin-8-one
7-hydroxy-2-[2-(trifluoromethyl)benzyl]-1,2,3,4-tetrahydro-8H-pyrido[1,2-a]pyrazin-8-one
7-hydroxy-2-[(3-phenyl-1H-pyrazol-4-yl)methyl]-1,2,3,4-tetrahydro-8H-pyrido[1,2-a]pyrazin-8-one
2-(2,6-dimethoxybenzyl)-7-hydroxy-1,2,3,4-tetrahydro-8H-pyrido[1,2-a]pyrazin-8-one
7-hydroxy-2-(4-phenoxybenzyl)-1,2,3,4-tetrahydro-8H-pyrido[1,2-a]pyrazin-8-one
2-(2,3-dihydro-1,4-benzodioxin-6-ylmethyl)-7-hydroxy-1,2,3,4-tetrahydro-8H-pyrido[1,2-a]pyrazin-8-one
2-[3-(1,3-benzodioxol-5-yl)-2-methyl propyl]-7-hydroxy-1,2,3,4-tetrahydro-8H-pyrido[1,2-a]pyrazin-8-one
7-hydroxy-2-(4-methoxybenzyl)-1,2,3,4-tetrahydro-8H-pyrido[1,2-a]pyrazin-8-one
7-hydroxy-2-(2-methoxybenzyl)-1,2,3,4-tetrahydro-8H-pyrido[1,2-a]pyrazin-8-one
2-[4-(benzyloxy)benzyl]-7-hydroxy-1,2,3,4-tetrahydro-8H-pyrido[1,2-a]pyrazin-8-one
2-[3-(benzyloxy)benzyl]-7-hydroxy-1,2,3,4-tetrahydro-8H-pyrido[1,2-a]pyrazin-8-one
2-(2,1,3-benzothiadiazol-5-ylmethyl)-7-hydroxy-1,2,3,4-tetrahydro-8H-pyrido[1,2-a]pyrazin-8-one
2-[2-(benzyloxy)benzyl]-7-hydroxy-1,2,3,4-tetrahydro-8H-pyrido[1,2-a]pyrazin-8-one
7-hydroxy-2-{[6-(4-methylphenyl)imidazo[2,1-b][1,3]thiazol-5-yl]methyl}-1,2,3,4-tetrahydro-8H-pyrido[1,2-a]pyrazin-8-one
2-(2-chloro-4-fluorobenzyl)-7-hydroxy-1,2,3,4-tetrahydro-8H-pyrido[1,2-a]pyrazin-8-one
2-(2-chlorobenzyl)-7-hydroxy-1,2,3,4-tetrahydro-8H-pyrido[1,2-a]pyrazin-8-one
2-(2-chloro-6-fluorobenzyl)-7-hydroxy-1,2,3,4-tetrahydro-8H-pyrido[1,2-a]pyrazin-8-one
2-(2,6-dichlorobenzyl)-7-hydroxy-1,2,3,4-tetrahydro-8H-pyrido[1,2-a]pyrazin-8-one
2-(2,4-dichlorobenzyl)-7-hydroxy-1,2,3,4-tetrahydro-8H-pyrido[1,2-a]pyrazin-8-one
2-(2,6-difluorobenzyl)-7-hydroxy-1,2,3,4-tetrahydro-8H-pyrido[1,2-a]pyrazin-8-one
2-[(4-bromo-2-chloro-phenyl)methyl]-7-hydroxy-3,4-dihydro-1H-pyrido[1,2-a]pyrazin-8-one
2-[(2-chloro-4-cyclopropyl-phenyl)methyl]-7-hydroxy-3,4-dihydro-1H-pyrido[1,2-a]pyrazin-8-one
2-[(2-chlorophenyl)methyl]-7-hydroxy-3,3-dimethyl-1,4-dihydropyrido[1,2-a]pyrazin-8-one
2-[(2,4-dichloro-5-nitro-phenyl)methyl]-7-hydroxy-3,4-dihydro-1H-pyrido[1,2-a]pyrazin-8-one
7-hydroxy-2-[1-(2-methylphenyl)ethyl]-1,2,3,4-tetrahydro-8H-pyrido[1,2-a]pyrazin-8-one
2-[1-(4-chlorophenyl)ethyl]-7-hydroxy-1,2,3,4-tetrahydro-8H-pyrido[1,2-a]pyrazin-8-one
2-[1-(2,5-dichlorophenyl)ethyl]-7-hydroxy-1,2,3,4-tetrahydro-8H-pyrido[1,2-a]pyrazin-8-one
7-hydroxy-2-{1-[4-(trifluoromethyl)phenyl]ethyl}-1,2,3,4-tetrahydro-8H-pyrido[1,2-a]pyrazin-8-one
7-hydroxy-2-[1-(3-methylphenyl)ethyl]-1,2,3,4-tetrahydro-8H-pyrido[1,2-a]pyrazin-8-one
2-[1-(3-chlorophenyl)ethyl]-7-hydroxy-1,2,3,4-tetrahydro-8H-pyrido[1,2-a]pyrazin-8-one
2-(4-chloro-2,3-dihydro-1H-inden-1-yl)-7-hydroxy-1,2,3,4-tetrahydro-8H-pyrido[1,2-a]pyrazin-8-one
2-[1-(2,6-dimethoxyphenyl)ethyl]-7-hydroxy-1,2,3,4-tetrahydro-8H-pyrido[1,2-a]pyrazin-8-one
7-hydroxy-2-[1-(2,3,5-trifluorophenyl)ethyl]-1,2,3,4-tetrahydro-8H-pyrido[1,2-a]pyrazin-8-one
2-[1-(2-chlorophenyl)ethyl]-7-hydroxy-1,2,3,4-tetrahydro-8H-pyrido[1,2-a]pyrazin-8-one
2-{1-[2-(benzyloxy)phenyl]ethyl}-7-hydroxy-1,2,3,4-tetrahydro-8H-pyrido[1,2-a]pyrazin-8-one
7-hydroxy-2-(1-phenylpentyl)-1,2,3,4-tetrahydro-8H-pyrido[1,2-a]pyrazin-8-one
2-(7-fluoro-2,3-dihydro-1H-inden-1-yl)-7-hydroxy-1,2,3,4-tetrahydro-8H-pyrido[1,2-a]pyrazin-8-one
7-hydroxy-2-(2-phenyl-3,4-dihydro-2H-chromen-4-yl)-1,2,3,4-tetrahydro-8H-pyrido[1,2-a]pyrazin-8-one
2-[1-(3-fluorophenyl)ethyl]-7-hydroxy-1,2,3,4-tetrahydro-8H-pyrido[1,2-a]pyrazin-8-one
2-[cyclopentyl(phenyl)methyl]-7-hydroxy-1,2,3,4-tetrahydro-8H-pyrido[1,2-a]pyrazin-8-one
7-hydroxy-2-[1-(3-methoxyphenyl)ethyl]-1,2,3,4-tetrahydro-8H-pyrido[1,2-a]pyrazin-8-one
2-(2,3-dihydro-1H-inden-1-yl)-7-hydroxy-1,2,3,4-tetrahydro-8H-pyrido[1,2-a]pyrazin-8-one
2-[1-(3-chloro-2,6-difluorophenyl)ethyl]-7-hydroxy-1,2,3,4-tetrahydro-8H-pyrido[1,2-a]pyrazin-8-one
7-hydroxy-2-(6,7,8,9-tetrahydro-5H-benzo[7]annulen-5-yl)-1,2,3,4-tetrahydro-8H-pyrido[1,2-a]pyrazin-8-one
2-[1-(2,5-dimethylphenyl)ethyl]-7-hydroxy-1,2,3,4-tetrahydro-8H-pyrido[1,2-a]pyrazin-8-one
2-(1,2-diphenylethyl)-7-hydroxy-1,2,3,4-tetrahydro-8H-pyrido[1,2-a]pyrazin-8-one
7-hydroxy-2-(1-phenylpropyl)-1,2,3,4-tetrahydro-8H-pyrido[1,2-a]pyrazin-8-one
7-hydroxy-2-(1,2,3,4-tetrahydronaphthalen-1-yl)-1,2,3,4-tetrahydro-8H-pyrido[1,2-a]pyrazin-8-one
7-hydroxy-2-(7-methoxy-1,2,3,4-tetrahydronaphthalen-1-yl)-1,2,3,4-tetrahydro-8H-pyrido[1,2-a]pyrazin-8-one
7-hydroxy-2-(4-methyl-2,3-dihydro-1H-inden-1-yl)-1,2,3,4-tetrahydro-8H-pyrido[1,2-a]pyrazin-8-one
7-hydroxy-2-(1-phenylbutyl)-1,2,3,4-tetrahydro-8H-pyrido[1,2-a]pyrazin-8-one
4-[1-(7-hydroxy-8-oxo-1,3,4,8-tetrahydro-2H-pyrido[1,2-a]pyrazin-2-yl)ethyl]benzonitrile
3-[1-(7-hydroxy-8-oxo-1,3,4,8-tetrahydro-2H-pyrido[1,2-a]pyrazin-2-yl)ethyl]benzonitrile
N-{3-[1-(7-hydroxy-8-oxo-1,3,4,8-tetrahydro-2H-pyrido[1,2-a]pyrazin-2-yl)ethyl]phenyl}acetamide
2-[1-(2,5-difluorophenyl)ethyl]-7-hydroxy-1,2,3,4-tetrahydro-8H-pyrido[1,2-a]pyrazin-8-one
2-[1-(2-fluorophenyl)ethyl]-7-hydroxy-1,2,3,4-tetrahydro-8H-pyrido[1,2-a]pyrazin-8-one
2-[1-(4-fluorophenyl)ethyl]-7-hydroxy-1,2,3,4-tetrahydro-8H-pyrido[1,2-a]pyrazin-8-one
7-hydroxy-2-(2-hydroxy-1-phenylethyl)-1,2,3,4-tetrahydro-8H-pyrido[1,2-a]pyrazin-8-one
7-hydroxy-2-(2,2,2-trifluoro-1-phenylethyl)-1,2,3,4-tetrahydro-8H-pyrido[1,2-a]pyrazin-8-one
7-hydroxy-2-[(2-phenyl-1,3-thiazol-4-yl)methyl]-1,2,3,4-tetrahydro-8H-pyrido[1,2-a]pyrazin-8-one
2-[(3,5-dimethyl-1-phenyl-1H-pyrazol-4-yl)methyl]-7-hydroxy-1,2,3,4-tetrahydro-8H-pyrido[1,2-a]pyrazin-8-one 7-hydroxy-2-(1-phenylcyclopropyl)-3,4-dihydro-1H-pyrido[1,2-a]pyrazin-8-one
2-(2-fluoro-1-phenyl-ethyl)-7-hydroxy-3,4-dihydro-1H-pyrido[1,2-a]pyrazin-8-one
2-[1-(2-chlorophenyl)cyclopropyl]-7-hydroxy-3,4-dihydro-1H-pyrido[1,2-a]pyrazin-8-one
2-(2,2-difluoro-1-phenyl-ethyl)-7-hydroxy-3,4-dihydro-1H-pyrido[1,2-a]pyrazin-8-one
2-(1,3-benzothiazol-2-yl)-7-hydroxy-3,4-dihydro-1H-pyrido[1,2-a]pyrazin-8-one
7-hydroxy-2-(2-phenylcyclopropyl)-3,4-dihydro-1H-pyrido[1,2-a]pyrazin-8-one
7-hydroxy-2-(5-quinolyl)-3,4-dihydro-1H-pyrido[1,2-a]pyrazin-8-one
7-hydroxy-2-(3-phenyloxetan-3-yl)-3,4-dihydro-1H-pyrido[1,2-a]pyrazin-8-one
7-hydroxy-2-phenyl-1,2,3,4-tetrahydro-8H-pyrido[1,2-a]pyrazin-8-one
7-hydroxy-2-(3-methylphenyl)-1,2,3,4-tetrahydro-8H-pyrido[1,2-a]pyrazin-8-one
7-hydroxy-2-[2-(trifluoromethoxy)phenyl]-1,2,3,4-tetrahydro-8H-pyrido[1,2-a]pyrazin-8-one
1,2-dibenzyl-7-hydroxy-1,2,3,4-tetrahydro-8H-pyrido[1,2-a]pyrazin-8-one
2-benzyl-7-hydroxy-1-phenyl-1,2,3,4-tetrahydro-8H-pyrido[1,2-a]pyrazin-8-one
2-(2,6-dichlorobenzyl)-7-hydroxy-1-phenyl-1,2,3,4-tetrahydro-8H-pyrido[1,2-a]pyrazin-8-one
(1R)-2-(4-ethylbenzyl)-7-hydroxy-1-phenyl-1,2,3,4-tetrahydro-8H-pyrido[1,2-a]pyrazin-8-one
(1S)-2-(4-ethylbenzyl)-7-hydroxy-1-phenyl-1,2,3,4-tetrahydro-8H-pyrido[1,2-a]pyrazin-8-one
2-(4-ethylbenzyl)-7-hydroxy-1-(propan-2-yl)-1,2,3,4-tetrahydro-8H-pyrido[1,2-a]pyrazin-8-one
2-(2,6-dimethylbenzyl)-7-hydroxy-1-methyl-1,2,3,4-tetrahydro-8H-pyrido[1,2-a]pyrazin-8-one
2-(4-ethylbenzyl)-7-hydroxy-1-methyl-1,2,3,4-tetrahydro-8H-pyrido[1,2-a]pyrazin-8-one
1-(4-fluorophenyl)-7-hydroxy-2-(quinolin-8-ylmethyl)-1,2,3,4-tetrahydro-8H-pyrido[1,2-a]pyrazin-8-one
2-(2,6-dimethylbenzyl)-1-(4-fluorophenyl)-7-hydroxy-1,2,3,4-tetrahydro-8H-pyrido[1,2-a]pyrazin-8-one
2-(4-ethylbenzyl)-7-hydroxy-1-(tetrahydro-2H-pyran-4-yl)-1,2,3,4-tetrahydro-8H-pyrido[1,2-a]pyrazin-8-one
2-(4-ethylbenzyl)-7-hydroxy-1-[3-(pyridin-3-yl)phenyl]-1,2,3,4-tetrahydro-8H-pyrido[1,2-a]pyrazin-8-one
2-benzyl-7-hydroxy-3-phenyl-1,2,3,4-tetrahydro-8H-pyrido[1,2-a]pyrazin-8-one
2,3-dibenzyl-7-hydroxy-1,2,3,4-tetrahydro-8H-pyrido[1,2-a]pyrazin-8-one
3-benzyl-2-(2,6-dichlorobenzyl)-7-hydroxy-1,2,3,4-tetrahydro-8H-pyrido[1,2-a]pyrazin-8-one
7-hydroxy-3-methyl-2-[4-(trifluoromethoxy)benzyl]-1,2,3,4-tetrahydro-8H-pyrido[1,2-a]pyrazin-8-one
2-benzyl-7-hydroxy-3-methyl-1,2,3,4-tetrahydro-8H-pyrido[1,2-a]pyrazin-8-one
2-benzyl-7-hydroxy-3-(2-phenylethyl)-1,2,3,4-tetrahydro-8H-pyrido[1,2-a]pyrazin-8-one
9-chloro-2-(2-chloro-6-fluorobenzyl)-7-hydroxy-1,2,3,4-tetrahydro-8H-pyrido[1,2-a]pyrazin-8-one
6-fluoro-7-hydroxy-2-[[4-(trifluoromethoxy)phenyl]methyl]-3,4-dihydro-1H-pyrido[1,2-a]pyrazin-8-one
2-[(2-chlorophenyl)methyl]-6-fluoro-7-hydroxy-3,4-dihydro-1H-pyrido[1,2-a]pyrazin-8-one
9-chloro-2-(4-ethylbenzyl)-7-hydroxy-1,2,3,4-tetrahydro-8H-pyrido[1,2-a]pyrazin-8-one
9-chloro-2-[(2-chlorophenyl)methyl]-7-hydroxy-3,4-dihydro-1H-pyrido[1,2-a]pyrazin-8-one
9-bromo-2-(4-ethyl benzyl)-7-hydroxy-1,2,3,4-tetrahydro-8H-pyrido[1,2-a]pyrazin-8-one
9-bromo-2-[(2-chlorophenyl)methyl]-7-hydroxy-3,4-dihydro-1H-pyrido[1,2-a]pyrazin-8-one
2-[(2-chlorophenyl)methyl]-7-hydroxy-9-iodo-3,4-dihydro-1H-pyrido[1,2-a]pyrazin-8-one
9-cyclopropyl-2-(4-ethylbenzyl)-7-hydroxy-1,2,3,4-tetrahydro-8H-pyrido[1,2-a]pyrazin-8-one
2-[(2-chlorophenyl)methyl]-9-cyclopropyl-7-hydroxy-3,4-dihydro-1H-pyrido[1,2-a]pyrazin-8-one.

The compounds for use in the instant method may be selected from any one or any combination of compounds designated 1-142 herein.

For use in the method, the compound or compounds of the present invention, described above, is typically provided as a pharmaceutical composition wherein the compound or compounds is present in combination with a pharmaceutically acceptable carrier as described herein. Such pharmaceutical compositions are also provided by this disclosure.

For use in the method, the compound(s) of the present invention, described above, may also be used in combination with another additional therapeutic agent.

The methods of the present invention may be used to treat or prevent a neurological or psychiatric disorder. In particular, exemplary embodiments of the invention include methods of treating or preventing schizophrenia, major depression, a depressive phase of bipolar disorder, attention deficit disorder, attention deficit/hyperactivity disorder, substance dependency, or increased appetite associated with smoking cessation or antipsychotic use. Other significant indications include age-associated cognitive symptoms, impulse control disorders, including compulsive gambling, sexual behavior, and other compulsive destructive behaviors.

In addition to the psychiatric indications, the methods of the invention may also be used to treat neurological disorders. In one embodiment, the method of the present invention comprises administering an effective amount of a compound described herein above in combination with L-DOPA for treatment of Parkinson's disease. The compound can be administered in combination with L-DOPA, concurrently or separately, with or without an aromatic L-amino acid decarboxylase inhibitor (AADC) such as carbidopa, to prevent or inhibit COMT-mediated metabolism of L-DOPA.

III. Compounds

Also disclosed herein are the novel 7-hydroxy-tetrahydropyridopyrazinone derivatives described above which, preferably, are inhibitors of catechol O-methyltransferase (COMT) enzyme, and which are useful in the treatment or prevention of neurological or psychiatric disorders or diseases in which COMT is involved. The compounds of the invention are characterized by their activity to inhibit the enzyme COMT. In preferred embodiments, the compounds of the present invention are effective to inhibit the enzyme COMT, in an assay which determines the inhibitory concentration ($IC_{50}$) for the conversion of the methyl donor S-adenosyl methionine to S-adenosyl homocysteine (SAH) as described herein, with a $pIC_{50}$ superior or equal to 4.5. In increasingly preferred embodiments, the $pIC_{50}$ as so determined is superior or equal to 6.0. In a more preferred embodiment, the $pIC_{50}$ as so determined is superior or equal to 7.0.

The ability of compounds within the scope of this invention to inhibit the activity of catechol-O-methyltransferase (COMT) may be determined by methods known to those in the art for measuring COMT inhibition. One method for measuring COMT activity uses a homogenous time-resolved fluorescent (HTRF) assay (Lina et al, 2012; kit from CisBio, Codolet, France). This assay measures the production of-S-adenosyl homocysteine (SAH) from the methyl donor S-adenosyl methionine. Using this assay preferred compounds of the invention have a $pIC_{50}$ superior or equal to 4.5. In increasingly preferred embodiments, the $pIC_{50}$ as so determined is superior or equal to 6.0. In a more preferred embodiment, the $pIC_{50}$ as so determined is superior or equal to 7.0.

Provided herein are COMT-inhibiting compounds in accordance with formula I, or pharmaceutically acceptable salts thereof:

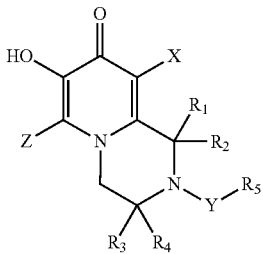

I wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_5$ is selected from aryl, heteroaryl, heterocycle, $C_1$-$C_{10}$ alkyl or $C_1$-$C_{10}$ cycloaklyl, optionally substituted with one or more groups selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and NHC(O)R, wherein R is $C_1$-$C_4$ alkyl; and Y is $(CR_6R_7)_n$, wherein n is from 0-3, and each $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or when $R_5$ is phenyl, one of $R_6$ or $R_7$ comes together with $R_5$ to form a bicycle.

In another embodiment are COMT-inhibiting compounds in accordance with formula Ia, or pharmaceutically acceptable salts thereof:

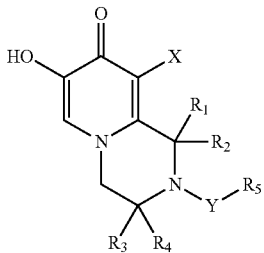

Ia wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_5$ is selected from aryl, heteroaryl, heterocycle, $C_1$-$C_{10}$ alkyl or $C_1$-$C_{10}$ cycloaklyl, optionally substituted with one or more groups selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and NHC(O)R, wherein R is $C_1$-$C_4$ alkyl; and Y is $(CR_6R_7)_n$, wherein n is from 0-3, and each $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; or when $R_5$ is phenyl, one of $R_6$ or $R_7$ comes together with $R_5$ to form a bicycle.

In another embodiment, the invention provides COMT-inhibiting compounds in accordance with formula II, or pharmaceutically acceptable salts thereof:

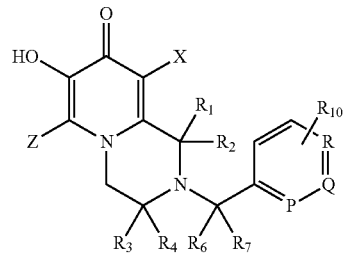

II wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; P, Q and R are each independently selected from CH and N; $R_{10}$ can be at one more positions on the ring, and at each occurrence is independently selected from hydrogen; mono-, di-, or trihalomethyl; $C_1$-$C_4$ alkyl, $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P, Q or R to form a bicycle; and $R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or one of $R_6$ or $R_7$ comes together with P to form a bicycle.

In a particular embodiment, X is H. In another particular embodiment, $R_1$, $R_2$, $R_3$ and $R_4$ are hydrogen. In still another particular embodiment, three of $R_1$, $R_2$, $R_3$ and $R_4$ are hydrogen. In yet another particular embodiment, $R_1$, $R_2$, $R_3$, $R_4$, $R_6$ and $R_7$ are each hydrogen.

In a preferred embodiment, X is H; $R_1$, $R_2$, $R_3$, $R_4$, $R_6$ and $R_7$ are hydrogen, and P, Q and R are all CH. In another preferred embodiment, X is H; three of $R_1$, $R_2$, $R_3$, $R_4$, $R_6$ and $R_7$ are each hydrogen and P, Q and R are all CH. In still another preferred embodiment, X is H; three of $R_1$, $R_2$, $R_3$ and $R_4$ are hydrogen; one of $R_6$ or $R_7$ is hydrogen; and P, Q and R are all CH.

In another embodiment, the invention provides COMT-inhibiting compounds in accordance with formula IIa, or pharmaceutically acceptable salts thereof:

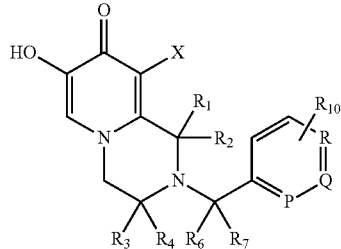

IIa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; P, Q and R are each independently selected from CH and N;

$R_{10}$ can be at one more more positions on the ring, and at each occurrence is independently selected from hydrogen; mono-, di-, or trihalomethyl; $C_1$-$C_4$ alkyl, $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P, Q or R to form a bicycle; and $R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; or one of $R_6$ or $R_7$ comes together with P to form a bicycle.

In a particular embodiment, X is H. In another particular embodiment, $R_1$, $R_2$, $R_3$ and $R_4$ are hydrogen. In still another particular embodiment, three of $R_1$, $R_2$, $R_3$ and $R_4$ are hydrogen. In yet another particular embodiment, $R_1$, $R_2$, $R_3$, $R_4$, $R_6$ and $R_7$ are each hydrogen.

In a preferred embodiment, X is H; $R_1$, $R_2$, $R_3$, $R_4$, $R_6$ and $R_7$ are hydrogen, and P, Q and R are all C. In another preferred embodiment, X is H; three of $R_1$, $R_2$, $R_3$, $R_4$, $R_6$ and $R_7$ are each hydrogen and P, Q and R are all C. In still another preferred embodiment, X is H; three of $R_1$, $R_2$, $R_3$ and $R_4$ are hydrogen; one of $R_6$ or $R_7$ is hydrogen; and P, Q and R are all CH.

In another embodiment, the invention provides COMT-inhibiting compounds in accordance with formula IIb, or pharmaceutically acceptable salts thereof:

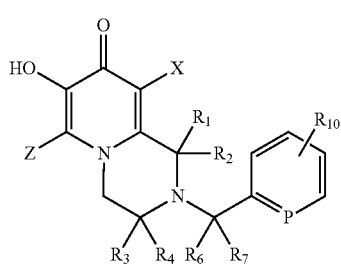

IIb wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; P is CH;

$R_{10}$ can be at one more positions on the ring, and at each occurrence is independently selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P to form a bicycle; and $R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or one of $R_6$ or $R_7$ comes together with P to form a bicycle.

In a particular embodiment, Z is fluoro and X is H. In another particular embodiment, $R_1$, $R_2$, $R_3$ and $R_4$ are hydrogen. In yet another particular embodiment, $R_1$, $R_2$, $R_3$, $R_4$, $R_6$, $R_7$ are each hydrogen.

In a preferred embodiment, Z is fluoro and X is H and $R_1$, $R_2$, $R_3$, $R_4$, $R_6$ and $R_7$ are hydrogen. In yet another preferred embodiment, X is H; $R_1$, $R_2$, $R_3$, $R_4$, $R_6$, $R_7$ and $R_{100}$ is selected from optionally substituted phenyl or methyl.

In exemplary embodiments, a compound is selected from the following:

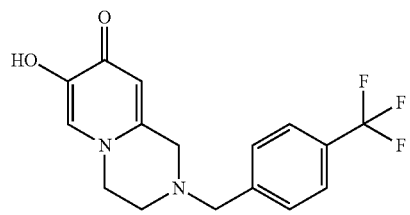

2

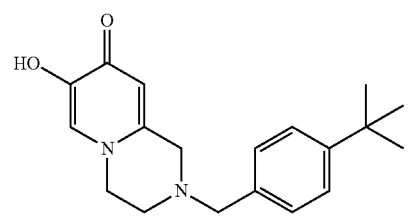

7

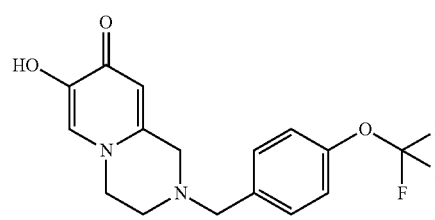

8

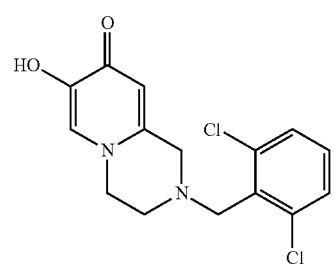

60

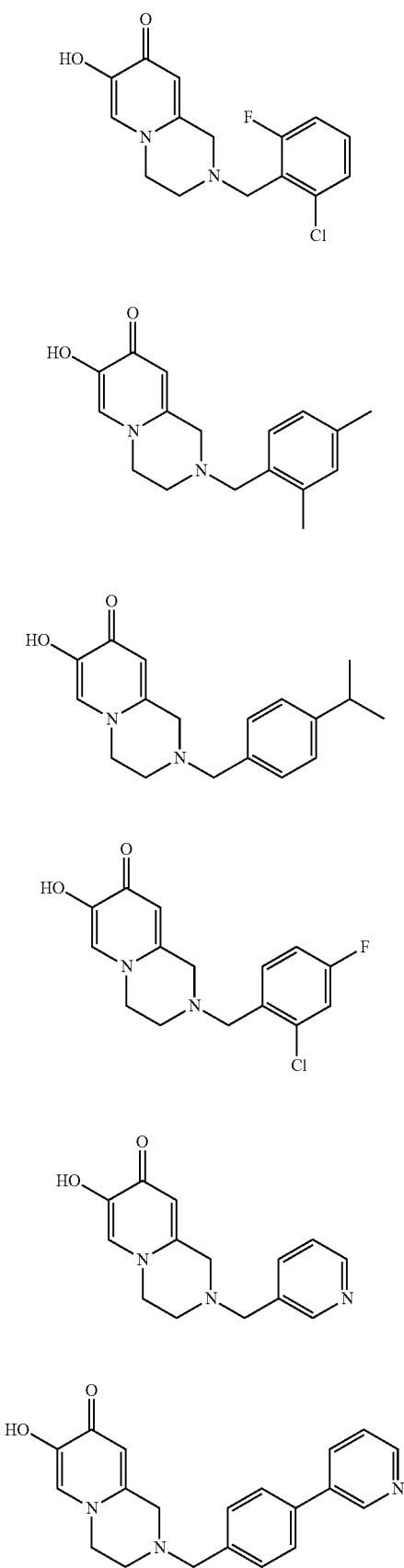
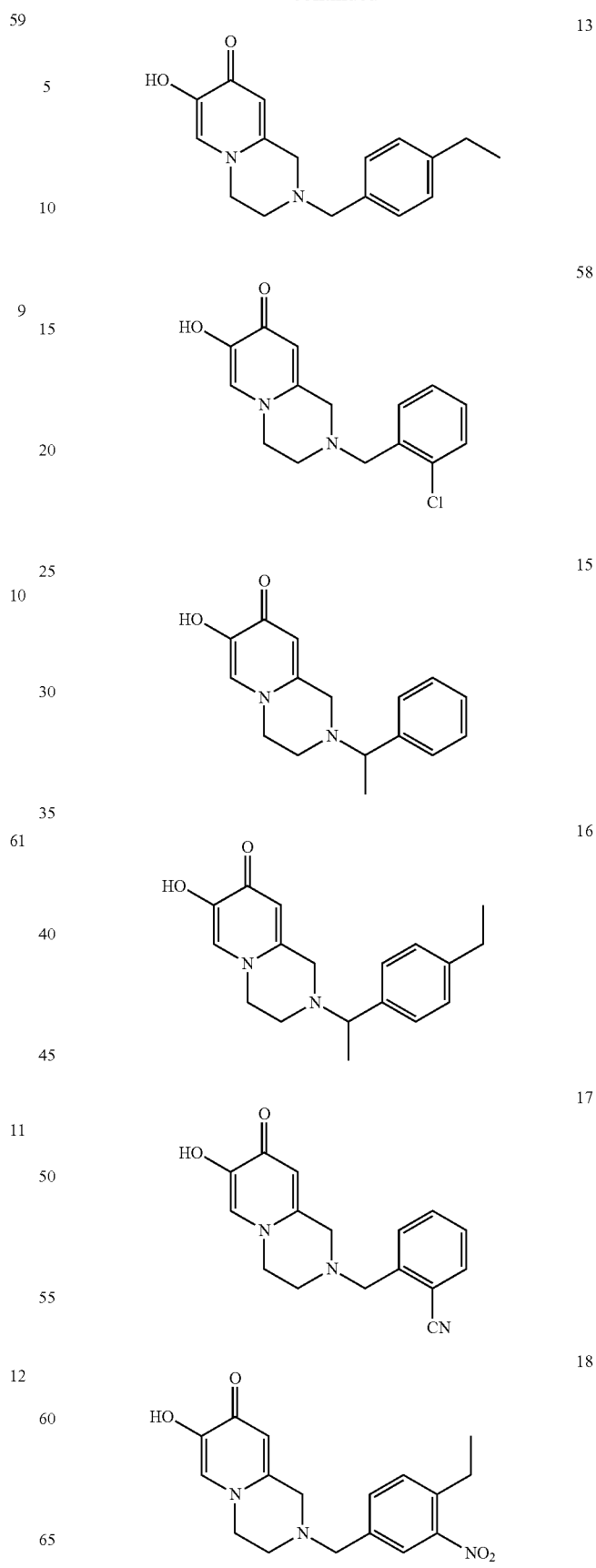

21
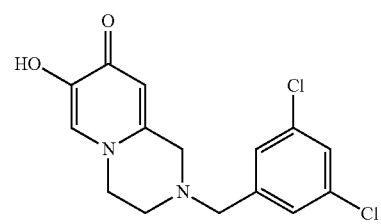
23
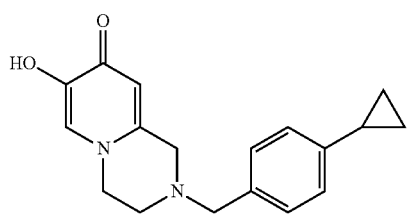
25
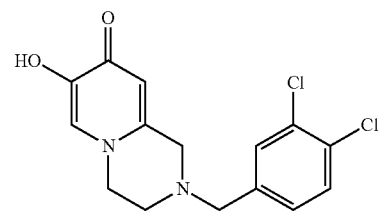
27
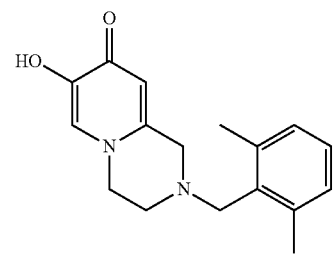
28
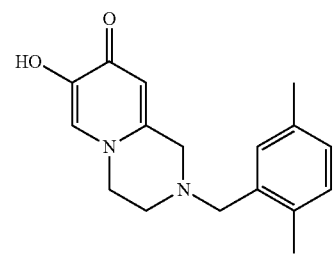
32
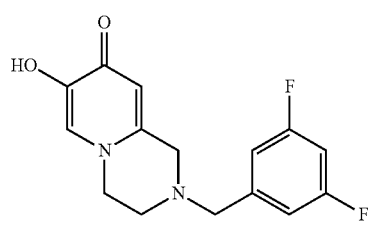
33
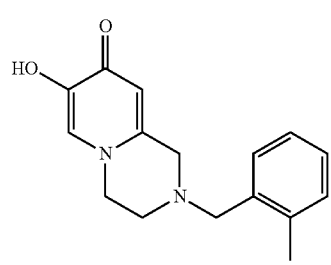
57
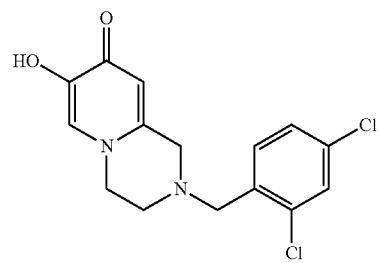
62
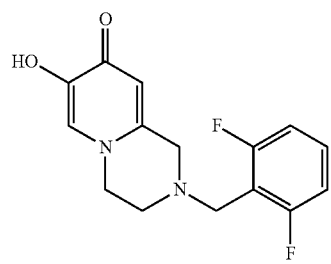
36
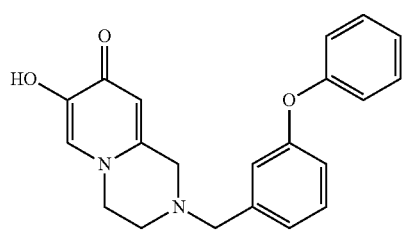
37
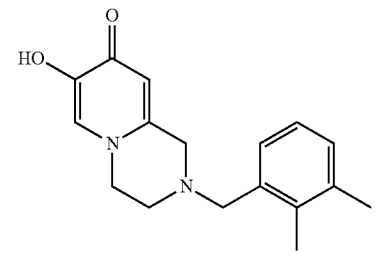
44
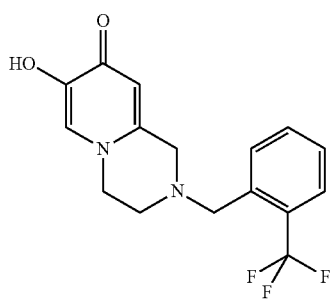

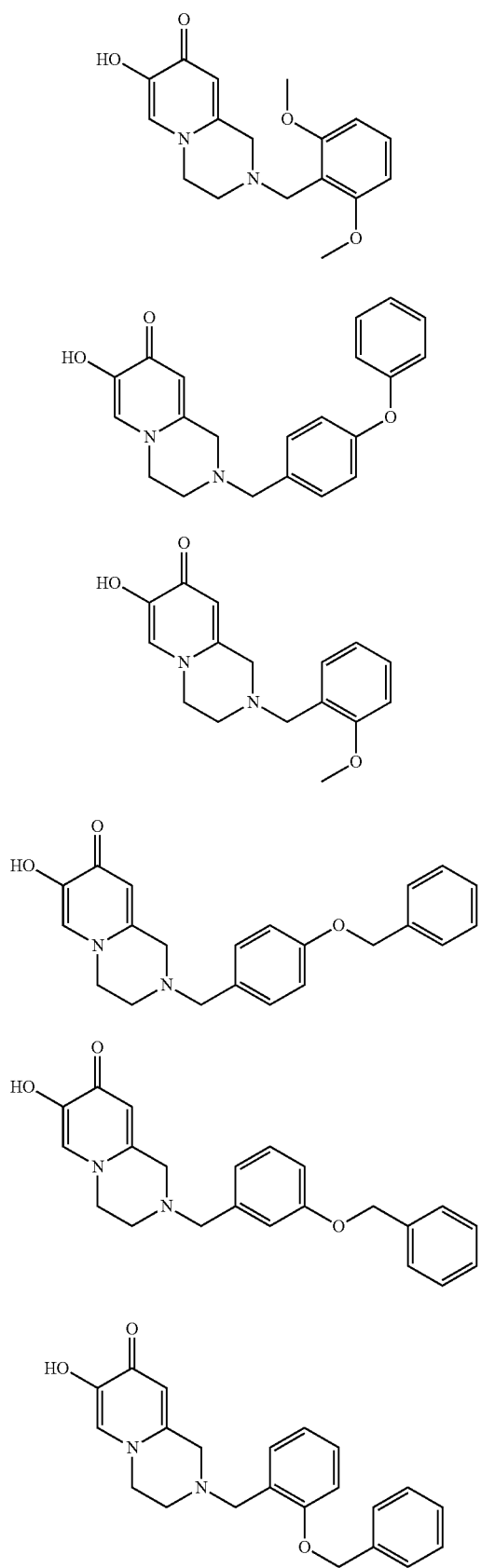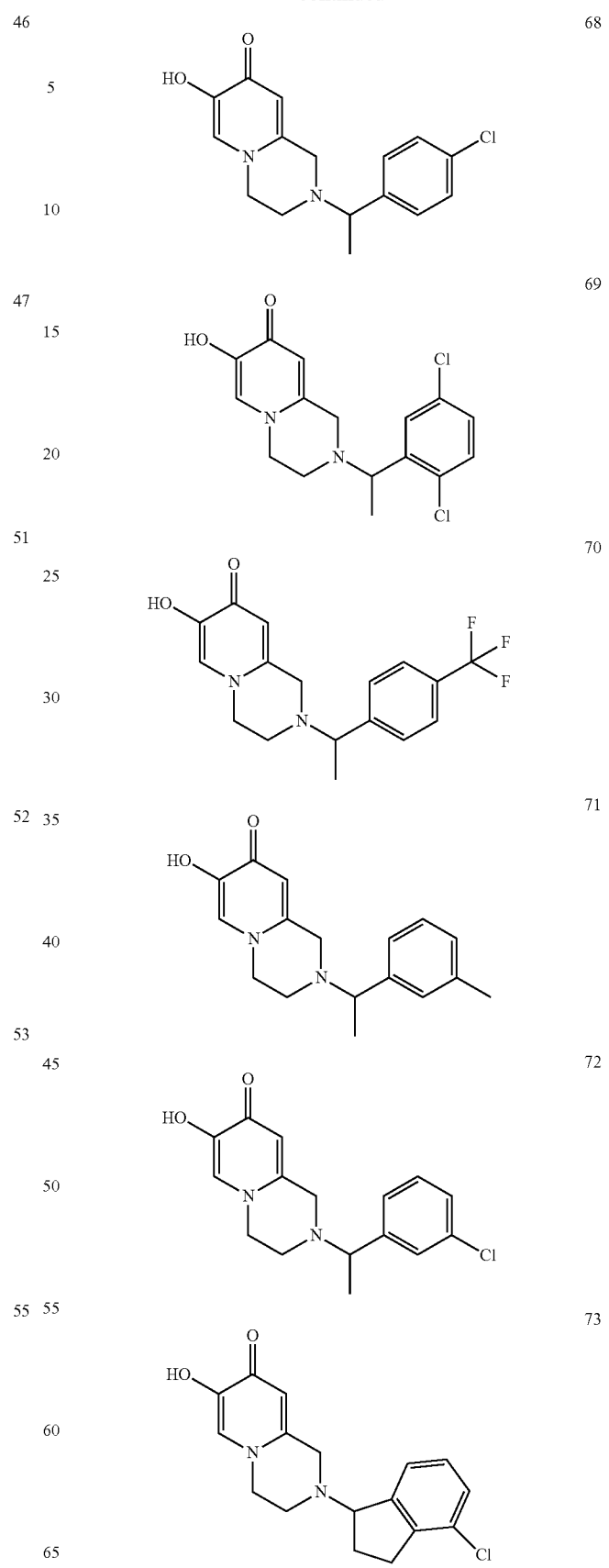

74
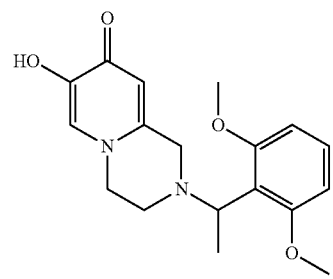
75
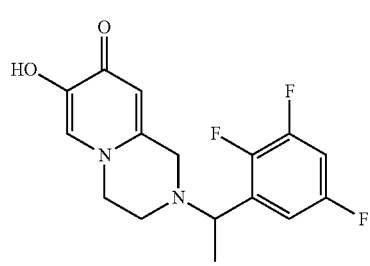
76
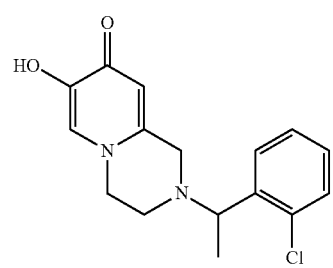
77
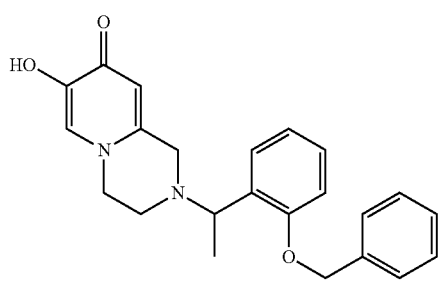
78
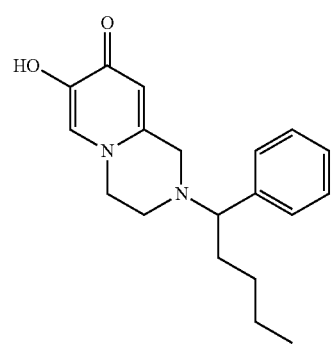
79
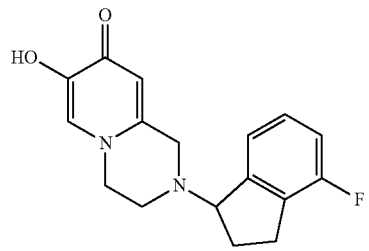
81
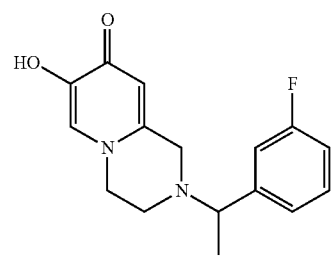
82
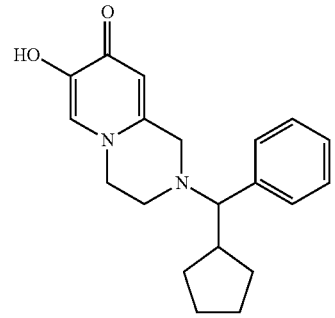
83
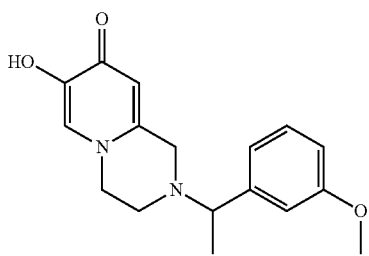
84
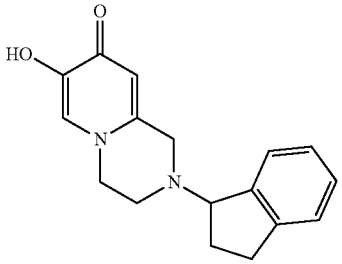
85
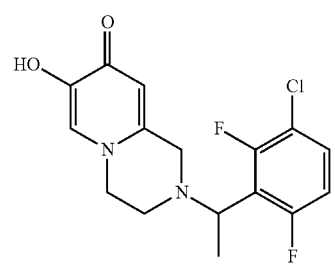

86
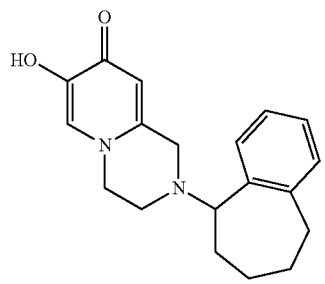
87
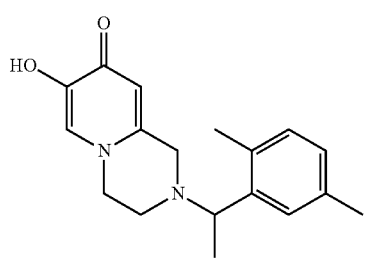
88
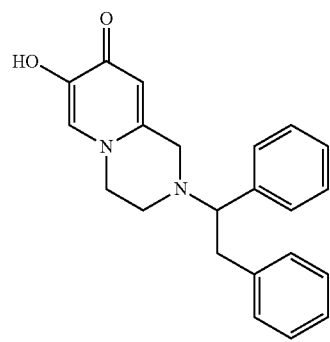
89
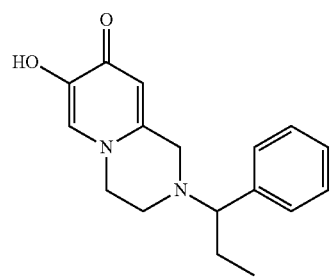
90
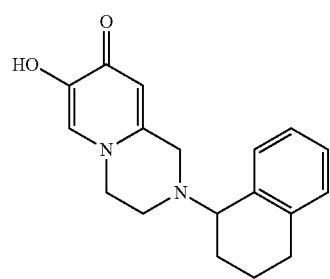
91
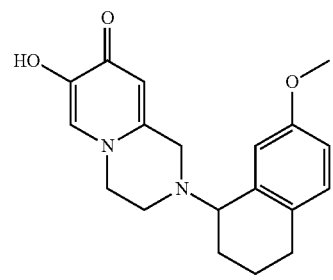
92
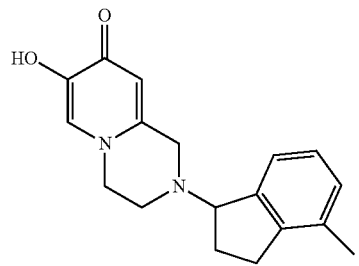
93
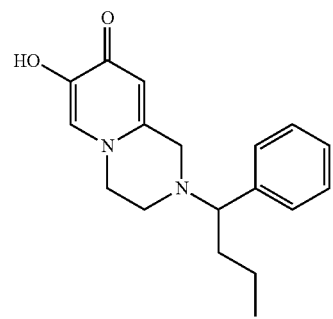
94
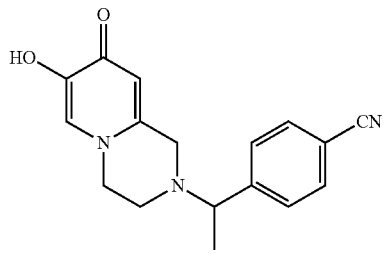
95
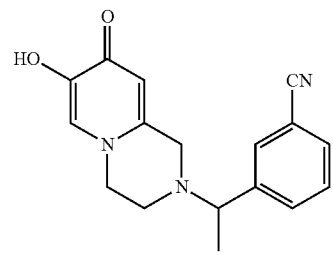
96
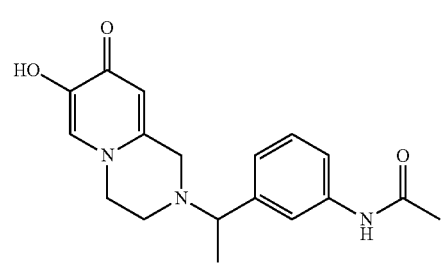

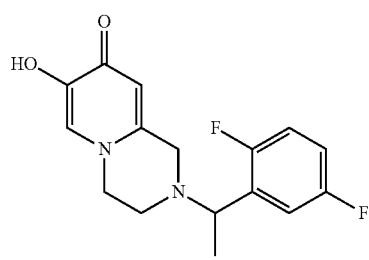
97
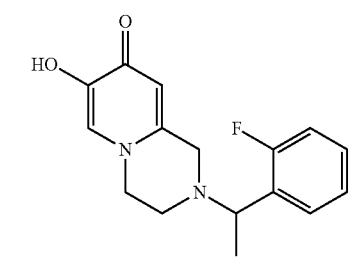
98
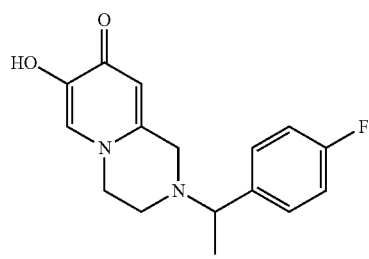
99
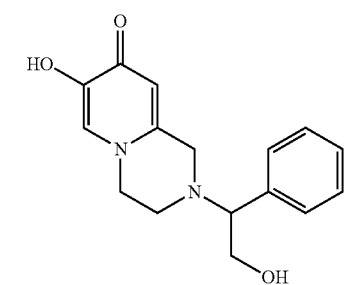
100
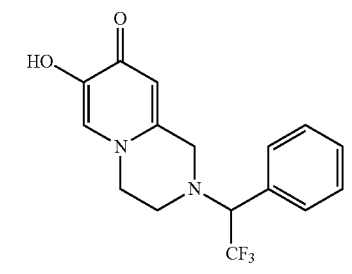
101
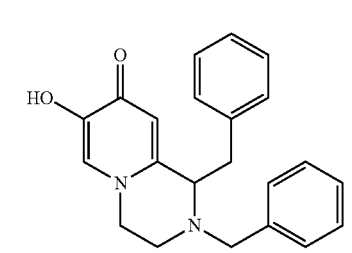
115
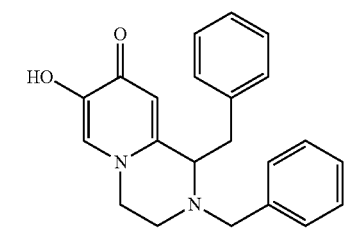
116
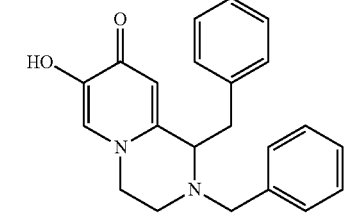
117
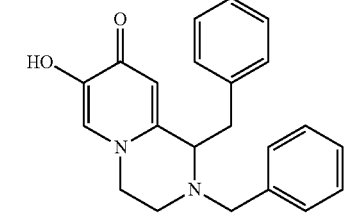
118
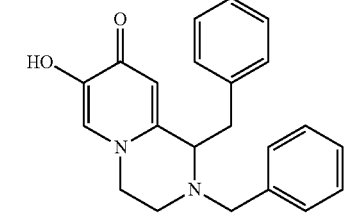
119

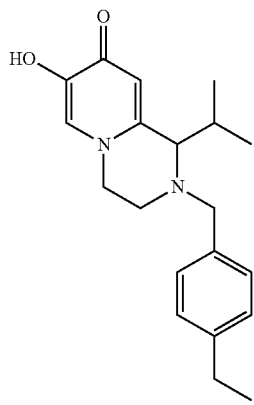
120
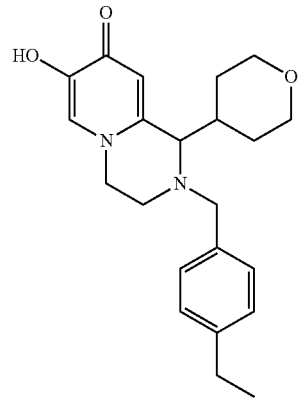
125
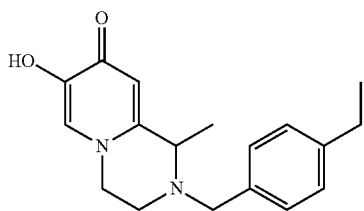
121
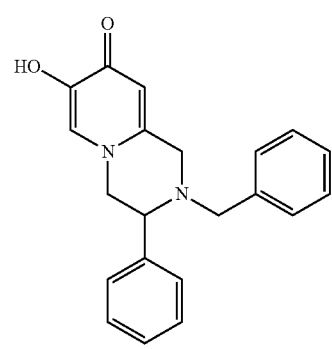
126
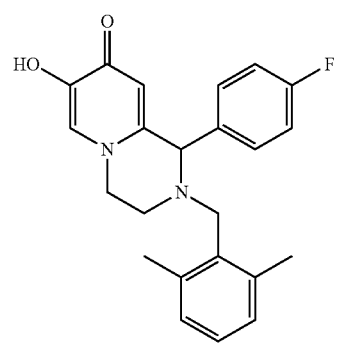
122
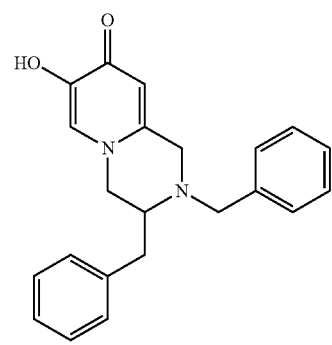
127
124
128

129
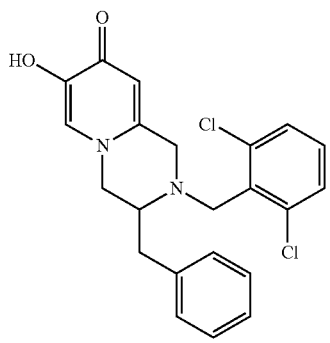
130
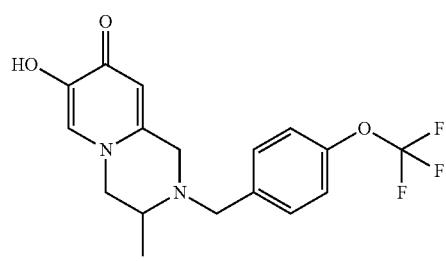
131
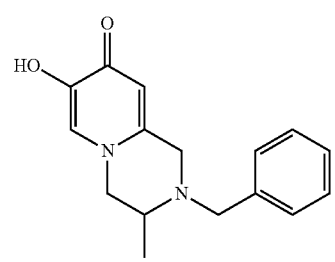
132
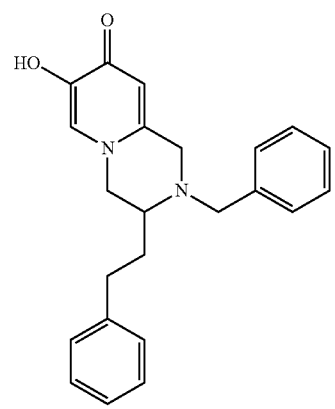
133
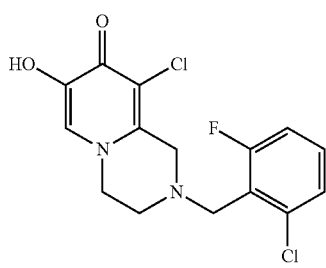
136
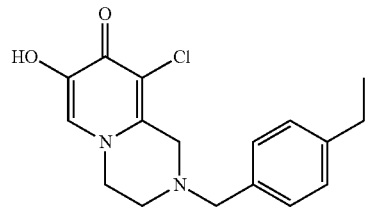
138
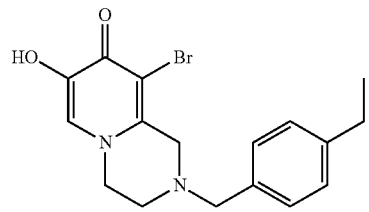
141
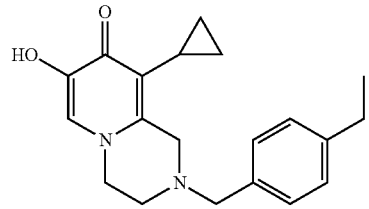
14
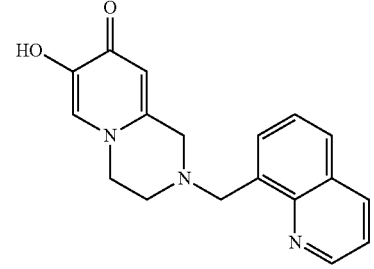
35
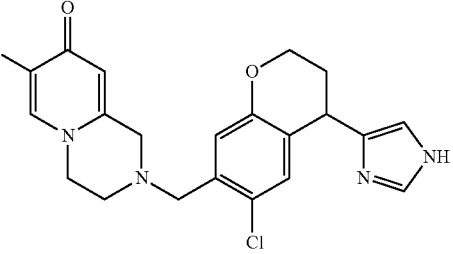
48
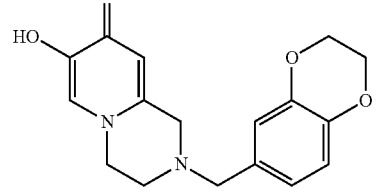
54
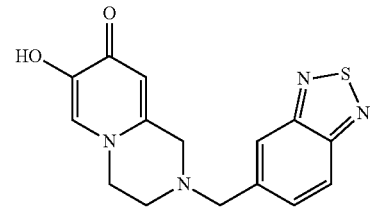

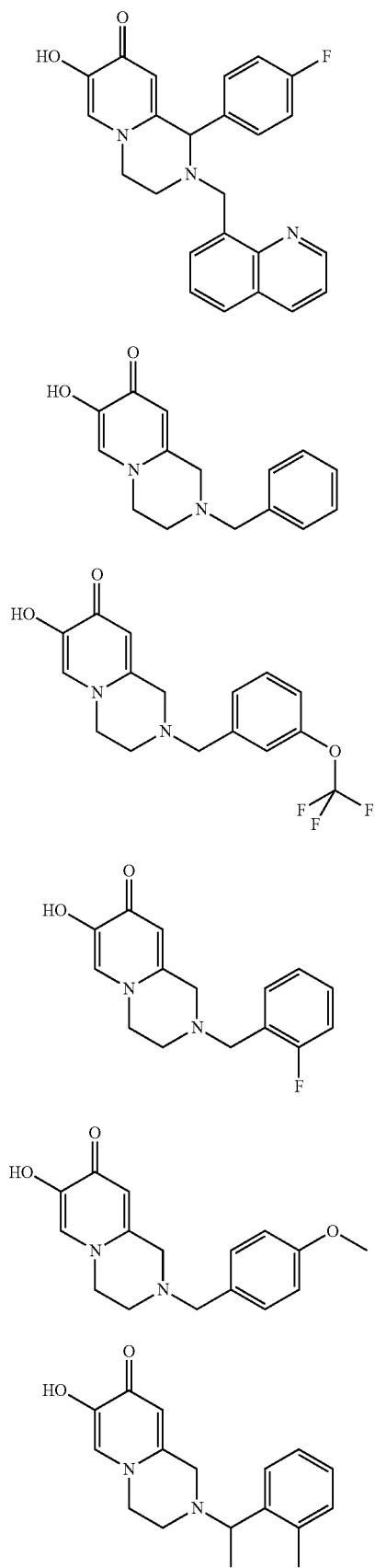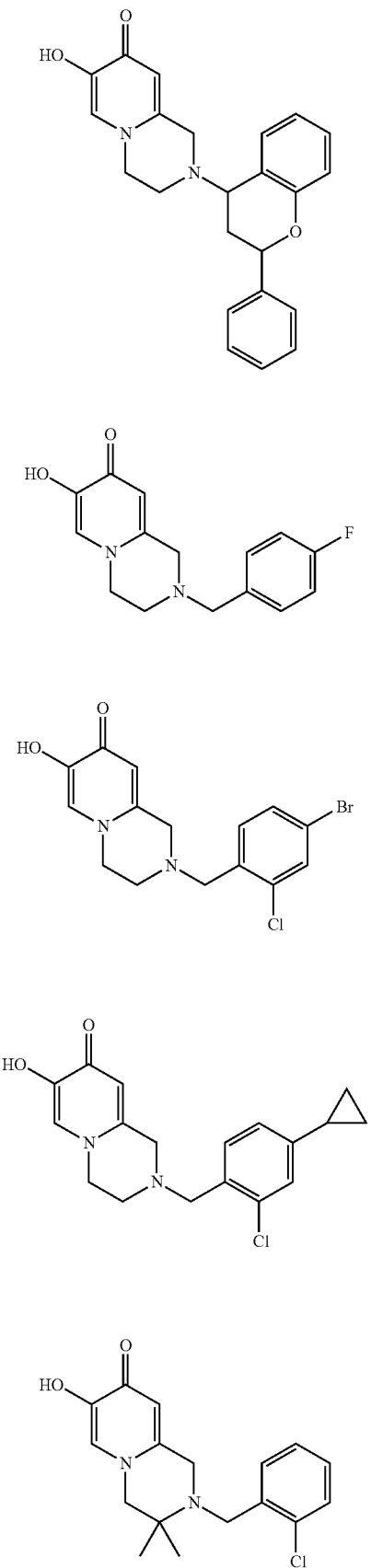

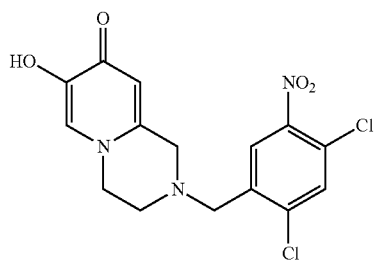
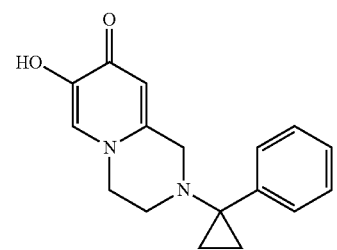
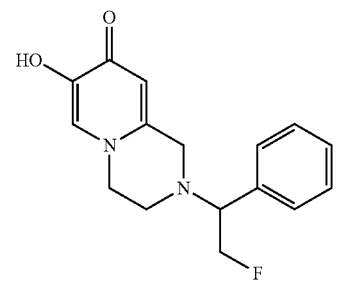
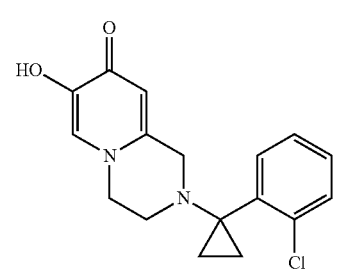
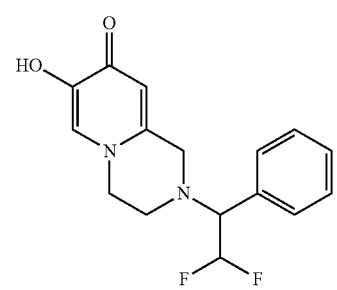
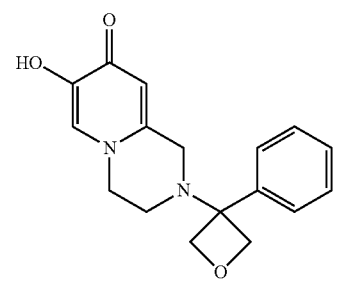
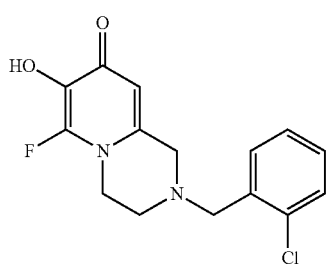
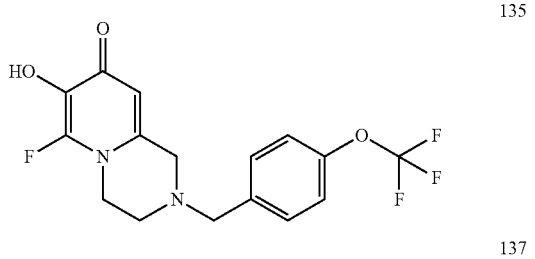
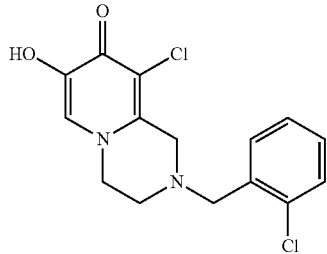
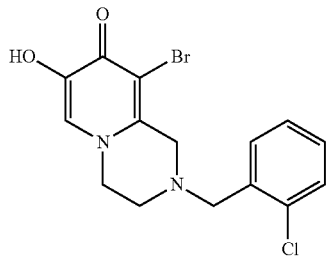
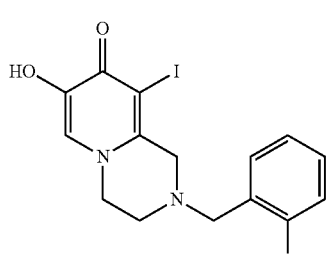
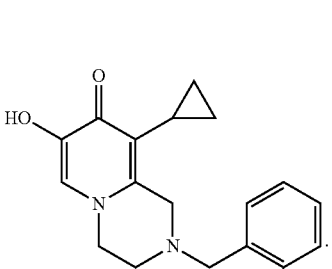

In another embodiment, the invention provides COMT-inhibiting compounds in accordance with formula III, or pharmaceutically acceptable salts thereof:

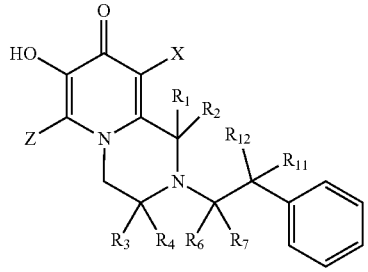

III wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; and $R_6$, $R_7$, $R_{11}$ and $R_{12}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; $R_6$ and $R_7$; $R_{11}$ and $R_{12}$; $R_6$ or $R_7$ and $R_{11}$ or $R_{12}$ may also come together to form a $C_3$-$C_6$ cycloalkyl.

In a particular embodiment, X is H. In another particular embodiment, $R_1$, $R_2$, $R_3$ and $R_4$ are hydrogen. In yet another particular embodiment, $R_1$, $R_2$, $R_3$, $R_4$, $R_6$, $R_7$, $R_{11}$ and $R_{12}$ are each hydrogen.

In a preferred embodiment, X is H and $R_1$, $R_2$, $R_3$, $R_4$, $R_6$ and $R_7$ are hydrogen. In yet another preferred embodiment, X is H; $R_1$, $R_2$, $R_3$, $R_4$, $R_6$, $R_7$ and $R_{11}$ are hydrogen and $R_{12}$ is selected from phenyl or methyl.

In another embodiment, the invention provides COMT-inhibiting compounds in accordance with formula IIIa, or pharmaceutically acceptable salts thereof:

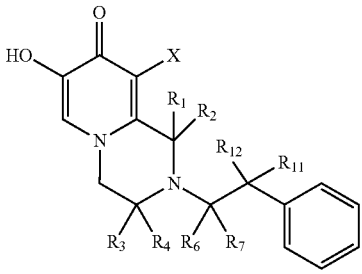

IIIa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; and $R_6$, $R_7$, $R_{11}$ and $R_{12}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl.

In a particular embodiment, X is H. In another particular embodiment, $R_1$, $R_2$, $R_3$ and $R_4$ are hydrogen. In yet another particular embodiment, $R_1$, $R_2$, $R_3$, $R_4$, $R_6$, $R_7$, $R_{11}$ and $R_{12}$ are each hydrogen.

In a preferred embodiment, X is H and $R_1$, $R_2$, $R_3$, $R_4$, $R_6$ and $R_7$ are hydrogen. In yet another another preferred embodiment, X is H; $R_1$, $R_2$, $R_3$, $R_4$, $R_6$, $R_7$ and $R_{11}$ are hydrogen and $R_{12}$ is selected from phenyl or methyl.

In exemplary embodiments, a compound is selected from the following:

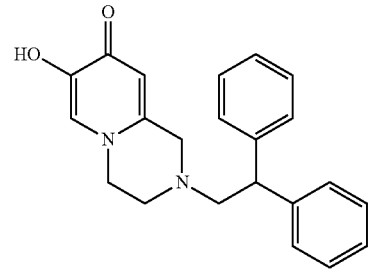

19

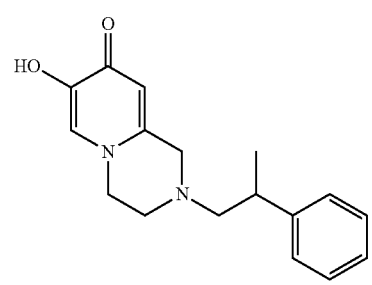

31

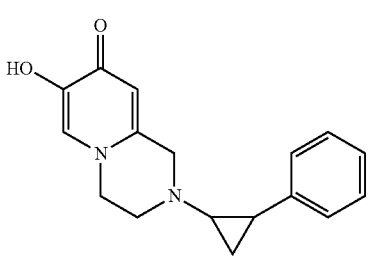

109

In another embodiment, the invention provides COMT-inhibiting compounds in accordance with formula IV, or pharmaceutically acceptable salts thereof:

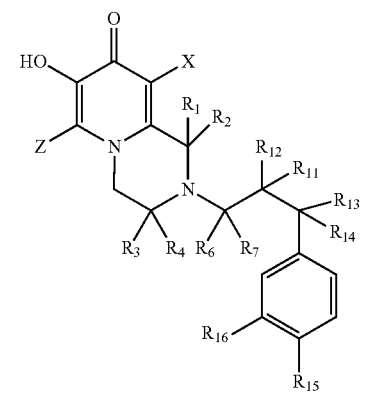

IV wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$, $R_7$, $R_{11}$, $R_{12}$ $R_{13}$ and $R_{14}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl and aryl; $R_6$ and $R_7$, $R_{11}$ and $R_{12}$, $R_{13}$ and $R_{14}$, $R_6$ or $R_7$ and $R_{11}$ or $R_{12}$, $R_6$ or $R_7$ and $R_{13}$ or $R_{14}$, $R_{11}$ or $R_{12}$ and $R_{13}$ or $R_{14}$ may also come together to form a $C_3$-$C_6$ cycloalkyl; and $R_{15}$ and $R_{16}$ are each hydrogen or come together to form a ring.

In a particular embodiment, X is H. In another particular embodiment, $R_1$, $R_2$, $R_3$ and $R_4$ are hydrogen. In still another particular embodiment, $R_1$, $R_2$, $R_3$, $R_4$, $R_6$, $R_7$, $R_{11}$, $R_{12}$, $R_{13}$ and $R_{14}$ are each hydrogen.

In a preferred embodiment, X is H; $R_1$, $R_2$, $R_3$, $R_4$, $R_6$, $R_7$, $R_{11}$, $R_{12}$, $R_{13}$, $R_{14}$, $R_{15}$ and $R_{16}$ are hydrogen. In yet another preferred embodiment, X is H; $R_1$, $R_2$, $R_3$, $R_4$, $R_6$, $R_7$, $R_{11}$, $R_{13}$ and $R_{14}$ are hydrogen; $R_{12}$ is methyl; and $R_{15}$—$R_{16}$ form a dioxolane.

In another embodiment, the invention provides COMT-inhibiting compounds in accordance with formula IVa, or pharmaceutically acceptable salts thereof:

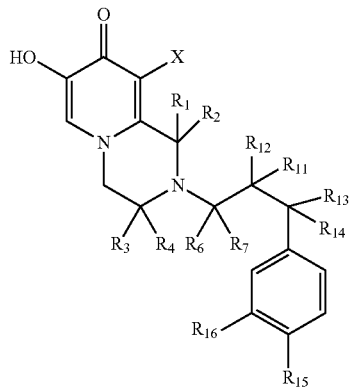

IVa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$, $R_7$, $R_{11}$, $R_{12}$, $R_{13}$ and $R_{14}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; and $R_{15}$ and $R_{16}$ are each hydrogen or come together to form a ring.

In a particular embodiment, X is H. In another particular embodiment, $R_1$, $R_2$, $R_3$ and $R_4$ are hydrogen. In still another particular embodiment, $R_1$, $R_2$, $R_3$, $R_4$, $R_6$, $R_7$, $R_{11}$, $R_{12}$, $R_{13}$ and $R_{14}$ are each hydrogen.

In a preferred embodiment, X is H; $R_1$, $R_2$, $R_3$, $R_4$, $R_6$, $R_7$, $R_{11}$, $R_{12}$, $R_{13}$, $R_{14}$, $R_{15}$ and $R_{16}$ are hydrogen. In yet another preferred embodiment, X is H; $R_1$, $R_2$, $R_3$, $R_4$, $R_6$, $R_7$, $R_{11}$, $R_{13}$ and $R_{14}$ are hydrogen; $R_{12}$ is methyl; and $R_{15}$—$R_{16}$ form a dioxolane.

In exemplary embodiments, a compound is selected from the following:

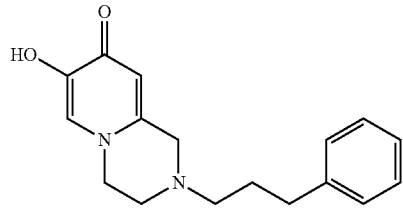

30

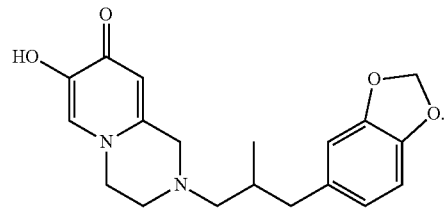

49

In another embodiment, the invention provides COMT-inhibiting compounds in accordance with formula V, or pharmaceutically acceptable salts thereof:

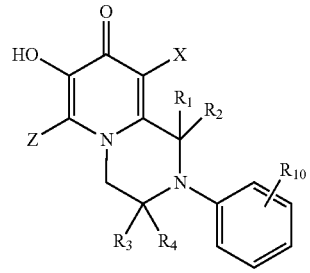

V wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; and $R_{10}$ can be at one or more positions on the ring, and at each occurrence is independently selected from the group consisting of hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl.

In a preferred embodiment, X is H; $R_1$, $R_2$, $R_3$, and $R_4$ are hydrogen; and $R_{10}$ is selected from hydrogen, $C_1$-$C_4$ alkyl and mono-, di- or trihalomethyl. In a more specific embodiment, $R_{10}$ is hydrogen. In an alternative specific embodiment, $R_{10}$ is methyl. In yet another alternative specific embodiment, $R_{10}$ is trifluoromethyl.

In another embodiment, the invention provides COMT-inhibiting compounds in accordance with formula Va, or pharmaceutically acceptable salts thereof:

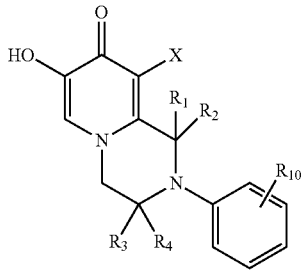

Va wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; and $R_{10}$ can be at one or more positions on the ring, and at each occurrence is independently selected from the group consisting of hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl.

In a preferred embodiment, X is H; $R_1$, $R_2$, $R_3$, and $R_4$ are hydrogen; and $R_{10}$ is selected from hydrogen, $C_1$-$C_4$ alkyl and mono-, di- or trihalomethyl. In a more specific embodiment, $R_{100}$ is hydrogen. In an alternative specific embodiment, $R_{10}$ is methyl. In yet another alternative specific embodiment, $R_{100}$ is trifluoromethyl.

In exemplary embodiments, a compound is selected from the following:

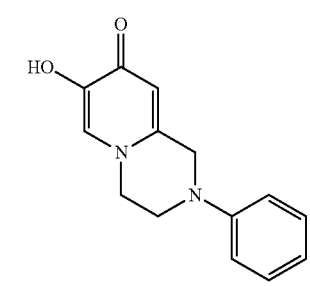

112

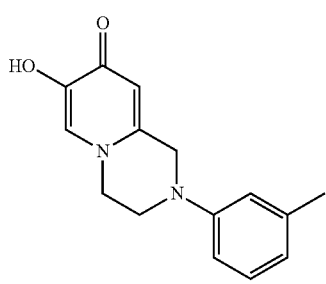

113

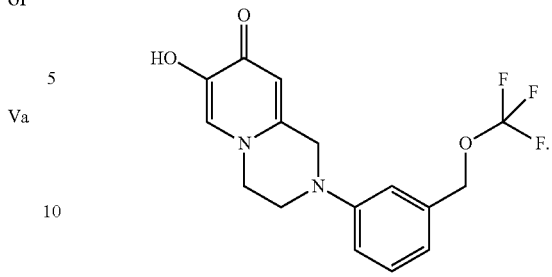

114

In another embodiment, the invention provides COMT-inhibiting compounds in accordance with formula VI, or pharmaceutically acceptable salts thereof:

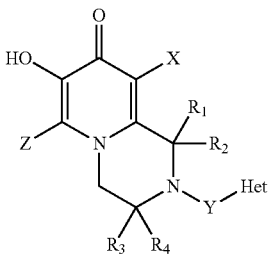

VI wherein:

X is selected from hydrogen; chloro; bromo, iodo and cyclopropyl;

Z is selected from hydrogen and fluoro.

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; Y is $(CR_6R_7)_n$, wherein n is from 0-3, and $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl Het is a heterocycle. Het may be connected to the $R_6$/$R_7$ carbon at any position of the heterocycle, provided it provides proper valency. In particular embodiments, the heterocycle is aromatic. Examples of heteroaromatics include, but are not limited to indole; 1H-pyrazole; benzothiazole; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole 2-phenylthiazole and 3,5-dimethyl-1-phenyl-1H-pyrazole.

In a preferred embodiment, X is H; $R_1$, $R_2$, $R_3$, $R_4$, $R_6$ and $R_7$, are hydrogen, and Het is selected from the group consisting of 1H-pyrazole; benzothiazole; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole 2-phenylthiazole and 3,5-dimethyl-1-phenyl-1H-pyrazole.

In another embodiment, the invention provides COMT-inhibiting compounds in accordance with formula VIa, or pharmaceutically acceptable salts thereof:

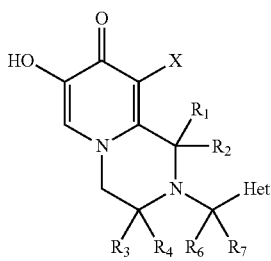

VIa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$ and $R_7$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; and Het is a heterocycle. Het may be connected to the $R_6/R_7$ carbon at any position of the heterocycle, provided it provides proper valency. In particular embodiments, the heterocycle is aromatic. Exemplary heteroaromatics include, but are not limited to indole; 1H-pyrazole; benzothiazole; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole 2-phenylthiazole and 3,5-dimethyl-1-phenyl-1H-pyrazole.

In a preferred embodiment, X is H; $R_1$, $R_2$, $R_3$, $R_4$, $R_6$ and $R_7$, are hydrogen, and Het is selected from the group consisting of 1H-pyrazole; benzothiazole; 5-chloro-1,3-dimethyl-1H-pyrazole; 4H-chromen-4-one; 1H-indazole; 3-(thiophen-2-yl)-1H-pyrazole; 3-phenyl-1H-pyrazole; 6-(p-tolyl)imidazo[2,1-b]thiazole 2-phenylthiazole and 3,5-dimethyl-1-phenyl-1H-pyrazole.

In exemplary embodiments, a compound is selected from the following:

29

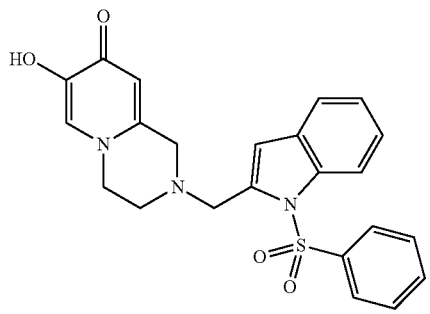

34

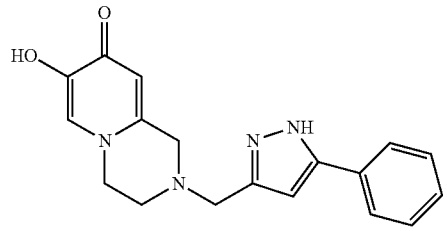

38

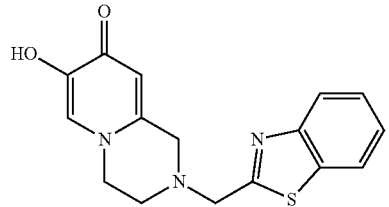

40

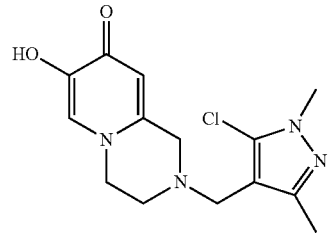

41

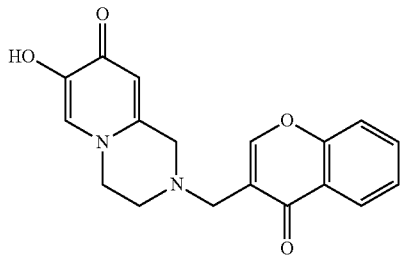

42

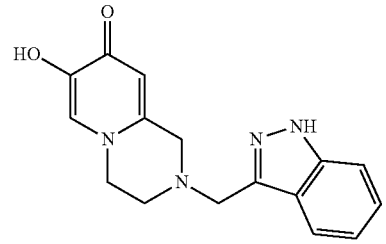

43

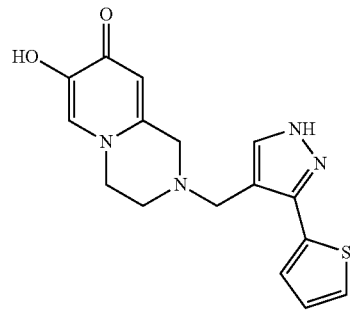

In another embodiment, the invention provides COMT-inhibiting compounds in accordance with formula VII, or pharmaceutically acceptable salts thereof:

VII wherein:
X is selected from hydrogen; chloro; bromo, iodo and cyclopropyl;
Z is selected from hydrogen and fluoro.
$R_1$ and $R_2$ are each independently selected from hydrogen; $C_{1-4}$ alkyl; aryl; substituted aryl; arylalkyl and heterocycle;
$R_3$ and $R_4$ are each independently selected from hydrogen; $C_1$-$C_4$ alkyl; aryl and arylalkyl;
$R_6$ and $R_7$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; and $R_{17}$ and $R_{18}$ are selected from $C_1$-$C_4$ alkyl or come together to form a 5-10 membered cycloalkane, which can optionally be further substituted with $C_1$-$C_8$ alkyl or cycloalkyl.

In a preferred embodiment, X is H; $R_1$, $R_2$, $R_3$, $R_4$, $R_6$ and $R_7$ are hydrogen, and $R_{17}$ and $R_{18}$ are methyl. In another preferred embodiment, X is H; $R_1$, $R_2$, $R_3$, $R_4$, $R_6$ and $R_7$ are hydrogen, and $R_{17}$ and $R_{18}$ come together to form a 6, 7 or 8 membered cycloalkane, which is further substituted with $C_1$-$C_8$ alkyl or cycloalkyl.

In another embodiment, the invention provides COMT-inhibiting compounds in accordance with formula VIIa, or pharmaceutically acceptable salts thereof:

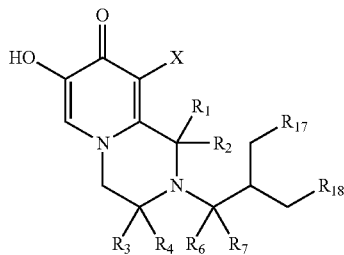

VIIa wherein:

X is selected from hydrogen; chloride; bromide and cyclopropyl;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$ and $R_7$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; and $R_{17}$ and $R_{18}$ are selected from $C_1$-$C_4$ alkyl or come together to form a 5-10 membered cycloalkane, which can optionally be further substituted with $C_1$-$C_8$ alkyl or cycloalkyl.

In a preferred embodiment, X is H; $R_1$, $R_2$, $R_3$, $R_4$, $R_6$ and $R_7$ are hydrogen, and $R_{17}$ and $R_{18}$ are methyl. In another preferred embodiment, X is H; $R_1$, $R_2$, $R_3$, $R_4$, $R_6$ and $R_7$ are hydrogen, and $R_{17}$ and $R_{18}$ come together to form a 6, 7 or 8 membered cycloalkane, which is further substituted with $C_1$-$C_8$ alkyl or cycloalkyl.

In exemplary embodiments, a compound is selected from the following:

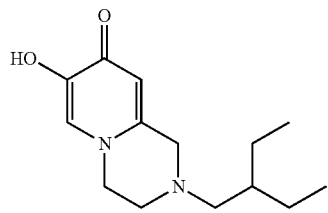

20

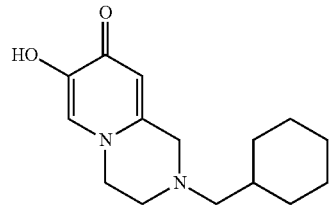

22

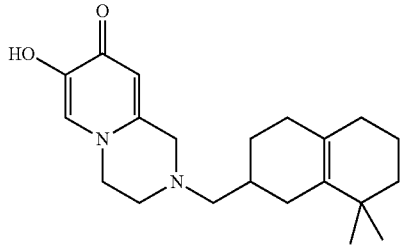

24

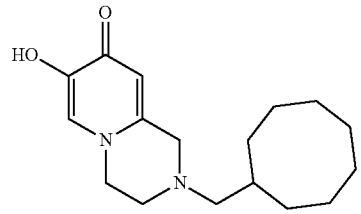

26

In particular embodiments, COMT-inhibiting compounds of the present invention are selected from the following:

2-benzyl-7-hydroxy-1,2,3,4-tetrahydro-8H-pyrido[1,2-a]pyrazin-8-one 7-hydroxy-2-[4-(trifluoromethyl)benzyl]-1,2,3,4-tetrahydro-8H-pyrido[1,2-a]pyrazin-8-one 2-[(4-fluorophenyl)methyl]-7-hydroxy-3,4-dihydro-1H-pyrido[1,2-a]pyrazin-8-one 2-[2-(benzotriazol-1-yl)ethyl]-7-hydroxy-3,4-dihydro-1H-pyrido[1,2-a]pyrazin-8-one 2-[2-(benzotriazol-2-yl)ethyl]-7-hydroxy-3,4-dihydro-1H-pyrido[1,2-a]pyrazin-8-one 7-hydroxy-2-[3-(trifluoromethoxy)benzyl]-1,2,3,4-tetrahydro-8H-pyrido[1,2-a]pyrazin-8-one 2-(4-tert-butylbenzyl)-7-hydroxy-1,2,3,4-tetrahydro-8H-pyrido[1,2-a]pyrazin-8-one 7-hydroxy-2-[4-(trifluoromethoxy)benzyl]-1,2,3,4-tetrahydro-8H-pyrido[1,2-a]pyrazin-8-one 2-(2,4-dimethylbenzyl)-7-hydroxy-1,2,3,4-tetrahydro-8H-pyrido[1,2-a]pyrazin-8-one 7-hydroxy-2-[4-(propan-2-yl)benzyl]-1,2,3,4-tetrahydro-8H-pyrido[1,2-a]pyrazin-8-one 7-hydroxy-2-(pyridin-2-ylmethyl)-1,2,3,4-tetrahydro-8H-pyrido[1,2-a]pyrazin-8-one 7-hydroxy-2-[4-(pyridin-3-yl)benzyl]-1,2,3,4-tetrahydro-8H-pyrido[1,2-a]pyrazin-8-one 2-(4-ethylbenzyl)-7-hydroxy-1,2,3,4-tetrahydro-8H-pyrido[1,2-a]pyrazin-8-one 7-hydroxy-2-(quinolin-8-ylmethyl)-1,2,3,4-tetrahydro-8H-pyrido[1,2-a]pyrazin-8-one 7-hydroxy-2-(1-phenylethyl)-1,2,3,4-tetrahydro-8H-pyrido[1,2-a]pyrazin-8-one 2-[1-(4-ethylphenyl)ethyl]-7-hydroxy-1,2,3,4-tetrahydro-8H-pyrido[1,2-a]pyrazin-8-one 2-[(7-hydroxy-8-oxo-1,3,4,8-tetrahydro-2H-pyrido[1,2-a]pyrazin-2-yl)methyl]benzonitrile 2-(4-ethyl-3-nitrobenzyl)-7-hydroxy-1,2,3,4-tetrahydro-8H-pyrido[1,2-a]pyrazin-8-one
2-(2,2-diphenylethyl)-7-hydroxy-1,2,3,4-tetrahydro-8H-pyrido[1,2-a]pyrazin-8-one
2-(2-ethylbutyl)-7-hydroxy-1,2,3,4-tetrahydro-8H-pyrido[1,2-a]pyrazin-8-one
2-(3,5-dichlorobenzyl)-7-hydroxy-1,2,3,4-tetrahydro-8H-pyrido[1,2-a]pyrazin-8-one
2-(cyclohexylmethyl)-7-hydroxy-1,2,3,4-tetrahydro-8H-pyrido[1,2-a]pyrazin-8-one
2-(4-cyclopropyl benzyl)-7-hydroxy-1,2,3,4-tetrahydro-8H-pyrido[1,2-a]pyrazin-8-one
2-[(8,8-dimethyl-1,2,3,4,5,6,7,8-octahydronaphthalen-2-yl)methyl]-7-hydroxy-1,2,3,4-tetrahydro-8H-pyrido[1,2-a]pyrazin-8-one
2-(3,4-dichlorobenzyl)-7-hydroxy-1,2,3,4-tetrahydro-8H-pyrido[1,2-a]pyrazin-8-one
2-(cyclooctylmethyl)-7-hydroxy-1,2,3,4-tetrahydro-8H-pyrido[1,2-a]pyrazin-8-one
2-(2,6-dimethylbenzyl)-7-hydroxy-1,2,3,4-tetrahydro-8H-pyrido[1,2-a]pyrazin-8-one
2-(2,5-dimethylbenzyl)-7-hydroxy-1,2,3,4-tetrahydro-8H-pyrido[1,2-a]pyrazin-8-one
7-hydroxy-2-{[1-(phenylsulfonyl)-1H-indol-2-yl]methyl}-1,2,3,4-tetrahydro-8H-pyrido[1,2-a]pyrazin-8-one
7-hydroxy-2-(3-phenylpropyl)-1,2,3,4-tetrahydro-8H-pyrido[1,2-a]pyrazin-8-one
7-hydroxy-2-(2-phenylpropyl)-1,2,3,4-tetrahydro-8H-pyrido[1,2-a]pyrazin-8-one
2-(3,5-difluorobenzyl)-7-hydroxy-1,2,3,4-tetrahydro-8H-pyrido[1,2-a]pyrazin-8-one
7-hydroxy-2-(2-methylbenzyl)-1,2,3,4-tetrahydro-8H-pyrido[1,2-a]pyrazin-8-one
7-hydroxy-2-[(5-phenyl-1H-pyrazol-3-yl)methyl]-1,2,3,4-tetrahydro-8H-pyrido[1,2-a]pyrazin-8-one
2-{[6-chloro-4-(1H-imidazol-4-yl)-3,4-dihydro-2H-chromen-8-yl]methyl}-7-hydroxy-1,2,3,4-tetrahydro-8H-pyrido[1,2-a]pyrazin-8-one
7-hydroxy-2-(3-phenoxybenzyl)-1,2,3,4-tetrahydro-8H-pyrido[1,2-a]pyrazin-8-one
2-(2,3-dimethylbenzyl)-7-hydroxy-1,2,3,4-tetrahydro-8H-pyrido[1,2-a]pyrazin-8-one
2-(1,3-benzothiazol-2-ylmethyl)-7-hydroxy-1,2,3,4-tetrahydro-8H-pyrido[1,2-a]pyrazin-8-one
2-(2-fluorobenzyl)-7-hydroxy-1,2,3,4-tetrahydro-8H-pyrido[1,2-a]pyrazin-8-one
2-[(5-chloro-1,3-dimethyl-1H-pyrazol-4-yl)methyl]-7-hydroxy-1,2,3,4-tetrahydro-8H-pyrido[1,2-a]pyrazin-8-one
7-hydroxy-2-[(4-oxo-4H-chromen-3-yl)methyl]-1,2,3,4-tetrahydro-8H-pyrido[1,2-a]pyrazin-8-one
7-hydroxy-2-(1H-indazol-3-ylmethyl)-1,2,3,4-tetrahydro-8H-pyrido[1,2-a]pyrazin-8-one
7-hydroxy-2-{[3-(thiophen-2-yl)-1H-pyrazol-4-yl]methyl}-1,2,3,4-tetrahydro-8H-pyrido[1,2-a]pyrazin-8-one
7-hydroxy-2-[2-(trifluoromethyl)benzyl]-1,2,3,4-tetrahydro-8H-pyrido[1,2-a]pyrazin-8-one
7-hydroxy-2-[(3-phenyl-1H-pyrazol-4-yl)methyl]-1,2,3,4-tetrahydro-8H-pyrido[1,2-a]pyrazin-8-one
2-(2,6-dimethoxybenzyl)-7-hydroxy-1,2,3,4-tetrahydro-8H-pyrido[1,2-a]pyrazin-8-one
7-hydroxy-2-(4-phenoxybenzyl)-1,2,3,4-tetrahydro-8H-pyrido[1,2-a]pyrazin-8-one
2-(2,3-dihydro-1,4-benzodioxin-6-ylmethyl)-7-hydroxy-1,2,3,4-tetrahydro-8H-pyrido[1,2-a]pyrazin-8-one
2-[3-(1,3-benzodioxol-5-yl)-2-methyl propyl]-7-hydroxy-1,2,3,4-tetrahydro-8H-pyrido[1,2-a]pyrazin-8-one
7-hydroxy-2-(4-methoxybenzyl)-1,2,3,4-tetrahydro-8H-pyrido[1,2-a]pyrazin-8-one
7-hydroxy-2-(2-methoxybenzyl)-1,2,3,4-tetrahydro-8H-pyrido[1,2-a]pyrazin-8-one
2-[4-(benzyloxy)benzyl]-7-hydroxy-1,2,3,4-tetrahydro-8H-pyrido[1,2-a]pyrazin-8-one
2-[3-(benzyloxy)benzyl]-7-hydroxy-1,2,3,4-tetrahydro-8H-pyrido[1,2-a]pyrazin-8-one
2-(2,1,3-benzothiadiazol-5-ylmethyl)-7-hydroxy-1,2,3,4-tetrahydro-8H-pyrido[1,2-a]pyrazin-8-one
2-[2-(benzyloxy)benzyl]-7-hydroxy-1,2,3,4-tetrahydro-8H-pyrido[1,2-a]pyrazin-8-one
7-hydroxy-2-{[6-(4-methylphenyl)imidazo[2,1-b][1,3]thiazol-5-yl]methyl}-1,2,3,4-tetrahydro-8H-pyrido[1,2-a]pyrazin-8-one
2-(2-chloro-4-fluorobenzyl)-7-hydroxy-1,2,3,4-tetrahydro-8H-pyrido[1,2-a]pyrazin-8-one
2-(2-chlorobenzyl)-7-hydroxy-1,2,3,4-tetrahydro-8H-pyrido[1,2-a]pyrazin-8-one
2-(2-chloro-6-fluorobenzyl)-7-hydroxy-1,2,3,4-tetrahydro-8H-pyrido[1,2-a]pyrazin-8-one
2-(2,6-dichlorobenzyl)-7-hydroxy-1,2,3,4-tetrahydro-8H-pyrido[1,2-a]pyrazin-8-one
2-(2,4-dichlorobenzyl)-7-hydroxy-1,2,3,4-tetrahydro-8H-pyrido[1,2-a]pyrazin-8-one
2-(2,6-difluorobenzyl)-7-hydroxy-1,2,3,4-tetrahydro-8H-pyrido[1,2-a]pyrazin-8-one
2-[(4-bromo-2-chloro-phenyl)methyl]-7-hydroxy-3,4-dihydro-1H-pyrido[1,2-a]pyrazin-8-one
2-[(2-chloro-4-cyclopropyl-phenyl)methyl]-7-hydroxy-3,4-dihydro-1H-pyrido[1,2-a]pyrazin-8-one
2-[(2-chlorophenyl)methyl]-7-hydroxy-3,3-dimethyl-1,4-dihydropyrido[1,2-a]pyrazin-8-one
2-[(2,4-dichloro-5-nitro-phenyl)methyl]-7-hydroxy-3,4-dihydro-1H-pyrido[1,2-a]pyrazin-8-one
7-hydroxy-2-[1-(2-methylphenyl)ethyl]-1,2,3,4-tetrahydro-8H-pyrido[1,2-a]pyrazin-8-one
2-[1-(4-chlorophenyl)ethyl]-7-hydroxy-1,2,3,4-tetrahydro-8H-pyrido[1,2-a]pyrazin-8-one
2-[1-(2,5-dichlorophenyl)ethyl]-7-hydroxy-1,2,3,4-tetrahydro-8H-pyrido[1,2-a]pyrazin-8-one
7-hydroxy-2-{1-[4-(trifluoromethyl)phenyl]ethyl}-1,2,3,4-tetrahydro-8H-pyrido[1,2-a]pyrazin-8-one
7-hydroxy-2-[1-(3-methylphenyl)ethyl]-1,2,3,4-tetrahydro-8H-pyrido[1,2-a]pyrazin-8-one
2-[1-(3-chlorophenyl)ethyl]-7-hydroxy-1,2,3,4-tetrahydro-8H-pyrido[1,2-a]pyrazin-8-one
2-(4-chloro-2,3-dihydro-1H-inden-1-yl)-7-hydroxy-1,2,3,4-tetrahydro-8H-pyrido[1,2-a]pyrazin-8-one
2-[1-(2,6-dimethoxyphenyl)ethyl]-7-hydroxy-1,2,3,4-tetrahydro-8H-pyrido[1,2-a]pyrazin-8-one
7-hydroxy-2-[1-(2,3,5-trifluorophenyl)ethyl]-1,2,3,4-tetrahydro-8H-pyrido[1,2-a]pyrazin-8-one
2-[1-(2-chlorophenyl)ethyl]-7-hydroxy-1,2,3,4-tetrahydro-8H-pyrido[1,2-a]pyrazin-8-one
2-{1-[2-(benzyloxy)phenyl]ethyl}-7-hydroxy-1,2,3,4-tetrahydro-8H-pyrido[1,2-a]pyrazin-8-one
7-hydroxy-2-(1-phenylpentyl)-1,2,3,4-tetrahydro-8H-pyrido[1,2-a]pyrazin-8-one
2-(7-fluoro-2,3-dihydro-1H-inden-1-yl)-7-hydroxy-1,2,3,4-tetrahydro-8H-pyrido[1,2-a]pyrazin-8-one
7-hydroxy-2-(2-phenyl-3,4-dihydro-2H-chromen-4-yl)-1,2,3,4-tetrahydro-8H-pyrido[1,2-a]pyrazin-8-one
2-[1-(3-fluorophenyl)ethyl]-7-hydroxy-1,2,3,4-tetrahydro-8H-pyrido[1,2-a]pyrazin-8-one
2-[cyclopentyl(phenyl)methyl]-7-hydroxy-1,2,3,4-tetrahydro-8H-pyrido[1,2-a]pyrazin-8-one 7-hydroxy-2-[1-(3-methoxyphenyl)ethyl]-1,2,3,4-tetrahydro-8H-pyrido[1,2-a]pyrazin-8-one 2-(2,3-dihydro-1H-inden-1-yl)-7-hydroxy-1,2,3,4-tetrahydro-8H-pyrido[1,2-a]pyrazin-8-one 2-[1-(3-chloro-2,6-difluorophenyl)ethyl]-7-hydroxy-1,2,3,4-tetrahydro-8H-pyrido[1,2-a]pyrazin-8-one 7-hydroxy-2-(6,7,8,9-tetrahydro-5H-benzo[7]annulen-5-yl)-1,2,3,4-tetrahydro-8H-pyrido[1,2-a]pyrazin-8-one 2-[1-(2,5-dimethylphenyl)ethyl]-7-hydroxy-1,2,3,4-tetrahydro-8H-pyrido[1,2-a]pyrazin-8-one 2-(1,2-diphenylethyl)-7-hydroxy-1,2,3,4-tetrahydro-8H-pyrido[1,2-a]pyrazin-8-one 7-hydroxy-2-(1-phenylpropyl)-1,2,3,4-tetrahydro-8H-pyrido[1,2-a]pyrazin-8-one 7-hydroxy-2-(1,2,3,4-tetrahydronaphthalen-1-yl)-1,2,3,4-tetrahydro-8H-pyrido[1,2-a]pyrazin-8-one 7-hydroxy-2-(7-methoxy-1,2,3,4-tetrahydronaphthalen-1-yl)-1,2,3,4-tetrahydro-8H-pyrido[1,2-a]pyrazin-8-one 7-hydroxy-2-(4-methyl-2,3-dihydro-1H-inden-1-yl)-1,2,3,4-tetrahydro-8H-pyrido[1,2-a]pyrazin-8-one 7-hydroxy-2-(1-phenylbutyl)-1,2,3,4-tetrahydro-8H-pyrido[1,2-a]pyrazin-8-one 4-[1-(7-hydroxy-8-oxo-1,3,4,8-tetrahydro-2H-pyrido[1,2-a]pyrazin-2-yl)ethyl]benzonitrile 3-[1-(7-hydroxy-8-oxo-1,3,4,8-tetrahydro-2H-pyrido[1,2-a]pyrazin-2-yl)ethyl]benzonitrile N-{3-[1-(7-hydroxy-8-oxo-1,3,4,8-tetrahydro-2H-pyrido[1,2-a]pyrazin-2-yl)ethyl]phenyl}acetamide 2-[1-(2,5-difluorophenyl)ethyl]-7-hydroxy-1,2,3,4-tetrahydro-8H-pyrido[1,2-a]pyrazin-8-one 2-[1-(2-fluorophenyl)ethyl]-7-hydroxy-1,2,3,4-tetrahydro-8H-pyrido[1,2-a]pyrazin-8-one 2-[1-(4-fluorophenyl)ethyl]-7-hydroxy-1,2,3,4-tetrahydro-8H-pyrido[1,2-a]pyrazin-8-one 7-hydroxy-2-(2-hydroxy-1-phenylethyl)-1,2,3,4-tetrahydro-8H-pyrido[1,2-a]pyrazin-8-one 7-hydroxy-2-(2,2,2-trifluoro-1-phenylethyl)-1,2,3,4-tetrahydro-8H-pyrido[1,2-a]pyrazin-8-one 7-hydroxy-2-[(2-phenyl-1,3-thiazol-4-yl)methyl]-1,2,3,4-tetrahydro-8H-pyrido[1,2-a]pyrazin-8-one 2-[(3,5-dimethyl-1-phenyl-1H-pyrazol-4-yl)methyl]-7-hydroxy-1,2,3,4-tetrahydro-8H-pyrido[1,2-a]pyrazin-8-one 7-hydroxy-2-(1-phenylcyclopropyl)-3,4-dihydro-1H-pyrido[1,2-a]pyrazin-8-one 2-(2-fluoro-1-phenyl-ethyl)-7-hydroxy-3,4-dihydro-1H-pyrido[1,2-a]pyrazin-8-one 2-[1-(2-chlorophenyl)cyclopropyl]-7-hydroxy-3,4-dihydro-1H-pyrido[1,2-a]pyrazin-8-one 2-(2,2-difluoro-1-phenyl-ethyl)-7-hydroxy-3,4-dihydro-1H-pyrido[1,2-a]pyrazin-8-one 2-(1,3-benzothiazol-2-yl)-7-hydroxy-3,4-dihydro-1H-pyrido[1,2-a]pyrazin-8-one 7-hydroxy-2-(2-phenylcyclopropyl)-3,4-dihydro-1H-pyrido[1,2-a]pyrazin-8-one 7-hydroxy-2-(5-quinolyl)-3,4-dihydro-1H-pyrido[1,2-a]pyrazin-8-one 7-hydroxy-2-(3-phenyloxetan-3-yl)-3,4-dihydro-1H-pyrido[1,2-a]pyrazin-8-one 7-hydroxy-2-phenyl-1,2,3,4-tetrahydro-8H-pyrido[1,2-a]pyrazin-8-one 7-hydroxy-2-(3-methylphenyl)-1,2,3,4-tetrahydro-8H-pyrido[1,2-a]pyrazin-8-one 7-hydroxy-2-[2-(trifluoromethoxy)phenyl]-1,2,3,4-tetrahydro-8H-pyrido[1,2-a]pyrazin-8-one 1,2-dibenzyl-7-hydroxy-1,2,3,4-tetrahydro-8H-pyrido[1,2-a]pyrazin-8-one 2-benzyl-7-hydroxy-1-phenyl-1,2,3,4-tetrahydro-8H-pyrido[1,2-a]pyrazin-8-one 2-(2,6-dichlorobenzyl)-7-hydroxy-1-phenyl-1,2,3,4-tetrahydro-8H-pyrido[1,2-a]pyrazin-8-one (1R)-2-(4-ethylbenzyl)-7-hydroxy-1-phenyl-1,2,3,4-tetrahydro-8H-pyrido[1,2-a]pyrazin-8-one (1S)-2-(4-ethylbenzyl)-7-hydroxy-1-phenyl-1,2,3,4-tetrahydro-8H-pyrido[1,2-a]pyrazin-8-one 2-(4-ethylbenzyl)-7-hydroxy-1-(propan-2-yl)-1,2,3,4-tetrahydro-8H-pyrido[1,2-a]pyrazin-8-one 2-(2,6-dimethylbenzyl)-7-hydroxy-1-methyl-1,2,3,4-tetrahydro-8H-pyrido[1,2-a]pyrazin-8-one 2-(4-ethylbenzyl)-7-hydroxy-1-methyl-1,2,3,4-tetrahydro-8H-pyrido[1,2-a]pyrazin-8-one 1-(4-fluorophenyl)-7-hydroxy-2-(quinolin-8-ylmethyl)-1,2,3,4-tetrahydro-8H-pyrido[1,2-a]pyrazin-8-one 2-(2,6-dimethylbenzyl)-1-(4-fluorophenyl)-7-hydroxy-1,2,3,4-tetrahydro-8H-pyrido[1,2-a]pyrazin-8-one 2-(4-ethylbenzyl)-7-hydroxy-1-(tetrahydro-2H-pyran-4-yl)-1,2,3,4-tetrahydro-8H-pyrido[1,2-a]pyrazin-8-one 2-(4-ethylbenzyl)-7-hydroxy-1-[3-(pyridin-3-yl)phenyl]-1,2,3,4-tetrahydro-8H-pyrido[1,2-a]pyrazin-8-one 2-benzyl-7-hydroxy-3-phenyl-1,2,3,4-tetrahydro-8H-pyrido[1,2-a]pyrazin-8-one 2,3-dibenzyl-7-hydroxy-1,2,3,4-tetrahydro-8H-pyrido[1,2-a]pyrazin-8-one 3-benzyl-2-(2,6-dichlorobenzyl)-7-hydroxy-1,2,3,4-tetrahydro-8H-pyrido[1,2-a]pyrazin-8-one 7-hydroxy-3-methyl-2-[4-(trifluoromethoxy)benzyl]-1,2,3,4-tetrahydro-8H-pyrido[1,2-a]pyrazin-8-one 2-benzyl-7-hydroxy-3-methyl-1,2,3,4-tetrahydro-8H-pyrido[1,2-a]pyrazin-8-one 2-benzyl-7-hydroxy-3-(2-phenylethyl)-1,2,3,4-tetrahydro-8H-pyrido[1,2-a]pyrazin-8-one 9-chloro-2-(2-chloro-6-fluorobenzyl)-7-hydroxy-1,2,3,4-tetrahydro-8H-pyrido[1,2-a]pyrazin-8-one 6-fluoro-7-hydroxy-2-[[4-(trifluoromethoxy)phenyl]methyl]-3,4-dihydro-1H-pyrido[1,2-a]pyrazin-8-one 2-[(2-chlorophenyl)methyl]-6-fluoro-7-hydroxy-3,4-dihydro-1H-pyrido[1,2-a]pyrazin-8-one 9-chloro-2-(4-ethylbenzyl)-7-hydroxy-1,2,3,4-tetrahydro-8H-pyrido[1,2-a]pyrazin-8-one 9-chloro-2-[(2-chlorophenyl)methyl]-7-hydroxy-3,4-dihydro-1H-pyrido[1,2-a]pyrazin-8-one 9-bromo-2-(4-ethyl benzyl)-7-hydroxy-1,2,3,4-tetrahydro-8H-pyrido[1,2-a]pyrazin-8-one 9-bromo-2-[(2-chlorophenyl)methyl]-7-hydroxy-3,4-dihydro-1H-pyrido[1,2-a]pyrazin-8-one 2-[(2-chlorophenyl)methyl]-7-hydroxy-9-iodo-3,4-dihydro-1H-pyrido[1,2-a]pyrazin-8-one 9-cyclopropyl-2-(4-ethylbenzyl)-7-hydroxy-1,2,3,4-tetrahydro-8H-pyrido[1,2-a]pyrazin-8-one and 2-[(2-chlorophenyl)methyl]-9-cyclopropyl-7-hydroxy-3,4-dihydro-1H-pyrido[1,2-a]pyrazin-8-one.

In some embodiments, the present invention provides prodrugs of the compounds described herein. The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce the active compounds.

Prodrugs may be prepared by any variety of synthetic methods or appropriate adaptations presented in the chemical literature or as in synthetic or organic chemistry text books, such as those provide in Green's Protective Groups in Organic Synthesis, Wiley, $4^{th}$ Edition (2007) Peter G. M. Wuts and Theodora W. Green; March's Advanced Organic Chemistry: Reactions, Mechanisms, and Structure, Wiley, 6th Edition (2007) Michael B. Smith and Domino Reactions in Organic Synthesis, Wiley (2006) Lutz F. Tietze, hereby incorporated by reference. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association), also hereby incorporated by reference.

Prodrugs in accordance with the invention can, for example, be produced by replacing appropriate functionalities present in the compounds disclosed herein with certain moieties known to those skilled in the art as 'pro-moieties' as described, for example, in Design of Prodrugs by H. Bundgaard (Elsevier, 1985).

Some non-limiting examples of prodrugs in accordance with the invention include: (i) where the exemplary compound contains a carboxylic acid functionality which is functionalized into a suitably metabolically labile group (esters, carbamates, etc.); (ii) where the exemplary compound contains an alcohol functionality which is functionalized into a suitably metabolically labile group (ethers, esters, carbamates, acetals, ketals, etc.); and (iii) where the exemplary compound contains a primary or secondary amino functionality, or an amide which are functionalized into a suitably metabolically labile group, e.g., a hydrolysable group (amides, carbamates, ureas, phosphonates, sulfonates, etc.). Further examples of replacement groups in accordance with the foregoing examples and examples of other prodrug types may be found in the aforementioned references.

IV. Indications

As discussed above, the COMT-inhibiting compounds of the present invention can be used for treating neuropsychiatric and neurological diseases for which inhibiting COMT provides a therapeutic benefit.

Significant psychiatric indications, as discussed above, include, but are not limited to ADHD, obsessive-compulsive disorder, alcoholism and other addictions, depression, bipolar disorder, age-associated cognitive symptoms, impulse control disorders, including compulsive gambling, sexual behavior, and other compulsive destructive behaviors, in particular, schizophrenia. Among the preferred neurological diseases is treating Parkinson's disease, preferably when co-administered with L-DOPA, with or without an aromatic L-amino acid decarboxylase inhibitor (AADC) such as carbidopa, by preventing COMT-mediated metabolism of L-DOPA.

In one embodiment, a method for treating conditions in which inhibition of COMT enzyme is beneficial comprises administering to a patient in need thereof a COMT-inhibiting compound described hereinabove for use in the present methods. Such conditions include, but are not limited to, those provided in WO 2011/109254, the contents of which are incorporated herein by reference.

In a specific embodiment, a method for treating schizophrenia or psychosis comprises administering to a patient in need thereof a COMT-inhibiting compound described hereinabove for use in the present methods. The Diagnostic and Statistical Manual of Mental Disorders (DSM-IV-TR) (2000, American Psychiatric Association, Washington, D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, *cannabis*, cocaine, hallucinogens, inhalants, opioids, phencyclidine, ketamine and other dissociative anaesthetics, and other psychostimulants), psychosis/psychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, a method for treating cognitive disorders comprises administering to a patient in need thereof a COMT-inhibiting compound described hereinabove for use in the present methods. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), mild cognitive impairment, multi-infarct dementia, Lewy body dementia, AIDS-related dementia, and frontotemporal dementia, delirium, amnestic disorders or age related cognitive decline.

In another specific embodiment, a method for treating anxiety disorders comprises administering to a patient in need thereof a COMT-inhibiting compound described hereinabove for use in the present methods. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, a method for treating substance-related disorders and addictive behaviors comprises administering to a patient in need thereof a COMT-inhibiting compound described hereinabove for use in the present methods. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, *cannabis*, cocaine, hallucinogens, inhalants, nicotine, opioids, phencyclidine, sedatives, hypnotics or anxiolytics.

In another specific embodiment, a method for treating obesity or eating disorders associated with excessive food intake, and complications associated therewith, comprises administering to a patient in need thereof a COMT-inhibiting compound described hereinabove for use in the present methods. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, a method for treating mood and depressive disorders comprises administering to a patient in need thereof a COMT-inhibiting compound described hereinabove for use in the present methods. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, a method for treating pain comprises administering to a patient in need thereof a COMT-inhibiting compound described hereinabove for use in the present methods. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, the COMT-inhibiting compounds described hereinabove for use in the present methods can be used to treat other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with traumatic brain injury, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballismus), myoclonus (including, generalised myoclonus and focal myoclonus), tics (including, simple tics, complex tics and symptomatic tics), dystonia (including, generalised, idiopathic, drug-induced, symptomatic, paroxysmal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In particularly desirable embodiments, the COMT-inhibiting compounds, including the compounds of the present invention, are useful for treating Alzheimer's disease. Accordingly, a method for treating Alzheimer's disease comprises administering to a patient in need thereof a COMT-inhibiting compound described hereinabove for the present methods.

In other particularly desirable embodiments, the COMT-inhibiting compounds, including the compounds of the present invention, are useful for treating Parkinson's disease. Accordingly, a method for treating Parkinson's disease comprises administering to a patient in need thereof a COMT-inhibiting compound described hereinabove for the present methods.

In yet other particularly desirable embodiments, the COMT-inhibiting compounds, including the compounds of the present invention, are useful for treating mild cognitive impairment. Accordingly, a method for treating mild cognitive impairment comprises administering to a patient in need thereof a COMT-inhibiting compound described hereinabove for the present methods.

In still other particularly desirable embodiments, the COMT-inhibiting compounds, including the compounds of the present invention, are useful for treating cognitive, learning and mental related disorders in patients with neurodegeneration associated with traumatic brain injury. Accordingly, a method for treating cognitive, learning and mental related disorders in patients with neurodegeneration associated with traumatic brain injury comprises administering a COMT-inhibiting compound described hereinabove for the present methods.

In further particularly desirable embodiments, the COMT-inhibiting compounds, including the compounds of the present invention, are useful for treating schizophrenia. Accordingly, a method for treating schizophrenia comprises administering to a patient in need thereof a COMT-inhibiting compound described hereinabove for the present methods.

The subject COMT-inhibiting compounds, including the compounds of the present invention, are useful in methods for the prevention, treatment, control, amelioration, or reduction of risk of the diseases, disorders and conditions noted herein.

V. Combination Therapies

The subject COMT-inhibiting compounds, including the compounds of the present invention, are further useful in a method for the prevention or treatment of the aforementioned diseases, disorders and conditions in combination with other agents. In many instances, the combination of the drugs together is safer or more effective than either drug alone; the compounds of the present invention and the other active ingredients may often be used in lower doses than when each is used singly. The drug(s) in the combination may be administered contemporaneously or sequentially (i.e. one preceding or following the other, at any appropriate time interval). When administered contemporaneously, the drugs may be administered separately, or a single dosage form may contain both active agents.

Accordingly, the subject compounds may be used in combination with other agents which are known to be beneficial in the subject indications, or other drugs that affect receptors or enzymes that either increase the efficacy, safety, convenience, or reduce unwanted side effects or toxicity of the compounds of the present invention. It will be appreciated that any of the drugs listed herein may be in the form of a pharmaceutically acceptable salt.

In a particularly preferred embodiment, the subject compound is employed in combination with levodopa, with or without a selective extracerebral decarboxylase inhibitor such as carbidopa or benserazide. In other embodiments, the COMT inhibitor of the invention is administered in combination with anticholinergics such as biperiden and trihexyphenidyl (benzhexol) hydrochloride, other COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with a neuroleptic or antipsychotic agent, or pharmaceutically acceptable salts thereof. Classes of neuroleptic agents include phenothiazines; thioxanthenes; heterocyclic dibenzazepines; butyrophenones; diphenylbutylpiperidines; indolones, such as acepromazine, amisulpride, amoxapine, aripiprazole, asenapine, benperidol, bifeprunox, blonanserin, brexpiprazole, bromperidol, bupropion, busprione, capuride, cariprazine, carpipramine, chlorpromazine, chlorprothixene, clocapramine, clopenthixol, cloperidone, clotiapine, clozapine, cyamemazine, dexclamol, divalproex, dixyrazine, droperidol, flupentixol tiotixene, flupentixol, fluphenazine, fluphenazine, fluspirilene, haloperidol, hydroxyzine, iloperidone, levomepromazine, loxapine, lurasidone, melperone, mesoridazine, molindone, moperone, mosapramine, nefazodone, nemonapride, olanzapine, paliperidone, penfluridol, perazine, pericyazine, perlapine, perospirone, perphenazine, perphenazine, phenelzine, pimavanserin, pimozide, pipamperone, pipotiazine, prochlorperazine, promazine, promethazine, prothipendyl, quetiapine, remoxipride, risperidone, roletamide, sertindole, sulpiride, sultopride, thioproperazine, thioridazine, thiothixene, timiperone, tranylcypromaine, trazodone, trepipam, trifluoperazine, triflupromazine, trimipramine, veralipride, zicronapine, ziprasidone, zotepine, or zuclopenthixol.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, butabarbital, butalbital, capuride, carbocloral, chloral betaine, chloral hydrate, clonazepam, clorazepate, chlordiazepoxide, clorethate, cyprazepam, desipramine, dexclamol, diazepam, dichloralphenazone, divalproex, diphenhydramine, doxepin, estazolam, ethchlorvynol, etomidate, fenobam, flupentixol, fiurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nisobamate, nitrazepam, nortriptyline, oxazepam, paraldehyde, paroxetine, pentobarbital, perlapine, phenelzine, phenobarbital, prazepam, propofol, protriptyline, quazepam, reclazepam, roletamide, secobarbital, sertraline, suproclone, temazepam, tracazolate, tranylcypromaine, trazodone, triazolam, trepipam, tricetamide, triclofos, trimetozine, trimipramine, uldazepam, venlafaxine, zaleplon, zolazepam, or zolpidem.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, β-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide; venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

VI. Formulation and Administration

The invention provides a method for administering a COMT inhibiting compound as provided herein to a patient suffering from a condition, or prone to a condition, that is responsive to treatment or prevention with the compound. The method comprises administering, e.g. orally or parenterally, a therapeutically effective amount of the compound, preferably provided as part of a pharmaceutical preparation.

In some embodiments, a prodrug of the COMT inhibiting compound is administered.

The invention also provides pharmaceutical preparations comprising a COMT-inhibiting compound as provided herein in combination with a pharmaceutical excipient.

Modes of administration include administration by injection, e.g. parenteral, intravenous, intraarterial, intramuscular, subcutaneous, and intrathecal, as well as pulmonary, rectal, transdermal, transmucosal, and oral delivery.

In addition to primates, such as humans, a variety of other mammals can be treated according to the method of the present invention. For instance, mammals including, but not limited to, cows, sheep, goats, horses, dogs, cats, guinea pigs, or other bovine, ovine, equine, canine, feline, or rodent, such as mouse, species can be treated. However, the method can also be practiced in other species, such as avian species (e.g., chickens).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Suitable formulation types for parenteral administration include ready-for-injection solutions, dry powders for combination with a solvent prior to use, suspensions ready for injection, dry insoluble compositions for combination with a vehicle prior to use, emulsions and liquid concentrates for dilution prior to administration.

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include, but are not limited to, water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and *arachis* oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

Exemplary excipients include, without limitation, carbohydrates, inorganic salts, antimicrobial agents, antioxidants, surfactants, buffers, acids, bases, and combinations thereof. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer including, but not limited to, citric acid, sodium chloride, potassium chloride, sodium sulfate, potassium nitrate, sodium phosphate monobasic, sodium phosphate dibasic, and combinations thereof.

A surfactant may be present as an excipient. Exemplary surfactants include, but are not limited to, polysorbates such as Tween 20 and Tween 80 and pluronics such as F68 and F88 (both available from BASF, Mount Olive, N.J.); sorbitan esters; lipids, such as phospholipids such as lecithin and other phosphatidyl cholines, phosphatidyl ethanolamines (although preferably not in liposomal form), and fatty acids and fatty esters.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

For pressurized compositions, the liquid carrier can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically, as a solution, cream, or lotion, by formulation with pharmaceutically acceptable vehicles containing the active compound. The compositions can be in a form suitable for use in transdermal devices.

The compositions of this invention may be orally administered, in formulations such as capsules, tablets, powders or granules, or as suspensions or solutions in water or non-aqueous media. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The amount of the compound in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the COMT-inhibiting compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then further exploring the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

The foregoing pharmaceutical excipients, along with other excipients, are described in "Remington: The Science & Practice of Pharmacy", 21st ed., Williams & Williams, (2005), the "Physician's Desk Reference", 67th ed., PDR Network, Montvale, N.J. (2013), and Kibbe, A. H., "Handbook of Pharmaceutical Excipients", 7th Edition, Pharmaceutical Press, Washington, D.C., 2012.

The dose of the compounds according to the invention to be administered, both unit dosage and dosing schedule, will vary depend upon the age, weight, and general condition of the subject, as well as the desired therapeutic effect, the route of administration, and the duration of the treatment. The compounds of the invention are administered to the patient in therapeutically effective amounts. Methods are known to those skilled in the art to adjust the dose to obtain maximal benefit. Generally, dosage levels of between 0.001 to 10 mg/kg of body weight daily are administered to the patient. The dosage range will generally be about 0.5 mg to 1.0 g per patient per day, which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. The compounds may be administered on a regimen of 1 to 4 times per day, such as once or twice per day.

These and other aspects of the invention will be realized upon closer inspection of the specification as a whole.

EXAMPLES

The present compounds can be prepared and evaluated according to procedures provided in the following Examples. The following Examples further describe, but do not limit, the scope of the invention.

COMT Inhibition Assay Procedure

The ability of compounds to inhibit the activity of catechol-O-methyltransferase (COMT) was determined by a homogenous time-resolved fluorescent (HTRF) assay (Lina et al, 2012; kit from CisBio, Codolet, France). This assay measures the production of S-adenosyl homocysteine (SAH) from the methyl donor S-adenosyl methionine. Recombinant human membrane bound COMT (MB-COMT; M51A variant) was expressed in HEK 293F cells using 293Fectin (Life Technologies, Gent, Belgium) and membranes prepared. The membranes were re-suspended in buffer (20 mM Tris/HCl pH 7; 10 mM glycerol; 2 mM $MgCl_2$; 10 mM NaCl), aliquoted and stored at −80° C. Recombinant human soluble COMT(S-COMT), Val158 variant and a hexa-His tag on the N-terminus, was purified using Ni-NTA chromatography, the His tag removed and stored in buffer as above.

For the human MB-COMT assay, membranes (62 ng/well) were incubated with SAM (20 μM final, CisBio) and dopamine (1.5 μM final; Sigma H8502, Diegem, Belgium) in the presence or absence of varying concentrations (typically 10 concentrations ranging from 10 μM to 0.1 nM) of compound for 40 min at 37° C. in 384-well microtiter plates (10 μl per well final volume). The reaction was terminated by the addition of acylation buffer and the amount of SAH produced determined according to manufacturer's instructions. Specific inhibition as that inhibited by a high concentration of tolcapone and all experiments were validated using a control curve to tolcapone.

The human S-COMT assay was performed as above except that 0.15 ng enzyme/well was incubated with SAM (201M final) and dopamine (100 μM final) for 15 min at 37° C. and SAH production determined.

HTRF readings were performed using a Perkin Elmer Envision and results expressed as concentration of SAH produced using a standard curve. Results were analyzed using non-linear regression to the 4-parameter logistic equation and pIC50 (−log 10 concentration of drug which inhibits enzyme activity/SAH production by 50%) determined.

As the data herein indicate, a broad variety of compounds of formula I were found effective as COMT inhibitors at low concentrations. $pIC_{50}$ values for exemplary compounds of formula I (see below for compound names and structures) are provided in Table 1 below. Any compound with a $pIC_{50}$ superior or equal to 4.5 in this assay, as described above, is deemed a COMT inhibitor. In the Table 1 below, a single plus (+) is associated with a $pIC_{50}$ of from about 4.5 to 6; two plus signs (++) is associated with a $pIC_{50}$ of from about 6 to 7; and three plus signs (+++) is associated with a $pIC_{50}$ of above about 7.

TABLE 1

| Example | Activity range |
| --- | --- |
| 1 | ++ |
| 2 | ++ |
| 3 | + |
| 4 | + |
| 5 | + |
| 6 | +++ |
| 7 | +++ |
| 8 | +++ |
| 9 | +++ |
| 10 | +++ |
| 11 | ++ |
| 12 | ++ |
| 13 | +++ |
| 14 | +++ |
| 15 | ++ |
| 16 | +++ |
| 17 | ++ |
| 18 | +++ |
| 19 | ++ |
| 20 | ++ |
| 21 | +++ |
| 22 | ++ |
| 23 | +++ |
| 24 | +++ |
| 25 | +++ |
| 26 | ++ |
| 27 | +++ |
| 28 | +++ |
| 29 | +++ |
| 30 | ++ |
| 31 | ++ |
| 32 | ++ |
| 33 | +++ |
| 34 | ++ |
| 35 | ++ |
| 36 | +++ |
| 37 | +++ |
| 38 | ++ |
| 39 | +++ |
| 40 | ++ |
| 41 | ++ |
| 42 | ++ |
| 43 | ++ |
| 44 | +++ |
| 45 | ++ |
| 46 | ++ |
| 47 | +++ |
| 48 | ++ |
| 49 | ++ |
| 50 | ++ |
| 51 | ++ |
| 52 | +++ |
| 53 | +++ |
| 54 | ++ |
| 55 | ++ |
| 56 | ++ |
| 57 | +++ |
| 58 | +++ |
| 59 | +++ |
| 60 | +++ |
| 61 | +++ |
| 62 | +++ |
| 63 | +++ |
| 64 | +++ |
| 65 | ++ |
| 66 | +++ |
| 67 | +++ |
| 68 | ++ |
| 69 | +++ |
| 70 | ++ |
| 71 | ++ |
| 72 | ++ |
| 73 | +++ |
| 74 | ++ |
| 75 | +++ |
| 76 | +++ |
| 77 | +++ |
| 78 | +++ |
| 79 | +++ |
| 80 | ++ |
| 81 | ++ |
| 82 | +++ |
| 83 | ++ |
| 84 | ++ |
| 85 | +++ |
| 86 | +++ |
| 87 | +++ |
| 88 | +++ |
| 89 | ++ |
| 90 | +++ |
| 91 | +++ |
| 92 | +++ |
| 93 | ++ |
| 94 | ++ |
| 95 | ++ |
| 96 | ++ |
| 97 | +++ |
| 98 | ++ |
| 99 | ++ |
| 100 | + |
| 101 | +++ |
| 102 | ++ |
| 103 | ++ |
| 104 | +++ |
| 105 | +++ |
| 106 | +++ |
| 107 | +++ |
| 108 | ++ |
| 109 | ++ |
| 110 | + |
| 111 | ++ |
| 112 | +++ |
| 113 | ++ |
| 114 | ++ |
| 115 | ++ |
| 116 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |
| 128 | ++ |
| 129 | ++ |
| 130 | ++ |
| 131 | ++ |
| 132 | +++ |
| 133 | +++ |
| 134 | ++ |
| 135 | ++ |
| 136 | +++ |

TABLE 1-continued

| Example | Activity range |
| --- | --- |
| 137 | +++ |
| 138 | +++ |
| 139 | +++ |
| 140 | + |
| 141 | ++ |
| 142 | +++ |

Synthetic Procedures

Exemplary compounds were prepared via several general synthetic routes set forth in the Examples below. Any of the disclosed compounds of the present invention can be prepared according to one or more of these synthetic routes or specific examples, or via modifications thereof accessible to the person of ordinary skill in the art.

Intermediate 1: 7-benzyloxy-1,2,3,4-tetrahydro-pyrido[1,2-a]pyrazin-8-one

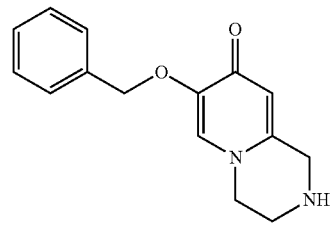 [SMILES: O=c1cc2n(cc1OCc1ccccc1)CCNC2]

Step 1: Preparation of 1-(2-aminoethyl)-5-benzyloxy-2-(hydroxymethyl)pyridin-4-one

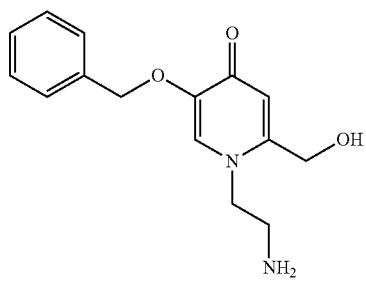 [SMILES: NCCn1cc(OCc2ccccc2)c(=O)cc1CO]

Ethylenediamine (45.3 g, 754 mmol, 50.9 mL) was added to a suspension of 5-(benzyloxy)-2-(hydroxymethyl)-4H-pyran-4-one (35 g, 151 mmol) in ethanol (350 mL). The mixture was heated at 90° C. for 1.5 h. The reaction mixture was concentrated to yield the title intermediate as a brown viscous oil (46.4 g, quant.) used as such in the next experiment without further purification. MS, ES$^+$ m/z 275.2 [M+H]$^+$.

Method A

Step 2a: Preparation of 7-benzyloxy-3,4-dihydro-pyrido[1,2-a]pyrazin-8-one

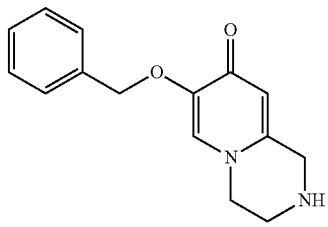 [SMILES: O=c1cc2n(cc1OCc1ccccc1)CCNC2]

1-(2-aminoethyl)-5-benzyloxy-2-(hydroxymethyl)pyridin-4-one (49 g, 179 mmol) was dissolved in CHCl$_3$ (400 mL) and MnO$_2$ (78 g, 893 mmol) was added to the mixture and heated overnight at 60° C. The reaction mixture was filtered and the residue was concentrated to yield the title intermediate used in the next step without further purification. MS, ES$^+$ m/z 255.5 [M+H]$^+$.

Step 2b: Preparation of 7-benzyloxy-1,2,3,4-tetrahydropyrido[1,2-a]pyrazin-8-one 7-benzyloxy-3,4-dihydropyrido[1,2-a]pyrazin-8-one (46.4 g, 182 mmol) was dissolved in MeOH (500 mL). NaBH4 (20.71 g, 547 mmol) was added portionwise to the mixture and the mixture was stirred over 48 h at rt. The reaction mixture was then concentrated to give a residue (10 g) that was purified by chromatography (SiO$_2$, DCM:MeOH:NH$_3$ (7 N) (90:9:1) to yield the title intermediate as a yellow solid (23.4 g, 50%). MS, ES$^+$ m/z 257.2 [M+H]$^+$.

$^1$H-NMR (300 MHz, DMSO-d$_6$) ᶞ 7.45-7.22 (m, 6H), 5.90 (s, 1H), 4.96 (s, 2H), 3.74 (t, J=5.6 Hz, 2H), 3.70 (br.s., 2H), 3.00 (t, J=5.6 Hz, 2H), 2.57 (br.s., 1H), 1H-NMR (300 MHz, MeOD) ᶞ 7.48-7.42 (m, 3H), 7.38-7.26 (m, 3H), 6.25 (s, 1H), 5.06 (s, 1H), 3.97-3.81 (m, 4H), 3.28 (t, J=5.6 Hz, 2H).

Intermediate 2: 7-[(4-methoxyphenyl)methoxy]-1,2,3,4-tetrahydropyrido[1,2-a]pyrazin-8-one

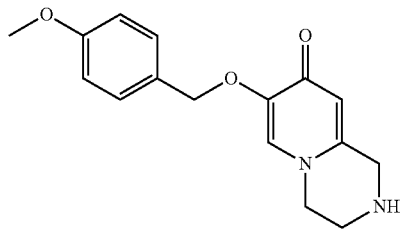 [SMILES: COc1ccc(COc2cn3c(cc2=O)CNCC3)cc1]

Step 1: Preparation of 2-(hydroxymethyl)-5-((4-methoxybenzyl)oxy)-4Hpyran-4-one

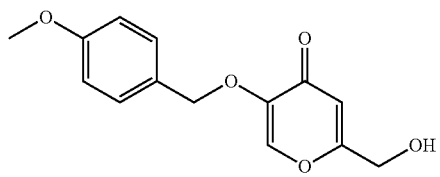 [SMILES: COc1ccc(COc2coc(CO)cc2=O)cc1]

To a suspension of Kojic acid (25.4 g, 179 mmol) in anhydrous DMF (450 mL) was added potassium carbonate (29.6 g, 214 mmol) and alpha-chloro-4-methoxytoluene (30.8 g, 197 mmol, 26.7 mL) and the resulting suspension was stirred at 80° C. for 4 h. The reaction mixture was evaporated in vacuo (oil pump, high vacuum) and water (500 mL) was added. The resulting suspension was stirred for 30 minutes. The solids were filtered off and dried under air current for 30 minutes, then triturated from heptane:diethyl ether (1:1, 300 mL) and dried in a vacuum oven (40° C.) overnight to yield 38.44 g of the title intermediate as a brown solid used in the next step without any further purification.

Step 2: Preparation of 1-(2-aminoethyl)-2-(hydroxymethyl)-5-((4-methoxybenzyl)oxy)pyridin-4(1H)-one

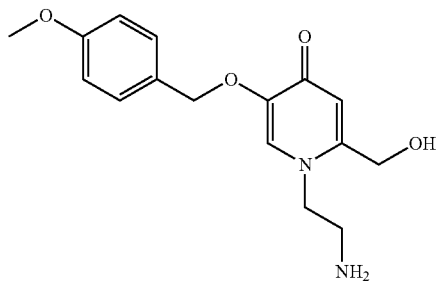 [SMILES: COc1ccc(COc2cn(CCN)c(CO)cc2=O)cc1]

Ethylenediamine (38.2 g, 635 mmol, 42.9 mL) was added to a suspension of 2-hydroxymethyl-5-((4-methoxybenzyl)oxy)-4H-pyran-4-one (33.3 g, 127 mmol) in Ethanol (400 mL). The reaction mixture was stirred for 4 h at 90° C. and then stirred overnight at rt. The reaction mixture was concentrated to yield the title intermediate (50.3 g) as a brown viscous oil used in the next step without any further purification. MS, ES+ m/z 305.2 [M+H]+.

Step 3: Preparation of 7-((4-methoxybenzyl)oxy)-3H-pyrido[1,2-a]pyrazin-8(4H)-one

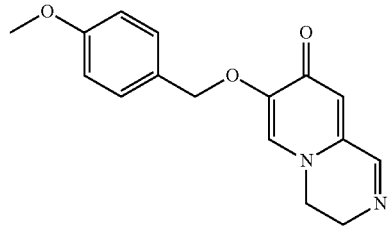 [SMILES: COc1ccc(COc2cn3c(cc2=O)C=NCC3)cc1]

1-(2-aminoethyl)-2-(hydroxymethyl)-5-((4-methoxybenzyl)oxy)pyridin-4(1H)-one (38.6 g, 127 mmol) was dissolved in chloroform (400 mL) and stirred for a few minutes. $MnO_2$ (55.1 g, 634 mmol) was added to the mixture was stirred at 60° C. overnight. The reaction mixture was filtered and the residue was concentrated to yield the title intermediate (47.5 g). MS, ES+ m/z 285.2 [M+H]+.

Step 4: Preparation of 7-[(4-methoxyphenyl)methoxy]-1,2,3,4-tetrahydropyrido[1,2-a]pyrazin-8-one

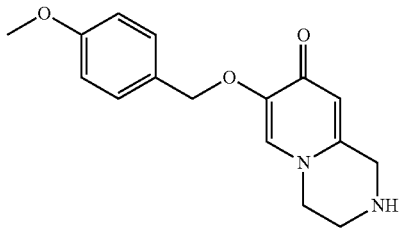 [SMILES: COc1ccc(COc2cn3c(cc2=O)CNCC3)cc1]

To a cooled (ice bath) solution of 7-[(4-methoxyphenyl)methoxy]-3,4-dihydropyrido[1,2-a]pyrazin-8-one (5.0 g, 17.59 mmol) in MeOH (100 mL) was added $NaBH_4$ (672 mg, 1 eq.) and the resulting mixture was stirred at rt for 14 h. The reaction mixture was filtered on a bed of celite/silicagel/celite and rinsed with MeOH (3×10 mL). The solvent was evaporated to give a pale yellow solid (6.1 g). This solid was then dissolved in a DCM/MeOH (9:1). The mixture was then washed with an aq. saturated solution of NaCl. The organic layers were dried on $MgSO_4$ and concentrated under vacuum to yield the title intermediate as a yellow solid (4.6 g, 90%). MS, ES+ m/z 287.2 [M+H]+.
1H-NMR (300 MHz, DMSO-$d_6$) ? 7.35 (s, 1H), 7.31 (d, J=4.3 Hz, 2H), 6.91 (d, J=4.3 Hz, 2H), 5.88 (s, 1H), 4.89 (s 2H), 3.75-3.71 (m, 4H), 3.73 (s, 3H), 3.01 (t, J=5.9, 2H), 1H-NMR (300 MHz, MeOD) ? 7.42 (s, 1H), 7.36 (d, J=4.3 Hz, 2H), 6.90 (d, J=4.3 Hz, 2H), 6.25 (s, 1H), 5.05 (s 2H), 3.97-3.92 (m, 4H), 3.78 (s, 3H), 3.19 (t, J=5.9, 2H).

Intermediate 3: 5-benzyloxy-1-(2-chloroethyl)-2-(chloromethyl)pyridin-4-one

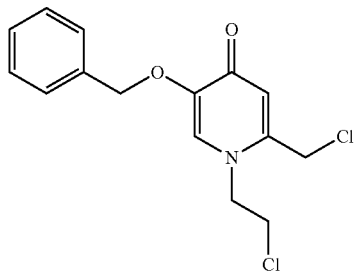 [SMILES: O=c1cc(CCl)n(CCCl)cc1OCc1ccccc1]

Step 1: Preparation of 5-benzyloxy-1-(2-hydroxyethyl)-2-(hydroxymethyl)pyridin-4-one

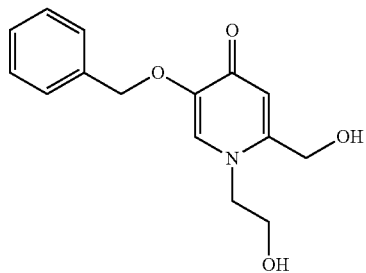 [SMILES: O=c1cc(CO)n(CCO)cc1OCc1ccccc1]

To a suspension of 5-benzyloxy-2-(hydroxymethyl) pyran-4-one (9.90 g, 42.7 mmol) in EtOH (20 mL) was added ethanolamine (3.0 mL, 49.2 mmol). The resulting mixture was stirred at reflux (bath oil heated at 110° C.) for 4.5 h and then at room temperature overnight. Ethanolamine (0.5 mL) was added and the mixture was stirred at reflux for another 1 h. The mixture was cooled to rt, then filtered. The collected solid was washed with Et$_2$O (3×15 mL) to yield the title intermediate as a beige solid (9.7 g, 83%). This intermediate is used in the next step without further purification. MS, ES$^+$ m/z 275 [M+H]$^+$.

Step 2: Preparation of 5-benzyloxy-1-(2-chloroethyl)-2-(chloromethyl)pyridin-4-one Method B

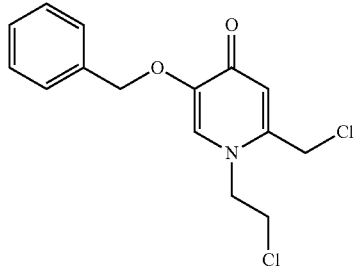 [SMILES: O=c1cc(CCl)n(CCCl)cc1OCc1ccccc1]

A mixture of 5-benzyloxy-1-(2-hydroxyethyl)-2-(hydroxymethyl)pyridin-4-one (980 mg, 3.56 mmol) in CHCl$_3$ (6 mL) with SOCl$_2$ (2 mL) was stirred at 50° C. for 2 h. Evaporation of the solvents under vacuum (40° C. overnight) gave 1.1 g of a beige brown solid (quant.). MS, ES$^+$ m/z 312 (M+H)$^+$. This intermediate is used in the next step without further purification.

Intermediate 4: 5-benzyloxy-4-oxo-pyran-2-carbaldehyde

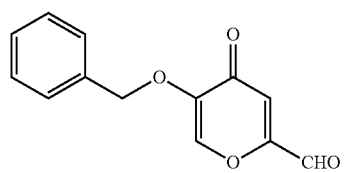 [SMILES: O=Cc1cc(=O)c(OCc2ccccc2)co1]

MnO$_2$ (18.7 g, 216 mmol) was added to a suspension of 5-benzyloxy-2-(hydroxymethyl)pyran-4-one (43.1 mmol, 10 g) in toluene (150 mL). The mixture was heated at 100° C. for 14 h. The mixture was cooled to rt, filtered on a bed of celite then concentrated to yield the title intermediate as a colorless oil (6.0 g, 60%). This intermediate is used in the next step without further purification Intermediate 5: N-[[5-benzyloxy-1-[2-[tert-butyl(dimethyl)silyl]oxyethyl]-4-oxo-2-pyridyl]methylene]-2-methyl-propane-2-sulfinamide

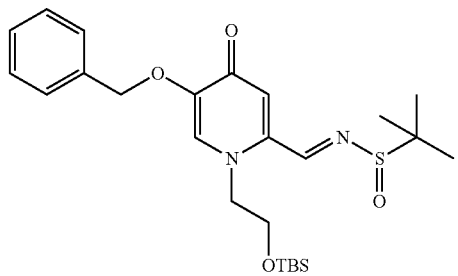 [SMILES: CC(C)(C)S(=O)/N=C/c1cc(=O)c(OCc2ccccc2)cn1CCO[Si](C)(C)C(C)(C)C]

Step 1: Preparation of 5-benzyloxy-1-[2-[tert-butyl(dimethyl)silyl]oxyethyl]-2-(hydroxymethyl)pyridin-4-one

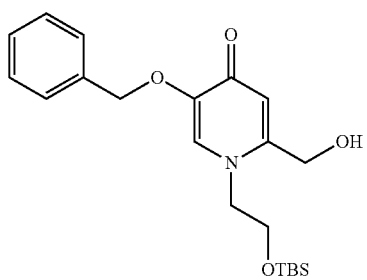 [SMILES: CC(C)(C)[Si](C)(C)OCCn1cc(OCc2ccccc2)c(=O)cc1CO]

5-benzyloxy-2-(hydroxymethyl)pyran-4-one (55.2 g, 238 mmol) was suspended in water (180 ml). 2-[tert-butyl(dimethyl)silyl]oxyethanamine (50 g, 285 mmol) and an aq. solution of NaOH (23.8 ml, 23.8 mmol, 1N) was added and the mixture was stirred at 60° C. for 2 h, then an additional amount of 2-[tert-butyl(dimethyl)silyl]oxyethanamine (50 g, 285 mmol) was added and the mixture was stirred at 60° C. for 14 h. Water was added, the mixture decanted and iPrOH (100 mL) was added. Ether was added (100 mL), until a beige precipitate was formed. The precipitate was filtered off, washed with ether and dried. The mother liquor was concentrated and ether was added. The precipitate was filtered off, washed with ether and combined with the first batch to afford the title intermediate as an off-white solid (43.5 g). MS, ES$^+$ m/z, 390.2 (M+H)$^+$.

Step 2: Preparation of 5-benzyloxy-1-[2-[tert-butyl(dimethyl)silyl]oxyethyl]-4-oxo-pyridine-2-carbaldehyde

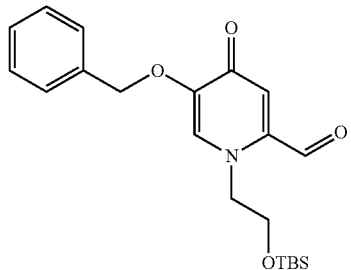 [SMILES: CC(C)(C)[Si](C)(C)OCCn1cc(OCc2ccccc2)c(=O)cc1C=O]

5-benzyloxy-1-[2-[tert-butyl(dimethyl)silyl]oxyethyl]-2-(hydroxymethyl)pyridin-4-one (43.8 g, 112 mmol) was dissolved in DCM (700 ml). Dess-Martin periodinane (52.5 g, 124 mmol) was added and the mixture was stirred at rt for 2 h. The mixture was washed with an aq. sat. solution of sodium bicarbonate (2×). The organic layer was dried with sodium sulfate and concentrated to afford a yellow solid (56.5 g). Purification by chromatography (SiO$_2$, gradient up to 5% MeOH in DCM) gave the title intermediate as a yellow oil (51 g). MS, ES$^+$ m/z, 388.2 (M+H)$^+$.

Step 3: Preparation of N-[[5-benzyloxy-1-[2-[tert-butyl(dimethyl)silyl]oxyethyl]-4-oxo-2-pyridyl]methylene]-2-methyl-propane-2-sulfinamide

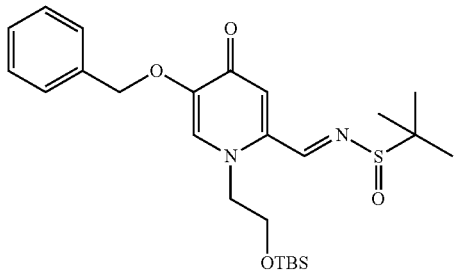 [SMILES: CC(C)(C)S(=O)/N=C/c1cc(=O)c(OCc2ccccc2)cn1CCO[Si](C)(C)C(C)(C)C]

5-benzyloxy-1-[2-[tert-butyl(dimethyl)silyl]oxyethyl]-2-(hydroxymethyl)pyridin-4-one (51 g, 132 mmol) and 2-methylpropane-2-sulfinamide (19.14 g, 158 mmol) were dissolved in DCM (1 L). Titanium (IV) isopropoxide (46.3 mL, 158 mmol) was added and the mixture was stirred overnight. The reaction mixture was concentrated (87 g crude) and filtered over a plug of silica (10% MeOH in DCM) to afford the title intermediate as a yellow solid/oil (65.95 g, 95%). MS, ES$^+$ m/z, 491.2 (M+H)$^+$. $^1$H-NMR (300 MHz, DMSO-d$_6$) ⌐ 8.51 (s, 1H), 7.75 (s, 1H), 7.44-7.27 (m, 5H), 6.73 (s, 1H), 5.04 (s, 2H), 4.44-4.23 (m, 2H), 3.91-3.71 (m, 2H), 1.18 (s, 9H), 0.73 (s, 9H), 0.15 (s, 3H), 0.14 (s, 3H).

Intermediate 6: 7-benzyloxy-1-methyl-1,2,3,4-tetrahydropyrido[1,2-a]pyrazin-8-one

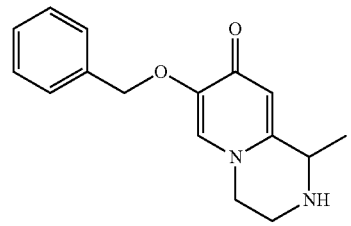 [SMILES: CC1NCCn2cc(OCc3ccccc3)c(=O)cc21]

Step 1: Preparation of N-[1-[5-benzyloxy-1-[2-[tert-butyl(dimethyl)silyl]oxyethyl]-4-oxo-2-pyridyl]ethyl]-2-methyl-propane-2-sulfinamide

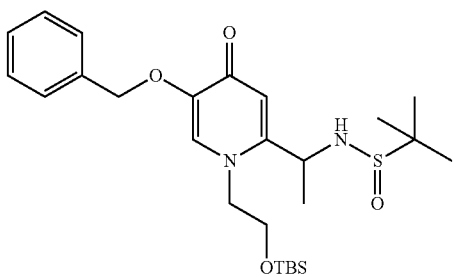 [SMILES: CC(NS(=O)C(C)(C)C)c1cc(=O)c(OCc2ccccc2)cn1CCO[Si](C)(C)C(C)(C)C]

N-[[5-benzyloxy-1-[2-[tert-butyl(dimethyl)silyl]oxyethyl]-4-oxo-2-pyridyl]methylene]-2-methyl-propane-2-sulfinamide (Intermediate 5, 20 g, 40.8 mmol) was dissolved in THF (dry) (500 mL), the mixture was cooled to −15° C. under a nitrogen atmosphere. Methylmagnesium bromide (1 N in THF, 122 mmol, 122 mL) was added and the mixture was stirred 1 h and slowly warmed to 12° C. The mixture was added to aq. sat. solution of ammonium chloride, extracted with EtOAc. The combined organic layers were dried with Na$_2$SO$_4$ filtered and concentrated under reduced pressure to give a white solid. Purification by chromatography (SiO$_2$, 5-10% MeOH in DCM) yielded the title intermediate (9.98 g, 48%). MS, ES$^+$ m/z, 507.4 (M+H)$^+$.

Step 2: Preparation of N-[1-[5-benzyloxy-1-(2-hydroxyethyl)-4-oxo-2-pyridyl]ethyl]-2-methyl-propane-2-sulfinamide

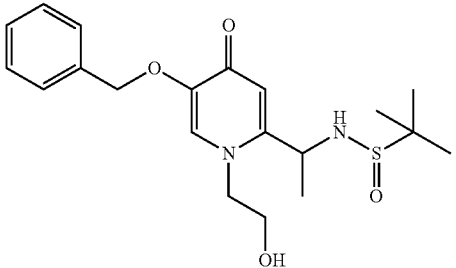 [SMILES: CC(NS(=O)C(C)(C)C)c1cc(=O)c(OCc2ccccc2)cn1CCO]

N-[1-[5-benzyloxy-1-[2-[tert-butyl(dimethyl)silyl]oxyethyl]-4-oxo-2-pyridyl]ethyl]-2-methyl-propane-2-sulfinamide (9.98 g, 19.69 mmol) was dissolved in anhydrous DMF (100 mL). Cesium fluoride (5.98 g, 39.4 mmol) was added to the stirred mixture and stirring was continued at room temperature for 20 h. The reaction mixture was added to a water/aq. sat. solution of NH$_4$Cl (1:1) and extracted with EtOAc. The organic phase was evaporated under vacuum. The remaining aqueous phase were evaporated to dryness under reduced pressure (0.5 Torr) and stripped with toluene (100 mL), affording a yellow oil batch combined with the evaporated organic phase. This material was taken up in DCM:MeOH (1:1) and filtered over SiO$_2$ (eluting with DCM:MeOH (1:1)) to yield the title intermediate (6.86 g, 89%). MS, ES$^+$ m/z, 393.2 (M+H)$^+$.

Step 3: Preparation of 7-benzyloxy-2-tert-butylsulfinyl-1-methyl-3,4-dihydro-1H-pyrido[1,2-a]pyrazin-8-one

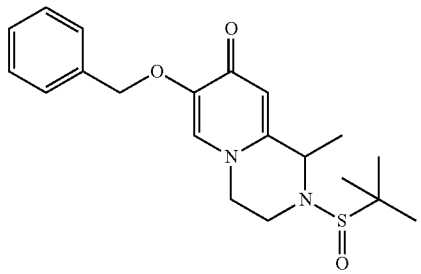 [SMILES: CC1c2cc(=O)c(OCc3ccccc3)cn2CCN1S(=O)C(C)(C)C]

A solution of N-[1-[5-benzyloxy-1-(2-hydroxyethyl)-4-oxo-2-pyridyl]ethyl]-2-methyl-propane-2-sulfinamide (6.68 g, 17.02 mmol) and triphenylphosphine (4.46 g, 17.02 mmol) in anhydrous THF (100 mL) was cooled to 0° C. The reaction mixture was stirred and DIAD (4.16 g, 20.57 mmol, 4 mL) was added in 100 µL portions, until an orange color persisted. The reaction mixture was stirred at room temperature over the weekend. The reaction mixture was then cooled to 0° C. and another portion of triphenylphosphine (4 g, 15.25 mmol) and DIAD (4.16 g, 20.57 mmol, 4 ml) were added. Reaction mixture was stirred for 1 h while slowly warming to room temperature. The reaction mixture was evaporated to dryness to obtain a red oil (23.5 g). Material was taken up in 50 mL MeOH and purified by automated reversed phase chromatography (8 runs of 8 mL MeOH solution, 120 g C18, water:CH3CN). The collected fractions were freeze-dried to yield the title intermediate (4.32 g, 68%). MS, ES$^+$ m/z, 375.2 (M+H)$^+$.

Step 4: Preparation of 7-benzyloxy-1-methyl-1,2,3,4-tetrahydropyrido[1,2-a]pyrazin-8-one A solution of 7-benzyloxy-2-tert-butylsulfinyl-1-methyl-3,4-dihydro-1H-pyrido[1,2-a]pyrazin-8-one (4.23 g, 11.30 mmol) in MeOH (50 mL) was cooled in an ice bath. A solution of HCl (4 N in dioxane, 13.55 mmol, 3.39 mL) was added dropwise and the stirring was continued for 15 min, while keeping the flask in the ice bath. Diethyl ether (50 mL) was added to the reaction mixture and the stirring continued for 30 minutes. The white precipitate was collected by filtration. The filtrates were then evaporated to dryness and the residue was combined with the collected solid. The material was taken up in MeOH:DCM (1:9, 50 mL). A solution of NH$_3$ in MeOH (7 N, 2.3 mL) was added and hydromatrix (50 g) was added. The mixture was evaporated to dryness under reduced pressure and charged on a SiO$_2$ column (100 g silica, DCM:MeOH (95:5)) until molybdate staining revealed no side products anymore. Subsequently, the product was eluted with DCM:MeOH:NH3/MeOH (8:2: 0.1) to give the title intermediate (1.95 g, 65%). MS, ES$^+$ m/z, 271.2 (M+H)$^+$. $^1$H-NMR (300 MHz, MeOD) ☒ ☒ 7.46 (m, 3H), 7.38-7.24 (m, 3H), 6.62 (s, 1H), 5.09 (s, 2H), 4.12-3.95 (m, 3H), 3.36-3.31 (m, 1H, coincides with solvent residual peak), 3.23-3.14 (m, 1H), 1.49 (d, J=3.8 Hz).

Intermediate 7: 7-benzyloxy-1-tetrahydropyran-4-yl-1,2,3,4-tetrahydropyrido[1,2-a]pyrazin-8-one

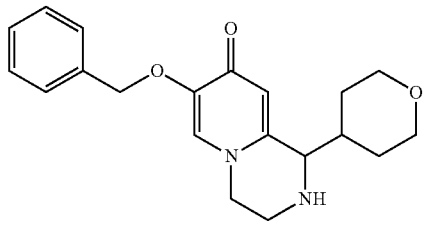 [SMILES: O=c1cc2n(cc1OCc1ccccc1)CCNC2C1CCOCC1]

Step 1: Preparation of N-[[5-benzyloxy-1-[2-[tert-butyl(dimethyl)silyl]oxyethyl]-4-oxo-2-pyridyl]-tetrahydropyran-4-yl-methyl]-2-methyl-propane-2-sulfinamide

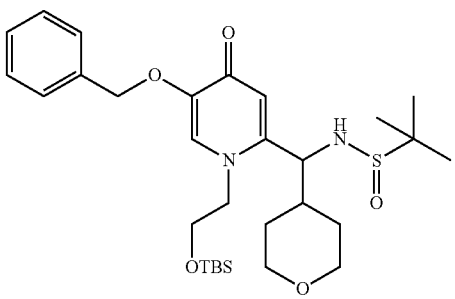 [SMILES: CC(C)(C)S(=O)NC(c1cc(=O)c(OCc2ccccc2)cn1CCO[Si](C)(C)C(C)(C)C)C1CCOCC1]

Under nitrogen atmosphere, magnesium (6.05 g, 249 mmol) was suspended in THF (30 ml). A catalytic amount of iodine and dibromoethane (0.4 ml) were added. The mixture was heated to 60° C. and 4-chlorotetrahydro-2H-pyran (5 g, 41.5 mmol) in THF (5 ml) was added dropwise. The mixture was stirred at 60° C. for 2.5 h. The mixture was cooled to 0° C. and N-[[5-benzyloxy-1-[2-[tert-butyl(dimethyl)silyl]oxyethyl]-4-oxo-2-pyridyl]methylene]-2-methyl-propane-2-sulfinamide (Intermediate 5, 6.78 g, 13.82 mmol) in THF (20 ml) was added. The resulting mixture was stirred at rt for 45 min. The reaction was quenched with ammonium chloride solution and extracted with EtOAc (2×). The combined organic layers were washed with brine, dried with sodium sulfate and concentrated to afford the title intermediate as an orange gum (8.7 g). Purification by chromatography (SiO$_2$, 10% MeOH in DCM) gave the title intermediate as an orange oil (7.3 g, 56%). MS, ES$^+$ m/z, 577 (M+H)$^+$.

Step 2: Preparation of N-[[5-benzyloxy-1-(2-hydroxyethyl)-4-oxo-2-pyridyl]-tetrahydropyran-4-yl-methyl]-2-methyl-propane-2-sulfinamide

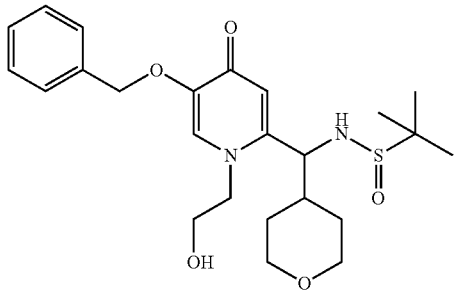 [SMILES: CC(C)(C)S(=O)NC(c1cc(=O)c(OCc2ccccc2)cn1CCO)C1CCOCC1]

N-[[5-benzyloxy-1-[2-[tert-butyl(di methyl)silyl]oxyethyl]-4-oxo-2-pyridyl]-tetrahydropyran-4-yl-methyl]-2-methyl-propane-2-sulfinamide (7.3 g, 7.59 mmol) was dissolved in DMF (50 mL). Cesium fluoride (3.5 g, 22.78 mmol) was added and the mixture was stirred at rt for 3 h. Additional Cesium fluoride (5 g) was added and the mixture was stirred over the weekend at rt. The mixture was concentrated and stripped with toluene to afford a yellow oil (8.3 g). Purification by chromatography (SiO$_2$, 5% MeOH in DCM) afforded the title intermediate (2.12 g, 48%). MS, ES$^+$ m/z, 463.2 (M+H)$^+$.

Step 3: Preparation of 7-benzyloxy-2-tert-butylsulfinyl-1-tetrahydropyran-4-yl-3,4-dihydro-1H-pyrido[1,2-a]pyrazin-8-one

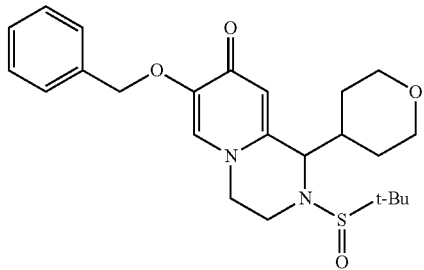 [SMILES: CC(C)(C)S(=O)N1CCn2cc(OCc3ccccc3)c(=O)cc2C1C1CCOCC1]

N-[[5-benzyloxy-1-(2-hydroxyethyl)-4-oxo-2-pyridyl]-tetrahydropyran-4-yl-methyl]-2-methyl-propane-2-sulfinamide (2.1 g, 3.63 mmol) and triphenylphosphine (1.1 g, 4.19 mmol) were dissolved in THF (30 mL). The mixture was cooled to 0° C. and DIAD (0.8 ml, 4.11 mmol) was added until an orange color persisted. The mixture was allowed to reach rt and stirred overnight. Additional triphenylphosphine (1.1 g, 4.19 mmol) and DIAD (0.8 mL, 4.11 mmol) were added and the mixture was stirred at rt for 2 h. The mixture was concentrated to afford an orange oil. Purification by chromatography (SiO$_2$, 5% MeOH in DCM) afforded an orange gum (1.95 g, 90%). MS, ES$^+$ m/z, 445.2 (M+H)$^+$.

Step 4: Preparation of 7-benzyloxy-1-tetrahydropyran-4-yl-1,2,3,4-tetrahydropyrido[1,2-a]pyrazin-8-one N-[[5-benzyloxy-1-(2-hydroxyethyl)-4-oxo-2-pyridyl]-tetrahydropyran-4-yl-methyl]-2-methyl-propane-2-sulfinamide (1.95 g, 3.27 mmol) was dissolved in MeOH (4 mL). HCl (4 N in dioxane, 1.2 ml, 4.9 mmol) was added and the mixture was stirred at rt for 30 min. The mixture was concentrated, dissolved in MeOH (4 mL)/7N ammonia in MeOH (2 ml) and stirred for 15 min. The resulting mixture was coated onto silica and purified with flash column chromatography (7.5% MeOH in DCM) to afford the title intermediate as a white foam (492 mg, 42%). MS, ES m/z, 341.2 (M+H)$^+$. $^1$H-NMR (300 MHz, DMSO-d$_6$) ☐ 7.43-7.28 (m, 6H), 6.05 (s, 1H), 4.95 (s, 2H), 3.87-3.74 (m, 4H), 3.61 (d, J=2.7 Hz, 1H), 3.29-3.19 (m, 1H, overlap with solvent residual peak), 3.14-3.07 (m, 1H), 2.94-2.85 (m, 1H), 2.61 (bs, 1H), 2.04-1.90 (m, 1H), 1.50 (qd, J1=6.2 Hz, J2=2.1 Hz, 1H), 1.41-1.28 (m, 3H), Intermediate 8: 7-benzyloxy-3-phenyl-1,2,3,4-tetrahydropyrido[1,2-a]pyrazin-8-one

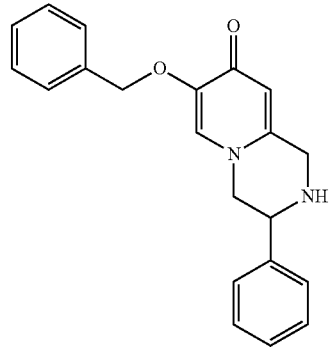 [SMILES: O=c1cc2n(cc1OCc1ccccc1)CC(c1ccccc1)NC2]

Step 1: Preparation of 1-(2-amino-2-phenyl-ethyl)-5-benzyloxy-2-(hydroxymethyl)pyridin-4-one

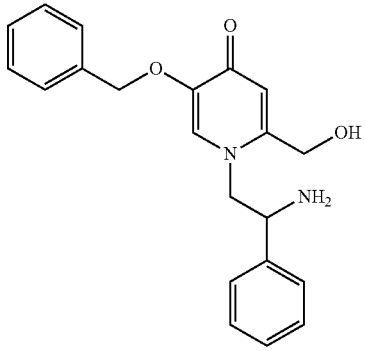 [SMILES: NC(Cn1cc(OCc2ccccc2)c(=O)cc1CO)c1ccccc1]

Method C 1-phenyl-ethane-1,2-diamine (10.34 mmol, 1.482 g, 1.2 eq.) was added to a solution of 5-benzyloxy-2-(hydroxymethyl)pyran-4-one (8.6 mmol, 2.0 g) in EtOH (15 mL) and the mixture was heated at 90° C. for 14 h. 1-phenyl-ethane-1,2-diamine (0.2 g) was added and the mixture was stirred for another 14 h. Water was added, then the mixture was extracted with EtOAc. The combined organic layers were dried over MgSO4, filtered and concentrated to give a residue (3.4 g). Purification by chromatography (gradient from 3% methanolic ammonia in DCM up to 10%) gave the title intermediate (1.33 g, 45%). MS, ES$^+$ m/z, 351.3 (M+H)$^+$.

Step 2: Preparation of 7-benzyloxy-3-phenyl-1,2,3,4-tetrahydropyrido[1,2-a]pyrazin-8-one The title intermediate was prepared according to Method A using 1-(2-amino-2-phenyl-ethyl)-5-benzyloxy-2-(hydroxymethyl)pyridin-4-one as a yellow oil. (77%). MS, ES$^+$ m/z, 333.3 (M+H)$^+$.

Intermediate 9: 3-benzyl-7-benzyloxy-1,2,3,4-tetrahydropyrido[1,2-a]pyrazin-8-one

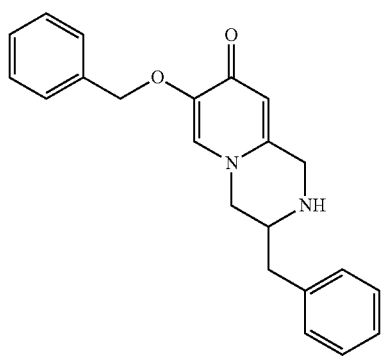 [SMILES: O=c1cc2n(cc1OCc1ccccc1)CC(Cc1ccccc1)NC2]

Step 1: Preparation of 1-(2-amino-3-phenyl-propyl)-5-benzyloxy-2-(hydroxymethyl)pyridin-4-one

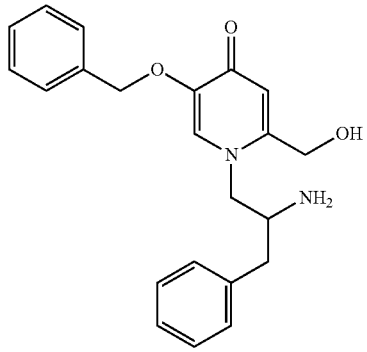 [SMILES: NC(Cc1ccccc1)Cn1cc(OCc2ccccc2)c(=O)cc1CO]

The title intermediate was prepared according to Method C using 3-phenylpropane-1,2-diamine, and isolated as a brown oil (used in the next step without purification). MS, ES$^+$ m/z, 365.3 (M+H)+.

Step 2: Preparation of 3-benzyl-7-benzyloxy-1,2,3,4-tetrahydropyrido[1,2-a]pyrazin-8-one The title intermediate was prepared according to Method A using 3-benzyl-7-benzyloxy-1,2,3,4-tetrahydropyrido[1,2-a]pyrazin-8-one involving a purification of the crude product by chromatography (SiO$_2$, 7% methanolic ammonia in DCM) (45%). MS, ES$^+$ m/z, 347.3 (M+H)$^+$.

Intermediate 10: 7-benzyloxy-3-methyl-1,2,3,4-tetrahydropyrido[1,2-a]pyrazin-8-one

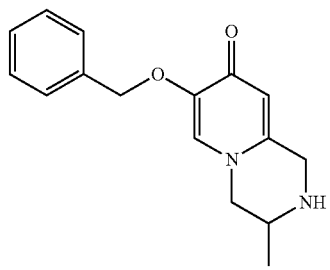 [SMILES: CC1Cn2cc(OCc3ccccc3)c(=O)cc2CN1]

Step 1: Preparation of 1-(2-aminopropyl)-5-benzyloxy-2-(hydroxymethyl)pyridin-4-one

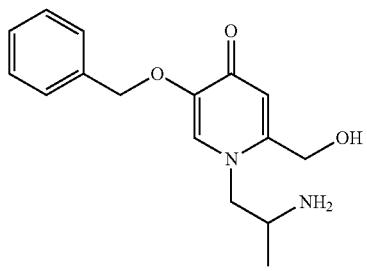 [SMILES: CC(N)Cn1cc(OCc2ccccc2)c(=O)cc1CO]

The title intermediate was prepared according to Method C using 1,2-diaminopropane as a brown oil (56%). The crude product was purified by chromatography (SiO$_2$, DCM-MeOH—NH4OH 88-10.8-1.2). MS, ES$^+$ m/z, 289.2 (M+H)$^+$.

Step 2: Preparation of 7-benzyloxy-3-methyl-1,2,3,4-tetrahydropyrido[1,2-a]pyrazin-8-one The title intermediate was prepared according to Method A using 1-(2-aminopropyl)-5-benzyloxy-2-(hydroxymethyl)pyridin-4-one as a yellow solid (77%), used in the next step without any further purification.

Intermediate 11: 7-benzyloxy-3,3-dimethyl-1,2,3,4-tetrahydropyrido[1,2-a]pyrazin-8-one

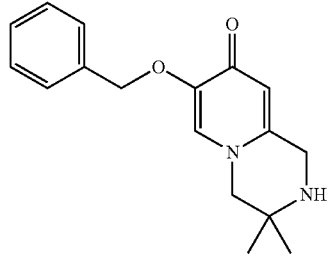 [SMILES: CC1(C)Cn2cc(OCc3ccccc3)c(=O)cc2CN1]

Step 1: Preparation of 1-(2-amino-2-methylpropyl)-5-benzyloxy-2-(hydroxymethyl)pyridin-4-one

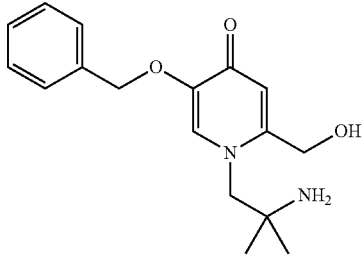 [SMILES: CC(C)(N)Cn1cc(OCc2ccccc2)c(=O)cc1CO]

The title intermediate was prepared according to Method C using 1,2-diamino-2-methylpropane. The crude product was purified by chromatography (SiO$_2$, 0-50% MeOH/DCM) to give 1-(2-amino-2-methylpropyl)-5-benzyloxy-2-(hydroxymethyl)pyridin-4-one as a tan gum (27%). MS, ES$^+$ m/z, 303.2 (M+H)$^+$.

$^1$H NMR (400 MHz, DMSO-d$_6$) δ ppm 7.53 (s, 1H) 7.30-7.42 (m, 5H) 6.23 (s, 1H) 5.01 (s, 2H) 4.42 (s, 2H) 3.75 (s, 2H) 0.96 (s, 6H)

Step 2: Preparation of 7-benzyloxy-3,3-dimethyl-1,2,3,4-tetrahydropyrido[1,2-a]pyrazin-8-one The title intermediate was prepared according to Method A using 1-(2-amino-2-methylpropyl)-5-benzyloxy-2-(hydroxymethyl)pyridin-4-one. The crude product was purified by chromatography (SiO$_2$, 0-50% MeOH/DCM) to give 7-benzyloxy-3,3-dimethyl-1,2,3,4-tetrahydropyrido[1,2-a]pyrazin-8-one as a yellow solid (49%). MS, ES$^+$ m/z, 285.2 (M+H)$^+$.

$^1$H NMR (400 MHz, DMSO-d$_6$) δ ppm 7.30-7.44 (m, 6H) 5.98 (s, 1H) 4.97 (s, 2H) 3.75 (s, 2H) 3.58 (s, 2H) 1.06 (s, 6H).

Example 1: 2-benzyl-7-hydroxy-1,2,3,4-tetrahydro-8H-pyrido[1,2-a]pyrazin-8-one

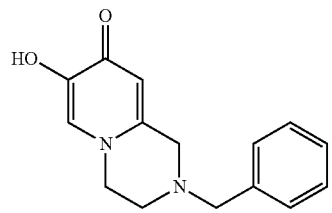 [SMILES: O=c1cc2n(cc1O)CCN(Cc1ccccc1)C2]

Step 1: Preparation of 2-benzyl-7-hydroxy-1,2,3,4-tetrahydro-8H-pyrido[1,2-a]pyrazin-8-one Method D

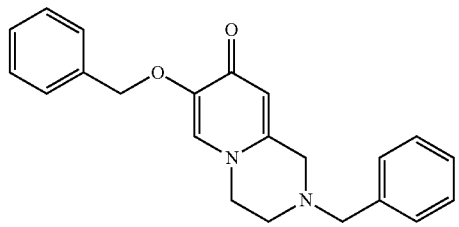 [SMILES: O=c1cc2n(cc1OCc1ccccc1)CCN(Cc1ccccc1)C2]

7-benzyloxy-1,2,3,4-tetrahydropyrido[1,2-a]pyrazin-8-one (Intermediate 1, 55 mg, 0.22 mmol) was dissolved in EtOH (1 mL). Benzyl bromide (30 µL, 0.25 mmol) and an aq. solution of NaOH (0.25 mL, 0.25 mmol, 1 N) were added. The mixture was stirred at 60° C. for 1 h. The reaction mixture was cooled to rt, then extracted with DCM (10 mL). The combined org. layers were washed with an aq. sat. solution of NaCl, dried over MgSO4, filtered and concentrated under vacuum. The residue was purified by column chromatography (SiO$_2$, gradient up to 10% methanolic ammonia in DCM) to yield the title intermediate as a light yellow oil (62 mg, 83%). MS, ES$^+$ m/z, 347.4 (M+H)$^+$.

Step 2: Preparation of 2-benzyl-7-hydroxy-1,2,3,4-tetrahydro-8H-pyrido[1,2-a]pyrazin-8-one Method E 2-benzyl-7-benzyloxy-3,4-dihydro-1H-pyrido[1,2-a]pyrazin-8-one (99 mg, 0.27 mmol) was dissolved in an aq. solution of HCl (7 mL, 5 N) and heated 1 h at 100° C. The mixture was cooled to rt, then washed with CHCl$_3$ (2×3 mL). The aq. phase was evaporated under vacuum to yield the title intermediate as a white solid (12 mg, 22%). High-Res MS, ES$^+$ m/z, 257.1276 (M+H)$^+$ (obs.), 257.129 (M+H)$^+$ (calc.).

The following compound 2 has been synthesized according to Methods D followed by Method E:

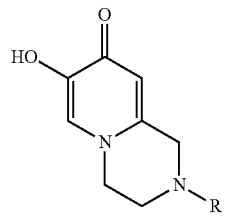

| Example | Name | R | Analytical data | Preparation Information |
|---|---|---|---|---|
| 2 | 7-hydroxy-2-[4-(trifluoromethyl)benzyl]-1,2,3,4-tetrahydro-8H-pyrido[1,2-a]pyrazin-8-one | 4-(trifluoromethyl)benzyl | High-Res MS ES+, 325.1144 (M + H)+ (obs.), 325.1164 (M + H)+ (calc.) | Method D using 4-(trifluoromethyl)benzyl bromide, followed by Method E. |
| 3 | 2-[(4-fluorophenyl)methyl]-7-hydroxy-3,4-dihydro-1H-pyrido[1,2-a]pyrazin-8-one | 4-fluorobenzyl | MS, ES+ m/z, 275.2 (M + H)+. 1H NMR (400 MHz, DMSO-d6) δ ppm 8.02 (s, 1 H) 7.44 (dd, J = 8.59, 5.81 Hz, 2 H) 7.17-7.27 (m, 2 H) 7.02 (s, 1 H) 4.38 (t, J = 5.43 Hz, 2 H) 3.93 (s, 2 H) 3.83 (s, 2 H) 3.03 (t, J = 5.31 Hz, 2 H) | Method D using 4-fluoromethylbenzyl bromide, followed by Method E. |
| 4 | 2-[2-(benzotriazol-1-yl)ethyl]-7-hydroxy-3,4-dihydro-1H-pyrido[1,2-a]pyrazin-8-one | benzotriazol-1-ylethyl | MS, ES+ m/z, 312.2 (M + H)+. 1H NMR (400 MHz, DMSO-d6) δ ppm 8.02-8.08 (m, 2 H) 7.97 (d, 1 H) 7.53-7.59 (m, 1 H) 7.38-7.44 (m, 1 H) 7.09 (s, 1 H) 4.99 (t, 2 H) 4.30 (t, 2 H) 4.08 (br. s., 2 H) 3.20 (br. s., 2 H) 3.14 (br. s., 2 H) | Method D using 1-(2-bromoethyl)benzotriazole, followed by Method E. |
| 5 | 2-[2-(benzotriazol-2-yl)ethyl]-7-hydroxy-3,4-dihydro-1H-pyrido[1,2-a]pyrazin-8-one | benzotriazol-2-ylethyl | MS, ES+ m/z, 312.2 (M + H)+. 1H NMR (400 MHz, DMSO-d6) δ ppm 8.07 (s, 1 H) 7.90-7.96 (m, 2 H) 7.42-7.47 (m, 2 H) 7.15 (s, 1 H) 5.06 (t, 2 H) 4.35 (d, 2 H) 4.15 (br. s., 2 H) 3.41 (br. s., 2 H) 3.18 (br. s., 2 H) | Method D using 2-(2-bromoethyl)benzotriazole, followed by Method E. |

Example 6: 7-hydroxy-2-[3-(trifluoromethoxy)benzyl]-1,2,3,4-tetrahydro-8H-pyrido[1,2-a]pyrazin-8-one

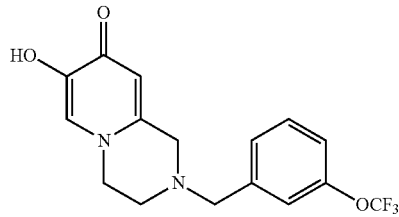 [SMILES: O=c1cc2n(cc1O)CCN(Cc1cccc(OC(F)(F)F)c1)C2]

Step 1: Preparation of 7-benzyloxy-2-[[4-(trifluoromethyl)phenyl]methyl]-3,4-dihydro-1H-pyrido[1,2-a]pyrazin-8-one Method F 7-benzyloxy-1,2,3,4-tetrahydropyrido[1,2-a]pyrazin-8-one (Intermediate 1, 150 mg, 0.59 mmol), 3-(trifluoromethoxy)benzaldehyde (130 μL, 0.86 mmol), 4A molecular sieve (<5 μm, 72 mg), Si—BH$_3$CN (Silicycle, 1.81 g, 1.6 mmol, 0.89 mmol/g) in EtOH (4 mL, 68.5 mmol) were dispersed in THF (2 mL). The mixture was stirred for 1 h at 40° C. before addition of HOAc (0.5 mL, 9 mmol). The mixture was stirred again for an additional 2.5 h at 40° C. Filtration on a bed of Celite (rinse with EtOAc, 3×20 mL). The liquors were evaporated under vacuum to give a yellow oil (306 mg). Purification by column chromatography (SiO$_2$, gradient 5% methanolic ammonia in up to 10%) yielded the title intermediate as a white solid (87 mg, 35%). MS, ES$^+$ m/z, 431.3 (M+H)$^+$.

Step 2: Preparation of 7-hydroxy-2-[3-(trifluoromethoxy)benzyl]-1,2,3,4-tetrahydro-8H-pyrido[1,2-a]pyrazin-8-one The title compound was prepared using 7-benzyloxy-2-[[4-(trifluoromethyl)phenyl]methyl]-3,4-dihydro-1H-pyrido[1,2-a]pyrazin-8-one following to Method E, as a white solid (86%). High-Res MS, ES$^+$, 341.1116 (M+H)$^+$ (obs.), 341.1113 (M+H)$^+$ (calc.).

The following compounds 4-17 have been synthesized according to Method F followed by Method E

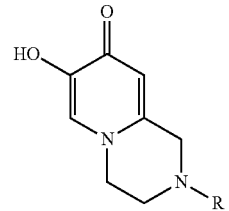

| Ex. | Name | R | Analytical data | Preparation Information |
|---|---|---|---|---|
| 7 | 2-(4-tert-butylbenzyl)-7-hydroxy-1,2,3,4-tetrahydro-8H-pyrido[1,2-a]pyrazin-8-one | 4-tert-butylbenzyl | High-Res MS, ES$^+$, 313.1917 (M + H)$^+$ (obs.), 313.1916 (M + H)$^+$ (calc.). | Method F using 4-tert-butylbenzaldehyde, followed by Method E |
| 8 | 7-hydroxy-2-[4-(trifluoromethoxy)benzyl]-1,2,3,4-tetrahydro-8H-pyrido[1,2-a]pyrazin-8-one | 4-(trifluoromethoxy)benzyl | High-Res MS, ES$^+$, 341.1118 (M + H)$^+$ (obs.), 341.1113 (M + H)$^+$ (calc.). | Method F using 4-(trifluoromethyl)benzaldehyde, followed by Method E |
| 9 | 2-(2,4-dimethylbenzyl)-7-hydroxy-1,2,3,4-tetrahydro-8H-pyrido[1,2-a]pyrazin-8-one | 2,4-dimethylbenzyl | High-Res MS ES$^+$, 284.1597 (M + H)$^+$ (obs.), 285.1603 (M + H)$^+$ (calc.). | Method F using 2,4-dimethylbenzaldehyde, followed by Method E |
| 10 | 7-hydroxy-2-[4-(propan-2-yl)benzyl]-1,2,3,4-tetrahydro-8H-pyrido[1,2-a]pyrazin-8-one | 4-isopropylbenzyl | High-Res MS ES$^+$, 299.1755 (M + H)$^+$ (obs.), 299.1759 (M + H)$^+$ (calc.). | Method F using 4-isopropylbenzaldehyde, followed by Method E |

-continued

| Ex. | Name | R | Analytical data | Preparation Information |
|---|---|---|---|---|
| 11 | 7-hydroxy-2-(pyridin-2-ylmethyl)-1,2,3,4-tetrahydro-8H-pyrido[1,2-a]pyrazin-8-one | pyridin-2-ylmethyl | High-Res MS, ES+, 258.1242 (M + H)+ (obs.), 258.1242 (M + H)+ (calc.). | Method F using pyridine-2-carbaldehyde, followed by Method E |
| 12 | 7-hydroxy-2-[4-(pyridin-3-yl)benzyl]-1,2,3,4-tetrahydro-8H-pyrido[1,2-a]pyrazin-8-one | 4-(pyridin-3-yl)benzyl | High-Res MS, ES+, 334.1541 (M + H)+ (obs.), 334.1555 (M + H)+ (calc.). | Method F using 4-(pyridine-3-yl)benzaldehyde, followed by Method E |
| 13 | 2-(4-ethylbenzyl)-7-hydroxy-1,2,3,4-tetrahydro-8H-pyrido[1,2-a]pyrazin-8-one | 4-ethylbenzyl | High-Res MS, ES+, 285.1612 (M + H)+ (obs.), 285.1603 (M + H)+ (calc.). | Method F using 4-ethylbenzaldehyde, followed by Method E |
| 14 | 7-hydroxy-2-(quinolin-8-ylmethyl)-1,2,3,4-tetrahydro-8H-pyrido[1,2-a]pyrazin-8-one | quinolin-8-ylmethyl | High-Res MS, ES+, 308.1383 (M + H)+ (obs.), 308.1399 (M + H)+ (calc.) | Method F using Intermediate 2 and quinoline-8-carbaldehyde, followed by Method E |
| 15 | 7-hydroxy-2-(1-phenylethyl)-1,2,3,4-tetrahydro-8H-pyrido[1,2-a]pyrazin-8-one | 1-phenylethyl | High-Res MS, ES+, 271.1434 (M + H)+ (obs.), 271.1447 (M + H)+ (calc.) | Method F using acetophenone, purification by chromatography (SiO$_2$, 10% methanolic ammonia in DCM), followed by Method E |
| 16 | 2-[1-(4-ethylphenyl)ethyl]-7-hydroxy-1,2,3,4-tetrahydro-8H-pyrido[1,2-a]pyrazin-8-one | 1-(4-ethylphenyl)ethyl | High-Res MS, ES+, 299.1747 (M + H)+ (obs.), 299.1759 (M + H)+ (calc.). | Method F using 4'-ethylacetophenone, purification by chromatography (SiO$_2$, 10% methanolic ammonia in DCM), followed by Method E |

Example 17: 2-[(7-hydroxy-8-oxo-1,3,4,8-tetrahydro-2H-pyrido[1,2-a]pyrazin-2-yl)methyl]benzonitrile

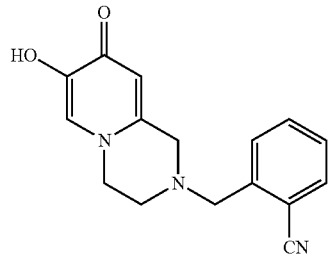 [SMILES: N#Cc1ccccc1CN1CCn2cc(O)c(=O)cc2C1]

Step 1: Preparation of 2-[[7-[(4-methoxyphenyl)methoxy]-8-oxo-3,4-dihydro-1H-pyrido[1,2-a]pyrazin-2-yl]methyl]benzonitrile

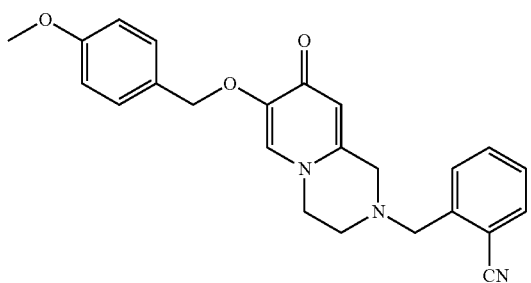 [SMILES: COc1ccc(COc2cn3c(cc2=O)CN(Cc2ccccc2C#N)CC3)cc1]

The title intermediate was prepared following to Method C starting from intermediate 2 and 2-cyanobenzaldehyde (yield: 44%). MS, ES+, 402.1 (M+H)+.

Step 2: Preparation of 2-[(7-hydroxy-8-oxo-1,3,4,8-tetrahydro-2H-pyrido[1,2-a]pyrazin-2-yl)methyl]benzonitrile

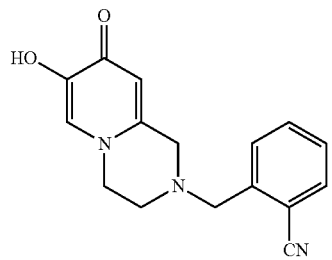 [SMILES: N#Cc1ccccc1CN1CCn2cc(O)c(=O)cc2C1]

TFA (0.4 mL) was added to a solution of 2-[[7-[(4-methoxyphenyl)methoxy]-8-oxo-3,4-dihydro-1H-pyrido[1,2-a]pyrazin-2-yl]methyl]benzonitrile (185 mg, 0.46 mmol) in DCM (2 mL). The mixture was stirred at rt for 1 h. Evaporation of the solvent under vacuum gave a residue that was purified by reverse phase chromatography to yield the title compound as a beige solid (65 mg, 35%). MS, ES+, 282 (M+H)+.

Example 18: 2-(4-ethyl-3-nitrobenzyl)-7-hydroxy-1,2,3,4-tetrahydro-8H-pyrido[1,2-a]pyrazin-8-one

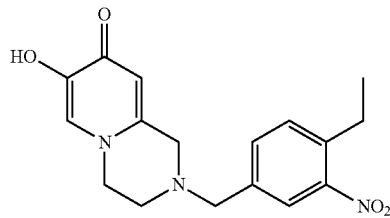 [SMILES: CCc1ccc(CN2CCn3cc(O)c(=O)cc3C2)cc1[N+](=O)[O-]]

2-[(4-ethylphenyl)methyl]-7-hydroxy-3,4-dihydro-1H-pyrido[1,2-a]pyrazin-8-one (Example 13, 0.25 mmol, 70 mg) was poured in sulfuric acid (0.5 mL). Fuming nitric acid (0.26 mmol, 17 mg, 1.1 eq., 11 µL) was added and the resulting mixture stirred at rt for 10 min. Water (2 mL) was added and the mixture was neutralized to pH 7 by the addition of an aq. solution of $K_2CO_3$, then $NaHCO_3$. The precipitate was filtered, dried under vacuum to yield the title compound as an orange solid (38 mg, 47%). MS, ES+, 330.29 (M+H)+.

Example 19: 2-(2,2-diphenylethyl)-7-hydroxy-1,2,3,4-tetrahydro-8H-pyrido[1,2-a]pyrazin-8-one

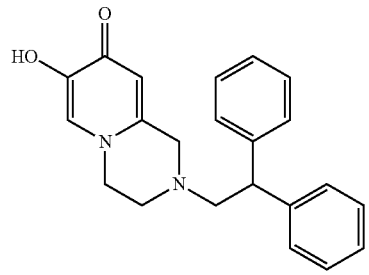 [SMILES: O=c1cc2n(cc1O)CCN(CC(c1ccccc1)c1ccccc1)C2]

Method G 0.6 mL of THF, 0.3 mL of EtOH and 0.1 mL of HOAc were added to 7-benzyloxy-1,2,3,4-tetrahydropyrido[1,2-a]pyrazin-8-one (Intermediate 1, 19.2 mg, 0.075 mmol). 2,2-diphenylacetaldehyde (22 mg, 1.5 eq.) followed by Si—$BH_3CN$ (Silicycle, 250 mg, 0.223 mmol, 3 eq.) were added. The resulting reaction mixture was stirred overnight at rt. The mixture was filtered, evaporated. The residue was then dissolved in $CH_3CN$ (2 mL) and purified by reverse phase preparative chromatography.

An aq. solution of HCl (1 mL, 6 N) was added to the purified and evaporated fractions and the mixture was heated at 100° C. for 1.5 h. The solvent was evaporated under vacuum. The residue was dissolved in $CH_3CN/H_2O$ 75:25 (2 mL) and the solvents evaporated under vacuum to yield the title compound as a colorless film (28.4 mg). High-Res MS, ES+, 347.1765 (M+H)+ (obs.), 347.1759 (M+H)+ (calc.).

The following compounds 21-52 have been synthesized according to Methods G

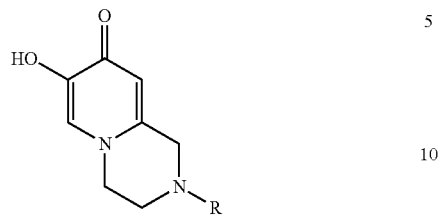

| Ex. | Name | R | Analytical data | Preparation Information |
|---|---|---|---|---|
| 20 | 2-(2-ethylbutyl)-7-hydroxy-1,2,3,4-tetrahydro-8H-pyrido[1,2-a]pyrazin-8-one | (2-ethylbutyl) | High-Res MS, ES+, 251.1755 (M + H)+ (obs.), 251.1759 (M + H)+ (calc.). | Method G using 2-ethylbutyraldehyde |
| 21 | 2-(3,5-dichlorobenzyl)-7-hydroxy-1,2,3,4-tetrahydro-8H-pyrido[1,2-a]pyrazin-8-one | (3,5-dichlorobenzyl) | High-Res MS, ES+, 325.0521 (M + H)+ (obs.), 325.0511 (M + H)+ (calc.). | Method G using 3,5-dichlorobenzaldehyde |
| 22 | 2-(cyclohexylmethyl)-7-hydroxy-1,2,3,4-tetrahydro-8H-pyrido[1,2-a]pyrazin-8-one | (cyclohexylmethyl) | High-Res MS, ES+, 263.1747 (M + H)+ (obs.), 263.1759 (M + H)+ (calc.). | Method G using cyclohexanecarboxaldehyde |
| 23 | 2-(4-cyclopropylbenzyl)-7-hydroxy-1,2,3,4-tetrahydro-8H-pyrido[1,2-a]pyrazin-8-one | (4-cyclopropylbenzyl) | High-Res MS, ES+, 297.1603 (M + H)+ (obs.), 297.1603 (M + H)+ (calc.). | Method G using 4-cyclopropylbenzaldehyde |
| 24 | 2-[(8,8-dimethyl-1,2,3,4,5,6,7,8-octahydro-naphthalen-2-yl)methyl]-7-hydroxy-1,2,3,4-tetrahydro-8H-pyrido[1,2-a]pyrazin-8-one | (8,8-dimethyl-octahydronaphthalen-2-yl)methyl | High-Res MS, ES+, 343.2372 (M + H)+ (obs.), 343.2386 (M + H)+ (calc.). | Method G using 1,2,3,4,5,6,7,8-octahydro-8,8-dimethyl-2-naphthaldehyde |
| 25 | 2-(3,4-dichlorobenzyl)-7-hydroxy-1,2,3,4-tetrahydro-8H-pyrido[1,2-a]pyrazin-8-one | (3,4-dichlorobenzyl) | High-Res MS, ES+, 325.0516 (M + H)+ (obs.), 325.0511 (M + H)+ (calcd.). | Method G using 3,4-dichlorobenzaldehyde |

-continued

| Ex. | Name | R | Analytical data | Preparation Information |
|---|---|---|---|---|
| 26 | 2-(cyclooctylmethyl)-7-hydroxy-1,2,3,4-tetrahydro-8H-pyrido[1,2-a]pyrazin-8-one | 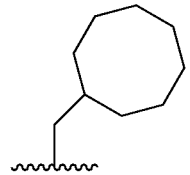 [SMILES: *CC1CCCCCCC1] | LCMS (Method D, ES+) RT, (M + H)+, 98.8% purity. | Method G using cyclooctane-carbaldehyde |
| 27 | 2-(2,6-dimethylbenzyl)-7-hydroxy-1,2,3,4-tetrahydro-8H-pyrido[1,2-a]pyrazin-8-one | 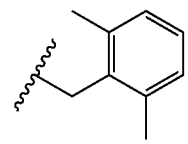 [SMILES: *Cc1c(C)cccc1C] | High-Res MS, ES+, 285.1591 (M + H)+ (obs.), 285.1603 (M + H)+ (calc.) | Method G using 2,6-dimethyl-benzaldehyde |
| 28 | 2-(2,5-dimethylbenzyl)-7-hydroxy-1,2,3,4-tetrahydro-8H-pyrido[1,2-a]pyrazin-8-one | 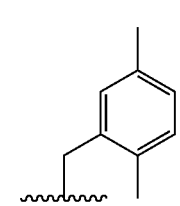 [SMILES: *Cc1cc(C)ccc1C] | High-Res MS, ES+, 285.1595 (M + H)+ (obs.), 285.1603 (M + H)+ (calc.). | Method G using 2,5-dimethyl-benzaldehyde |
| 29 | 7-hydroxy-2-{[1-(phenylsulfonyl)-1H-indol-2-yl]methyl}-1,2,3,4-tetrahydro-8H-pyrido[1,2-a]pyrazin-8-one | 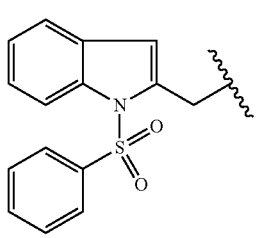 [SMILES: *Cc1cc2ccccc2n1S(=O)(=O)c1ccccc1] | High-Res MS, ES+, 436.1325 (M + H)+ (obs.), 436.1331 (M + H)+ (calc.). | Method G using 1-(phenylsulfonyl)-1h-indole-2-carbaldehyde |
| 30 | 7-hydroxy-2-(3-phenylpropyl)-1,2,3,4-tetrahydro-8H-pyrido[1,2-a]pyrazin-8-one | 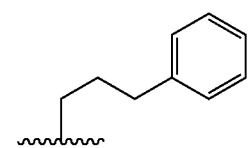 [SMILES: *CCCc1ccccc1] | High-Res MS, ES+, 285.1593 (M + H)+ (obs.), 285.1603 (M + H)+ (calc.). | Method G using 3-phenylpropion-aldehyde |
| 31 | 7-hydroxy-2-(2-phenylpropyl)-1,2,3,4-tetrahydro-8H-pyrido[1,2-a]pyrazin-8-one | 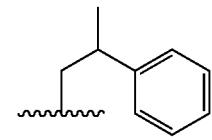 [SMILES: *CC(C)c1ccccc1] | High-Res MS, ES+, 285.1587 (M + H)+ (obs.), 285.1603 (M + H)+ (calc.). | Method G using 2-phenylpropion-aldehyde |
| 32 | 2-(3,5-difluorobenzyl)-7-hydroxy-1,2,3,4-tetrahydro-8H-pyrido[1,2-a]pyrazin-8-one | 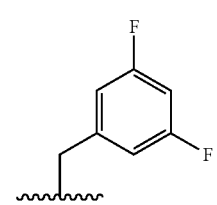 [SMILES: *Cc1cc(F)cc(F)c1] | High-Res MS, ES+, 293.1098 (M + H)+ (obs.), 293.1101 (M + H)+ (calc.). | Method G using 2,6-difluorobenz-aldehyde |
| 33 | 7-hydroxy-2-(2-methylbenzyl)-1,2,3,4-tetrahydro-8H-pyrido[1,2-a]pyrazin-8-one | 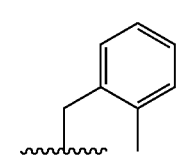 [SMILES: *Cc1ccccc1C] | High-Res MS, ES+, 271.1434 (M + H)+ (obs.), 271.1447 (M + H)+ (calc.). | Method G using 2-methylbenz-aldehyde |
| 34 | 7-hydroxy-2-[(5-phenyl-1H-pyrazol-3-yl)methyl]-1,2,3,4-tetrahydro-8H-pyrido[1,2-a]pyrazin-8-one... | 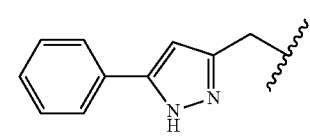 | High-Res MS, ES+, 323.1483 (M + H)+ (obs.), 323.1508 (M + H)+ (calc.). | Method G using 5-phenyl-1h-pyrazole-3-carbaldehyde |

| Ex. | Name | R | Analytical data | Preparation Information |
|---|---|---|---|---|
| | pyrido[1,2-a]pyrazin-8-one | | | |
| 35 | 2-{[6-chloro-4-(1H-imidazol-4-yl)-3,4-dihydro-2H-chromen-8-yl]methyl}-7-hydroxy-1,2,3,4-tetrahydro-8H-pyrido[1,2-a]pyrazin-8-one | 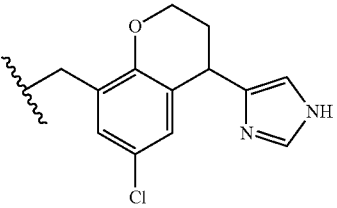 [SMILES: *Cc1cc(Cl)cc2c1OCCC2c1c[nH]cn1] | High-Res MS, ES+, 413.1355 (M + H)+ (obs.), 413.138 (M + H)+ (calc.). | Method G using 6-chloro-4-(1h-imidazol-4-yl)chromane-8-carbaldehyde |
| 36 | 7-hydroxy-2-(3-phenoxybenzyl)-1,2,3,4-tetrahydro-8H-pyrido[1,2-a]pyrazin-8-one | 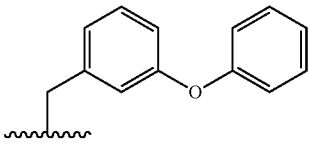 [SMILES: *Cc1cccc(Oc2ccccc2)c1] | High-Res MS, ES+, 349.1562 (M + H)+ (obs.), 349.1552 (M + H)+ (calc.). | Method G using 4-phenoxybenzaldehyde |
| 37 | 2-(2,3-dimethylbenzyl)-7-hydroxy-1,2,3,4-tetrahydro-8H-pyrido[1,2-a]pyrazin-8-one | 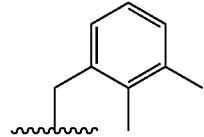 [SMILES: *Cc1cccc(C)c1C] | High-Res MS, ES+, 285.1581 (M + H)+ (obs.), 285.1603 (M + H)+ (calc.). | Method G using 2,3-dimethylbenzaldehyde |
| 38 | 2-(1,3-benzothiazol-2-ylmethyl)-7-hydroxy-1,2,3,4-tetrahydro-8H-pyrido[1,2-a]pyrazin-8-one | 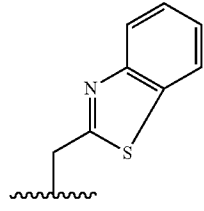 [SMILES: *Cc1nc2ccccc2s1] | High-Res MS, ES+), 314.0943 (M + H)+ (obs.), 314.0963 (M + H)+ (calc.) | Method G using 1,3-benzothiazole-2-carbaldehyde |
| 39 | 2-(2-fluorobenzyl)-7-hydroxy-1,2,3,4-tetrahydro-8H-pyrido[1,2-a]pyrazin-8-one | 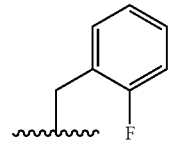 [SMILES: *Cc1ccccc1F] | High-Res MS, ES+, 275.1202 (M + H)+ (obs.), 275.1196 (M + H)+ (calc.) | Method G using 2-fluorobenzaldehyde |
| 40 | 2-[(5-chloro-1,3-dimethyl-1H-pyrazol-4-yl)methyl]-7-hydroxy-1,2,3,4-tetrahydro-8H-pyrido[1,2-a]pyrazin-8-one | 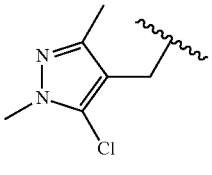 [SMILES: *Cc1c(C)nn(C)c1Cl] | High-Res MS, ES+, 309.1111 (M + H)+ (obs.), 309.1118 (M + H)+ (calc.). | Method G using 5-chloro-1,3-dimethyl-1h-pyrazole-4-carbaldehyde |
| 41 | 7-hydroxy-2-[(4-oxo-4H-chromen-3-yl)methyl]-1,2,3,4-tetrahydro-8H-pyrido[1,2-a]pyrazin-8-one | 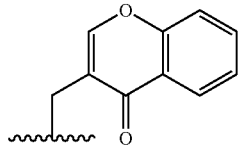 [SMILES: *Cc1coc2ccccc2c1=O] | High-Res MS, ES+, 325.1214 (M + H)+ (obs.), 325.1188 (M + H)+ (calc.). | Method G using chromone-3-carboxaldehyde |
| 42 | 7-hydroxy-2-(1H-indazol-3-ylmethyl)-1,2,3,4-tetrahydro-8H-pyrido[1,2-a]pyrazin-8-one | 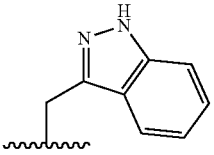 [SMILES: *Cc1n[nH]c2ccccc12] | High-Res MS, ES+, 297.1372 (M + H)+(obs.), 297.1351 (M + H)+ (calc.). | Method G using 1h-indazole-3-carbaldehyde |

-continued

| Ex. | Name | R | Analytical data | Preparation Information |
|---|---|---|---|---|
| 43 | 7-hydroxy-2-{[3-(thiophen-2-yl)-1H-pyrazol-4-yl]methyl}-1,2,3,4-tetrahydro-8H-pyrido[1,2-a]pyrazin-8-one | 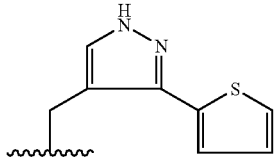 [SMILES: *Cc1c[nH]nc1-c1cccs1] | High-Res MS, ES$^+$, 329.1059 (M + H)$^+$ (obs.), 329.1072 (M + H)$^+$ (calc.). | Method G using 3-(2-thienyl)-1h-pyrazole-4-carbaldehyde |
| 44 | 7-hydroxy-2-[2-(trifluoromethyl)benzyl]-1,2,3,4-tetrahydro-8H-pyrido[1,2-a]pyrazin-8-one | 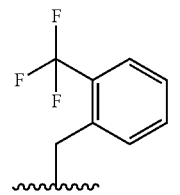 [SMILES: *Cc1ccccc1C(F)(F)F] | High-Res MS, ES$^+$, 325.1154 (M + H)$^+$ (obs.), 325.1164 (M + H)$^+$ (calc.). | Method G using 2-(trifluoromethyl)benzaldehyde |
| 45 | 7-hydroxy-2-[(3-phenyl-1H-pyrazol-4-yl)methyl]-1,2,3,4-tetrahydro-8H-pyrido[1,2-a]pyrazin-8-one | 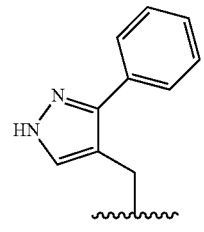 | High-Res MS, ES$^+$, 323.1494 (M + H)$^+$ (obs.), 323.1508 (M + H)$^+$ (calc.). | Method G using 3-phenyl-1h-pyrazole-4-carbaldehyde |
| 46 | 2-(2,6-dimethoxybenzyl)-7-hydroxy-1,2,3,4-tetrahydro-8H-pyrido[1,2-a]pyrazin-8-one | 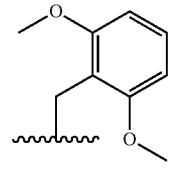 | High-Res MS, ES$^+$, 317.1486 (M + H)$^+$ (obs.), 317.1501 (M + H)$^+$ (calc.). | Method G using 2,6-dimethoxybenzaldehyde. |
| 47 | 7-hydroxy-2-(4-phenoxybenzyl)-1,2,3,4-tetrahydro-8H-pyrido[1,2-a]pyrazin-8-one | 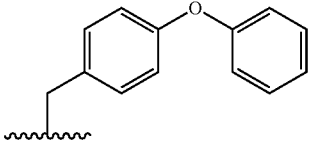 [SMILES: *Cc1ccc(Oc2ccccc2)cc1] | High-Res MS, ES$^+$), 349.1549 (M + H)$^+$ (obs.), 349.1552 (M + H)$^+$ (calc.). | Method G using 4-phenoxybenzaldehyde |
| 48 | 2-(2,3-dihydro-1,4-benzodioxin-6-ylmethyl)-7-hydroxy-1,2,3,4-tetrahydro-8H-pyrido[1,2-a]pyrazin-8-one | 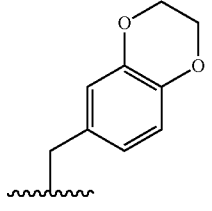 [SMILES: *Cc1ccc2c(c1)OCCO2] | High-Res MS, ES$^+$, 315.1329 (M + H)$^+$ (obs.), 315.1345 (M + H)$^+$ (calc.). | Method G using 2,3-dihydro-1,4-benzodioxine-6-carbaldehyde |
| 49 | 2-[3-(1,3-benzodioxol-5-yl)-2-methylpropyl]-7-hydroxy-1,2,3,4-tetrahydro-8H-a]pyrazin-8-one pyrido[1,2- | 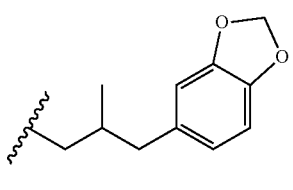 [SMILES: *CC(C)Cc1ccc2c(c1)OCO2] | High-Res MS, ES$^+$, 343.1656 (M + H)$^+$ (obs.), 343.1658 (M + H)$^+$ calc.). | Method G using 3-(1,3-benzodioxol-5-yl)-2-methyl-propanal |

Example 50: 7-hydroxy-2-(4-methoxybenzyl)-1,2,3,4-tetrahydro-8H-pyrido[1,2-a]pyrazin-8-one

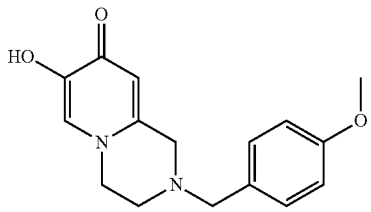 [SMILES: COc1ccc(CN2CCn3cc(O)c(=O)cc3C2)cc1]

Method H 0.6 mL of THF, 0.3 mL of EtOH and 0.1 mL of HOAc were added to 7-[(4-methoxyphenyl)methoxy]-1,2,3,4-tetrahydropyrido[1,2-a]pyrazin-8-one (Intermediate 2, 21.5 mg, 0.075 mmol). 4-methoxybenzaldehyde (22.1 mg, 1.5 eq.) followed by MP-BH$_3$CN (SOPACHEM, 35 mg, 0.1851 mmol, 2.5 eq.) were added. The resulting reaction mixture was stirred overnight at rt. The mixture was filtered, evaporated. The residue was then dissolved in CH$_3$CN (2 mL) and purified by reverse phase preparative chromatography. DCM (0.5 mL) and TFA (0.5 mL) were added to the purified and evaporated fractions and the mixture was stirred at rt for 2 h. The solvent was evaporated under vacuum. The residue was dissolved in CH$_3$CN/H$_2$O 90:10 (2 mL), filtered and the solvents evaporated under vacuum to yield the title compound as a colorless film (32.8 mg). High-Res MS, ES$^+$ 287.1391 (M+H)$^+$ (obs.), 287.1396 (M+H)$^+$ (calc.).

The following compounds 54-59 have been synthesized according to Method H

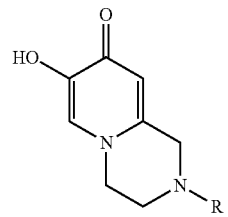

| Ex. | Name | R | Analytical data | Preparation Information |
|---|---|---|---|---|
| 51 | 7-hydroxy-2-(2-methoxybenzyl)-1,2,3,4-tetrahydro-8H-pyrido[1,2-a]pyrazin-8-one | 2-methoxybenzyl | High-Res MS, ES$^+$, 287.1399 (M + H)$^+$ (obs.), 287.1396 (M + H)$^+$ (calc.). | Method H using 4-methoxybenzaldehyde |
| 52 | 2-[4-(benzyloxy)benzyl]-7-hydroxy-1,2,3,4-tetrahydro-8H-pyrido[1,2-a]pyrazin-8-one | 4-(benzyloxy)benzyl | High-Res MS, ES$^+$, 363.1693 (M + H)$^+$ (obs.), 363.1709 (M + H)$^+$ (calc.). | Method H using 4-benzyloxybenzaldehyde |
| 53 | 2-[3-(benzyloxy)benzyl]-7-hydroxy-1,2,3,4-tetrahydro-8H-pyrido[1,2-a]pyrazin-8-one | 3-(benzyloxy)benzyl | High-Res MS, ES$^+$), 363.169 (M + H)$^+$ (obs.), 363.1709 (M + H)$^+$ (calc.). | Method H using 3-benzyloxybenzaldehyde |
| 54 | 2-(2,1,3-benzothiadiazol-5-ylmethyl)-7-hydroxy-1,2,3,4-tetrahydro-8H-pyrido[1,2-a]pyrazin-8-one | 2,1,3-benzothiadiazol-5-ylmethyl | High-Res MS, ES$^+$, 315.09 (M + H)$^+$ (obs.), 315.0916 (M + H)$^+$ (calc.). | Method H using 2,1,3-benzothiadiazole-5-carbaldehyde |
| 55 | 2-[2-(benzyloxy)benzyl]-7-hydroxy-1,2,3,4-tetrahydro-8H-pyrido[1,2-a]pyrazin-8-one | 2-(benzyloxy)benzyl | High-Res MS, ES$^+$, 363.1703 (M + H)$^+$ (obs.), 363.1709 (M + H)$^+$ (calc.). | Method H using 2-benzyloxybenzaldehyde |

| Ex. | Name | R | Analytical data | Preparation Information |
|---|---|---|---|---|
| 56 | 7-hydroxy-2-{[6-(4-methylphenyl)imidazo[2,1-b][1,3]thiazol-5-yl]methyl}-1,2,3,4-tetrahydro-8H-pyrido[1,2-a]pyrazin-8-one | (structure) | High-Res MS, ES+, 393.137 (M + H)+ (obs.), 393.1385 (M + H)+ (calc.). | Method H using 6-(4-methylphenyl)imidazo[2,1-b][1,3]thiazole-5-carbaldehyde |

Example 57: 7-hydroxy-2-[(2,4-dichlorophenyl)methyl]-1,2,3,4-tetrahydro-8H-pyrido[1,2-a]pyrazin-8-one

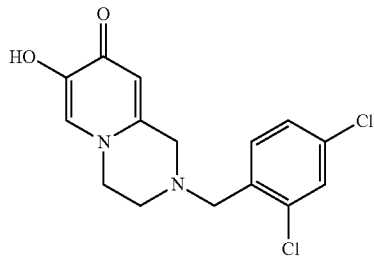 [SMILES: O=c1cc2n(cc1O)CCN(Cc1ccc(Cl)cc1Cl)C2]

Method I
Step 1

To a suspension of 7-[(4-methoxyphenyl)methoxy]-1,2,3,4-tetrahydropyrido[1,2-a]pyrazin-8-one (Intermediate 2, 150 mg, 0.52 mmol) in DCE (10 mL) was added 2,4-dichlorobenzaldehyde (101 mg, 0.58 mmol) and sodium triacetoxyborohydride (333 mg, 1.57 mmol). The resulting mixture was stirred at room temperature for 18 h. The contents were treated with 1 N NaOH, added 10% $Na_2CO_3$ and extracted with $CHCl_3$ (3×). The organic layers were combined, dried over $Na_2SO_4$, filtered and the solvent removed in vacuo to give a residue which was purified by automated normal-phase chromatography (0-40% MeOH/DCM, silica gel) to give 2-[(2,4-dichlorophenyl)methyl]-7-[(4-methoxyphenyl)methoxy]-3,4-dihydro-1H-pyrido[1,2-a]pyrazin-8-one (166 mg, 0.373 mmol, 71% yield) as an off-white foam. MS, ES+ m/z 445.0 [M+H]+.

1H NMR (400 MHz, DMSO-$d_6$) δ ppm 7.64 (d, 1H) 7.55 (d, 1H) 7.42-7.47 (m, 2H) 7.32-7.36 (m, 2H) 6.92-6.96 (m, 2H) 5.95 (s, 1H) 4.89 (s, 2H) 3.92 (t, 2H) 3.76 (s, 3H) 3.71 (s, 2H) 3.59 (s, 2H) 2.85 (t, 2H)

Step 2

To a solution of 2-[(2-chloro-4-fluorophenyl)methyl]-7-[(4-methoxyphenyl)methoxy]-3,4-dihydro-1H-pyrido[1,2-a]pyrazin-8-one (160 mg, 0.36 mmol) in EtOH (5 mL) was added 6 M HCl (3.27 mL, 19.6 mmol). The resulting mixture was stirred at 100° C. for 3 h, then allowed to reach room temperature with stirring overnight (for convenience). The solvent was removed in vacuo and the residue was triturated with Et2O (3×) and the triturants removed by decantation. The solid was dried under vacuum to give 2-[(2,4-dichlorophenyl)methyl]-7-hydroxy-3,4-dihydro-1H-pyrido[1,2-a]pyrazin-8-one hydrochloride (121 mg, 0.33 mmol, 93% yield) as an off-white solid. MS, ES+ m/z 325.0 [M+H]+.

$^1$H NMR (400 MHz, DMSO-$d_6$) δ ppm 11.26 (br. s., 1H) 8.12 (s, 1H) 7.68 (d, 1H) 7.63 (d, 1H) 7.49 (dd, 1H) 7.17 (s, 1H) 4.44 (t, 2H) 4.04 (br. s., 2H) 3.94 (br. s., 2H) 3.12 (br. s., 2H)

The following compounds 58-65 have been synthesized according to Method I

| Ex. | Name | Structure | Analytical data | Preparation Information |
|---|---|---|---|---|
| 58 | 2-[(2-chlorophenyl)methyl]-7-hydroxy-3,4-dihydro-1H-pyrido[1,2-a]pyrazin-8-one | (structure) | MS, ES+, 291.2 (M + H)+, $^1$H NMR (400 MHz, DMSO-$d_6$) δ ppm 11.34 (br. s., 1 H) 8.17 (s, 1 H) 7.68 (br. s., 1 H) 7.50-7.56 (m, 1 H) 7.38-7.45 (m, 2 H) 7.24 (s, 1 H) 4.50 (br. s., 2 H) 4.19 (br. s., 2 H) 4.10 (br. s., 2 H) 3.26 (br. s., 2 H) | Method I using 2-chlorobenzaldehyde and Intermediate 2 |

| Ex. | Name | Structure | Analytical data | Preparation Information |
|---|---|---|---|---|
| 59 | 2-[(2-chloro-6-fluorophenyl)methyl]-7-hydroxy-3,4-dihydro-1H-pyrido[1,2-a]pyrazin-8-one | 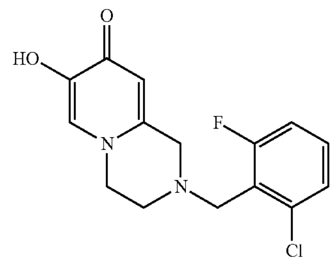 [SMILES: O=c1cc2n(cc1O)CCN(Cc1c(F)cccc1Cl)C2] | MS, ES+ 309.0 (M + H)+, 1H NMR (400 MHz, DMSO-d6) δ ppm 11.21 (br. s., 1 H) 8.07 (s, 1 H) 7.38-7.50 (m, 2 H) 7.27-7.33 (m, 1 H) 7.17 (s, 1 H) 4.36 (t,, 2 H) 4.00 (s, 2 H) 3.90 (s, 2 H) 3.06 (br. s., 2 H) | Method I using 2-chloro-4-fluorobenzaldehyde and Intermediate 2 |
| 60 | 2-[(2,6-dichlorophenyl)methyl]-7-hydroxy-3,4-dihydro-1H-pyrido[1,2-a]pyrazin-8-one | 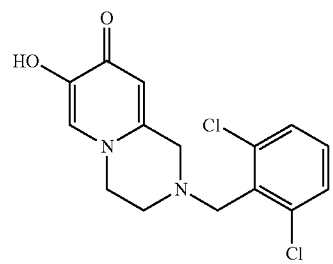 [SMILES: O=c1cc2n(cc1O)CCN(Cc1c(Cl)cccc1Cl)C2] | MS, ES+, 325.0 (M + H)+ 1H NMR (400 MHz, DMSO-d6) δ ppm 11.21 (br. s., 1 H) 8.06 (s, 1 H) 7.51-7.55 (m, 2 H) 7.37-7.43 (m, 1 H) 7.16 (s, 1 H) 4.33 (t, 2 H) 4.00 (s, 2 H) 3.95 (s, 2 H) 3.06 (t, 2 H) | Method I using 2,6-dichlorobenzaldehyde and Intermediate 2 |
| 61 | 2-[(2-chloro-4-fluorophenyl)methyl)]-7-hydroxy-3,4-dihydro-1H-pyrido[1,2-a]pyrazin-8-one | 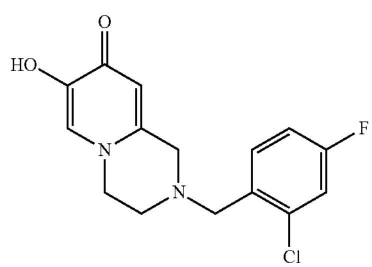 [SMILES: O=c1cc2n(cc1O)CCN(Cc1ccc(F)cc1Cl)C2] | MS, ES+, 309.0 (M + H)+, 1H NMR (40 0MHz, DMSO-d6) δ ppm 11.09-11.38 (m, 1 H) 8.10 (s, 1 H) 7.61-7.67 (m, 1 H) 7.51 (dd, 1 H) 7.29 (td, 1 H) 7.15 (s, 1 H) 4.43 (t, 2 H) 4.02 (br. s., 2H) 3.91 (br. s., 2 H) 3.10 (br. s., 2 H) | Method I using 2-chloro-4-fluorobenzaldehyde and Intermediate 2 |
| 62 | 2-[(2,6-difluorophenyl)methyl]-7-hydroxy-3,4-dihydro-1H-pyrido[1,2-a]pyrazin-8-one | 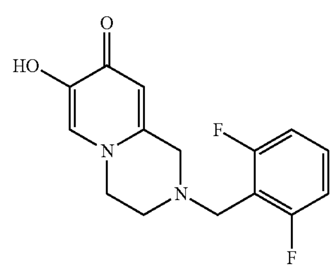 [SMILES: O=c1cc2n(cc1O)CCN(Cc1c(F)cccc1F)C2] | MS, ES+, 293.1 (M + H)+ 1H NMR (400 MHz, DMSO-d6) δ ppm 11.20 (br. s., 1 H) 8.06 (s, 1 H) 7.45-7.55 (m, 1 H) 7.12-7.22 (m, 3 H) 4.38 (t, 2 H) 3.97 (s, 2 H) 3.88 (s, 2 H) 3.04 (br. s., 2 H) | Method I using 2,6-difluorobenzaldehyde and Intermediate 2 |
| 63 | 2-[(4-bromo-2-chlorophenyl)methyl]-7-hydroxy-3,4-dihydro-1H-pyrido[1,2-a]pyrazin-8-one hydrochloride | 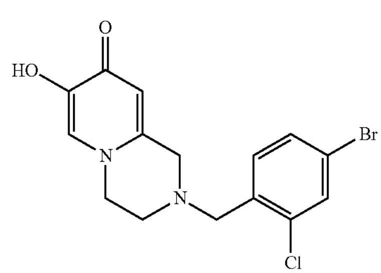 [SMILES: O=c1cc2n(cc1O)CCN(Cc1ccc(Br)cc1Cl)C2] | MS, ES+, 368.9 (M + H)+ 1H NMR (400 MHz, DMSO-d6) δ ppm 11.16 (br. s., 1 H) 8.07 (s, 1 H) 7.78 (d, 1 H) 7.58-7.62 (m, 1 H) 7.49-7.53 (m, 1 H) 7.10 (s, 1 H) 4.40 (t, 2 H) 3.96 (s, 2 H) 3.83 (s, 2 H) 3.04 (br. s., 2 H) | Method I using 4-bromo-2-chlorobenzaldehyde and Interemdiate 2 |

| Ex. | Name | Structure | Analytical data | Preparation Information |
|---|---|---|---|---|
| 64 | 2-[(2-chloro-4-cyclopropyl-phenyl)methyl]-7-hydroxy-3,4-dihydro-1H-pyrido[1,2-a]pyrazin-8-one hydrochloride | 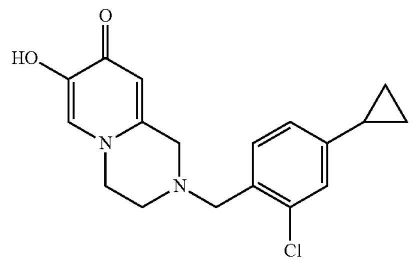 [SMILES: O=c1cc2n(cc1O)CCN(Cc1ccc(C3CC3)cc1Cl)C2] | MS, ES+, 331.0 (M + H)+ <br> 1H NMR (400 MHz, DMSO-d6) δ ppm 11.14 (br. s., 2 H) 8.06 (s, 1 H) 7.43 (d, 1 H) 7.21 (d, 1 H) 7.11 (s, 1 H) 7.07 (dd, 1 H) 4.40 (br. s., 2 H) 3.99 (br. s., 2 H) 3.86 (br. s., 3 H) 3.06 (br. s., 2 H) 1.90-1.99 (m, 1 H) 0.95-1.01 (m, 2 H) 0.68-0.74 (m, 2 H) | Method I using 2-chloro-4-cyclopropyl-benzaldehyde and Intermediate 2 |
| 65 | 2-[(2-chlorophenyl)methyl]-7-hydroxy-3,3-dimethyl-1,4-dihydropyrido[1,2-a]pyrazin-8-one | 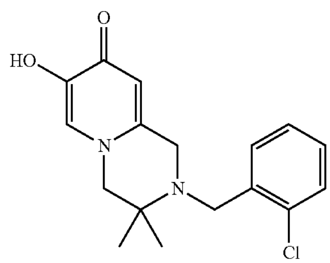 [SMILES: CC1(C)Cn2cc(O)c(=O)cc2CN1Cc1ccccc1Cl] | MS, ES+, 319.0 (M + H)+ <br> 1H NMR (400 MHz, DMSO-d6) δ ppm 11.28 (br. s., 1 H) 8.06 (s, 1 H) 7.63 (br. s., 1 H) 7.47 (d, 1 H) 7.31-7.41 (m, 2 H) 7.14 (s, 1 H) 4.30 (br. s., 2 H) 3.91 (br. s., 4 H) 1.22-1.31 (br. s., 6 H) | Method I using 2-chlorobenzaldehyde and Intermediate 11 |

Example 66: 2-[(2,4-dichloro-5-nitro-phenyl)methyl]-7-hydroxy-3,4-dihydro-1H-pyrido[1,2-a]pyrazin-8-one

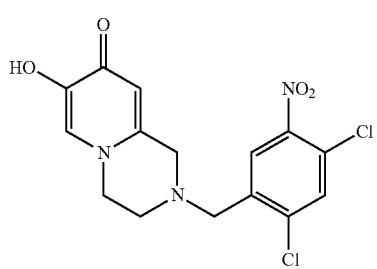 [SMILES: O=c1cc2n(cc1O)CCN(Cc1cc([N+](=O)[O-])c(Cl)cc1Cl)C2]

To a solution of 2-[(2,4-dichlorophenyl)methyl]-7-hydroxy-3,4-dihydro-1H-pyrido[1,2-a]pyrazin-8-one (Example 61, 30 mg, 0.083 mmol) in sulfuric acid (1 mL) was added potassium nitrate (16.8 mg, 0.17 mmol) in portions over 5 min. The resulting mixture was stirred for 30 min at 0° C., then quenched by adding cold water (3 mL) followed by careful addition of sat'd. NaHCO3. The aqueous phase was extracted with CHCl3 (3×). The organic layers were combined, dried over Na2SO4, filtered, and 0.5 mL 6N HCl was added to the filtrate. The solvent was removed in vacuo to give to yield the hydrochloride salt of the title compound as a yellow solid (25 mg, 74%). MS, ES+, 370.0 (M+H)+.

1H NMR (400 MHz, DMSO-d6) δ ppm 11.19 (br. s., 1H) 8.22 (s, 1H) 8.06-8.10 (m, 2H) 7.06 (s, 1H) 4.41 (br. s., 2H) 3.97 (br. s., 2H) 3.88 (br. s., 2H) 3.05 (br. s., 2H)

Example 67: 7-hydroxy-2-[1-(2-methylphenyl)ethyl]-1,2,3,4-tetrahydro-8H-pyrido[1,2-a]pyrazin-8-one

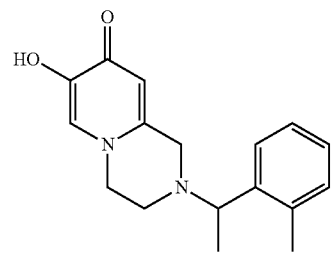 [SMILES: Cc1ccccc1C(C)N1CCn2cc(O)c(=O)cc2C1]

Method J

7-[(4-methoxyphenyl)methoxy]-1,2,3,4-tetrahydropyrido[1,2-a]pyrazin-8-one (Intermediate 2, 0.1 mmol, 0.1 mmol), 2'-methylacetophenone (14.8 mg, 0.110 mmol), MP-BH3CN (Sopachem, 80 mg, 0.199 mmol) were poured in a mixture EtOH (0.6 mL):THF (0.3 mL):HOAc (0.1 mL) and stirred overnight at rt, then at 60° C. for 14 h. MP-BH3CN (Sopachem, 40 mg, 0.050 mmol) and 2'-methylacetophenone (8 mg) was added. The mixture was heated at 70° C. overnight. The reaction mixture was filtered, evaporated. The residue was purified by reverse phase chromatography to yield the PMB protected intermediate (18 mg). This intermediate was dissolved in DCM (0.4 mL), TFA (0.4 mL) was added and the resulting mixture was stirred at rt for 30 min. The solvents were evaporated to yield the title compound as a brown oil (20 mg). High-Res MS, ES+, 285.1597 (M+H)+ (obs.), 285.1603 (M+H)+ (calc.).

The following compounds 68-97 have been synthesized according to Methods J. Examples 94-97 were repurified by reverse phase chromatography.

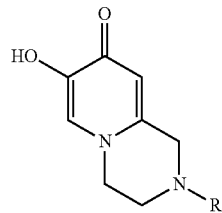

| Ex. | Name | R | Analytical data | Preparation Information |
|---|---|---|---|---|
| 68 | 2-[1-(4-chlorophenyl)ethyl]-7-hydroxy-1,2,3,4-tetrahydro-8H-pyrido[1,2-a]pyrazin-8-one | 4-chlorophenyl ethyl | High-Res MS, ES+, 305.1053 (M + H)+ (obs.), 305.1057 (M + H)+ (calc.). | Method J using 4'-chloroacetophenone |
| 69 | 2-[1-(2,5-dichlorophenyl)ethyl]-7-hydroxy-1,2,3,4-tetrahydro-8H-pyrido[1,2-a]pyrazin-8-one | 2,5-dichlorophenyl ethyl | High-Res MS, ES+, 339.0656 (M + H)+ (obs.), 339.0667 (M + H)+ (calc.). | Method J using 2',5'-dichloroacetophenone |
| 70 | 7-hydroxy-2-{1-[4-(trifluoromethyl)phenyl]ethyl}-1,2,3,4-tetrahydro-8H-pyrido[1,2-a]pyrazin-8-one | 4-(trifluoromethyl)phenyl ethyl | High-Res MS, ES+, 339.1321 (M + H)+ (obs.), 339.132 (M + H)+ (calc.). | Method J using 4'-(trifluoromethyl)acetophenone |
| 71 | 7-hydroxy-2-[1-(3-methylphenyl)ethyl]-1,2,3,4-tetrahydro-8H-pyrido[1,2-a]pyrazin-8-one | 3-methylphenyl ethyl | High-Res MS, ES+, 285.1599 (M + H)+ (obs.), 285.1603 (M + H)+ (calc.). | Method J using 3'-methylacetophenone |
| 72 | 2-[1-(3-chlorophenyl)ethyl]-7-hydroxy-1,2,3,4-tetrahydro-8H-pyrido[1,2-a]pyrazin-8-one | 3-chlorophenyl ethyl | High-Res MS, ES+, 305.1041 (M + H)+ (obs.), 305.1057 (M + H)+ (calc.). | Method J using 3'-chloroacetophenone |
| 73 | 2-(4-chloro-2,3-dihydro-1H-inden-1-yl)-7-hydroxy-1,2,3,4-tetrahydro-8H-pyrido[1,2-a]pyrazin-8-one | 4-chloro-indanyl | High-Res MS, ES+, 317.1044 (M + H)+ (obs.), 317.1057 (M + H)+ (calc.). | Method J using 4-chloro-1-indanone |

| Ex. | Name | R | Analytical data | Preparation Information |
|---|---|---|---|---|
| 74 | 2-[1-(2,6-dimethoxy-phenyl)ethyl]-7-hydroxy-1,2,3,4-tetrahydro-8H-pyrido[1,2-a]pyrazin-8-one | 2,6-dimethoxyphenyl with ethyl linker | High-Res MS, ES$^+$, 331.1638 (M + H)$^+$ (obs.), 331.1658 (M + H)$^+$ (calc.). | Method J using 2',6'-dimethoxy-acetophenone |
| 75 | 7-hydroxy-2-[1-(2,3,5-trifluorophenyl)ethyl]-1,2,3,4-tetrahydro-8H-pyrido[1,2-a]pyrazin-8-one | 2,3,5-trifluorophenyl with ethyl linker | High-Res MS, ES$^+$, 325.1161 (M + H)$^+$ (obs.), 325.1164 (M + H)$^+$ (calc.). | Method J using 2',3',5'-trifluoro-acetophenone |
| 76 | 2-[1-(2-chlorophenyl)eth-yl]-7-hydroxy-1,2,3,4-tetrahydro-8H-pyrido[1,2-a]pyrazin-8-one | 2-chlorophenyl with ethyl linker | High-Res MS, ES$^+$, 305.1039 (M + H)$^+$ (obs), 305.1057 (M + H)$^+$ (calc.). | Method J using 2-chloro-acetophenone |
| 77 | 2-{1-[2-(benzyloxy)phe-nyl]ethyl}-7-hydroxy-1,2,3,4-tetrahydro-8H-pyrido[1,2-a]pyrazin-8-one | 2-(benzyloxy)phenyl with ethyl linker | High-Res MS, ES$^+$, 377.1847 (M + H)$^+$ (obs.), 377.1865 (M + H)$^+$ (calc.). | Method J using 2'-benzyloxy-acetophenone |
| 78 | 7-hydroxy-2-(1-phenylpentyl)-1,2,3,4-tetrahydro-8H-pyrido[1,2-a]pyrazin-8-one | phenyl with pentyl linker | High-Res MS, ES$^+$, 313.1911 (M + H)$^+$ (obs.), 313.1916 (M + H)$^+$ (calc.). | Method J using valerophenone |
| 79 | 2-(7-fluoro-2,3-dihydro-1H-inden-1-yl)-7-hydroxy-1,2,3,4-tetrahydro-8H-pyrido[1,2-a]pyrazin-8-one | 7-fluoroindanyl | High-Res MS, ES$^+$, 301.1338 (M + H)$^+$ (obs.), 301.1352 (M + H)$^+$ (calc.). | Method J using 7-fluoro-1-indanone |
| 80 | 7-hydroxy-2-(2-phenyl-3,4-dihydro-2H-chromen-4-yl)-1,2,3,4-tetrahydro-8H-pyrido[1,2-a]pyrazin-8-one | 2-phenylchroman-4-yl | LCMS (Method D, ES$^+$) RT, (M + H)$^+$, 95% purity. | Method J using flavanone |
| 81 | 2-[1-(3-fluorophenyl)eth-yl]-7-hydroxy-1,2,3,4-tetrahydro-8H-pyrido[1,2-a]pyrazin-8-one | 3-fluorophenyl with ethyl linker | High-Res MS, ES$^+$, 289.1344 (M + H)$^+$ (obs.), 289.1352 (M + H)$^+$ (calc.). | Method J using 3'-fluoroaceto-phenone |

| Ex. | Name | R | Analytical data | Preparation Information |
|---|---|---|---|---|
| 82 | 2-[cyclopentyl(phenyl)methyl]-7-hydroxy-1,2,3,4-tetrahydro-8H-pyrido[1,2-a]pyrazin-8-one | 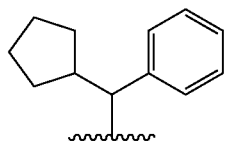 [SMILES: *C(c1ccccc1)C1CCCC1] | High-Res MS, ES+, 325.1905 (M + H)+ (obs.), 325.1916 (M + H)+ (calc.). | Method J using cyclopentyl phenyl ketone |
| 83 | 7-hydroxy-2-[1-(3-methoxyphenyl)ethyl]-1,2,3,4-tetrahydro-8H-pyrido[1,2-a]pyrazin-8-one | 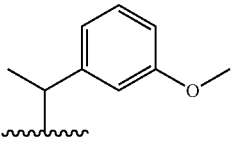 [SMILES: *C(C)c1cccc(OC)c1] | High-Res MS, ES+, 301.1534 (M + H)+ (obs.), 301.1552 (M + H)+ (calc.). | Method J using 3'-methoxy-acetophenone |
| 84 | 2-(2,3-dihydro-1H-inden-1-yl)-7-hydroxy-1,2,3,4-tetrahydro-8H-pyrido[1,2-a]pyrazin-8-one | 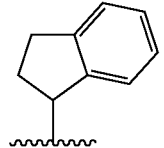 [SMILES: *C1CCc2ccccc21] | High-Res MS, ES+, 283.1427 (M + H)+ (obs.), 283.1447 (M + H)+ (calc.). | Method J using 1-indanone |
| 85 | 2-[1-(3-chloro-2,6-difluorophenyl)ethyl]-7-hydroxy-1,2,3,4-tetrahydro-8H-pyrido[1,2-a]pyrazin-8-one | 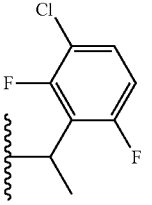 | High-Res MS, ES+, 341.0881 (M + H)+ (obs.), 341.0868 (M + H)+ (calc.). | Method J using 3'-chloro-2',6'-difluoro-acetophenone |
| 86 | 7-hydroxy-2-(6,7,8,9-tetrahydro-5H-benzo[7]annulen-5-yl)-1,2,3,4-tetrahydro-8H-pyrido[1,2-a]pyrazin-8-one | 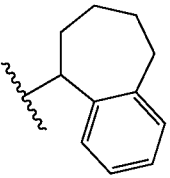 [SMILES: *C1CCCCc2ccccc21] | High-Res MS, ES+, 311.1765 (M + H)+ (obs.), 311.1759 (M + H)+ (calc.). | Method J using 1-benzosuberone |
| 87 | 2-[1-(2,5-dimethylphenyl)ethyl]-7-hydroxy-1,2,3,4-tetrahydro-8H-pyrido[1,2-a]pyrazin-8-one | 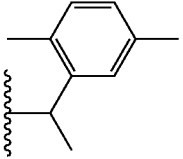 [SMILES: *C(C)c1cc(C)ccc1C] | High-Res MS, ES+, 299.1744 (M + H)+ (obs.), 299.1759 (M + H)+ (calc.). | Method J using 2',5'-dimethyl-acetophenone |
| 88 | 2-(1,2-diphenylethyl)-7-hydroxy-1,2,3,4-tetrahydro-8H-pyrido[1,2-a]pyrazin-8-one | 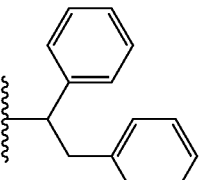 | High-Res MS, ES+, 347.1757 (M + H)+ (obs.), 347.1759 (M + H)+ (calc.). | Method J using deoxybenzoin |
| 89 | 7-hydroxy-2-(1-phenylpropyl)-1,2,3,4-tetrahydro-8H-pyrido[1,2-a]pyrazin-8-one | 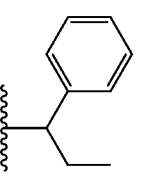 [SMILES: *C(CC)c1ccccc1] | High-Res MS, ES+, 285.1589 (M + H)+ (obs.), 285.1603 (M + H)+ (calc.). | Method J using propiophenone |

-continued

| Ex. | Name | R | Analytical data | Preparation Information |
|---|---|---|---|---|
| 90 | 7-hydroxy-2-(1,2,3,4-tetrahydronaph-thalen-1-yl)-1,2,3,4-tetrahydro-8H-pyrido[1,2-a]pyrazin-8-one | | High-Res MS, ES⁺, 297.1606 (M + H)⁺ (obs.), 297.1603 (M + H)⁺ (calc.). | Method J using 1-tetralone |
| 91 | 7-hydroxy-2-(7-methoxy-1,2,3,4-tetrahydro-naphthalen-1-yl)-1,2,3,4-tetrahydro-8H-pyrido[1,2-a]pyrazin-8-one | | High-Res MS, ES⁺, 327.1693 (M + H)⁺ (obs.), 327.1709 (M + H)⁺ (calc.). | Method J using 7-methoxy-1-tetralone |
| 92 | 7-hydroxy-2-(4-methyl-2,3-dihdyro-1H-inden-1-yl)-1,2,3,4-tetrahydro-8H-pyrido[1,2-a]pyrazin-8-one | | High-Res MS, ES⁺, 297.1601 (M + H)⁺ (obs.), 297.1603 (M + H)⁺ (calc.). | Method J using 4-methyl-1-indanone |
| 93 | 7-hydroxy-2-(1-phenylbutyl)-1,2,3,4-tetrahydro-8H-pyrido[1,2-a]pyrazin-8-one | | High-Res MS, ES⁺, 299.1752 (M + H)⁺ (obs.), 299.1759 (M + H)⁺ (calc.). | Method J using butyrophenone |
| 94 | 4-[1-(7-hydroxy-8-oxo-1,3,4,8-tetrahydro-2H-pyrido[1,2-a]pyrazin-2-yl)ethyl]benzonitrile | | High-Res MS, ES⁺, 296.1386 (M + H)⁺ (obs.), 296.1399 (M + H)⁺ (calc.) | Method J using 4-acetylbenzonitrile |
| 95 | 3-[1-(7-hydroxy-8-oxo 1,3,4,8-tetrahydro-2H-pyrido[1,2-a]pyrazin-2-yl)ethyl]benzo-nitrile | | High-Res MS, ES⁺, 296.1383 (M + H)⁺ (obs.), 296.1399 (M + H)⁺ (calc.). | Method J using 3-acetylbenzonitrile |
| 96 | N-{3-[1-(7-hydroxy-8-oxo-1,3,4,8-tetrahydro-2H-pyrido[1,2-a]pyrazin-2-yl)ethyl]phenyl}acetamide | | High-Res MS, ES⁺, 328.1646 (M + H)⁺ (obs.), 328.1661 (M + H)⁺ (calc.) | Method J using 3'-acetamido-acetophenone |

| Ex. | Name | R | Analytical data | Preparation Information |
|---|---|---|---|---|
| 97 | 2-[1-(2,5-difluorophenyl)ethyl]-7-hydroxy-1,2,3,4-tetrahydro-8H-pyrido[1,2-a]pyrazin-8-one | 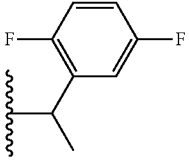 | High-Res MS, ES+, 307.1252 (M + H)+ (obs.), 307.1258 (M + H)+ (calc.) | Method J using 2',5'-difluoro-acetophenone |

Example 98: 2-[1-(2-fluorophenyl)ethyl]-7-hydroxy-1,2,3,4-tetrahydro-8H-pyrido[1,2-a]pyrazin-8-one

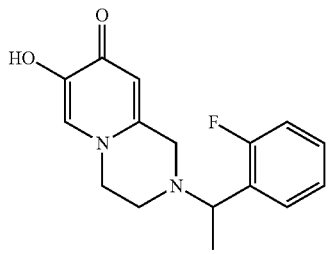 [SMILES: CC(c1ccccc1F)N1CCn2cc(O)c(=O)cc2C1]

Method K

Step 1: Preparation of 7-benzyloxy-2-[1-(2-fluorophenyl)ethyl]-3,4-dihydro-1H-pyrido[1,2-a]pyrazin-8-one

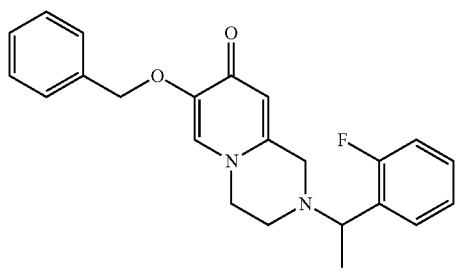 [SMILES: CC(c1ccccc1F)N1CCn2cc(OCc3ccccc3)c(=O)cc2C1]

5-benzyloxy-1-(2-chloroethyl)-2-(chloromethyl)pyridin-4-one (Intermediate 3, 0.32 mmol, 101 mg), sodium iodide (0.16 mmol, 24 mg, 0.50 eq.), NEt₃ (4 eq., 1.32 mmol, 135 mg), (1-(2-fluorophenyl)ethanamine, 2.0 eq., 0.660 mmol) were placed in CH₃CN (2 mL). The reaction mixture was heated at 125° C. for 2.5 h. Addition of water (2 mL) and extraction with DCM (2 mL). The organic phase was evaporated under vacuum and purified by reverse phase preparative chromatography to yield the title intermediate (101 mg as a yellow oil (83%).

MS, ES+, 379.2 (M+H)+.

Step 2: Preparation of 2-[1-(2-fluorophenyl)ethyl]-7-hydroxy-1,2,3,4-tetrahydro-8H-pyrido[1,2-a]pyrazin-8-one An aq. solution of HCl (2 mL, 5 N) was added to 7-benzyloxy-2-[1-(2-fluorophenyl)ethyl]-3,4-dihydro-1H-pyrido[1,2-a]pyrazin-8-one (101 mg, 0.27 mmol) and the mixture was heated for 2 h at 95° C. The mixture was then evaporated under vacuum. The residue was then triturated with ether, filtered then dried under vacuum.

MS, ES+, 289.3 (M+H)+.

The following compounds 92-96 have been synthesized according to Methods K

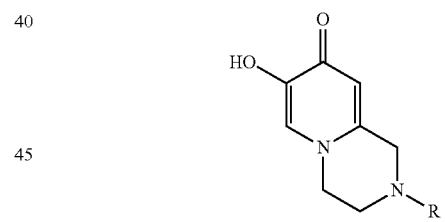

| Ex. | Name | R | Analytical data | Preparation Information |
|---|---|---|---|---|
| 99 | 2-[1-(4-fluorophenyl)ethyl]-7-hydroxy-1,2,3,4-tetrahydro-8H-pyrido[1,2-a]pyrazin-8-one | 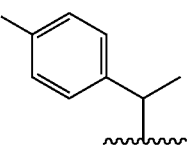 | MS, ES+, 289.2 (M + H)+, | Method K using 1-(4-fluorophenyl)ethanamine |
| 100 | 7-hydroxy-2-(2-hydroxy-1-phenylethyl)-1,2,3,4-tetrahydro-8H-pyrido[1,2-a]pyrazin-8-one | 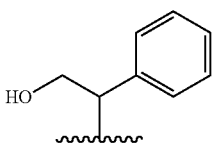 [SMILES: *C(CO)c1ccccc1] | MS, ES+ 287.2 (M + H)+, | Method K using dl-2-phenylglycinol |

-continued

| Ex. Name | R | Analytical data | Preparation Information |
|---|---|---|---|
| 101 7-hydroxy-2-(2,2,2-trifluoro-1-phenylethyl)-1,2,3,4-tetrahydro-8H-pyrido[1,2-a]pyrazin-8-one | (structure: 2,2,2-trifluoro-1-phenylethyl) | MS, ES$^+$, 325.2 (M + H)$^+$ | Method K using 2,2,2-trifluoro-1-phenyl-ethylamine |
| 102 7-hydroxy-2-[(2-phenyl-1,3-thiazol-4-yl)methyl]-1,2,3,4-tetrahydro-8H-pyrido[1,2-a]pyrazin-8-one | (structure: (2-phenyl-1,3-thiazol-4-yl)methyl) | MS, ES$^+$, 340.3 (M + H)$^+$, | Method K using (2-phenyl-1,3-thiazol-4-yl)methylamine |
| 103 2-[(3,5-dimethyl-1-phenyl-1H-pyrazol-4-yl)methyl]-7-hydroxy-1,2,3,4-tetrahydro-8H-pyrido[1,2-a]pyrazin-8-one | (structure: (3,5-dimethyl-1-phenyl-1H-pyrazol-4-yl)methyl) | MS, ES$^+$, 351.3 (M + H)$^+$ | Method K using c-(3,5-dimethyl-1-phenyl-1h-pyrazol-4-yl)-methylamine |
| 104 7-hydroxy-2-(1-phenylcyclopropyl)-3,4-dihydro-1H-pyrido[1,2-a]pyrazin-8-one | (structure: 1-phenylcyclopropyl) | MS, ES$^+$, 283.1 (M + H)$^+$<br>$^1$H NMR (400 MHz, DMSO-d$_6$) δ ppm 11.08 (br. s., 1 H) 7.99 (s, 1 H) 7.37-7.44 (m, 4 H) 7.30-7.36 (m, 1 H) 7.11 (s, 1 H) 4.30 (t, 2 H)<br><br>3.88 (s, 2 H) 2.95-3.01 (m, 2 H) 1.03-1.08 (m, 2 H) 0.86-0.90 (m, 2 H) | Method K using 1-phenylcyclopropylamine |
| 105 2-(2-fluoro-1-phenyl-ethyl)-7-hydroxy-3,4-dihydro-1H-pyrido[1,2-a]pyrazin-8-one | (structure: 2-fluoro-1-phenyl-ethyl) | MS, ES$^+$, 289.1 (M + H)$^+$<br>$^1$H NMR (400 MHz, DMSO-d$_6$) δ ppm 7.9 (s, 1H) 7.44-7.39 (m, 5H) 6.86 (s, 1H) 4.96-4.67 (m, 3H) 4.31-4.25 (m, 2H) 4.02-3.80 (m, 2H)<br><br>3.01-2.86 (m, 2H) | Method K using 2-fluoro-1-phenyl-ethylamine |
| 106 2-[1-(2-chlorophenyl)cyclopropyl]-7-hydroxy-3,4-dihydro-1H-pyrido[1,2-a]pyrazin-8-one | (structure: 1-(2-chlorophenyl)cyclopropyl) | MS, ES$^+$, 317.0 (M + H)$^+$<br>$^1$H NMR (400 MHz, DMSO-d$_6$) δ ppm 7.99 (s, 1 H) 7.56 (dd, 1 H) 7.47-7.51 (m, 1 H) 7.34-7.43 (m, 2 H) 7.10 (s, 1 H) 4.29 (t, 2 H) 3.95 (s, 2 H) 3.09 (t, 2 H) 1.18-1.22 (m, 2 H) 0.94-0.99 (m, 2 H) | Method K using 1-(2-chlorophenyl)cyclopropylamine |
| 107 2-(2,2-difluoro-1-phenyl-ethyl)-7-hydroxy-3,4-dihydro-1H-pyrido[1,2-a]pyrazin-8-one | (structure: 2,2-difluoro-1-phenyl-ethyl) | MS, ES$^+$, 307.0 (M + H)$^+$<br>$^1$H NMR (400 MHz, DMSO-d$_6$) δ ppm 7.9 (s, 1H) 7.54-7.40 (m, 5H) 7.33-7.08 (m, 1H) 6.87 (s, 1H) 6.83-6.54 (m, 1H) 4.35-4.15 (m, 2H)<br><br>3.92 (quart., 2H) 3.11-3.03 (m, 1H) 2.92-2.83 (m, 1H). | Method K using 2,2-difluoro-1-phenyl-ethylamine |
| 108 2-(1,3-benzothiazol-2-yl)-7-hydroxy-3,4-dihydro-1H-pyrido[1,2-a]pyrazin-8-one | (structure: 1,3-benzothiazol-2-yl) | MS, ES$^+$, 300.1 (M + H)$^+$<br>$^1$H NMR (400 MHz, DMSO-d$_6$) δ ppm 11.27 (br. s., 1 H) 8.30 (s, 1 H) 7.87 (d, 1 H) 7.55 (d, 1 H) 7.42 (s, 1 H) 7.31-7.38 (m, 1 H) 7.12-7.18 (m, 1 H) 5.05 (s, 2 H) 4.66 (t, 2 H) 3.97-4.02 (m, 2 H) | Method K using 1,3-benzothiazol-2-amine |

-continued

| Ex. Name | R | Analytical data | Preparation Information |
|---|---|---|---|
| 109 7-hydroxy-2-(2-phenylcyclopropyl)-3,4-dihydro-1H-pyrido[1,2-a]pyrazin-8-one | (cyclopropyl-phenyl) | MS, ES$^+$, 283.1 (M + H)$^+$ $^1$H NMR (400 MHz, DMSO-d$_6$) δ ppm 8.03 (s, 1H) 7.26-7.24 (m, 2H) 7.20-7.17 (m, 3H) 7.06 (s, 1H) 4.38-4.30 (m, 2H) 4.11-3.95 (m, 2H) 3.20-3.05 (m, 2H) 2.22 (s, 1H), 2.11-2.03 (m, 2H) 1.17-1.04 (m, 2H). | Method K using 2-phenylcyclopropylamine |
| 110 7-hydroxy-2-(5-quinolyl)-3,4-dihydro-1H-pyrido[1,2-a]pyrazin-8-one | (quinolyl) | MS, ES$^+$, 294.0 (M + H)$^+$ $^1$H NMR (400 MHz, DMSO-d$_6$) δ ppm 11.31 (br. s., 1 H) 9.20 (d, 1 H) 9.07 (d, 1 H) 8.28 (s, 1 H) 8.07 (d, 1 H) 7.97-8.04 (m, 1 H) 7.92 (dd, 1 H) 7.53 (d, 1 H) 7.29 (s, 1 H) 4.67 (s, 4 H) 3.71 (d, 2 H) | Method K using 5-aminoquinoline |
| 111 7-hydroxy-2-(3-phenyloxetan-3-yl)-3,4-dihydro-1H-pyrido[1,2-a]pyrazin-8-one | (oxetanyl-phenyl-methyl) | MS, ES$^+$, 299.0 (M + H)$^+$ $^1$H NMR (400 MHz, DMSO-d$_6$) δ ppm 8.09 (s, 1H) 7.81-7.35 (m, 5H) 7.15 (s, 1H) 5.12 (br. s., 4H) 4.36 (t, 2H) 3.64 (s, 2H) 2.70 (t, 2H). | Method K using 3-phenyloxetan-3-amine |

Example 112: 7-hydroxy-2-phenyl-1,2,3,4-tetrahydro-8H-pyrido[1,2-a]pyrazin-8-one

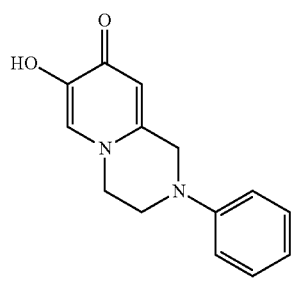 [SMILES: O=c1cc2n(cc1O)CCN(c1ccccc1)C2]

Step 1: Preparation of 1-(2-anilinoethyl)-5-benzyloxy-2-(hydroxymethyl)pyridin-4-one A suspension of 5-benzyloxy-2-(hydroxymethyl)pyran-4-one (100 mg, 0.43 mmol) and N'-phenylethane-1,2-diamine (84.51 µL, 0.65 mmol) in water (2 mL) was heated under microwave conditions at 150° C. for 90 min. The solvent was removed in vacuo and the residue treated with 10% Na$_2$CO$_3$ and CHCl$_3$ and passed through a phase separator tube. After removing the organic solvent in vacuo, the residue was purified by automated normal-phase chromatography (0-20% MeOH/DCM, 4 g silica gel cartridge). The product-containing fractions were combined and the solvent removed in vacuo to give 1-(2-anilinoethyl)-5-benzyloxy-2-(hydroxymethyl)pyridin-4-one (58 mg, 38% yield) as a tan solid. MS, ES$^+$, 351 (M+H)$^+$, $^1$H NMR (400 MHz, DMSO-d$_6$) δ 7.49 (s, 1H), 7.31-7.40 (m, 5H), 7.08 (t, 2H, J=7.7 Hz), 6.52-6.60 (m, 3H), 6.20 (s, 1H), 5.80 (t, 1H, J=6.1 Hz), 5.62 (t, 1H, J=5.7 Hz), 4.92 (s, 2H), 4.36 (d, 2H, J=5.8 Hz), 4.03 (t, 2H, J=6.2 Hz), 3.38 (m, 2H).

Step 2: Preparation of 7-benzyloxy-2-phenyl-3,4-dihydro-1H-pyrido[1,2-a]pyrazin-8-one To a solution of 1-(2-anilinoethyl)-5-benzyloxy-2-(hydroxymethyl)pyridin-4-one (55.mg, 0.16 mmol) in DME (5 mL) and chloroform (100 mL) was added thionyl chloride (500 µL, 6.9 mmol) in chloroform (100 mL) over 45 min at ambient temperature. The contents were allowed to stir for 3 days (for convenience), then 10 mL of 1M NaOH was added. The resulting mixture was allowed to stir for 24 h at ambient temperature, then at 50° C. for 24 h. The contents were transferred to a separatory funnel, the CHCl$_3$ layer removed and the aqueous layer washed with CHCl$_3$(2×). The organic layers were combined, dried over MgSO$_4$, filtered and the solvent removed in vacuo to give a residue which was purified by automated normal-phase chromatography (0-20% MeOH/DCM, 4 g silica gel cartridge). The product-containing fractions were combined and the solvent removed in vacuo to give 7-benzyloxy-2-phenyl-3,4-dihydro-1H-pyrido[1,2-a]pyrazin-8-one (32 mg, 61% yield) as a colorless glass. MS, ES$^+$, 333 (M+H)$^+$. $^1$H NMR (400 MHz, DMSO-d$_6$) δ 7.64 (s, 1H), 7.32-7.46 (m, 5H), 7.23-7.29 (m, 2H), 6.95 (d, 2H, J=8.8 Hz), 6.80 (t, 1H, J=7.3 Hz), 6.22 (s, 1H), 4.99 (s, 2H), 4.38 (s, 2H), 4.09-4.14 (m, 2H), 3.65 (t, 2H, J=5.6 Hz).

Step 3: Preparation of 7-hydroxy-2-phenyl-3,4-dihydro-1H-pyrido[1,2-a]pyrazin-8-one 7-benzyloxy-2-phenyl-3,4-dihydro-1H-pyrido[1,2-a]pyrazin-8-one (29.mg, 0.090 mmol) was stirred in 6M HCl (2.mL, 12 mmol) at 100° C. for 2 h. The solvents were removed in vacuo to give 7-hydroxy-2-phenyl-3,4-dihydro-1H-pyrido[1,2-a]pyrazin-8-one hydrochloride (24.5 mg, 0.089 mmol, 98% yield) as a brown solid. MS, ES$^+$, 243 (M+H)$^+$. $^1$H NMR (400 MHz, DMSO-d$_6$) δ 8.24 (s, 1H), 7.25-7.34 (m, 4H), 6.99-7.03 (m, 2H), 6.84 (t, 1H, J=7.3 Hz), 4.68 (s, 2H), 4.51-4.56 (m, 2H), 3.71-3.76 (m, 2H).

Example 113: 7-hydroxy-2-(3-methylphenyl)-1,2,3,4-tetrahydro-8H-pyrido[1,2-a]pyrazin-8-one

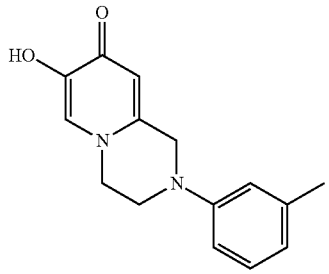 [SMILES: Cc1cccc(N2CCn3cc(O)c(=O)cc3C2)c1]

Method L

Step 1: Preparation of 7-benzyloxy-2-(o-tolyl)-3,4-dihydro-1H-pyrido[1,2-a]pyrazin-8-one Xantphos (45 mg, 0.078 mmol), Pd$_2$(dba)$_3$ (13 mg, 0.038 mmol) and potassium tert-butoxide (0.135 g, 1.17 mmol) were added to a suspension of 7-benzyloxy-1,2,3,4-tetrahydropyrido[1,2-a]pyrazin-8-one (Intermediate 1, 0.1 g, 0.39 mmol) and 3-bromotoluene (0.14 g, 0.78 mmol) in 1,4-dioxane (1 mL). The mixture was heated at 130° C. for 14 h, then cooled to rt and filtered. The filtered solid was washed with EtOAc and the combined filtrates were evaporated under vacuum. The residue was purified by chromatography (SiO$_2$, gradient from 100% DCM up to 7% methanolic ammonia in DCM) to yield the title intermediate as a yellow solid (83 mg, 61%).
MS, ES$^+$, 347 (M+H)$^+$.

Step 2: Preparation of 7-hydroxy-2-(3-methylphenyl)-1,2,3,4-tetrahydro-8H-pyrido[1,2-a]pyrazin-8-one An aq. solution of HCl (2 mL, 5 N) was added to 7-benzyloxy-2-(m-tolyl)-3,4-dihydro-1H-pyrido[1,2-a]pyrazin-8-one (83 mg, 0.24 mmol) and the mixture heated at 100° C. for 30 min., then cooled to rt. The reaction mixture was washed with CH$_3$Cl, treated with Norite®, filtered and evaporated to give a residue (30 mg, brown solid). Purification by reverse phase preparative chromatography yielded the title compound as a brown solid (22 mg, 24%). MS, ES$^+$, 257 (M+H)$^+$.

Example 114: 7-hydroxy-2-[2-(trifluoromethoxy)phenyl]-1,2,3,4-tetrahydro-8H-pyrido[1,2-a]pyrazin-8-one

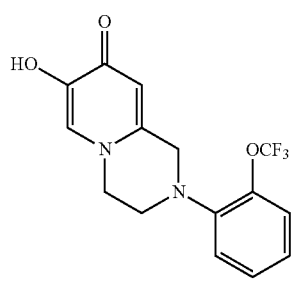 [SMILES: O=c1cc2n(cc1O)CCN(c1ccccc1OC(F)(F)F)C2]

The title compound has been prepared according to Method L, but using 1-bromo-2-(trifluoromethoxy)benzene. Purification of the intermediate by chromatography (SiO$_2$, gradient from 100% DCM up to 7% methanolic ammonia in DCM) yielded the intermediate as a yellow solid (127 mg) used in the next step without any further purification. MS, ES$^+$, 417.3 (M+H)$^+$. HCl treatment (Method E) gave the title compound. MS, ES$^+$, 327.2 (M+H)$^+$. $^1$H NMR (400 MHz, D$_2$O) δ 7.97 (s, 1H), 7.38 (m, 1H), 7.31 (t, 1H, J=7.6 Hz), 7.19 (m, 2H), 7.08 (s, 0H), 4.50 (s, 2H), 4.43 (m, 2H), 3.65 (m, 2H).

Example 115: 1,2-dibenzyl-7-hydroxy-1,2,3,4-tetrahydro-8H-pyrido[1,2-a]pyrazin-8-one

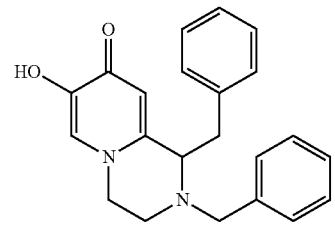 [SMILES: O=c1cc2n(cc1O)CCN(Cc1ccccc1)C2Cc1ccccc1]

Step 1: Preparation of 5-benzyloxy-2-(1-hydroxy-2-phenyl-ethyl)pyran-4-one

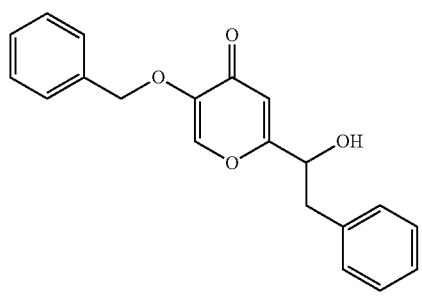 [SMILES: O=c1cc(C(O)Cc2ccccc2)occ1OCc1ccccc1]

A solution of benzylmagnesium bromide (0.6 M, 1.2 eq., 10.4 mmol, 17.4 mL) in THF was added dropwise (in ca. 20 min) to a solution of 5-benzyloxy-4-oxo-pyran-2-carbaldehyde (Intermediate 4, 8.7 mmol, 2.0 g) in THF (20 mL) cooled at −70° C. The mixture was warmed to rt. Water was added, then the mixture was extracted with EtOAc. The combined organic layers were dried over MgSO$_4$, filtered and concentrated under vacuum to give a brown oil (3.27 g). Purification by chromatography (SiO$_2$, 5% methanolic ammonia in DCM) gave the title intermediate (1.47 g, 52%). MS, ES$^+$, 323.3 (M+H)$^+$.

Step 2: Preparation of 1-(2-aminoethyl)-5-benzyloxy-2-(1-hydroxy-2-phenyl-ethyl)pyridin-4-one

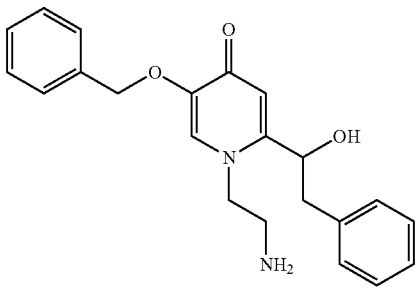 [SMILES: NCCn1cc(OCc2ccccc2)c(=O)cc1C(O)Cc1ccccc1]

Ethylenediamine (13.7 mmol, 0.830 g, 3 eq.) was added to a solution of 5-benzyloxy-2-(1-hydroxy-2-phenyl-ethyl)pyran-4-one (4.56 mmol, 1.47 g, 1 eq.) in EtOH (5 mL) and the mixture was heated to 90° C. for 15.5 h. The reaction mixture was concentrated under vacuum. The residue was taken up in a mixture of EtOAc/MeOH 90/10, washed with H$_2$O. The aqueous layer was extracted with n-BuOH. The combined org. layers were dried over MgSO$_4$, filtered and concentrated to yield a brown oil (1.83 g, quant.) used in the next step without any further purification.

Step 3: Preparation of 1-benzyl-7-benzyloxy-1,2,3,4-tetrahydropyrido[1,2-a]pyrazin-8-one

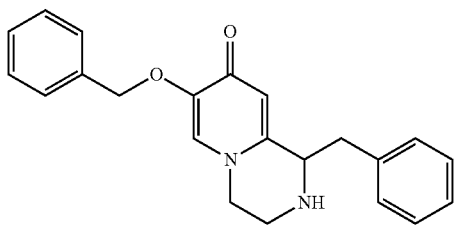 [SMILES: O=c1cc2n(cc1OCc1ccccc1)CCNC2Cc1ccccc1]

Method M

SOCl$_2$ (15 mmol, 1.8 g, 3.1 eq.) was added to a solution of 1-(2-aminoethyl)-5-benzyloxy-2-(1-hydroxy-2-phenyl-ethyl)pyridin-4-one (4.9 mmol, 1.8 g, 1.0 eq.) in DCM (10 mL). The mixture was stirred at rt for 1 h. then evaporated under vacuum to yield a brown oil. This residue was taken up in n-BuOH and an aq. solution of NaHCO$_3$ was added until the pH is 9. The mixture was then stirred for 14 h. at rt.

The reaction mixture was decanted, and the aq. layer was extracted with n-BuOH. The org. phase was dried over MgSO$_4$, filtered and concentrated to yield a black oil (1.5 g). Purification by chromatography (SiO$_2$, 10% methanolic ammonia in DCM) yielded the title intermediate as a brown oil (0.7 g) MS, ES$^+$, 347.3 (M+H)$^+$.

Step 4: Preparation of 1,2-dibenzyl-7-benzyloxy-3,4-dihydro-1H-pyrido[1,2-a]pyrazin-8-one

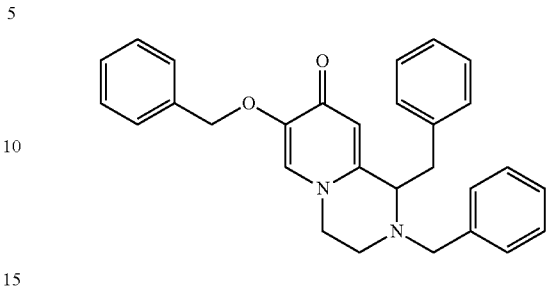

Method N

Benzaldehyde (0.58 mmol, 0.061 g, 2.0 eq.) and molecular sieve 4A (<5 μm, 0.3 g) were added to a solution of 1-benzyl-7-benzyloxy-1,2,3,4-tetrahydropyrido[1,2-a]pyrazin-8-one (0.29 mmol, 0.1 g, 1.0 eq.) in MeOH (4 mL). The mixture was stirred 1 h at rt, then HOAc (0.58 mmol, 0.035 g, 2.0 eq.) followed by sodium cyanoborohydride (0.87 mmol, 0.054 g, 3.0 eq.). The mixture was then stirred 14 h at rt. The mixture was filtered and concentrated. The residue was taken up in DCM, washed with H2O then dried over MgSO$_4$, filtered and concentrated under vacuum to give a residue. Purification by chromatography (SiO$_2$, from 3% methanolic ammonia up to 10% in DCM) yielded the title intermediate (30 mg). MS, ES$^+$, 337.4 (M+H)$^+$

Step 5: Preparation of: 1,2-dibenzyl-7-hydroxy-1,2,3,4-tetrahydro-8H-pyrido[1,2-a]pyrazin-8-one An aq. solution of HCl (2 mL, 5 N) was added to a solution of 1,2-dibenzyl-7-benzyloxy-3,4-dihydro-1H-pyrido[1,2-a]pyrazin-8-one (0.034 mmol, 0.015 g, 1.0 eq.) in dioxane (1 mL). The mixture was stirred at 90° C. for 1 h then cooled to rt. The reaction mixture was washed with CHCl$_3$ (2×2 mL). The aq. phase was filtered on Celite, then concentrated under vacuum to give a brown solid. Purification by reverse phase preparative chromatography yielded the title compound (9 mg). High-Res MS, ES$^+$, 347.1764 (M+H)$^+$ (obs.), 347.1759 (M+H)$^+$ (calc.).

Example 116: 2-benzyl-7-hydroxy-1-phenyl-1,2,3,4-tetrahydro-8H-pyrido[1,2-a]pyrazin-8-one

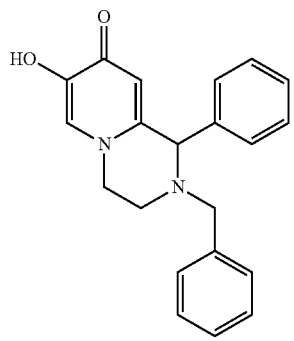 [SMILES: O=c1cc2n(cc1O)CCN(Cc1ccccc1)C2c1ccccc1]

Step 1: Preparation of 5-benzyloxy-2-[hydroxy(phenyl)methyl]pyran-4-one

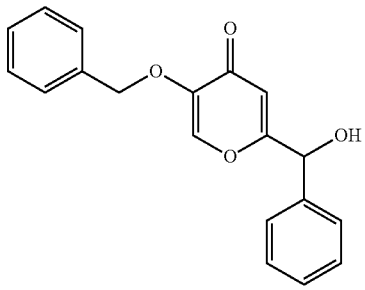 [SMILES: O=c1cc(C(O)c2ccccc2)occ1OCc1ccccc1]

Method O

A solution of phenylmagnesium chloride (2 M in THF, 6.53 mL, 13.0 mmol, 1.5 eq.) was added dropwise to a cold (−70° C.) solution of 5-benzyloxy-4-oxo-pyran-2-carbaldehyde (Intermediate 4, 8.7 mmol, 2.0 g, 1.0 eq.) in THF (20 mL). The mixture was stirred and the temperature allowed to warm up to −30° C. $H_2O$ was then added (10 mL), the mixture allowed to reach rt. The mixture was extracted with EtOAc. The combined org. layers were washed with $H_2O$, then dried over $MgSO_4$, filtered and evaporated to give an oil (4.0 g). This residue was triturated with $Et_2O$ and the precipitate formed filtered to yield the title intermediate (1.44 g, 54%) used in the next step without any further purification. MS, $ES^+$, 309.2 $(M+H)^+$.

Step 2: Preparation of 1-(2-aminoethyl)-5-benzyloxy-2-[hydroxy(phenyl)methyl]pyridin-4-one

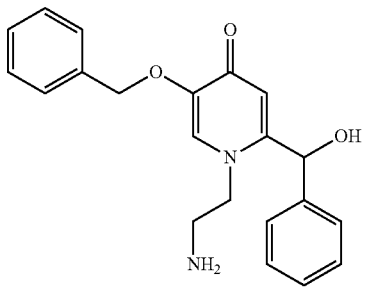 [SMILES: NCCn1cc(OCc2ccccc2)c(=O)cc1C(O)c1ccccc1]

Method P

Ethylenediamine (0.84 g, 3 eq.) and 5-benzyloxy-2-[hydroxy(phenyl)methyl]pyran-4-one (4.61 mmol, 1.42 g, 1.0 eq.) were heated at 70° C. for 4 h. The mixture was cooled to rt, concentrated and the residue was purified by chromatography ($SiO_2$, 10% methanolic ammonia in DCM) to yield the title intermediate as a brown oil (0.9 g, 60%). MS, $ES^+$, 351.3 $(M+H)^+$.

Step 3: Preparation of 7-benzyloxy-1-phenyl-1,2,3,4-tetrahydropyrido[1,2-a]pyrazin-8-one

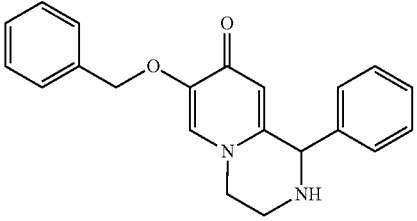 [SMILES: O=c1cc2n(cc1OCc1ccccc1)CCNC2c1ccccc1]

The title intermediate was prepared according to Method A, using 1-(2-aminoethyl)-5-benzyloxy-2-[hydroxy(phenyl)methyl]pyridin-4-one (0.9 g, 2.6 mmol) and longer reaction time (heated 48 h at 60° C.).

The residue obtained was dissolved in MeOH (12 mL) and sodium borohydride (100 mg, 3 mmol) were added and the mixture stirred at rt for 1 h. Another portion of sodium borohydride (100 mg) were added and the mixture stirred at rt for 14 h. The reaction mixture was concentrated to give a residue (700 mg). Purification by chromatography ($SiO_2$, 10% methanolic ammonia in DCM) yielded the title intermediate (417 mg). MS, $ES^+$, 333.3 $(M+H)^+$.

Step 4: Preparation of 2-benzyl-7-benzyloxy-1-phenyl-3,4-dihydro-1H-pyrido[1,2-a]pyrazin-8-one

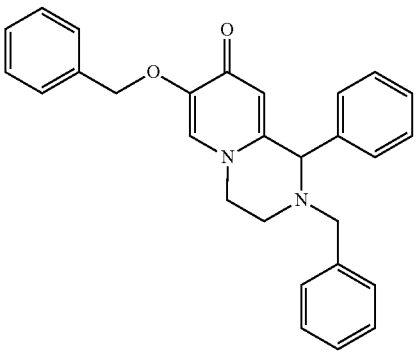 [SMILES: O=c1cc2n(cc1OCc1ccccc1)CCN(Cc1ccccc1)C2c1ccccc1]

Method Q 7-benzyloxy-1-phenyl-1,2,3,4-tetrahydropyrido[1,2-a]pyrazin-8-one (0.42 mmol, 140 mg), potassium carbonate (0.87 mmol, 121 mg, 2.05 eq.), sodium iodide (ca. 1 mg) and benzyl bromide (0.35 mmol, 59 mg, 0.8 eq., dissolved in $CH_3CN$ 1 mL) were stirred 14 h at rt in $CH_3CN$ (1.5 mL). Then DMF (2 mL) were added and the resulting reaction mixture stirred another 14 h at rt.

$H_2O$ was then added, the mixture was extracted with EtOAc. The combined org. layers were washed with $H_2O$, then dried over $MgSO_4$, filtered and evaporated to give a residue (100 mg). Purification by chromatography ($SiO_2$, gradient from DCM up to 10% methanolic ammonia in DCM) yielded the title intermediate (120 mg). MS, $ES^+$, 423.3 $(M+H)^+$.

Step 5: Preparation of 2-benzyl-7-hydroxy-1-phenyl-1,2,3,4-tetrahydro-8H-pyrido[1,2-a]pyrazin-8-one An aq. solution of HCl (3 mL, 5 N) was added to 2-benzyl-7-benzyloxy-1-phenyl-3,4-dihydro-1H-pyrido[1, 2-a]pyrazin-8-one (0.28 mmol, 120 mg) and the mixture heated at 90° C. for 2 h, then cooled to rt. The precipitate was filtered, washed with Et₂O, dried under vacuum to yield the title compound (62 mg) High-Res MS, ES⁺, 333.1613 (M+H)⁺ (obs.), 333.1603 (M+H)⁺ (calc.).

Example 117: 2-(2,6-dichlorobenzyl)-7-hydroxy-1-phenyl-1,2,3,4-tetrahydro-8H-pyrido[1,2-a]pyrazin-8-one

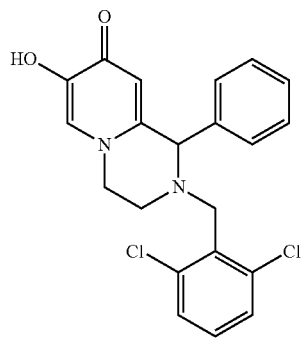 [SMILES: O=c1cc2n(cc1O)CCN(Cc1c(Cl)cccc1Cl)C2c1ccccc1]

The title compound was prepared according to method Q, but using 2,6-dichlorobenzyl bromide.

High-Res MS, ES⁺, 401.0815 (M+H)⁺ (obs.), 401.0823 (M+H)⁺ (calc.).

Example 118: (1R)-2-(4-ethylbenzyl)-7-hydroxy-1-phenyl-1,2,3,4-tetrahydro-8H-pyrido[1,2-a]pyrazin-8-one

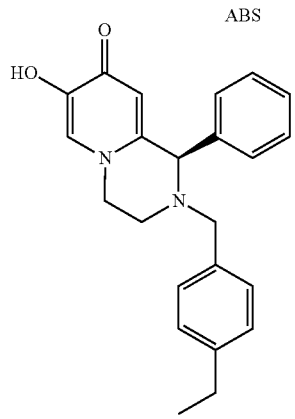 [SMILES: "ABS" ; CCc1ccc(CN2CCn3cc(O)c(=O)cc3[C@H]2c2ccccc2)cc1]

Step 1: Preparation of 7-benzyloxy-2-[(4-ethylphenyl)methyl]-1-phenyl-3,4-dihydro-1H-pyrido[1,2-a]pyrazin-8-one

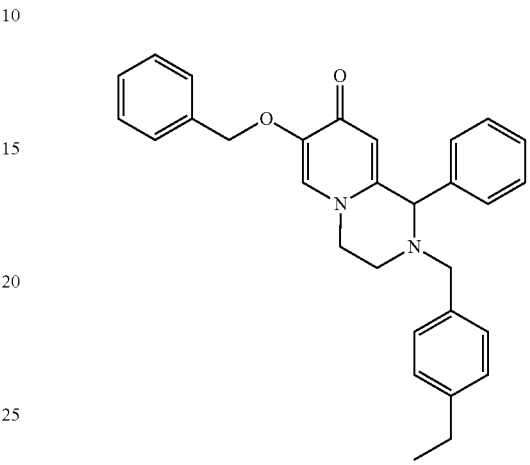

The title intermediate (240 mg) was prepared according to Method N, using 7-benzyloxy-1-phenyl-1,2,3,4-tetrahydropyrido[1,2-a]pyrazin-8-one (200 mg, 0.60 mmol), 4-ethylbenzaldehyde (205 mg, 1.5 mmol, 2.5. eq.) and Si—BH₃CN (Silicycle, 1.5 g, 1.3 mmol, 2.2 eq.). MS, ES⁺, 451.3 (M+H)⁺.

Step 2: Preparation of (1R)-2-(4-ethylbenzyl)-7-hydroxy-1-phenyl-1,2,3,4-tetrahydro-8H-pyrido[1,2-a]pyrazin-8-one 7-benzyloxy-2-[(4-ethylphenyl)methyl]-1-phenyl-3,4-dihydro-1H-pyrido[1,2-a]pyrazin-8-one (240 mg) was purified by chiral chromatography (SFC conditions on ChiralCel OD (50×266 mm, 360 mL/min, 25° C., CO₂+40% EtOH, conc: 20 g/l), to give 100 mg of the first eluting enantiomer (RT 7.13 min) as a brown oil, attributed to (1R)-2-[(4-ethylphenyl)methyl]-7-hydroxy-1-phenyl-3,4-dihydro-1H-pyrido[1,2-a]pyrazin-8-one and 110 mg of the second eluting enantiomer, attributed to (1S)-2-[(4-ethylphenyl)methyl]-7-hydroxy-1-phenyl-3,4-dihydro-1H-pyrido[1,2-a]pyrazin-8-one (RT 11.5 min) as a brown oil. ChiralCel OD-H, 50% EtOH in n-heptane (5 um, 240×4.6 mm, 1.0 mL/min) RT 6.4 min (100% purity). ChiralCel OD-H, 50% EtOH in n-heptane (5 um, 240×4.6 mm, 1.0 mL/min) RT 10.2 min (100% purity).

(1R)-2-[(4-ethylphenyl)methyl]-7-hydroxy-1-phenyl-3,4-dihydro-1H-pyrido[1,2-a]pyrazin-8-one (100 mg, 0.22 mmol) was reacted following Method E to yield the title compound (25 mg).

High-Res MS, ES⁺, 361.1903 (M+H)⁺ (obs.), 361.1916 (M+H)⁺ (calc.).

Example 119: (1S)-2-(4-ethylbenzyl)-7-hydroxy-1-phenyl-1,2,3,4-tetrahydro-8H-pyrido[1,2-a]pyrazin-8-one

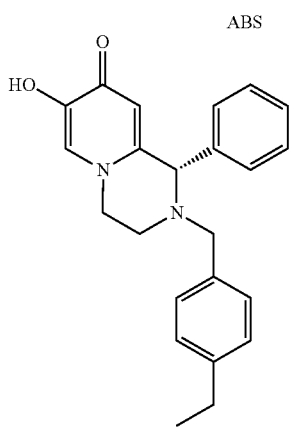 [SMILES: "ABS" ; CCc1ccc(CN2CCn3cc(O)c(=O)cc3[C@@H]2c2ccccc2)cc1]

(1S)-2-[(4-ethylphenyl)methyl]-7-hydroxy-1-phenyl-3,4-dihydro-1H-pyrido[1,2-a]pyrazin-8-one (100 mg, 0.22 mmol) was reacted following Method E to yield the title compound (31 mg, 38%). High-Res MS, ES$^+$, 361.1933 (M+H)$^+$ (obs.), 361.1916 (M+H)$^+$ (calc.).

Example 120: 2-(4-ethylbenzyl)-7-hydroxy-1-(propan-2-yl)-1,2,3,4-tetrahydro-8H-pyrido[1,2-a]pyrazin-8-one

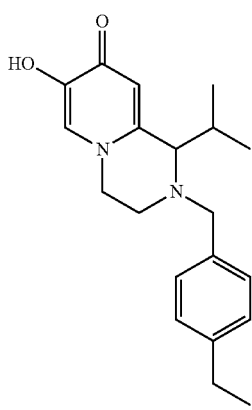 [SMILES: CCc1ccc(CN2CCn3cc(O)c(=O)cc3C2C(C)C)cc1]

Step 1: Preparation of tert-butyl 7-benzyloxy-8-oxo-3,4-dihydro-1H-pyrido[1,2-a]pyrazine-2-carboxylate

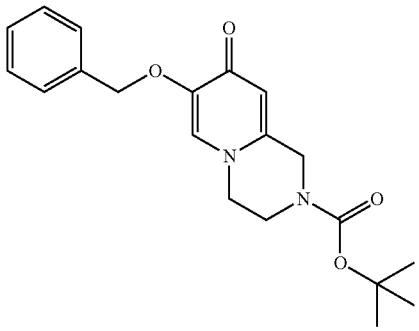 [SMILES: CC(C)(C)OC(=O)N1CCn2cc(OCc3ccccc3)c(=O)cc2C1]

Di-tert-butyl dicarbonate (258 mg, 1.5 eq., 1.2 mmol) was added to a suspension of 7-benzyloxy-1,2,3,4-tetrahydropyrido[1,2-a]pyrazin-8-one (200 mg, 0.78 mmol) and DMAP (0.1 eq., 0.078 mmol) in THF (10 mL) and the reaction mixture was stirred 2 days at rt. H$_2$O was added, the mixture was extracted with EtOAc. The combined org. layers were washed with H$_2$O, then dried over MgSO$_4$, filtered and evaporated. The residue was purified by reverse phase chromatography to yield the title intermediate (100 mg). MS, ES$^+$), 357.1 (M+H)$^+$.

Step 2: Preparation of tert-butyl 7-benzyloxy-1-isopropyl-8-oxo-3,4-dihydro-1H-pyrido[1,2-a]pyrazine-2-carboxylate

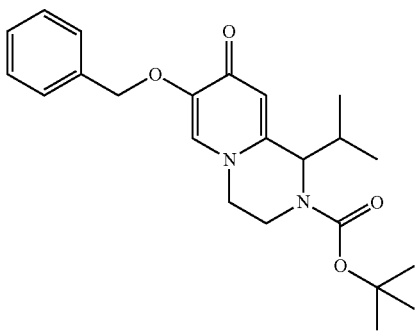 [SMILES: CC(C)C1c2cc(=O)c(OCc3ccccc3)cn2CCN1C(=O)OC(C)(C)C]

sec-butyllithium (1.2 eq., 0.33 mmol, 1.4 M, 0.240 mL) was added dropwise to a cold (−78° C.) solution of tert-butyl 7-benzyloxy-8-oxo-3,4-dihydro-1H-pyrido[1,2-a]pyrazine-2-carboxylate (100 mg, 0.28 mmol) in anhydrous THF (5 mL) and the resulting reaction mixture was stirred 30 min at −78° C. 2-iodopropane (143 mg, 3 eq., 0.84 mmol) was then added dropwise and the mixture was allowed to reach rt and stirred for 14 h. An aq. solution of NaHCO$_3$ was added and the mixture extracted with EtOAc. The combined org. phases were dried over MgSO$_4$, filtered and evaporated under vacuum to give a yellow oil (80 mg). The residue was purified by reverse phase chromatography to yield the title intermediate (20 mg). MS, ES$^+$, 399.2 (M+H)$^+$.

Step 3: Preparation of 7-benzyloxy-1-isopropyl-1,2,3,4-tetrahydropyrido[1,2-a]pyrazin-8-one

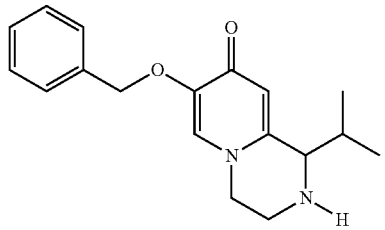 [SMILES: CC(C)C1NCCn2cc(OCc3ccccc3)c(=O)cc21]

TFA (3 mL) was added to a solution of tert-butyl 7-benzyloxy-1-isopropyl-8-oxo-3,4-dihydro-1H-pyrido[1,2-a]pyrazine-2-carboxylate (300 mg, 0.75 mmol) in DCM (3 mL). The mixture was stirred at rt for 2 h. The solvents were evaporated to yield the title intermediate as a brown oil (350 mg) used in the next step without further purification. MS, ES$^+$, 299.1 (M+H)$^+$.

Step 4: Preparation of 7-benzyloxy-2-[(4-ethylphenyl)methyl]-1-isopropyl-3,4-dihydro-1H-pyrido[1,2-a]pyrazin-8-one

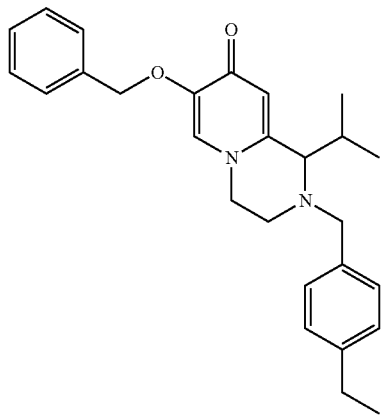 [SMILES: CCc1ccc(CN2CCn3cc(OCc4ccccc4)c(=O)cc3C2C(C)C)cc1]

The title intermediate was prepared according to Method C using 7-benzyloxy-1-isopropyl-1,2,3,4-tetrahydropyrido[1,2-a]pyrazin-8-one and 4-ethylbenzaldehyde. The crude product was purified by reverse phase chromatography (SiO2, DCM-MeOH—NH$_4$OH 97-2.7-0.3) to yield the title intermediate as a yellow oil (57%).

Step 5: Preparation of 2-(4-ethylbenzyl)-7-hydroxy-1-(propan-2-yl)-1,2,3,4-tetrahydro-8H-pyrido[1,2-a]pyrazin-8-one The title compound was prepared according to Method E, using 7-benzyloxy-2-[(4-ethylphenyl)methyl]-1-isopropyl-3,4-dihydro-1H-pyrido[1,2-a]pyrazin-8-one, affording the title compound as a yellow solid MS, ES$^+$), 327 (M+H)$^+$.

Example 121: 2-(2,6-dimethylbenzyl)-7-hydroxy-1-methyl-1,2,3,4-tetrahydro-8H-pyrido[1,2-a]pyrazin-8-one

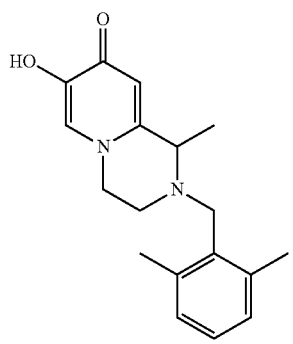 [SMILES: Cc1cccc(C)c1CN1CCn2cc(O)c(=O)cc2C1C]

Step 1: Preparation of 7-benzyloxy-2-[(2,6-dimethylphenyl)methyl]-1-methyl-3,4-dihydro-1H-pyrido[1,2-a]pyrazin-8-one

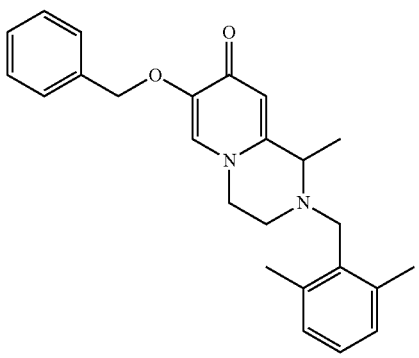 [SMILES: Cc1cccc(C)c1CN1CCn2cc(OCc3ccccc3)c(=O)cc2C1C]

The title compound was prepared according to Method F using 7-benzyloxy-1-methyl-1,2,3,4-tetrahydropyrido[1,2-a]pyrazin-8-one and 2,6-dimethylbenzaldehyde (Intermediate 5), reaction at 40° C. for 40 h. The crude product was purified by chromatography (SiO$_2$, gradient from 100% DCM up to 6% methanolic ammonia in DCM) to give the title intermediate as a colorless oil (60 mg). MS, ES$^+$, 389.3 (M+H)$^+$.

Step 2: Preparation of 2-(2,6-dimethylbenzyl)-7-hydroxy-1-methyl-1,2,3,4-tetrahydro-8H-pyrido[1,2-a]pyrazin-8-one The title compound was prepared according to Method E from 7-benzyloxy-2-[(2,6-dimethylphenyl)methyl]-1-methyl-3,4-dihydro-1H-pyrido[1,2-a]pyrazin-8-one to give the title compound as a yellow solid.
MS, ES⁺, 299.27 (M+H)⁺.

Example 122: 2-(4-ethylbenzyl)-7-hydroxy-1-methyl-1,2,3,4-tetrahydro-8H-pyrido[1,2-a]pyrazin-8-one

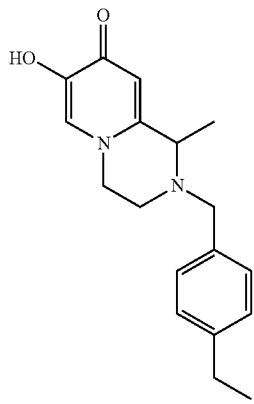 [SMILES: CCc1ccc(CN2CCn3cc(O)c(=O)cc3C2C)cc1]

The title compound was prepared according to Method F using 7-benzyloxy-1-methyl-1,2,3,4-tetrahydropyrido[1,2-a]pyrazin-8-one (Intermediate 5) and 4-ethylbenzaldehyde (quant.) followed by Method E using 7-benzyloxy-2-[(4-ethylphenyl)methyl]-1-methyl-3,4-dihydro-1H-pyrido[1,2-a]pyrazin-8-one.
MS, ES⁺, 299.2 (M+H)⁺.

Example 123: 1-(4-fluorophenyl)-7-hydroxy-2-(quinolin-8-ylmethyl)-1,2,3,4-tetrahydro-8H-pyrido[1,2-a]pyrazin-8-one

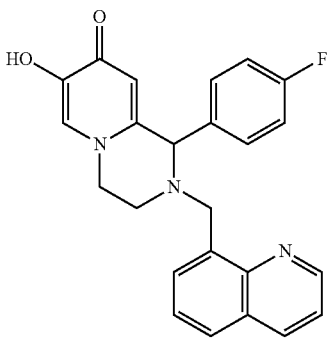 [SMILES: O=c1cc2n(cc1O)CCN(Cc1cccc3cccnc13)C2c1ccc(F)cc1]

Step 1: Preparation of 5-benzyloxy-2-[(4-fluorophenyl)-hydroxy-methy]pyran-4-one

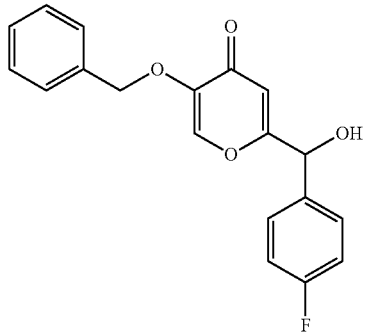 [SMILES: O=c1cc(C(O)c2ccc(F)cc2)occ1OCc1ccccc1]

The title intermediate was prepared according to Method O using 4-fluorophenylmagnesium bromide. MS, ES⁺, 327.2 (M+H)⁺.

Step 2: Preparation of 1-(2-aminoethyl)-5-benzyloxy-2-[(4-fluorophenyl)-hydroxy-methyl]pyridin-4-one

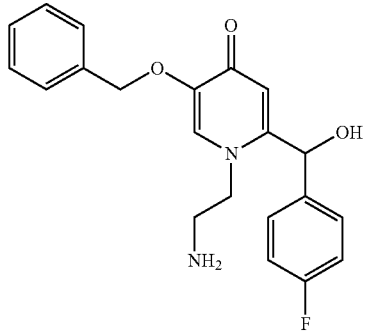 [SMILES: NCCn1cc(OCc2ccccc2)c(=O)cc1C(O)c1ccc(F)cc1]

The title intermediate was prepared according to Method P using 5-benzyloxy-2-[(4-fluorophenyl)-hydroxy-methyl]pyran-4-one as a brown oil. MS, ES⁺, 369.3 (M+H)⁺.

Step 3: Preparation of 7-benzyloxy-1-(4-fluorophenyl)-1,2,3,4-tetrahydropyrido[1,2-a]pyrazin-8-one

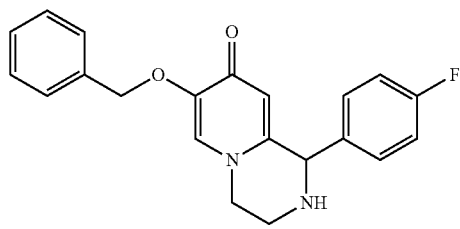 [SMILES: O=c1cc2n(cc1OCc1ccccc1)CCNC2c1ccc(F)cc1]

The title intermediate was prepared according to Method A using 1-(2-aminoethyl)-5-benzyloxy-2-[(4-fluorophenyl)-hydroxy-methyl]pyridin-4-one as a brown oil. MS, ES⁺, 349.3 (M+H)⁺.

Step 4: Preparation of 7-benzyloxy-1-(4-fluorophenyl)-2-(8-quinolylmethyl)-3,4-dihydro-1H-pyrido[1,2-a]pyrazin-8-one

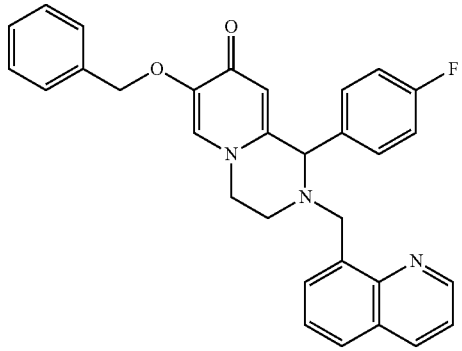 [SMILES: O=c1cc2n(cc1OCc1ccccc1)CCN(Cc1cccc3cccnc13)C2c1ccc(F)cc1]

The title intermediate was prepared according to Method F using 7-benzyloxy-1-(4-fluorophenyl)-1,2,3,4-tetrahydropyrido[1,2-a]pyrazin-8-one and quinoline-8-carbaldehyde as a yellow oil. MS, ES$^+$, 492.3 (M+H)$^+$.

Step 5: Preparation of 1-(4-fluorophenyl)-7-hydroxy-2-(quinolin-8-ylmethyl)-1,2,3,4-tetrahydro-8H-pyrido[1,2-a]pyrazin-8-one The title compound was prepared according to Method E from 7-benzyloxy-1-(4-fluorophenyl)-2-(8-quinolylmethyl)-3,4-dihydro-1H-pyrido[1,2-a]pyrazin-8-one to give the title compound as an orange solid.
MS, ES$^+$, 402.3 (M+H)$^+$.

Example 124: 2-(2,6-dimethylbenzyl)-1-(4-fluorophenyl)-7-hydroxy-1,2,3,4-tetrahydro-8H-pyrido[1,2-a]pyrazin-8-one

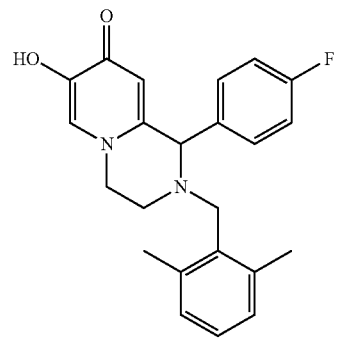 [SMILES: Cc1cccc(C)c1CN1CCn2cc(O)c(=O)cc2C1c1ccc(F)cc1]

Step 1: Preparation of 7-benzyloxy-2-[(2,6-dimethylphenyl)methyl]-1-(4-fluorophenyl)-3,4-dihydro-1H-pyrido[1,2-a]pyrazin-8-one

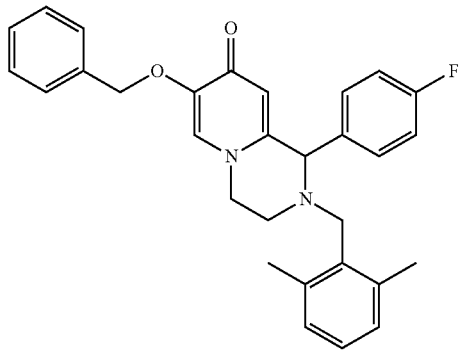 [SMILES: Cc1cccc(C)c1CN1CCn2cc(OCc3ccccc3)c(=O)cc2C1c1ccc(F)cc1]

The title intermediate was prepared according to Method F using 7-benzyloxy-1-(4-fluorophenyl)-1,2,3,4-tetrahydropyrido[1,2-a]pyrazin-8-one and 2,6-dimethylbenzaldehyde.
MS, ES$^+$, 469.3 (M+H)$^+$, Step 2: Preparation of 2-(2,6-dimethylbenzyl)-1-(4-fluorophenyl)-7-hydroxy-1,2,3,4-tetrahydro-8H-pyrido[1,2-a]pyrazin-8-one The title compound was prepared according to Method E using 7-benzyloxy-2-[(2,6-dimethylphenyl)methyl]-1-(4-fluorophenyl)-3,4-dihydro-1H-pyrido[1,2-a]pyrazin-8-one (57%).
MS, ES$^+$, 379.3 (M+H)$^+$.

Example 125: 2-(4-ethylbenzyl)-7-hydroxy-1-(tetrahydro-2H-pyran-4-yl)-1,2,3,4-tetrahydro-8H-pyrido[1,2-a]pyrazin-8-one

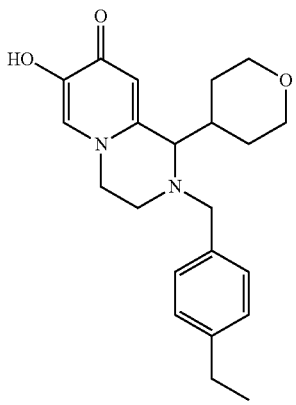 [SMILES: CCc1ccc(CN2CCn3cc(O)c(=O)cc3C2C2CCOCC2)cc1]

Step 1: Preparation of 7-benzyloxy-2-[(4-ethylphenyl)methyl]-1-tetrahydropyran-4-yl-3,4-dihydro-1H-pyrido[1,2-a]pyrazin-8-one

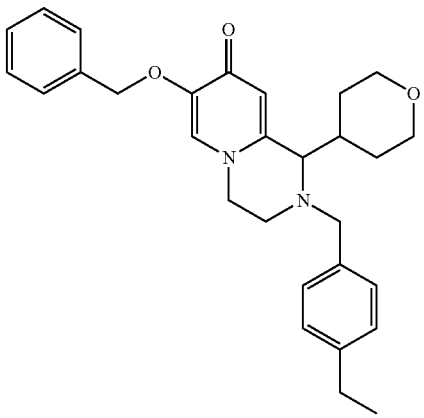 [SMILES: CCc1ccc(CN2CCn3cc(OCc4ccccc4)c(=O)cc3C2C2CCOCC2)cc1]

The title intermediate was prepared according to Method F using 7-benzyloxy-1-tetrahydropyran-4-yl-1,2,3,4-tetrahydropyrido[1,2-a]pyrazin-8-one (Intermediate 6) as a white solid (65%). MS, ES+, 459.4 (M+H)+.

Step 2: Preparation of 2-(4-ethylbenzyl)-7-hydroxy-1-(tetrahydro-2H-pyran-4-yl)-1,2,3,4-tetrahydro-8H-pyrido[1,2-a]pyrazin-8-one The title compound was prepared according to Method E using 7-benzyloxy-2-[(4-ethylphenyl)methyl]-1-tetrahydropyran-4-yl-3,4-dihydro-1H-pyrido[1,2-a]pyrazin-8-one as a pale yellow solid (93%).
MS, ES+, 369.32 (M+H)+.

Example 126: 2-(4-ethylbenzyl)-7-hydroxy-1-[3-(pyridin-3-yl)phenyl]-1,2,3,4-tetrahydro-8H-pyrido[1,2-a]pyrazin-8-one Step 1: Preparation of 5-benzyloxy-2-[(3-bromophenyl)-hydroxy-methyl]pyran-4-one

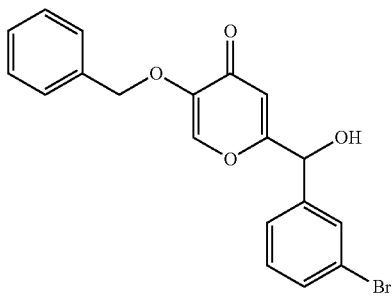 [SMILES: O=c1cc(C(O)c2cccc(Br)c2)occ1OCc1ccccc1]

I2 (ca. 5 mg) was added to a suspension of magnesium (26.1 mmol, 633 mg, 1.2 eq.) in anhydrous THF (5 mL). A solution of 1,3-dibromobenzene (26.1 mmol, 6.33 g, 1.2 eq.) in THF (10 mL) was added dropwise. The mixture was stirred at rt for 3 h then 1 h at reflux.
This solution was added dropwise onto a solution of 5-benzyloxy-4-oxo-pyran-2-carbaldehyde (21.7 mmol, 5.0 g, 1.0 eq.) in THF (100 mL) and the mixture was stirred 1 h at rt. An aq. solution of HCl (20 mL, 1 N) was added. The resulting reaction mixture was extracted with EtOAc. The combined org. layers were dried over MgSO4, filtered and evaporated to give a residue (13 g). Purification by chromatography (SiO2, DCM-MeOH—NH4OH 98-1.8-0.2) yielded the title intermediate (1.3 g). MS, ES+, 487.2 (M+H)+.

Step 2: Preparation of 1-(2-aminoethyl)-5-benzyloxy-2-[(3-bromophenyl)-hydroxy-methyl]pyridin-4-one

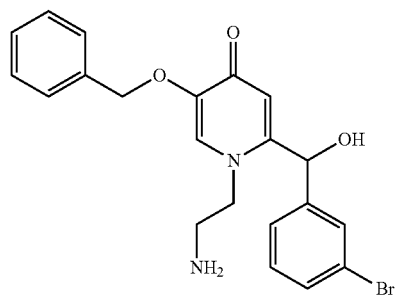 [SMILES: NCCn1cc(OCc2ccccc2)c(=O)cc1C(O)c1cccc(Br)c1]

Ethylenediamine (5.1 mmol, 0.3 g, 1.5 eq.) was added to a solution of 5-benzyloxy-2-[(3-bromophenyl)-hydroxy-methyl]pyran-4-one (3.4 mmol, 1.3 g) in EtOH (10 mL). The mixture was stirred at 40° C. for 48 h. The solvent was evaporated under vacuum to give a residue used in the next step without any further purification. MS, ES+, 429.2/431.2 (M+H)+.

Step 3: Preparation of 7-benzyloxy-1-(3-bromophenyl)-1,2,3,4-tetrahydropyrido[1,2-a]pyrazin-8-one

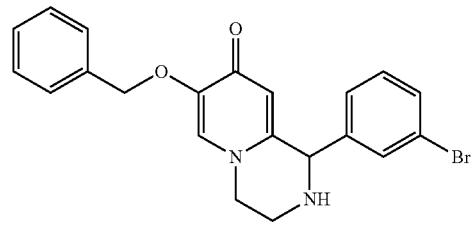 [SMILES: O=c1cc2n(cc1OCc1ccccc1)CCNC2c1cccc(Br)c1]

The title intermediate was prepared according to Method A using 1-(2-aminoethyl)-5-benzyloxy-2-[(3-bromophenyl)-hydroxy-methyl]pyridin-4-one, involving a purification by reverse phase chromatography.

Step 4: Preparation of 7-benzyloxy-1-(3-bromophenyl)-2-[(4-ethylphenyl)methyl]-3,4-dihydro-1H-pyrido[1,2-a]pyrazin-8-one

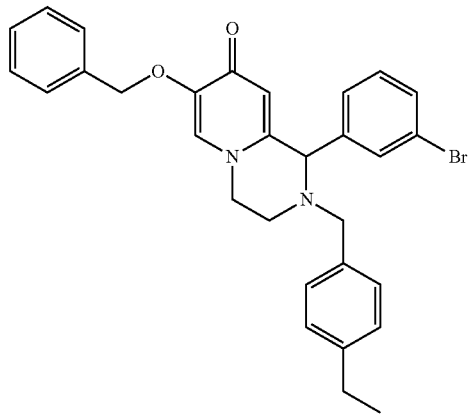 [SMILES: CCc1ccc(CN2CCn3cc(OCc4ccccc4)c(=O)cc3C2c2cccc(Br)c2)cc1]

The title intermediate was prepared according to Method F using 7-benzyloxy-1-(3-bromophenyl)-1,2,3,4-tetrahydro-pyrido[1,2-a]pyrazin-8-one (43%) involving a purification by chromatography (SiO2, gradient from DCM up to 10% methanolic ammonia in DCM). MS, ES+, 529.2/531.2 (M+H)+.

Step 5: Preparation of 7-benzyloxy-2-[(4-ethylphenyl)methyl]-1-[3-(3-pyridyl)phenyl]-3,4-dihydro-1H-pyrido[1,2-a]pyrazin-8-one

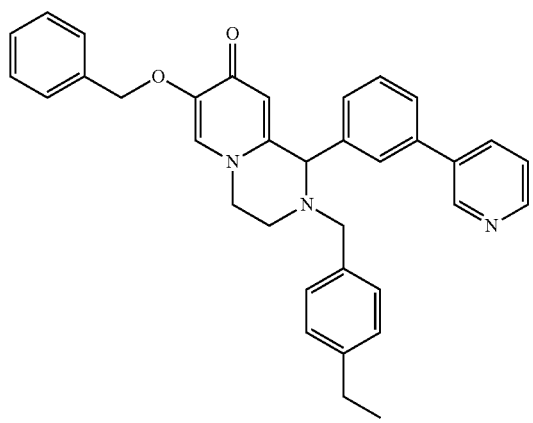 [SMILES: CCc1ccc(CN2CCn3cc(OCc4ccccc4)c(=O)cc3C2c2cccc(-c3cccnc3)c2)cc1]

7-benzyloxy-1-(3-bromophenyl)-2-[(4-ethylphenyl)methyl]-3,4-dihydro-1H-pyrido[1,2-a]pyrazin-8-one (0.19 mmol, 100 mg), pyridine-3-boronic acid (0.23 mmol, 29 mg, 1.2 eq.), cesium carbonate (2.29 mmol, 745 mg) and [1,1'-bis(diphenylphosphino)ferrocene]dichloropalladium (11) (0.009 mmol, 7 mg, 0.05 eq.) were placed in a mixture 10:1 dioxane:H2O (2 mL). The mixture was degassed then heated 3 h at 100° C. The reaction mixture was then cooled to rt. H2O was added and the mixture extracted with EtOAc. The combined org. layers were washed with a sat. solution of NaCl, dried over MgSO4, filtered and evaporated to give a residue (100 mg). Purification by chromatography (SiO2, gradient from DCM up to 10% methanolic ammonia) yielded the title intermediate as a brown oil (89 mg, 89%). MS, ES+, 528.2 (M+H)+.

Step 6: Preparation of 2-(4-ethylbenzyl)-7-hydroxy-1-[3-(pyridin-3-yl)phenyl]-1,2,3,4-tetrahydro-8H-pyrido[1,2-a]pyrazin-8-one The title compound was prepared according to Method E using 7-benzyloxy-2-[(4-ethylphenyl)methyl]-1-[3-(3-pyridyl)phenyl]-3,4-dihydro-1H-pyrido[1,2-a]pyrazin-8-one as a pale yellow solid.
MS, ES+, 438.2 (M+H)+.

Example 127: 2-benzyl-7-hydroxy-3-phenyl-1,2,3,4-tetrahydro-8H-pyrido[1,2-a]pyrazin-8-one

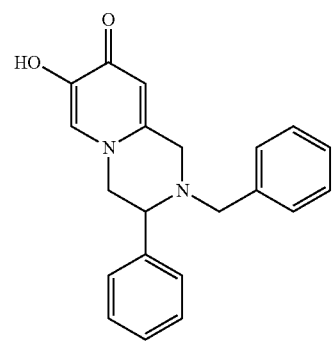 [SMILES: O=c1cc2n(cc1O)CC(c1ccccc1)N(Cc1ccccc1)C2]

Step 1: Preparation of 2-benzyl-7-benzyloxy-3-phenyl-3,4-dihydro-1H-pyrido[1,2-a]pyrazin-8-one

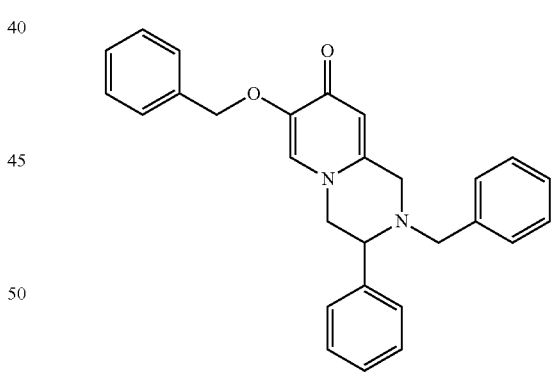

The title intermediate was prepared according to Method Q using 7-benzyloxy-3-phenyl-1,2,3,4-tetrahydropyrido[1,2-a]pyrazin-8-one (Intermediate 7) and benzyl bromide as a yellow oil. MS, ES+, 423.3 (M+H)+.

Step 2: Preparation of 2-benzyl-7-hydroxy-3-phenyl-1,2,3,4-tetrahydro-8H-pyrido[1,2-a]pyrazin-8-one The title compound was prepared according to Method E using of 2-benzyl-7-benzyloxy-3-phenyl-3,4-dihydro-1H-pyrido[1,2-a]pyrazin-8-one (26%). High-Res MS, ES+, 333.1604 (M+H) (obs.), 333.1603 (M+H)+ (calc.).

Example 128: 2,3-dibenzyl-7-hydroxy-1,2,3,4-tetrahydro-8H-pyrido[1,2-a]pyrazin-8-one

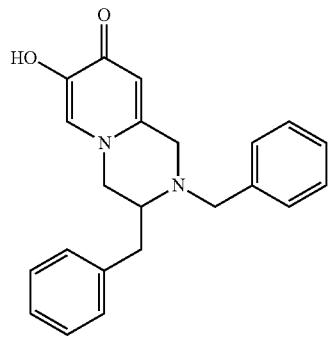 [SMILES: O=c1cc2n(cc1O)CC(Cc1ccccc1)N(Cc1ccccc1)C2]

Step 2: Preparation of 2,3-dibenzyl-7-hydroxy-1,2,3,4-tetrahydro-8H-pyrido[1,2-a]pyrazin-8-one

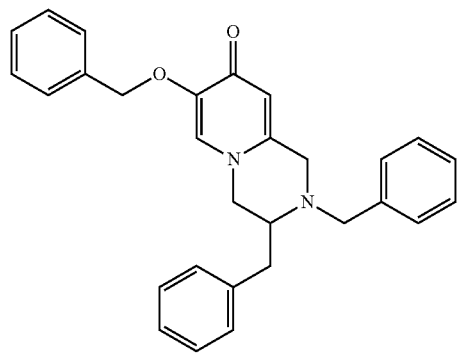 [SMILES: O=c1cc2n(cc1OCc1ccccc1)CC(Cc1ccccc1)N(Cc1ccccc1)C2]

The title compound was prepared according to Method E using 2,3-dibenzyl-7-benzyloxy-3,4-dihydro-1H-pyrido[1,2-a]pyrazin-8-one as an orange solid (quant.). High-Res MS, ES+, 347.175 (M+H)+ (obs.), 347.1759 (M+H)+ (calc.).

Example 129: 3-benzyl-2-(2,6-dichlorobenzyl)-7-hydroxy-1,2,3,4-tetrahydro-8H-pyrido[1,2-a]pyrazin-8-one

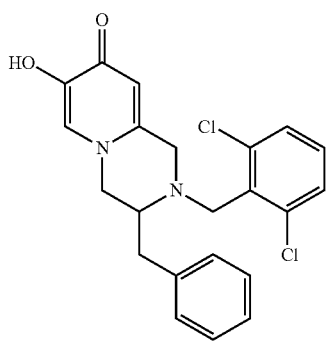 [SMILES: O=c1cc2n(cc1O)CC(Cc1ccccc1)N(Cc1c(Cl)cccc1Cl)C2]

Step 1: Preparation of 3-benzyl-7-benzyloxy-2-[(2,6-dichlorophenyl)methyl]-3,4-dihydro-1H-pyrido[1,2-a]pyrazin-8-one

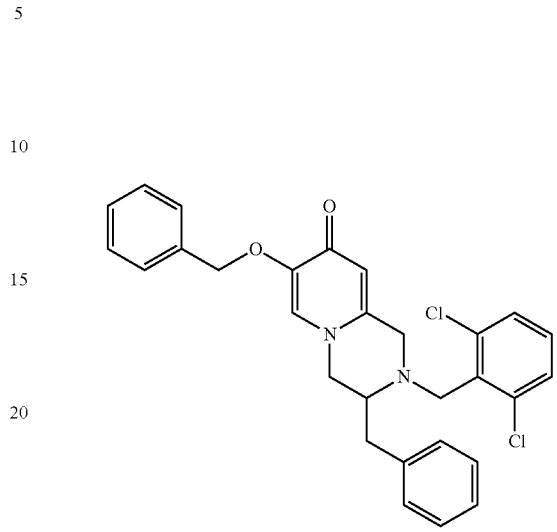

The title intermediate was prepared according to Method F using 3-benzyl-7-benzyloxy-1,2,3,4-tetrahydropyrido[1,2-a]pyrazin-8-one (Intermediate 8) and 2,6-dichlorobenzaldehyde involving a purification of the crude product by chromatography (SiO2, gradient from DCM up to 10% methanolic ammonia in DCM) as a colorless oil. MS, ES+, 505.3 (M+H)+.

Step 2: Preparation of 3-benzyl-2-(2,6-dichlorobenzyl)-7-hydroxy-1,2,3,4-tetrahydro-8H-pyrido[1,2-a]pyrazin-8-one The title compound was prepared according to Method E using 3-benzyl-7-benzyloxy-2-[(2,6-dichlorophenyl)methyl]-3,4-dihydro-1H-pyrido[1,2-a]pyrazin-8-one (18%). High-Res MS, ES+, 415.0984 (M+H)+ (obs.), 415.098 (M+H)+ (calc.).

Example 130: 7-hydroxy-3-methyl-2-[4-(trifluoromethoxy)benzyl]-1,2,3,4-tetrahydro-8H-pyrido[1,2-a]pyrazin-8-one

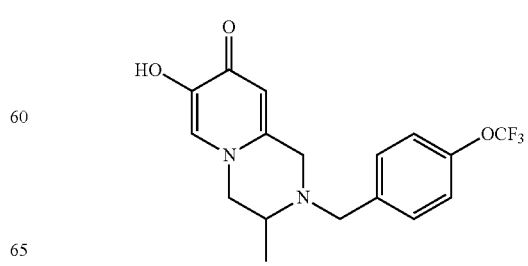

Step 1: Preparation of 7-benzyloxy-3-methyl-2-[[4-(trifluoromethoxy)phenyl]methyl]-3,4-dihydro-1H-pyrido[1,2-a]pyrazin-8-one

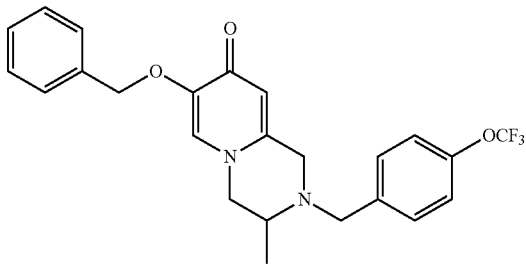 [SMILES: CC1Cn2cc(OCc3ccccc3)c(=O)cc2CN1Cc1ccc(OC(F)(F)F)cc1]

The title intermediate was prepared according to Method F using 7-benzyloxy-3-methyl-1,2,3,4-tetrahydropyrido[1,2-a]pyrazin-8-one (Intermediate 9) and 4-(trifluoromethoxy)benzaldehyde involving a purification of the crude product by chromatography (SiO$_2$, gradient from DCM up to 10% methanolic ammonia in DCM) as a colorless oil (61%). MS, ES$^+$, 445.3 (M+H)$^+$.

Step 2: Preparation of 7-hydroxy-3-methyl-2-[4-(trifluoromethoxy)benzyl]-1,2,3,4-tetrahydro-8H-pyrido[1,2-a]pyrazin-8-one The title compound was prepared according to Method E using 7-benzyloxy-3-methyl-2-[[4-(trifluoromethoxy)phenyl]methyl]-3,4-dihydro-1H-pyrido[1,2-a]pyrazin-8-one as a light yellow solid (66%).
High-Res MS, ES$^+$, 355.1269 (M+H)$^+$ (obs.), 355.127 (M+H)$^+$ (calc.).

Example 131: 2-benzyl-7-hydroxy-3-methyl-1,2,3,4-tetrahydro-8H-pyrido[1,2-a]pyrazin-8-one

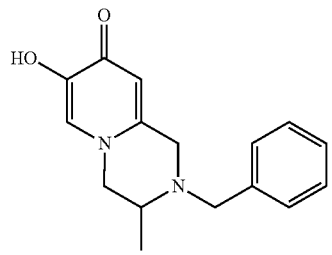 [SMILES: CC1Cn2cc(O)c(=O)cc2CN1Cc1ccccc1]

Step 1: Preparation of 2-benzyl-7-benzyloxy-3-methyl-3,4-dihydro-1H-pyrido[1,2-a]pyrazin-8-one

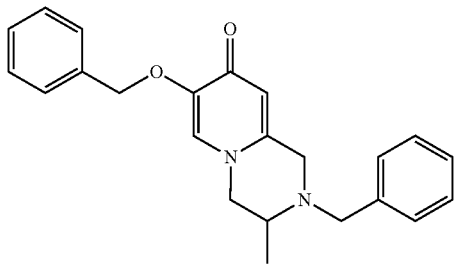 [SMILES: CC1Cn2cc(OCc3ccccc3)c(=O)cc2CN1Cc1ccccc1]

The title intermediate was prepared according to Method F using 7-benzyloxy-3-methyl-1,2,3,4-tetrahydropyrido[1,2-a]pyrazin-8-one (Intermediate 9) and benzaldehyde involving a purification of the crude product by chromatography (SiO$_2$, gradient from DCM up to 10% methanolic ammonia in DCM) as a colorless oil (90%). MS, ES$^+$, 361.3 (M+H)$^+$.

Step 2: Preparation of 2-benzyl-7-hydroxy-3-methyl-1,2,3,4-tetrahydro-8H-pyrido[1,2-a]pyrazin-8-one The title compound was prepared according to Method E using 2-benzyl-7-benzyloxy-3-methyl-3,4-dihydro-1H-pyrido[1,2-a]pyrazin-8-one as a light yellow solid (71%).
High-Res MS, ES$^+$, 271.1454 (M+H)$^+$ (obs.), 271.1447 (M+H)$^+$ (calc.).

Example 132: 2-benzyl-7-hydroxy-3-(2-phenyl-ethyl)-1,2,3,4-tetrahydro-8H-pyrido[1,2-a]pyrazin-8-one

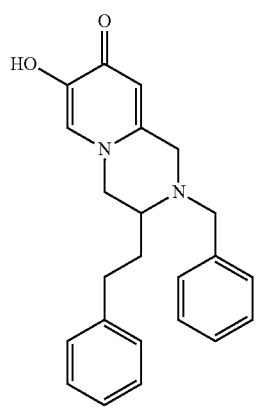 [SMILES: O=c1cc2n(cc1O)CC(CCc1ccccc1)N(Cc1ccccc1)C2]

Step 1: Preparation of 5-benzyloxy-2-(chloromethyl)-1-(2-chloro-4-phenyl-butyl)pyridin-4-one

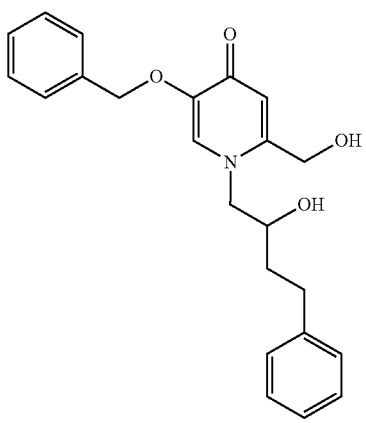 [SMILES: O=c1cc(CO)n(CC(O)CCc2ccccc2)cc1OCc1ccccc1]

The title intermediate was prepared according to Method C using 1-amino-4-phenylbutan-2-ol involving a purification of the crude product by chromatography (SiO$_2$, gradient from DCM up to 15% methanolic ammonia in DCM) as a yellow oil. MS, ES+, 380.3 (M+H)+.

Step 2: Preparation of 5-benzyloxy-2-(chloromethyl)-1-(2-chloro-4-phenyl-butyl)pyridin-4-one

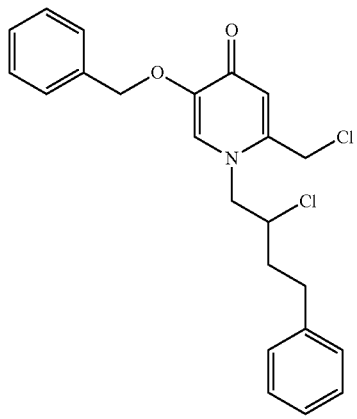 [SMILES: O=c1cc(CCl)n(CC(Cl)CCc2ccccc2)cc1OCc1ccccc1]

The title intermediate was prepared according to Method B using 5-benzyloxy-2-(chloromethyl)-1-(2-chloro-4-phenyl-butyl)pyridin-4-one at 60° C. as a dark beige powder used in the next step without any further purification. MS, ES+, 416.1/418.1 (M+H)+.

Step 3: Preparation of 2-benzyl-7-benzyloxy-3-phenethyl-3,4-dihydro-1H-pyrido[1,2-a]pyrazin-8-one

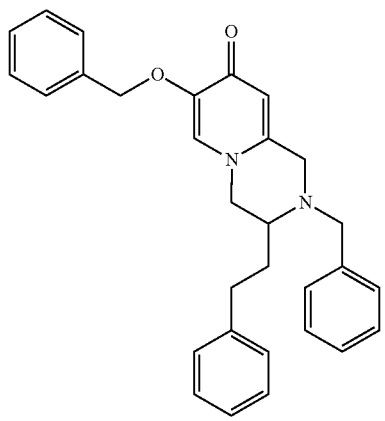 [SMILES: O=c1cc2n(cc1OCc1ccccc1)CC(CCc1ccccc1)N(Cc1ccccc1)C2]

The title intermediate was prepared according to Method K using 5-benzyloxy-2-(chloromethyl)-1-(2-chloro-4-phenyl-butyl)pyridin-4-one, benzylamine and triethylamine, involving a purification of the crude product by chromatography (SiO2, gradient from DCM up to 15% methanolic ammonia in DCM) as a dark yellow oil. MS, ES+, 451.2 (M+H)+.

Step 4: Preparation of: 2-benzyl-7-hydroxy-3-(2-phenylethyl)-1,2,3,4-tetrahydro-8H-pyrido[1,2-a]pyrazin-8-one The title compound was prepared according to Method E using 2-benzyl-7-benzyloxy-3-phenethyl-3,4-dihydro-1H-pyrido[1,2-a]pyrazin-8-one as a yellow solid (42%).

High-Res MS, ES+, 361.1907 (M+H)+ (obs.), 361.1916 (M+H)+ (calc.).

Example 133: 9-chloro-2-(2-chloro-6-fluorobenzyl)-7-hydroxy-1,2,3,4-tetrahydro-8H-pyrido[1,2-a]pyrazin-8-one

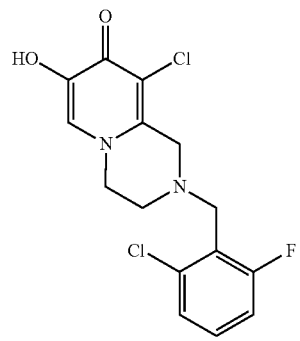 [SMILES: O=c1c(O)cn2c(c1Cl)CN(Cc1c(F)cccc1Cl)CC2]

Step 1: Preparation of 7-benzyloxy-9-chloro-2-[(2-chloro-6-fluoro-phenyl)methyl]-3,4-dihydro-1H-pyrido[1,2-a]pyrazin-8-one

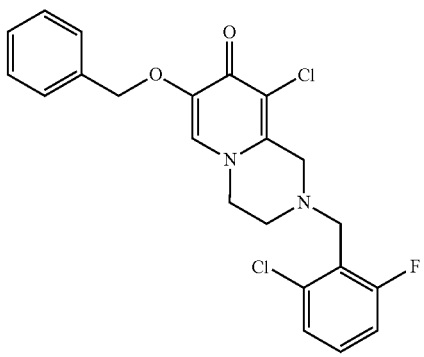 [SMILES: O=c1c(OCc2ccccc2)cn2c(c1Cl)CN(Cc1c(F)cccc1Cl)CC2]

7-benzyloxy-2-[(2-chloro-6-fluoro-phenyl)methyl]-3,4-dihydro-1H-pyrido[1,2-a]pyrazin-8-one (Intermediate prepared for the Example 7, 63 mg, 0.16 mmol) and N-chlorosuccinimide (22 mg, 0.16 mmol) were poured in CH3CN (1 mL). The solution was degassed for 2 min, then heated overnight at 50° C. DCM (1 mL) was added and the suspension filtered on a 5 um filter. The solvent was evaporated to yield a light yellow oil (45 mg) used in the next step without any further purification. MS, ES+, 433.2/435.2 (M+H)+.

Step 2: Preparation of 9-chloro-2-(2-chloro-6-fluorobenzyl)-7-hydroxy-1,2,3,4-tetrahydro-8H-pyrido[1,2-a]pyrazin-8-one The title compound was prepared according to Method E using 7-benzyloxy-9-chloro-2-[(2-chloro-6-fluoro-phenyl)methyl]-3,4-dihydro-1H-pyrido[1,2-a]pyrazin-8-one as an off white powder (quant.).

High-Res MS, ES+, 343.0398 (M+H)+ (obs.), 343.0416 (M+H)+ (calc.).

Example 134: 6-fluoro-7-hydroxy-2-[[2-chlorophenyl]methyl]-3,4-dihydro-1H-pyrido[1,2-a]pyrazin-8-one

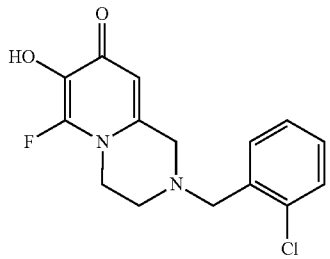 [SMILES: O=c1cc2n(c(F)c1O)CCN(Cc1ccccc1Cl)C2]

Step 1: Preparation of 6-bromo-2-fluoropyridin-3-ol

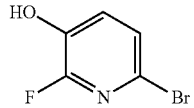

To a stirring solution of 2-fluoropyridin-3-ol (8.00 g, 70.7 mmol) in acetic acid (70 mL), potassium acetate (4.25 g, 70.7 mmol) was added. The solution was cooled to 0° C. after the potassium acetate had dissolved. Bromine (3.65 mL, 70.7 mmol) in acetic acid (10 mL) was added dropwise and the resulting mixture was stirred at room temperature for 1 h. Sodium sulfite (5 g) was added, followed by 1 N NaOH (30 mL). After the brown color of the solution disappeared, the solution was extracted with EtOAc (2×100 mL). The EtOAc extracts were combined, washed with water (100 mL), saturated NaHCO$_3$ (100 mL), brine (100 mL), dried over Na$_2$SO$_4$, filtered and the solvent removed in vacuo to give a residue which was purified by automated normal-phase chromatography (0-40% EtOAc/heptane) to give 6-bromo-2-fluoropyridin-3-ol (8.80 g, 45.8 mmol, 65% yield) as a white solid. MS (ES$^+$) m/z 191.9 [M+H]$^+$.

$^1$H NMR (400 MHz, CDCl$_3$) δ ppm 7.24-7.34 (m, 2H), 5.75 (br. s., 1H).

Step 2: Preparation of 6-bromo-2-fluoro-3-methoxypyridine

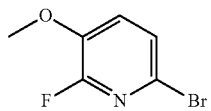

To a stirring solution of 6-bromo-2-fluoropyridin-3-ol (8.80 g, 45.8 mmol) in acetone (150 mL), potassium carbonate (12.67 g, 91.67 mmol) and iodomethane (5.71 mL, 91.7 mmol) were added. The resulting mixture was stirred under reflux overnight. The contents were filtered and the solvent removed in vacuo to give a residue which was purified by automated normal-phase chromatography (0-30% EtOAc/heptane) to give 6-bromo-2-fluoro-3-methoxypyridine (7.00 g, 34.0 mmol, 74% yield) as a white solid. MS (ES$^+$) m/z 206.0 [M+H]$^+$.

$^1$H NMR (400 MHz, CDCl$_3$) δ ppm 7.27-7.34 (m, 1H), 7.20 (dd, 1H), 3.88-3.95 (m, 3H).

Step 3: Preparation of 6-bromo-2-fluoro-3-methoxypyridin-4-ol

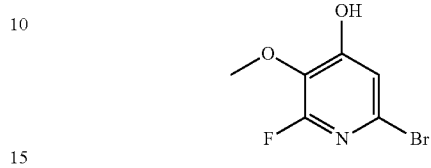

To a stirring solution of 6-bromo-2-fluoro-3-methoxypyridine (2.70 g, 13.1 mmol) in THF (50 mL) at −78° C., LDA (2 M in THF, 7.86 mL, 15.7 mmol) was added slowly. The resulting mixture was stirred at −78° C. for 1 h, then trimethyl borate (1.75 mL, 15.7 mmol) was added portionwise.

The resulting mixture was stirred at −78° C. for 1 h then allowed to reach room temperature with stirring over 1 h. Hydrogen peroxide (30%, 2.49 mL, 15.7 mmol) was added slowly to the contents, and the resulting mixture was stirred at room temperature for 1 h. Sodium sulfite (5 g) was added, followed by water (50 mL) and 1 N HCl (50 mL) and stirring continued for 1 h. The contents were extracted with EtOAc (2×150 mL). The EtOAc extracts were combined, washed with brine (200 mL), dried over Na$_2$SO$_4$, filtered and the solvent removed in vacuo to give an off-white solid, which was used without further purification.

Step 4: Preparation of 4-benzyloxy-6-bromo-2-fluoro-3-methoxypyridine

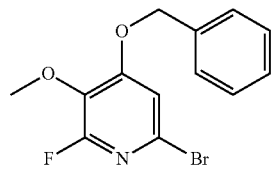 [SMILES: COc1c(OCc2ccccc2)cc(Br)nc1F]

To a stirring solution of crude 6-bromo-2-fluoro-3-methoxypyridin-4-ol (2.91 g, 13.1 mmol) in acetonitrile (50 mL), benzyl bromide (1.87 mL, 15.7 mmol) and potassium carbonate (3.98 g, 28.8 mmol) were added and the resulting mixture stirred at reflux overnight. After cooling to room temperature, the contents were filtered and washed with EtOAc. The filtrate was concentrated in vacuo to give a residue which was purified by automated normal-phase chromatography (0-20% EtOAc/heptane) to give 4-benzyloxy-6-bromo-2-fluoro-3-methoxypyridine (3.22 g, 10.3 mmol, 79% yield, two steps) as a white solid. MS (ES$^+$) m/z 312.0 [M+H]$^+$.

$^1$H NMR (400 MHz, CDCl$_3$) δ ppm 7.36-7.49 (m, 5H), 6.96-7.02 (m, 1H), 5.19 (s, 2H), 3.88-3.96 (m, 3H).

Step 5: Preparation of 4-benzyloxy-6-fluoro-5-methoxypyridine-2-carbaldehyde

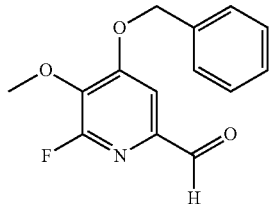 [SMILES: COc1c(OCc2ccccc2)cc(C=O)nc1F]

To a stirring solution of 4-benzyloxy-6-bromo-2-fluoro-3-methoxypyridine (4.10 g, 13.1 mmol) in Et$_2$O (60 mL) at −78° C., nBuLi (1.6 M in hexanes, 9.85 mL, 15.8 mmol) was added dropwise. After the resulting mixture was stirred at −78° C. for 40 min, DMF (1.52 mL, 19.7 mmol) was added and stirring continued for 2 h at −78° C. Saturated NH$_4$Cl (50 mL) was added and the resulting mixture extracted with EtOAc (2×150 mL). The EtOAc extracts were combined, washed with water (100 mL), brine (100 mL), dried over Na$_2$SO$_4$, filtered and the solvent removed in vacuo to give a residue which was purified by automated normal-phase chromatography (0-30% EtOAc/heptane) to give 4-benzyloxy-6-fluoro-5-methoxypyridine-2-carbaldehyde (1.85 g, 7.06 mmol, 54% yield) as an off-white solid. MS (ES$^+$) m/z 262.0 [M+H]$^+$.

$^1$H NMR (400 MHz, CDCl$_3$) δ ppm 9.77-9.84 (m, 1H), 7.52-7.58 (m, 1H), 7.35-7.49 (m, 5H), 5.22-5.30 (m, 2H), 4.03-4.10 (m, 3H).

Step 6: Preparation of 2-[(4-benzyloxy-6-fluoro-5-methoxy-2-pyridyl)methylamino]ethanol

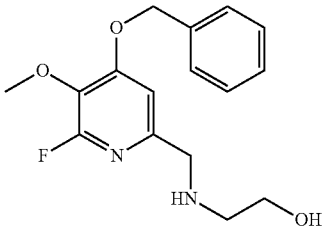 [SMILES: COc1c(OCc2ccccc2)cc(CNCCO)nc1F]

To a stirring solution of 4-benzyloxy-6-fluoro-5-methoxypyridine-2-carbaldehyde (1.85 g, 7.06 mmol) in MeOH (30 mL) at room temperature was added ethanolamine (0.52 g, 8.47 mmol). The contents were stirred at room temperature for 30 min, then NaBH$_4$ (0.40 g, 10.6 mmol) was added. After stirring 1 h, the reaction was complete and the solvent was removed in vacuo. Ethyl acetate (150 mL) was added then washed with 0.1 N NaOH (20 mL), brine (20 mL), dried over Na$_2$SO$_4$, filtered and the solvent removed in vacuo to give 2-[(4-benzyloxy-6-fluoro-5-methoxy-2-pyridyl)methylamino]ethanol (1.75 g, 5.71 mmol, 81% yield) as a colorless oil which was used without further purification.

Step 7: Preparation of tert-butyl N-[(4-benzyloxy-6-fluoro-5-methoxy-2-pyridyl)methyl]-N-(2-hydroxyethyl)carbamate

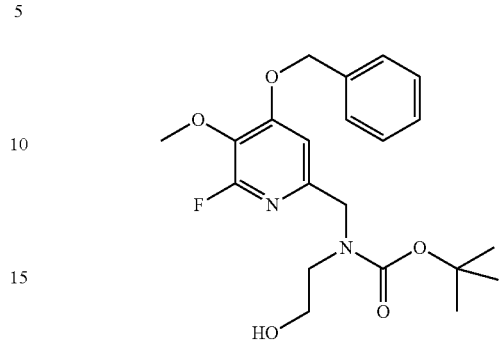

To a stirring solution of 2-[(4-benzyloxy-6-fluoro-5-methoxy-2-pyridyl)methylamino]ethanol (2.16 g, 7.06 mmol) in DCM (50 mL), was added triethylamine (1.96 mL, 14.1 mmol), followed by di-tert-butydicarbonate (2.00.g, 9.18 mmol). The resulting mixture was stirred at room temperature overnight, diluted with DCM (30 mL) and washed with 1 N HCl (2×30 mL), brine (20 mL), dried over Na$_2$SO$_4$, filtered and the solvent removed in vacuo to give a residue which was purified by automated normal-phase chromatography (0-60% EtOAc/heptane) to give tert-butyl N-[(4-benzyloxy-6-fluoro-5-methoxy-2-pyridyl)methyl]-N-(2-hydroxyethyl)carbamate (2.32 g, 5.72 mmol, 81% yield) as a colorless oil. MS (ES+) m/z 407.2 [M+H]$^+$.

$^1$H NMR (400 MHz, CDCl$_3$) δ ppm 7.33-7.46 (m, 5H), 6.69-6.90 (m, 1H), 5.20 (br. s., 2H), 4.32 (d, 2H), 3.93 (d, 3H), 3.78 (br. s., 2H), 3.46-3.55 (m, 2H).

Step 8: Preparation of 2-[(4-benzyloxy-6-fluoro-5-methoxy-2-pyridyl)methyl-tert-butoxycarbonyl-amino]ethyl methanesulfonate

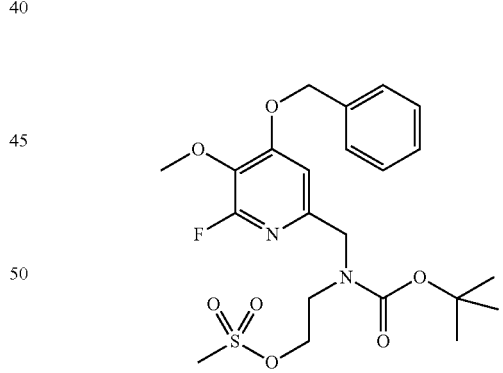

To a stirring solution of tert-butyl N-[(4-benzyloxy-6-fluoro-5-methoxy-2-pyridyl)methyl]-N-(2-hydroxyethyl)carbamate (2.32 g, 5.71 mmol) in DCM (50 mL) at 0° C. was added triethylamine (1.19 mL, 8.56 mmol) and methanesulfonyl chloride (0.53 mL, 6.85 mmol). The resulting mixture was stirred at 0° C. for 1 h, diluted with DCM (20 mL) and washed with 1 N HCl (3×20 mL), water (5 mL), brine (10 mL), dried over Na$_2$SO$_4$, filtered and the solvent removed in vacuo to give 2-[(4-benzyloxy-6-fluoro-5-methoxy-2-pyridyl)methyl-tert-butoxycarbonyl-amino] ethyl methanesulfonate (2.63 g, 5.43 mmol, 95% yield) as a colorless oil which was used without further purification.

Step 9: Preparation of 2-[tert-butoxycarbonyl-[(6-fluoro-4-hydroxy-5-methoxy-2-pyridyl)methyl]amino]ethyl methanesulfonate

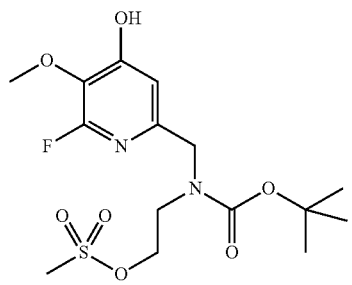 [SMILES: COc1c(O)cc(CN(CCOS(C)(=O)=O)C(=O)OC(C)(C)C)nc1F]

To a stirring solution of 2-[(4-benzyloxy-6-fluoro-5-methoxy-2-pyridyl)methyl-tert-butoxycarbonyl-amino] ethyl methanesulfonate (2.63 g, 5.43 mmol) in EtOAc (60 mL), was added 10% Pd/C (1.5 g, 1.42 mmol). After purging under vacuum, the contents were reacted for 2 h under $H_2$ at atmospheric pressure. The contents were filtered and the solvent removed in vacuo to give a residue which was used without further purification. MS (ES$^+$) m/z 395.0 [M+H]$^+$.

$^1$H NMR (400 MHz, DMSO-d$_6$) δ ppm 6.75 (s, 1H), 4.25-4.32 (s, 3H), 3.73-3.78 (s, 3H), 3.48-3.58 (m, 4H), 3.14-3.18 (m, 2H), 2.31-2.37 (m, 9H).

Step 10: Preparation of tert-butyl 6-fluoro-7-methoxy-8-oxo-3,4-dihydro-1H-pyrido[1,2-a]pyrazine-2-carboxylate

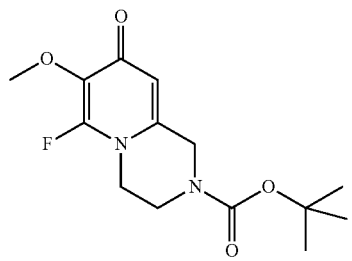 [SMILES: COc1c(F)n2c(cc1=O)CN(C(=O)OC(C)(C)C)CC2]

To a stirring solution of 2-[tert-butoxycarbonyl-[(6-fluoro-4-hydroxy-5-methoxy-2-pyridyl)methyl]amino]ethyl methanesulfonate (2.10 g, 5.32 mmol) in acetonitrile (30 mL), was added potassium carbonate (1.10 g, 7.99 mmol). The resulting mixture was stirred at room temperature overnight, diluted with ethyl acetate (60 mL), filtered through a pad of Celite and the solvent removed in vacuo to give a residue which was purified by automated normal-phase chromatography (0-5% MeOH/DCM) to give tert-butyl 6-fluoro-7-methoxy-8-oxo-3,4-dihydro-1H-pyrido[1,2-a]pyrazine-2-carboxylate (1.60 g, 5.36 mmol, 100% yield) as a colorless oil. MS (ES$^+$) m/z 299.2 [M+H]$^+$.

$^1$H NMR (400 MHz, CDCl$_3$) δ ppm 6.29 (s, 1H), 4.51 (s, 2H), 4.02-4.10 (m, 2H), 3.92-3.98 (m, 3H), 3.77-3.86 (m, 2H), 1.51 (s, 9H).

Step 11: Preparation of 6-fluoro-7-methoxy-1,2,3,4-tetrahydropyrido[1,2-a]pyrazin-8-one

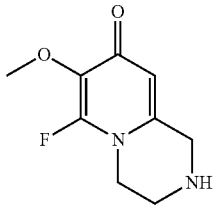

To a stirring solution of tert-butyl 6-fluoro-7-methoxy-8-oxo-3,4-dihydro-1H-pyrido[1,2-a]pyrazine-2-carboxylate (1.61 g, 5.40 mmol) in DCM (25 mL) was added TFA (25.mL). The resulting mixture was stirred at room temperature for 1 h and the solvent removed in vacuo to give 6-fluoro-7-methoxy-1,2,3,4-tetrahydropyrido[1,2-a] pyrazin-8-one trifluoroacetate as a colorless oil which was used without further purification.

Method R

Step 12a: Preparation of 2-[(2-chlorophenyl)methyl]-6-fluoro-7-methoxy-3,4-dihydro-1H-pyrido[1,2-a]pyrazin-8-one

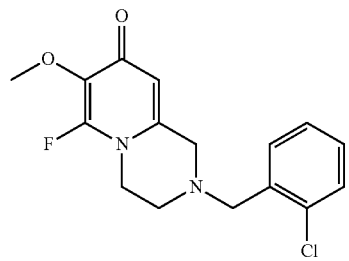 [SMILES: COc1c(F)n2c(cc1=O)CN(Cc1ccccc1Cl)CC2]

To a stirring solution of 6-fluoro-7-methoxy-1,2,3,4-tetrahydropyrido[1,2-a]pyrazin-8-one trifluoroacetate (290 mg, 0.58 mmol) in DCM (5 mL) was added 2-chlorobenzaldehyde (80 μL, 0.69 mmol) and two drops of acetic acid, followed by sodium triacetoxyborohydride (244 mg, 1.15 mmol). The resulting mixture was stirred at room temperature overnight, diluted with DCM (20 mL), washed with saturated NaHCO$_3$ (3×20 mL), brine (20 mL), dried over Na$_2$SO$_4$, filtered the solvent removed in vacuo to give a residue which was purified by automated normal-phase chromatography (0-5% MeOH/DCM) to give 2-[(2-chlorophenyl)methyl]-6-fluoro-7-methoxy-3,4-dihydro-1H-pyrido[1,2-a]pyrazin-8-one (83.0 mg, 0.257 mmol, 45% yield) as colorless oil. MS (ES+) m/z 323.0 [M+H]$^+$.

$^1$H NMR (400 MHz, DMSO-d$_6$) δ ppm 7.46-7.59 (m, 2H), 7.34-7.43 (m, 2H), 6.89 (s, 1H), 4.28 (br. s., 2H), 3.96 (s, 2H), 3.87 (s, 2H), 3.01-3.11 (m, 2H).

Step 12b: Preparation of 2-[(2-chlorophenyl)methyl]-6-fluoro-7-hydroxy-3,4-dihydro-1H-pyrido[1,2-a]pyrazin-8-one

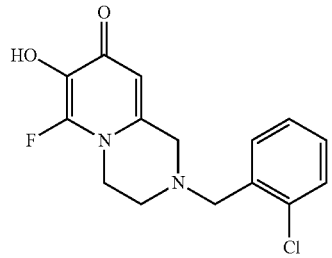 [SMILES: O=c1cc2n(c(F)c1O)CCN(Cc1ccccc1Cl)C2]

To a stirring solution of 2-[(2-chlorophenyl)methyl]-6-fluoro-7-methoxy-3,4-dihydro-1H-pyrido[1,2-a]pyrazin-8-one (78 mg, 0.24 mmol) in DCM (10 mL) at 0° C., was slowly added boron tribromide (1 M in DCM, 0.97 mL, 0.97 mmol). The resulting mixture was stirred at 0° C. for 1 h, allowed to reach room temperature and stirred for 3 h, then quenched with the addition of MeOH (3 mL). The solvent was removed in vacuo and the residue which was purified by automated normal-phase chromatography [0-10% (5% HOAc in MeOH)/DCM] to give the purified free base, was converted to its HCl salt by treating with HCl (2 M in Et20, 20 mL) and evaporated to dryness under vacuum to give 2-[(2-chlorophenyl)methyl]-6-fluoro-7-hydroxy-3,4-dihydro-1H-pyrido[1,2-a]pyrazin-8-one hydrochloride (65.0 mg, 0.188 mmol, 78% yield) as a pale purple solid. MS (ES+) m/z 309.0 [M+H]$^+$.

$^1$H NMR (400 MHz, DMSO-d$_6$) δ ppm 7.52 (dd, 3H), 7.44-7.49 (m, 1H), 7.29-7.40 (m, 2H), 6.02 (s, 1H), 3.94 (t, 2H), 3.71-3.77 (m, 5H), 3.62 (s, 2H), 2.89 (t, 2H).

Example 135: 2-[(4-(trifluoromethoxy)phenyl)methyl]-6-fluoro-7-hydroxy-3,4-dihydro-1H-pyrido[1,2-a]pyrazin-8-one

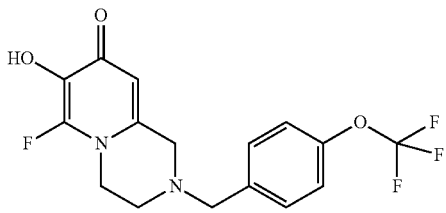 [SMILES: O=c1cc2n(c(F)c1O)CCN(Cc1ccc(OC(F)(F)F)cc1)C2]

The title compound was prepared according to Method R using 6-fluoro-7-methoxy-1,2,3,4-tetrahydropyrido[1,2-a]pyrazin-8-one trifluoroacetate and 4-(trifluoromethoxy)benzaldehyde, followed by demethylation with BBr$_3$ to give 2-[(4-(trifluoromethoxy)phenyl)methyl]-6-fluoro-7-hydroxy-3,4-dihydro-1H-pyrido[1,2-a]pyrazin-8-one hydrochloride (53%). MS, ES$^+$, 359.0 (M+H)$^+$.

$^1$H NMR (400 MHz, DMSO-d$_6$) δ ppm 7.54-7.70 (m, 2H), 7.32-7.49 (m, 2H), 6.98 (s, 1H), 4.41 (br. s., 2H), 4.13-4.30 (m, 4H), 3.35 (br. s., 2H).

Example 136: 9-chloro-2-(4-ethylbenzyl)-7-hydroxy-1,2,3,4-tetrahydro-8H-pyrido[1,2-a]pyrazin-8-one

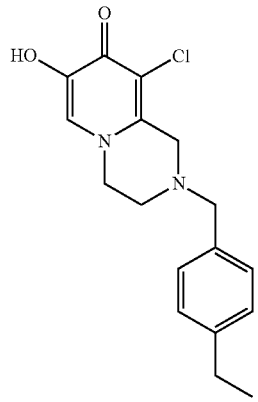 [SMILES: CCc1ccc(CN2CCn3cc(O)c(=O)c(Cl)c3C2)cc1]

Step 1: Preparation of 7-benzyloxy-9-chloro-2-[(4-ethylphenyl)methyl]-3,4-dihydro-1H-pyrido[1,2-a]pyrazin-8-one

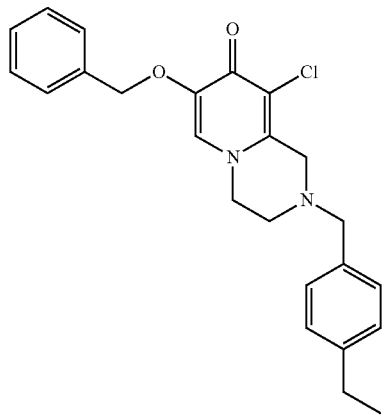 [SMILES: CCc1ccc(CN2CCn3cc(OCc4ccccc4)c(=O)c(Cl)c3C2)cc1]

N-chlorosuccinimide (1 equiv., 0.2670 mmol, 37.14 mg) was added to a solution of 7-benzyloxy-2-[(4-ethylphenyl)methyl]-3,4-dihydro-1H-pyrido[1,2-a]pyrazin-8-one (Intermediate prepared for the Example 13, 100 mg, 0.27 mmol) in CH$_3$CN (1 mL). The mixture was degassed and stirred 14 h at 50° C. The reaction mixture was allowed to cool to rt. The precipitate was filtered and the filtrates were evaporated to give the title intermediate as a brown oil (113 mg) used in the next step without further purification. MS, ES$^+$, 409.3 (M+H)$^+$.

Step 2: Preparation of 9-chloro-2-(4-ethylbenzyl)-7-hydroxy-1,2,3,4-tetrahydro-8H-pyrido[1,2-a]pyrazin-8-one The title compound was prepared according to Method E using 7-benzyloxy-2-[(4-ethylphenyl)methyl]-3,4-dihydro-1H-pyrido[1,2-a]pyrazin-8-one (63%).

MS, ES+, 319 (M+H)+.

Example 137: 9-chloro-2-[(2-chlorophenyl)methyl]-7-hydroxy-3,4-dihydro-1H-pyrido[1,2-a]pyrazin-8-one

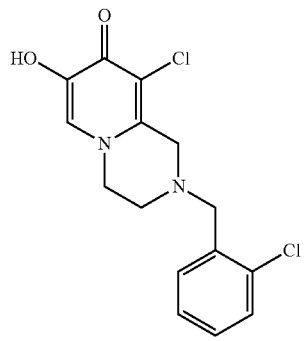

Step 1: Preparation of 9-chloro-2-[(2-chlorophenyl)methyl]-7-[(4-methoxyphenyl)methoxy]-3,4-dihydro-1H-pyrido[1,2-a]pyrazin-8-one

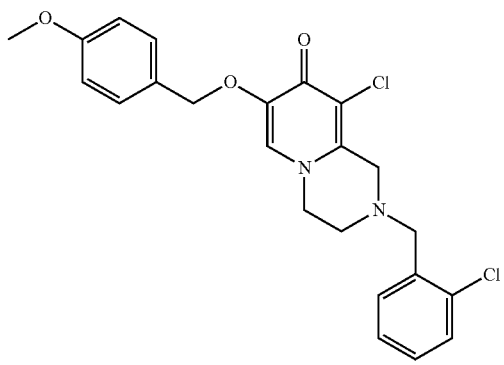 [SMILES: COc1ccc(COc2cn3c(c(Cl)c2=O)CN(Cc2ccccc2Cl)CC3)cc1]

N-chlorosuccinimide (68.2 mg, 0.511 mmol) was added to a solution of 2-[(2-chlorophenyl)methyl]-7-[(4-methoxyphenyl)methoxy]-3,4-dihydro-1H-pyrido[1,2-a]pyrazin-8-one (Intermediate prepared for the Example 58, 200 mg, 0.487 mmol) in CH$_3$CN (1 mL). The mixture was degassed and stirred 1 h at room temperature. The contents were poured into brine, extracted with DCM, dried over Na$_2$SO$_4$, filtered and the solvent removed in vacuo to give a residue which was purified by normal-phase chromatography to give the title intermediate as a yellow oil (50 mg). MS, ES+, 446.3 (M+H)+.

Step 2: Preparation of 9-chloro-2-[(2-chlorophenyl)methyl]-7-hydroxy-3,4-dihydro-1H-pyrido[1,2-a]pyrazin-8-one The title compound was prepared according to Method E using 9-chloro-2-[(2-chlorophenyl)methyl]-7-[(4-methoxyphenyl)methoxy]-3,4-dihydro-1H-pyrido[1,2-a]pyrazin-8-one (30%).

MS, ES+, 326.2 (M+H)+.
$^1$H NMR (400 MHz, DMSO-d$_6$) δ ppm 7.54-7.60 (m, 1H), 7.45-7.53 (m, 2H), 7.32-7.44 (m, 2H), 4.07 (t, 2H), 3.92 (s, 2H), 3.82 (s, 2H), 2.97 (br. s., 2H)

Example 138: 9-bromo-2-(4-ethylbenzyl)-7-hydroxy-1,2,3,4-tetrahydro-8H-pyrido[1,2-a]pyrazin-8-one

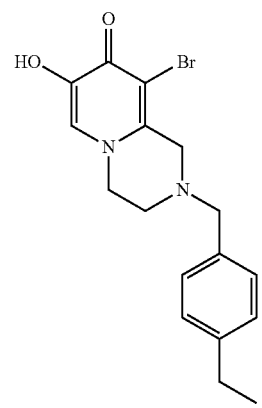 [SMILES: CCc1ccc(CN2CCn3cc(O)c(=O)c(Br)c3C2)cc1]

Step 1: Preparation of 7-benzyloxy-9-bromo-2-[(4-ethylphenyl)methyl]-3,4-dihydro-1H-pyrido[1,2-a]pyrazin-8-one

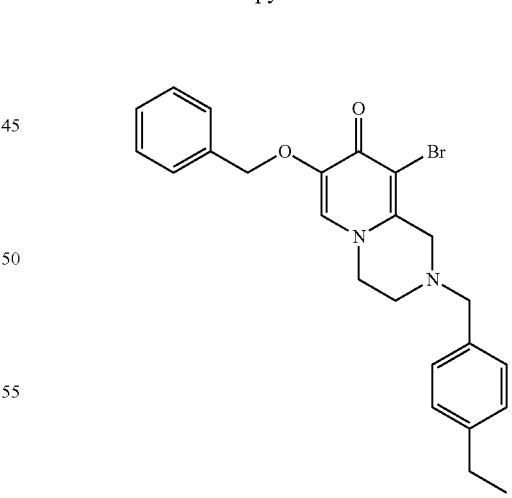

N-bromosuccinimide (428 mg, 1 eq., 2.4 mmol) was added to a solution of 7-benzyloxy-2-[(4-ethylphenyl)methyl]-3,4-dihydro-1H-pyrido[1,2-a]pyrazin-8-one (Intermediate prepared for the Example 13, 900 mg, 2.4 mmol) in CH$_3$CN (3 mL) and the mixture was stirred 1 h at 40° C. An aq. solution of NaHCO$_3$ was added and the mixture was extracted with DCM. The combined organic layers were dried over MgSO₄, filtered and evaporated to give a yellow oil (1.2 g). Purification by chromatography (SiO₂, DCM-MeOH—NH₄OH 97-2.7-0.3) to yield the title intermediate as a yellow solid (86%). MS, ES⁺, 451.3/453.2 (M+H)⁺.

Step 2: Preparation of 9-bromo-2-(4-ethylbenzyl)-7-hydroxy-1,2,3,4-tetrahydro-8H-pyrido[1,2-a]pyrazin-8-one The title compound was prepared according to Method E using 7-benzyloxy-9-bromo-2-[(4-ethylphenyl)methyl]-3,4-dihydro-1H-pyrido[1,2-a]pyrazin-8-one as a yellow solid (94%). MS, ES⁺, 363.2 (M+H)⁺.

Example 139: 9-bromo-2-[(2-chlorophenyl)methyl]-7-hydroxy-3,4-dihydro-1H-pyrido[1,2-a]pyrazin-8-one

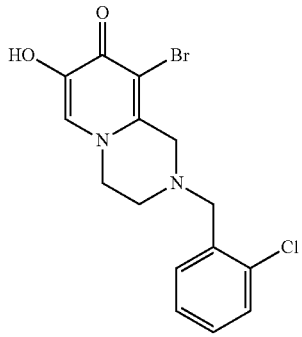 [SMILES: O=c1c(O)cn2c(c1I)CN(Cc1ccccc1Cl)CC2]

Step 1: Preparation of 9-bromo-2-[(2-chlorophenyl)methyl]-7-[(4-methoxyphenyl)methoxy]-3,4-dihydro-1H-pyrido[1,2-a]pyrazin-8-one

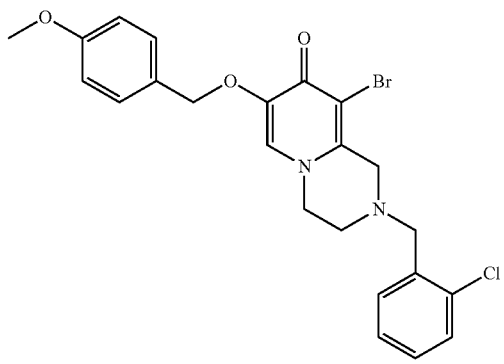

N-bromosuccinimide (0.91 g, 5.11 mmol) was added to a solution of 2-[(2-chlorophenyl)methyl]-7-[(4-methoxyphenyl)methoxy]-3,4-dihydro-1H-pyrido[1,2-a]pyrazin-8-one (Intermediate prepared for the Example 58, 200 mg, 0.487 mmol) in CHCl₃ (75 mL). The mixture was stirred 1 h at room temperature. The contents were poured into brine, extracted with DCM, dried over Na₂SO₄, filtered and the solvent removed in vacuo to give a residue which was purified by normal-phase chromatography to give the title intermediate as a yellow solid (1.5 g). MS, ES⁺, 490.0 (M+H)⁺.

Step 2: Preparation of 9-bromo-2-[(2-chlorophenyl)methyl]-7-hydroxy-3,4-dihydro-1H-pyrido[1,2-a]pyrazin-8-one The title compound was prepared according to Method E using 9-bromo-2-[(2-chlorophenyl)methyl]-7-[(4-methoxyphenyl)methoxy]-3,4-dihydro-1H-pyrido[1,2-a]pyrazin-8-one (80%).

MS, ES⁺, 370.1 (M+H)⁺.

¹H NMR (400 MHz, DMSO-d₆) δ ppm 7.49-7.63 (m, 3H), 7.40 (dd, 2H), 4.09-4.21 (m, 2H), 4.03 (s, 2H), 3.91 (s, 2H), 3.08 (d, 2H)

Example 140: 2-[(2-chlorophenyl)methyl]-7-hydroxy-9-iodo-3,4-dihydro-1H-pyrido[1,2-a]pyrazin-8-one

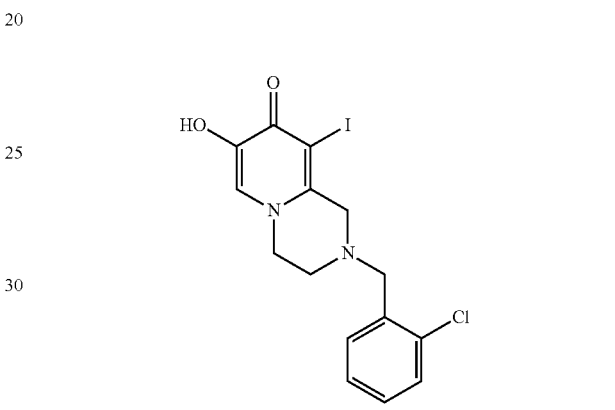

Step 1: Preparation of 2-[(2-chlorophenyl)methyl]-9-iodo-7-[(4-methoxyphenyl)methoxy]-3,4-dihydro-1H-pyrido[1,2-a]pyrazin-8-one

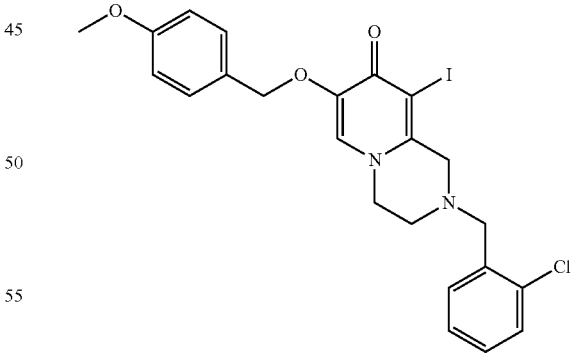

N-iodosuccinimide (152 mg, 0.678 mmol) was added to a solution of 2-[(2-chlorophenyl)methyl]-7-[(4-methoxyphenyl)methoxy]-3,4-dihydro-1H-pyrido[1,2-a]pyrazin-8-one (Intermediate prepared for the Example 58, 265 mg, 0.645 mmol) in HOAc (5 mL). The solvent was removed in vacuo to give a residue which was purified by normal-phase chromatography to give the title intermediate as a yellow solid (155 mg). MS, ES⁺, 537.3 (M+H)⁺.

Step 2: Preparation of 2-[(2-chlorophenyl)methyl]-7-hydroxy-9-iodo-3,4-dihydro-1H-pyrido[1,2-a]pyrazin-8-one The title compound was prepared according to Method E using 2-[(2-chlorophenyl)methyl]-9-iodo-7-[(4-methoxyphenyl)methoxy]-3,4-dihydro-1H-pyrido[1,2-a]pyrazin-8-one (74%).
MS, ES⁺, 417.2 (M+H)⁺.
¹H NMR (400 MHz, DMSO-d₆) δ ppm 7.75 (br. S., 2H), 7.41-7.63 (m, 3H), 4.28-4.44 (m, 4H), 4.14 (br. s., 2H), 3.32 (br. s., 2H)

Example 141: 9-cyclopropyl-2-(4-ethylbenzyl)-7-hydroxy-1,2,3,4-tetrahydro-8H-pyrido[1,2-a]pyrazin-8-one

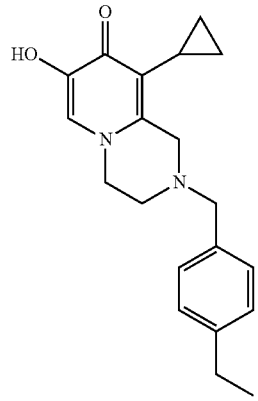 [SMILES: CCc1ccc(CN2CCn3cc(O)c(=O)c(C4CC4)c3C2)cc1]

Step 1: Preparation of 7-benzyloxy-9-cyclopropyl-2-[(4-ethylphenyl)methyl]-3,4-dihydro-1H-pyrido[1,2-a]pyrazin-8-one

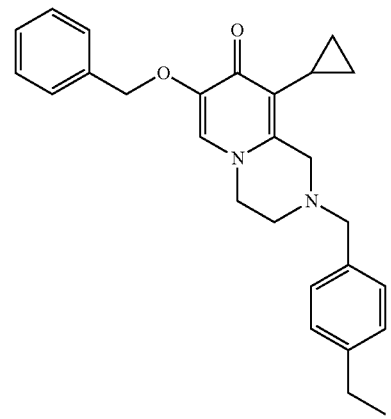 [SMILES: CCc1ccc(CN2CCn3cc(OCc4ccccc4)c(=O)c(C4CC4)c3C2)cc1]

7-benzyloxy-9-bromo-2-[(4-ethylphenyl)methyl]-3,4-dihydro-1H-pyrido[1,2-a]pyrazin-8-one (Intermediate formed for the preparation of Example 120, 100 mg, 0.22 mmol), cyclopropylboronic acid (5 eq., 1.10 mmol, 99.7 mg), [bis(diphenylphosphino)ferrocene]dichloropalladium (11) (3 eq., 0.66 mmol, 484 mg) and cesium carbonate (0.5 eq., 0.110 mmol, 35.9 mg) were placed in a mixture 1,4-dioxane (3 mL) and H₂O (1 mL). The mixture was degassed for 10 min. then heated 20 min. at 110° C. under microwave irradiation followed by 14 h at 100° C. (oil bath). The solvents were evaporated and the residue purified by chromatography (SiO₂, gradient from EtOAc up to 20% methanolic ammonia in EtOAc) to yield the title intermediate (30 mg, 33%). MS, ES⁺, 415.4 (M+H)⁺.

Step 2: Preparation of 9-cyclopropyl-2-(4-ethylbenzyl)-7-hydroxy-1,2,3,4-tetrahydro-8H-pyrido[1,2-a]pyrazin-8-one The title compound was prepared according to Method E using 7-benzyloxy-9-cyclopropyl-2-[(4-ethylphenyl)methyl]-3,4-dihydro-1H-pyrido[1,2-a]pyrazin-8-one (69%).
MS, ES⁺, 325.3 (M+H)⁺.

Example 142: 2-[(2-chlorophenyl)methyl]-9-cyclopropyl-7-hydroxy-3,4-dihydro-1H-pyrido[1,2-a]pyrazin-8-one

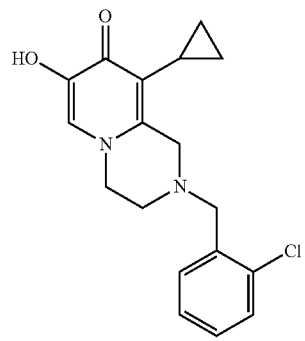 [SMILES: O=c1c(O)cn2c(c1C1CC1)CN(Cc1ccccc1Cl)CC2]

Step 1: Preparation of 2-[(2-chlorophenyl)methyl]-9-cyclopropyl-7-[(4-methoxyphenyl)methoxy]-3,4-dihydro-1H-pyrido[1,2-a]pyrazin-8-one

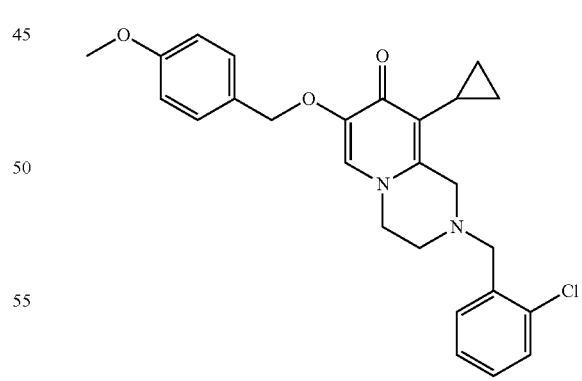

9-bromo-2-[(2-chlorophenyl)methyl]-7-[(4-methoxyphenyl)methoxy]-3,4-dihydro-1H-pyrido[1,2-a]pyrazin-8-one (Intermediate prepared for Example 139, 100 mg, 0.204 mmol), cyclopropylboronic acid (26.3 mg, 0.306 mmol), palladium (II) acetate (4.6 mg, 0.02 mmol), 2,2'-bis(diphenylphosphino)-1,1'-binaphthyl (25.4 mg, 0.04 mmol) and cesium carbonate (200 mg, 0.61 mmol) were suspended in 1,4-dioxane (4 mL). The mixture was degassed for 10 min.

then heated 18 h at 95° C. The solvents were evaporated and the residue purified by to give the title intermediate as a colorless oil. MS, ES+, 451.3 (M+H)+.

Step 2: Preparation of 2-[(2-chlorophenyl)methyl]-9-cyclopropyl-7-hydroxy-3,4-dihydro-1H-pyrido[1,2-a]pyrazin-8-one The title compound was prepared according to Method E using 2-[(2-chlorophenyl)methyl]-9-cyclopropyl-7-[(4-methoxyphenyl)methoxy]-3,4-dihydro-1H-pyrido[1,2-a]pyrazin-8-one and the crude product purified by HPLC (5%). MS, ES+, 331.2 (M+H)+.
$^1$H NMR (400 MHz, DMSO-d$_6$) δ ppm 7.90 (s, 1H), 7.48-7.64 (m, 2H), 7.38 (dd, 2H), 7.34-7.45 (m, 2H), 4.31-4.51 (m, 2H), 4.07 (s, 2H), 3.85-4.00 (m, 2H), 3.00 (d, 2H), 1.46-1.62 (m, 1H), 0.89-1.07 (m, 2H), 0.57-0.74 (m, 2H)

REFERENCES

Apud, J. A. and D. R. Weinberger (2007). "Treatment of cognitive deficits associated with schizophrenia—Potential role of catechol-O-methyltransferase inhibitors." CNS Drugs 21(7): 535-557.
Bonifacio, M. J., P. N. Palma et al. (2007). "Catechol-O-methyltransferase and its inhibitors in Parkinson's disease." CNS Drug Reviews 13(3): 352-379.
Borchardt, R. T., D. R. Thakker et al. (1976). "Catechol O-Methyltransferase 0.8. Structure-Activity-Relationships for Inhibition by 8-Hydroxyquinolines." Journal of Medicinal Chemistry 19(4): 558-560.
Ciliax, B. J., C. Heilman et al. (1995). "The Dopamine Transporter—Immunochemical Characterization and Localization in Brain." Journal of Neuroscience 15(3): 1714-1723.
Fatemi, S. H. and T. D. Folsom (2009). "The Neurodevelopmental Hypothesis of Schizophrenia, Revisited." Schizophrenia Bulletin 35(3): 528-548.
Goldman-Rakic, P. S., S. A. Castner et al. (2004). "Targeting the dopamine D-1 receptor in schizophrenia: insights for cognitive dysfunction." Psychopharmacology 174(1): 3-16.
Howes, O. D. and S. Kapur (2009). "The Dopamine Hypothesis of Schizophrenia: Version III—The Final Common Pathway." Schizophrenia Bulletin 35(3): 549-562.
Lin Y. et al. (2012), "Detecting S-adenosyl-l-methionine-induced conformational change of a histone methyltransferase using a homogeneous time-resolved fluorescence-based binding assay" Analytical Biochemistry, 423(1): 171-177. Kaenmaki, M., A. Tammimaki et al. (2010). "Quantitative role of COMT in dopamine clearance in the prefrontal cortex of freely moving mice." J Neurochem. 114(6): 1745-1755.
Lachman, H. M., D. F. Papolos et al. (1996). "Human catechol-O-methyltransferase pharmacogenetics: Description of a functional polymorphism and its potential application to neuropsychiatric disorders." Pharmacogenetics 6(3): 243-250.
Learmonth, D. A., L. E. Kiss et al. (2010). "The Chemistry of Catechol O-Methyltransferase Inhibitors." Basic Aspects of Catechol-O-Methyltransferase and the Clinical Applications of Its Inhibitors 95: 119-162.
Marenco, S. and D. R. Weinberger (2000). "The neurodevelopmental hypothesis of schizophrenia: Following a trail of evidence from cradle to grave." Development and Psychopathology 12(3): 501-527.
Nutt, J. G. and J. H. Fellman (1984). "Pharmacokinetics of Levodopa." Clinical Neuropharmacology 7(1): 35-49.
Nutt, J. G., W. R. Woodward et al. (1985). "The Effect of Carbidopa on the Pharmacokinetics of Intravenously Administered Levodopa—the Mechanism of Action in the Treatment of Parkinsonism." Annals of Neurology 18(5): 537-543.
Olanow, C. W. and P. B. Watkins (2007). "Tolcapone." Clinical Neuropharmacology 30(5): 287-294.
Pickard, B. (2011). "Progress in defining the biological causes of schizophrenia." Expert Reviews in Molecular Medicine 13.
Russ, H., et al. (1999). "Detection of tolcapone in the cerebrospinal fluid of Parkinsonian subjects." Naunyn-Schmiedeberg's Archives of Pharmacology 360(6): 719-720.
Yavich, L., M. M. Forsberg et al. (2007). "Site-specific role of catechol-O-methyltransferase in dopamine overflow within prefrontal cortex and dorsal striatum." Journal of Neuroscience 27(38): 10196-10202.

The invention claimed is:
1. A compound of formula I, or a pharmaceutically acceptable salt thereof:

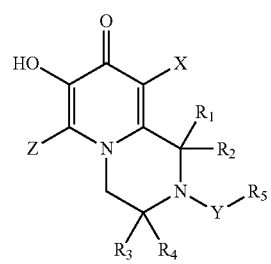

wherein:

X is selected from hydrogen; chloro; bromo, iodo and cyclopropyl;

Z is selected from hydrogen and fluoro;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_5$ is selected from aryl, heteroaryl, heterocycle, $C_1$-$C_{10}$ alkyl or C cycloaklyl, optionally substituted with one or more groups selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and NHC(O)R, wherein R is $C_1$-$C_4$ alkyl; and Y is $(CR_6R_7)_n$, wherein n is from 0-3, and $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or when $R_5$ is phenyl, one of $R_6$ or $R_7$ comes together with $R_5$ to form a bicycle.

2. The compound according to claim 1, wherein the compound is of formula II or a pharmaceutically acceptable salt thereof:

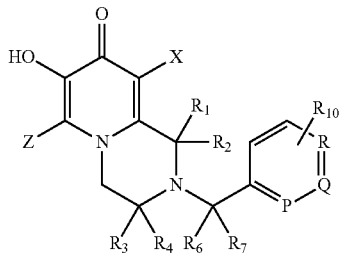

II wherein:
X is selected from hydrogen; chloro; bromo, iodo and cyclopropyl;
Z is selected from hydrogen and fluoro;
$R_1$ and $R_2$ are each independently selected from hydrogen; $C_{1-4}$ alkyl; aryl; substituted aryl; arylalkyl and heterocycle;
$R_3$ and $R_4$ are each independently selected from hydrogen; $C_1$-$C_4$ alkyl; aryl and arylalkyl;
P, Q and R are each independently selected from CH and N;
$R_{10}$ can be at one or more positions on the ring, and at each occurrence is independently selected from hydrogen; mono-, di-, or trihalomethyl; $C_1$-$C_4$ alkyl, $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P, Q or R to form a bicycle; and
$R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or one of $R_6$ or $R_7$ comes together with P to form a bicycle.

3. The compound according to claim 1, wherein the compound is of formula III or a pharmaceutically acceptable salt thereof:

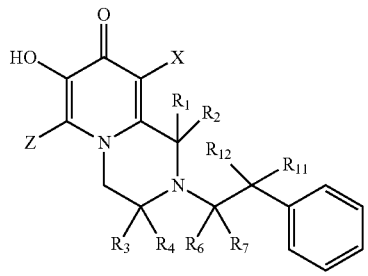

III wherein:
X is selected from hydrogen; chloro; bromo, iodo and cyclopropyl;
Z is selected from hydrogen and fluoro;
$R_1$ and $R_2$ are each independently selected from hydrogen; $C_{1-4}$ alkyl; aryl; substituted aryl; arylalkyl and heterocycle;
$R_3$ and $R_4$ are each independently selected from hydrogen; $C_1$-$C_4$ alkyl; aryl and arylalkyl; and $R_6$, $R_7$, $R_{11}$ and $R_{12}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; $R_6$ and $R_7$; $R_{11}$ and $R_{12}$; $R_6$ or $R_7$ and $R_{11}$ or $R_{12}$ may also come together to form a $C_3$-$C_6$ cycloalkyl.

4. The compound according to claim 1, wherein the compound is of formula IV or a pharmaceutically acceptable salt thereof:

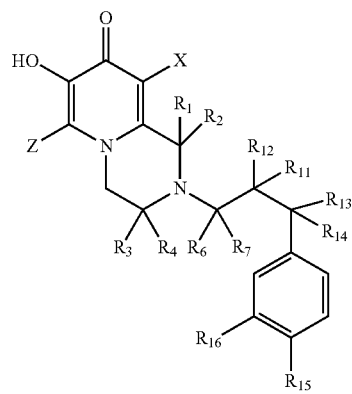

IV wherein:
X is selected from hydrogen; chloro; bromo, iodo and cyclopropyl;
Z is selected from hydrogen and fluoro;
$R_1$ and $R_2$ are each independently selected from hydrogen; $C_{1-4}$ alkyl; aryl; substituted aryl; arylakyl and heterocycle;
$R_3$ and $R_4$ are each independently selected from hydrogen; $C_1$-$C_4$ alkyl; aryl and arylalkyl;
$R_6$, $R_7$, $R_{11}$, $R_{12}$, $R_{13}$ and $R_{14}$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl and aryl; $R_6$ and $R_7$, $R_{11}$ and $R_{12}$, $R_{13}$ and $R_{14}$, $R_6$ or $R_7$ and $R_{11}$ or $R_{12}$, $R_6$ or $R_7$ and $R_{13}$ or $R_{14}$, $R_{11}$ or $R_{12}$ and $R_{13}$ or $R_{14}$ may also come together to form a $C_3$-$C_6$ cycloalkyl; and
$R_{15}$ and $R_{16}$ are each hydrogen or come together to form a ring.

5. The compound according to claim 1, wherein the compound is of formula V or a pharmaceutically acceptable salt thereof:

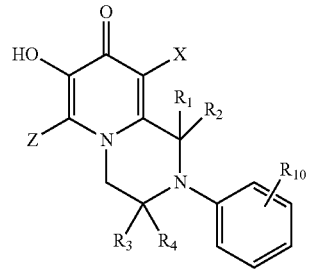

V wherein:

X is selected from hydrogen; chloro; bromo, iodo and cyclopropyl;

Z is selected from hydrogen and fluoro;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl; and $R_{10}$ can be at one or more positions on the ring, and at each occurrence is independently selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl.

6. The compound according to claim 1, wherein the compound is of formula VI or a pharmaceutically acceptable salt thereof:

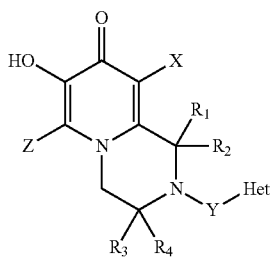

VI wherein:

X is selected from hydrogen; chloro; bromo, iodo and cyclopropyl;

Z is selected from hydrogen and fluoro;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

Y is $(CR_6R_7)_n$, wherein n is from 0-3, and $R_6$ and $R_7$ are independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl Het is a heterocycle.

7. The compound according to claim 2, wherein the compound is of IIb, wherein

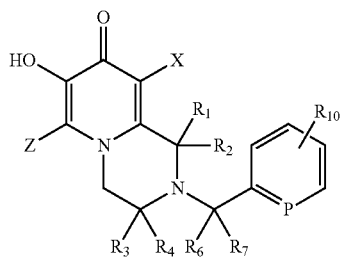

IIb wherein:

X is selected from hydrogen; chloro; bromo, iodo and cyclopropyl;

Z is selected from hydrogen and fluoro;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

P is CH;

$R_{10}$ can be at one or more positions on the ring, and at each occurrence is independently selected from hydrogen; mono-, di-, or trihalomethyl; $C_1$-$C_4$ alkyl; $C_3$-$C_{10}$ cycloalkyl; halo; heteroaryl; cyano; nitro; aryloxy; aryl; alkoxy; arylalkoxy and —NHC(O)R, wherein R is $C_1$-$C_4$ alkyl; or $R_{10}$ comes together with P to form a bicycle; and $R_6$ and $R_7$ are each independently selected from hydrogen; $C_1$-$C_6$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; or one of $R_6$ or $R_7$ comes together with P to form a bicycle.

8. The compound according to claim 1, wherein the compound is of formula VII or a pharmaceutically acceptable salt thereof:

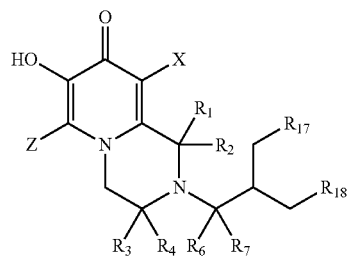

VII wherein:

X is selected from hydrogen; chloro; bromo, iodo and cyclopropyl;

Z is selected from hydrogen and fluoro;

$R_1$ and $R_2$ are each independently selected from hydrogen; $C_{1-4}$ alkyl; aryl; substituted aryl; arylalkyl and heterocycle;

$R_3$ and $R_4$ are each independently selected from hydrogen; $C_1$-$C_4$ alkyl; aryl and arylalkyl;

$R_6$ and $R_7$ are each independently selected from hydrogen; $C_1$-$C_4$ alkyl; $C_3$-$C_5$ cycloalkyl; $C_1$-$C_4$ alkylhydroxyl; mono-, di-, or trihaloalkyl; and aryl; $R_6$ and $R_7$ may also come together to form a $C_3$-$C_6$ cycloalkyl; and $R_{17}$ and $R_{18}$ are selected from $C_1$-$C_4$ alkyl or come together to form a 5-10 membered cycloalkane, which can optionally be further substituted with $C_1$-$C_8$ alkyl or cycloalkyl.

9. A compound selected from the group consisting of:

2-benzyl-7-hydroxy-1,2,3,4-tetrahydro-8H-pyrido[1,2-a]pyrazin-8-one;

7-hydroxy-2-[4-(trifluoromethyl)benzyl]-1,2,3,4-tetrahydro-8H-pyrido[1,2-a]pyrazin-8-one;

2-[(4-fluorophenyl)methyl]-7-hydroxy-3,4-dihydro-1H-pyrido[1,2-a]pyrazin-8-one;

2-[2-(benzotriazol-1-yl)ethyl]-7-hydroxy-3,4-dihydro-1H-pyrido[1,2-a]pyrazin-8-one;

2-[2-(benzotriazol-2-yl)ethyl]-7-hydroxy-3,4-dihydro-1H-pyrido[1,2-a]pyrazin-8-one;
7-hydroxy-2-[3-(trifluoromethoxy)benzyl]-1,2,3,4-tetrahydro-8H-pyrido[1,2-a]pyrazin-8-one;
2-(4-tert-butylbenzyl)-7-hydroxy-1,2,3,4-tetrahydro-8H-pyrido[1,2-a]pyrazin-8-one;
7-hydroxy-2-[4-(trifluoromethoxy)benzyl]-1,2,3,4-tetrahydro-8H-pyrido[1,2-a]pyrazin-8-one;
2-(2,4-dimethylbenzyl)-7-hydroxy-1,2,3,4-tetrahydro-8H-pyrido[1,2-a]pyrazin-8-one;
7-hydroxy-2-[4-(propan-2-yl)benzyl]-1,2,3,4-tetrahydro-8H-pyrido[1,2-a]pyrazin-8-one;
7-hydroxy-2-(pyridin-2-ylmethyl)-1,2,3,4-tetrahydro-8H-pyrido[1,2-a]pyrazin-8-one;
7-hydroxy-2-[4-(pyridin-3-yl)benzyl]-1,2,3,4-tetrahydro-8H-pyrido[1,2-a]pyrazin-8-one;
2-(4-ethylbenzyl)-7-hydroxy-1,2,3,4-tetrahydro-8H-pyrido[1,2-a]pyrazin-8-one;
7-hydroxy-2-(quinolin-8-ylmethyl)-1,2,3,4-tetrahydro-8H-pyrido[1,2-a]pyrazin-8-one;
7-hydroxy-2-(1-phenylethyl)-1,2,3,4-tetrahydro-8H-pyrido[1,2-a]pyrazin-8-one;
2-[1-(4-ethylphenyl)ethyl]-7-hydroxy-1,2,3,4-tetrahydro-8H-pyrido[1,2-a]pyrazin-8-one;
2-[(7-hydroxy-8-oxo-1,3,4,8-tetrahydro-2H-pyrido[1,2-a]pyrazin-2-yl)methyl]benzonitrile;
2-(4-ethyl-3-nitrobenzyl)-7-hydroxy-1,2,3,4-tetrahydro-8H-pyrido[1,2-a]pyrazin-8-one;
2-(2,2-diphenylethyl)-7-hydroxy-1,2,3,4-tetrahydro-8H-pyrido[1,2-a]pyrazin-8-one;
2-(2-ethylbutyl)-7-hydroxy-1,2,3,4-tetrahydro-8H-pyrido[1,2-a]pyrazin-8-one;
2-(3,5-dichlorobenzyl)-7-hydroxy-1,2,3,4-tetrahydro-8H-pyrido[1,2-a]pyrazin-8-one; 2-(cyclohexylmethyl)-7-hydroxy-1,2,3,4-tetrahydro-8H-pyrido[1,2-a]pyrazin-8-one;
2-(4-cyclopropylbenzyl)-7-hydroxy-1,2,3,4-tetrahydro-8H-pyrido[1,2-a]pyrazin-8-one;
2-[(8,8-dimethyl-1,2,3,4,5,6,7,8-octahydronaphthalen-2-yl)methyl]-7-hydroxy-1,2,3,4-tetrahydro-8H-pyrido[1,2-a]pyrazin-8-one;
2-(3,4-dichlorobenzyl)-7-hydroxy-1,2,3,4-tetrahydro-8H-pyrido[1,2-a]pyrazin-8-one;
2-(cyclooctylmethyl)-7-hydroxy-1,2,3,4-tetrahydro-8H-pyrido[1,2-a]pyrazin-8-one;
2-(2,6-dimethylbenzyl)-7-hydroxy-1,2,3,4-tetrahydro-8H-pyrido[1,2-a]pyrazin-8-one;
2-(2,5-dimethylbenzyl)-7-hydroxy-1,2,3,4-tetrahydro-8H-pyrido[1,2-a]pyrazin-8-one;
7-hydroxy-2-{[1-(phenylsulfonyl)-1H-indol-2-yl]methyl}-1,2,3,4-tetrahydro-8H-pyrido[1,2-a]pyrazin-8-one;
7-hydroxy-2-(3-phenylpropyl)-1,2,3,4-tetrahydro-8H-pyrido[1,2-a]pyrazin-8-one;
7-hydroxy-2-(2-phenylpropyl)-1,2,3,4-tetrahydro-8H-pyrido[1,2-a]pyrazin-8-one;
2-(3,5-difluorobenzyl)-7-hydroxy-1,2,3,4-tetrahydro-8H-pyrido[1,2-a]pyrazin-8-one;
7-hydroxy-2-(2-methylbenzyl)-1,2,3,4-tetrahydro-8H-pyrido[1,2-a]pyrazin-8-one;
7-hydroxy-2-[(5-phenyl-1H-pyrazol-3-yl)methyl]-1,2,3,4-tetrahydro-8H-pyrido[1,2-a]pyrazin-8-one;
2-{[6-chloro-4-(1H-imidazol-4-yl)-3,4-dihydro-2H-chromen-8-yl]methyl}-7-hydroxy-1,2,3,4-tetrahydro-8H-pyrido[1,2-a]pyrazin-8-one;
7-hydroxy-2-(3-phenoxybenzyl)-1,2,3,4-tetrahydro-8H-pyrido[1,2-a]pyrazin-8-one;
2-(2,3-dimethylbenzyl)-7-hydroxy-1,2,3,4-tetrahydro-8H-pyrido[1,2-a]pyrazin-8-one;
2-(1,3-benzothiazol-2-ylmethyl)-7-hydroxy-1,2,3,4-tetrahydro-8H-pyrido[1,2-a]pyrazin-8-one;
2-(2-fluorobenzyl)-7-hydroxy-1,2,3,4-tetrahydro-8H-pyrido[1,2-a]pyrazin-8-one;
2-[(5-chloro-1,3-dimethyl-1H-pyrazol-4-yl)methyl]-7-hydroxy-1,2,3,4-tetrahydro-8H-pyrido[1,2-a]pyrazin-8-one;
7-hydroxy-2-[(4-oxo-4H-chromen-3-yl)methyl]-1,2,3,4-tetrahydro-8H-pyrido[1,2-a]pyrazin-8-one;
7-hydroxy-2-(1H-indazol-3-ylmethyl)-1,2,3,4-tetrahydro-8H-pyrido[1,2-a]pyrazin-8-one;
7-hydroxy-2-{[3-(thiophen-2-yl)-1H-pyrazol-4-yl]methyl}-1,2,3,4-tetrahydro-8H-pyrido[1,2-a]pyrazin-8-one;
7-hydroxy-2-[2-(trifluoromethyl)benzyl]-1,2,3,4-tetrahydro-8H-pyrido[1,2-a]pyrazin-8-one;
7-hydroxy-2-[(3-phenyl-1H-pyrazol-4-yl)methyl]-1,2,3,4-tetrahydro-8H-pyrido[1,2-a]pyrazin-8-one;
2-(2,6-dimethoxybenzyl)-7-hydroxy-1,2,3,4-tetrahydro-8H-pyrido[1,2-a]pyrazin-8-one;
7-hydroxy-2-(4-phenoxybenzyl)-1,2,3,4-tetrahydro-8H-pyrido[1,2-a]pyrazin-8-one;
2-(2,3-dihydro-1,4-benzodioxin-6-ylmethyl)-7-hydroxy-1,2,3,4-tetrahydro-8H-pyrido[1,2-a]pyrazin-8-one;
2-[3-(1,3-benzodioxol-5-yl)-2-methylpropyl]-7-hydroxy-1,2,3,4-tetrahydro-8H-pyrido[1,2-a]pyrazin-8-one;
7-hydroxy-2-(4-methoxybenzyl)-1,2,3,4-tetrahydro-8H-pyrido[1,2-a]pyrazin-8-one;
7-hydroxy-2-(2-methoxybenzyl)-1,2,3,4-tetrahydro-8H-pyrido[1,2-a]pyrazin-8-one;
2-[4-(benzyloxy)benzyl]-7-hydroxy-1,2,3,4-tetrahydro-8H-pyrido[1,2-a]pyrazin-8-one;
2-[3-(benzyloxy)benzyl]-7-hydroxy-1,2,3,4-tetrahydro-8H-pyrido[1,2-a]pyrazin-8-one;
2-(2,1,3-benzothiadiazol-5-ylmethyl)-7-hydroxy-1,2,3,4-tetrahydro-8H-pyrido[1,2-a]pyrazin-8-one;
2-[2-(benzyloxy)benzyl]-7-hydroxy-1,2,3,4-tetrahydro-8H-pyrido[1,2-a]pyrazin-8-one;
7-hydroxy-2-{[6-(4-methylphenyl)imidazo[2,1-b][1,3]thiazol-5-yl]methyl}-1,2,3,4-tetrahydro-8H-pyrido[1,2-a]pyrazin-8-one;
2-(2-chloro-4-fluorobenzyl)-7-hydroxy-1,2,3,4-tetrahydro-8H-pyrido[1,2-a]pyrazin-8-one;
2-(2-chlorobenzyl)-7-hydroxy-1,2,3,4-tetrahydro-8H-pyrido[1,2-a]pyrazin-8-one;
2-(2-chloro-6-fluorobenzyl)-7-hydroxy-1,2,3,4-tetrahydro-8H-pyrido[1,2-a]pyrazin-8-one;
2-(2,6-dichlorobenzyl)-7-hydroxy-1,2,3,4-tetrahydro-8H-pyrido[1,2-a]pyrazin-8-one;
2-(2,4-dichlorobenzyl)-7-hydroxy-1,2,3,4-tetrahydro-8H-pyrido[1,2-a]pyrazin-8-one;
2-(2,6-difluorobenzyl)-7-hydroxy-1,2,3,4-tetrahydro-8H-pyrido[1,2-a]pyrazin-8-one;
2-[(4-bromo-2-chloro-phenyl)methyl]-7-hydroxy-3,4-dihydro-1H-pyrido[1,2-a]pyrazin-8-one;
2-[(2-chloro-4-cyclopropyl-phenyl)methyl]-7-hydroxy-3,4-dihydro-1H-pyrido[1,2-a]pyrazin-8-one;
2-[(2-chlorophenyl)methyl]-7-hydroxy-3,3-dimethyl-1,4-dihydropyrido[1,2-a]pyrazin-8-one;
2-[(2,4-dichloro-5-nitro-phenyl)methyl]-7-hydroxy-3,4-dihydro-1H-pyrido[1,2-a]pyrazin-8-one;
7-hydroxy-2-[1-(2-methylphenyl)ethyl]-1,2,3,4-tetrahydro-8H-pyrido[1,2-a]pyrazin-8-one;
2-[1-(4-chlorophenyl)ethyl]-7-hydroxy-1,2,3,4-tetrahydro-8H-pyrido[1,2-a]pyrazin-8-one;

2-[1-(2,5-dichlorophenyl)ethyl]-7-hydroxy-1,2,3,4-tetrahydro-8H-pyrido[1,2-a]pyrazin-8-one;
7-hydroxy-2-{1-[4-(trifluoromethyl)phenyl]ethyl}-1,2,3,4-tetrahydro-8H-pyrido[1,2-a]pyrazin-8-one;
7-hydroxy-2-[1-(3-methylphenyl)ethyl]-1,2,3,4-tetrahydro-8H-pyrido[1,2-a]pyrazin-8-one;
2-[1-(3-chlorophenyl)ethyl]-7-hydroxy-1,2,3,4-tetrahydro-8H-pyrido[1,2-a]pyrazin-8-one;
2-(4-chloro-2,3-dihydro-1H-inden-1-yl)-7-hydroxy-1,2,3,4-tetrahydro-8H-pyrido[1,2-a]pyrazin-8-one;
2-[1-(2,6-dimethoxyphenyl)ethyl]-7-hydroxy-1,2,3,4-tetrahydro-8H-pyrido[1,2-a]pyrazin-8-one;
7-hydroxy-2-[1-(2,3,5-trifluorophenyl)ethyl]-1,2,3,4-tetrahydro-8H-pyrido[1,2-a]pyrazin-8-one;
2-[1-(2-chlorophenyl)ethyl]-7-hydroxy-1,2,3,4-tetrahydro-8H-pyrido[1,2-a]pyrazin-8-one;
2-{1-[2-(benzyloxy)phenyl]ethyl}-7-hydroxy-1,2,3,4-tetrahydro-8H-pyrido[1,2-a]pyrazin-8-one;
7-hydroxy-2-(1-phenylpentyl)-1,2,3,4-tetrahydro-8H-pyrido[1,2-a]pyrazin-8-one;
2-(7-fluoro-2,3-dihydro-1H-inden-1-yl)-7-hydroxy-1,2,3,4-tetrahydro-8H-pyrido[1,2-a]pyrazin-8-one;
7-hydroxy-2-(2-phenyl-3,4-dihydro-2H-chromen-4-yl)-1,2,3,4-tetrahydro-8H-pyrido[1,2-a]pyrazin-8-one;
2-[1-(3-fluorophenyl)ethyl]-7-hydroxy-1,2,3,4-tetrahydro-8H-pyrido[1,2-a]pyrazin-8-one;
2-[cyclopentyl(phenyl)methyl]-7-hydroxy-1,2,3,4-tetrahydro-8H-pyrido[1,2-a]pyrazin-8-one;
7-hydroxy-2-[1-(3-methoxyphenyl)ethyl]-1,2,3,4-tetrahydro-8H-pyrido[1,2-a]pyrazin-8-one;
2-(2,3-dihydro-1H-inden-1-yl)-7-hydroxy-1,2,3,4-tetrahydro-8H-pyrido[1,2-a]pyrazin-8-one;
2-[1-(3-chloro-2,6-difluorophenyl)ethyl]-7-hydroxy-1,2,3,4-tetrahydro-8H-pyrido[1,2-a]pyrazin-8-one;
7-hydroxy-2-(6,7,8,9-tetrahydro-5H-benzo[7]annulen-5-yl)-1,2,3,4-tetrahydro-8H-pyrido[1,2-a]pyrazin-8-one;
2-[1-(2,5-dimethylphenyl)ethyl]-7-hydroxy-1,2,3,4-tetrahydro-8H-pyrido[1,2-a]pyrazin-8-one;
2-(1,2-diphenylethyl)-7-hydroxy-1,2,3,4-tetrahydro-8H-pyrido[1,2-a]pyrazin-8-one;
7-hydroxy-2-(1-phenylpropyl)-1,2,3,4-tetrahydro-8H-pyrido[1,2-a]pyrazin-8-one;
7-hydroxy-2-(1,2,3,4-tetrahydronaphthalen-1-yl)-1,2,3,4-tetrahydro-8H-pyrido[1,2-a]pyrazin-8-one;
7-hydroxy-2-(7-methoxy-1,2,3,4-tetrahydronaphthalen-1-yl)-1,2,3,4-tetrahydro-8H-pyrido[1,2-a]pyrazin-8-one;
7-hydroxy-2-(4-methyl-2,3-dihydro-1H-inden-1-yl)-1,2,3,4-tetrahydro-8H-pyrido[1,2-a]pyrazin-8-one;
7-hydroxy-2-(1-phenylbutyl)-1,2,3,4-tetrahydro-8H-pyrido[1,2-a]pyrazin-8-one;
4-[1-(7-hydroxy-8-oxo-1,3,4,8-tetrahydro-2H-pyrido[1,2-a]pyrazin-2-yl)ethyl]benzonitrile;
3-[1-(7-hydroxy-8-oxo-1,3,4,8-tetrahydro-2H-pyrido[1,2-a]pyrazin-2-yl)ethyl]benzonitrile;
N-{3-[1-(7-hydroxy-8-oxo-1,3,4,8-tetrahydro-2H-pyrido[1,2-a]pyrazin-2-yl)ethyl]phenyl}acetamide;
2-[1-(2,5-difluorophenyl)ethyl]-7-hydroxy-1,2,3,4-tetrahydro-8H-pyrido[1,2-a]pyrazin-8-one;
2-[1-(2-fluorophenyl)ethyl]-7-hydroxy-1,2,3,4-tetrahydro-8H-pyrido[1,2-a]pyrazin-8-one;
2-[1-(4-fluorophenyl)ethyl]-7-hydroxy-1,2,3,4-tetrahydro-8H-pyrido[1,2-a]pyrazin-8-one;
7-hydroxy-2-(2-hydroxy-1-phenylethyl)-1,2,3,4-tetrahydro-8H-pyrido[1,2-a]pyrazin-8-one;
7-hydroxy-2-(2,2,2-trifluoro-1-phenylethyl)-1,2,3,4-tetrahydro-8H-pyrido[1,2-a]pyrazin-8-one;
7-hydroxy-2-[(2-phenyl-1,3-thiazol-4-yl)methyl]-1,2,3,4-tetrahydro-8H-pyrido[1,2-a]pyrazin-8-one;
2-[(3,5-dimethyl-1-phenyl-1H-pyrazol-4-yl)methyl]-7-hydroxy-1,2,3,4-tetrahydro-8H-pyrido[1,2-a]pyrazin-8-one;
7-hydroxy-2-(1-phenylcyclopropyl)-3,4-dihydro-1H-pyrido[1,2-a]pyrazin-8-one;
2-(2-fluoro-1-phenyl-ethyl)-7-hydroxy-3,4-dihydro-1H-pyrido[1,2-a]pyrazin-8-one;
2-[1-(2-chlorophenyl)cyclopropyl]-7-hydroxy-3,4-dihydro-1H-pyrido[1,2-a]pyrazin-8-one;
2-(2,2-difluoro-1-phenyl-ethyl)-7-hydroxy-3,4-dihydro-1H-pyrido[1,2-a]pyrazin-8-one;
2-(1,3-benzothiazol-2-yl)-7-hydroxy-3,4-dihydro-1H-pyrido[1,2-a]pyrazin-8-one;
7-hydroxy-2-(2-phenylcyclopropyl)-3,4-dihydro-1H-pyrido[1,2-a]pyrazin-8-one;
7-hydroxy-2-(5-quinolyl)-3,4-dihydro-1H-pyrido[1,2-a]pyrazin-8-one;
7-hydroxy-2-(3-phenyloxetan-3-yl)-3,4-dihydro-1H-pyrido[1,2-a]pyrazin-8-one;
7-hydroxy-2-phenyl-1,2,3,4-tetrahydro-8H-pyrido[1,2-a]pyrazin-8-one;
7-hydroxy-2-(3-methylphenyl)-1,2,3,4-tetrahydro-8H-pyrido[1,2-a]pyrazin-8-one;
7-hydroxy-2-[2-(trifluoromethoxy)phenyl]-1,2,3,4-tetrahydro-8H-pyrido[1,2-a]pyrazin-8-one;
1,2-dibenzyl-7-hydroxy-1,2,3,4-tetrahydro-8H-pyrido[1,2-a]pyrazin-8-one;
2-benzyl-7-hydroxy-1-phenyl-1,2,3,4-tetrahydro-8H-pyrido[1,2-a]pyrazin-8-one;
2-(2,6-dichlorobenzyl)-7-hydroxy-1-phenyl-1,2,3,4-tetrahydro-8H-pyrido[1,2-a]pyrazin-8-one;
(1R)-2-(4-ethylbenzyl)-7-hydroxy-1-phenyl-1,2,3,4-tetrahydro-8H-pyrido[1,2-a]pyrazin-8-one;
(1 S)-2-(4-ethylbenzyl)-7-hydroxy-1-phenyl-1,2,3,4-tetrahydro-8H-pyrido[1,2-a]pyrazin-8-one;
2-(4-ethylbenzyl)-7-hydroxy-1-(propan-2-yl)-1,2,3,4-tetrahydro-8H-pyrido[1,2-a]pyrazin-8-one;
2-(2,6-dimethylbenzyl)-7-hydroxy-1-methyl-1,2,3,4-tetrahydro-8H-pyrido[1,2-a]pyrazin-8-one;
2-(4-ethylbenzyl)-7-hydroxy-1-methyl-1,2,3,4-tetrahydro-8H-pyrido[1,2-a]pyrazin-8-one;
1-(4-fluorophenyl)-7-hydroxy-2-(quinolin-8-ylmethyl)-1,2,3,4-tetrahydro-8H-pyrido[1,2-a]pyrazin-8-one;
2-(2,6-dimethylbenzyl)-1-(4-fluorophenyl)-7-hydroxy-1,2,3,4-tetrahydro-8H-pyrido[1,2-a]pyrazin-8-one;
2-(4-ethylbenzyl)-7-hydroxy-1-(tetrahydro-2H-pyran-4-yl)-1,2,3,4-tetrahydro-8H-pyrido[1,2-a]pyrazin-8-one;
2-(4-ethylbenzyl)-7-hydroxy-1-[3-(pyridin-3-yl)phenyl]-1,2,3,4-tetrahydro-8H-pyrido[1,2-a]pyrazin-8-one;
2-benzyl-7-hydroxy-3-phenyl-1,2,3,4-tetrahydro-8H-pyrido[1,2-a]pyrazin-8-one;
2,3-dibenzyl-7-hydroxy-1,2,3,4-tetrahydro-8H-pyrido[1,2-a]pyrazin-8-one;
3-benzyl-2-(2,6-dichlorobenzyl)-7-hydroxy-1,2,3,4-tetrahydro-8H-pyrido[1,2-a]pyrazin-8-one;
7-hydroxy-3-methyl-2[4-(trifluoromethoxy)benzyl]-1,2,3,4-tetrahydro-8H-pyrido[1,2-a]pyrazin-8-one;
2-benzyl-7-hydroxy-3-methyl-1,2,3,4-tetrahydro-8H-pyrido[1,2-a]pyrazin-8-one;
2-benzyl-7-hydroxy-3-(2-phenylethyl)-1,2,3,4-tetrahydro-8H-pyrido[1,2-a]pyrazin-8-one;
9-chloro-2-(2-chloro-6-fluorobenzyl)-7-hydroxy-1,2,3,4-tetrahydro-8H-pyrido[1,2-a]pyrazin-8-one;
6-fluoro-7-hydroxy-2[[4-(trifluoromethoxy)phenyl]methyl]-3,4-dihydro-1H-pyrido[1,2-a]pyrazin-8-one;

2-[(2-chlorophenyl)methyl]-6-fluoro-7-hydroxy-3,4-di-hydro-1H-pyrido[1,2-a]pyrazin-8-one;

9-chloro-2-(4-ethylbenzyl)-7-hydroxy-1,2,3,4-tetra-hydro-8H-pyrido[1,2-a]pyrazin-8-one;

9-chloro-2-[(2-chlorophenyl)methyl]-7-hydroxy-3,4-di-hydro-1H-pyrido[1,2-a]pyrazin-8-one;

9-bromo-2-(4-ethylbenzyl)-7-hydroxy-1,2,3,4-tetra-hydro-8H-pyrido[1,2-a]pyrazin-8-one;

9-bromo-2-[(2-chlorophenyl)methyl]-7-hydroxy-3,4-di-hydro-1H-pyrido[1,2-a]pyrazin-8-one;

2-[(2-chlorophenyl)methyl]-7-hydroxy-9-iodo-3,4-di-hydro-1H-pyrido[1,2-a]pyrazin-8-one;

9-cyclopropyl-2-(4-ethylbenzyl)-7-hydroxy-1,2,3,4-tetra-hydro-8H-pyrido[1,2-a]pyrazin-8-one; and 2-[(2-cholorophenyl)methyl]-7-hydroxy-3,4-dihydro-1H-pyrdio[1,2-a]pyrazin-8-one;

7-hydroxy-2-[(2,4-dicholorphenyl)methyl]-1,2,3,4-tetra-hydro-8H-pyrido[1,2-a]pyrazin-8-one;

2-[(2-chloropheny,l)methyl]-9-cyclopropyl-7-hydroxy-3,4-dihydro-1H-pyrido[1,2-a]pyrazin-8-one; and a pharmaceutically acceptable salt of any one thereof.

10. The compound according to claim 9, wherein the compound is 7-hydroxy-2-(6,7,8,9-tetrahydro-5H-benzo[7]annulen-5-yl)-1,2,3,4-tetrahydro-8H-pyrido[1,2-a]pyrazin-8-one or a pharmaceutically acceptable salt thereof.

11. The compound according to claim 9, wherein the compound is 7-hydroxy-2-(6,7,8,9-tetrahydro-5H-benzo[7]annulen-5-yl)-1,2,3,4-tetrahydro-8H-pyrido[1,2-a]pyrazin-8-one.

12. The compound according to claim 9, wherein the compound is 2[1-(2,5-dimethylphenyl)ethyl]-7-hydroxy-1,2,3,4-tetrahydro-8H-pyrido[1,2-a]pyrazin-8-one or a pharmaceutically acceptable salt thereof.

13. The compound according to claim 9, wherein the compound is 2[1-(2,5-dimethylphenyl)ethyl]-7-hydroxy-1,2,3,4-tetrahydro-8H-pyrido[1,2-a]pyrazin-8-one.

14. The compound according to claim 9, wherein the compound is 2-(1,2-diphenylethyl)-7-hydroxy-1,2,3,4-tetra-hydro-8H-pyrido[1,2-a]pyrazin-8-one or a pharmaceutically acceptable salt thereof.

15. The compound according to claim 9, wherein the compound is 2-(1,2-diphenylethyl)-7-hydroxy-1,2,3,4-tetra-hydro-8H-pyrido[1,2-a]pyrazin-8-one.

16. The compound according to claim 9, wherein the compound is 2-(4-ethylbenzyl)-7-hydroxy-1,2,3,4-tetrahydro-8H-pyrido[1,2-a]pyrazin-8-one or a pharmaceutically acceptable salt thereof.

17. The compound according to claim 9, wherein the compound is 2-(4-ethylbenzyl)-7-hydroxy-1,2,3,4-tetra-hydro-8H-pyrido[1,2-a]pyrazin-8-one.

18. The compound according to claim 9, wherein the compound is 2-(2,6-dimethylbenzyl)-7-hydroxy-1,2,3,4-tet-rahydro-8H-pyrido[1,2-a]pyrazin-8-one or a pharmaceuti-cally acceptable salt thereof.

19. The compound according to claim 9, wherein the compound is 2-(2,6-dimethylbenzyl)-7-hydroxy-1,2,3,4-tet-rahydro-8H-pyrido[1,2-a]pyrazin-8-one.

20. The compound according to claim 9, wherein the compound is 2-(2,5-dimethylbenzyl)-7-hydroxy-1,2,3,4-tet-rahydro-8H-pyrido[1,2-a]pyrazin-8-one or a pharmaceuti-cally acceptable salt thereof.

21. The compound according to claim 9, wherein the compound is 2-(2,5-dimethylbenzyl)-7-hydroxy-1,2,3,4-tet-rahydro-8H-pyrido[1,2-a]pyrazin-8-one.

22. The compound according to claim 9, wherein the compound is 7-hydroxy-2-[(2,4-dichlorophenyl)methyl]-1, 2,3,4-tetrahydro-8H-pyrido[1,2-a]pyrazin-8-one or a phar-maceutically acceptable salt thereof.

23. The compound according to claim 9, wherein the compound is 7-hydroxy-2-[(2,4-dichlorophenyl)methyl]-1, 2,3,4-tetrahydro-8H-pyrido[1,2-a]pyrazin-8-one.

24. The compound according to claim 9, wherein the compound is 242,6-dichlorobenzyl)-7-hydroxy-l-phenyl-1, 2,3,4-tetrahydro-8H-pyrido[1,2-a]pyrazin-8-one or a phar-maceutically acceptable salt thereof.

25. The compound according to claim 9, wherein the compound is 242,6-dichlorobenzyl)-7-hydroxy-l-phenyl-1, 2,3,4-tetrahydro-8H-pyrido[1,2-a]pyrazin-8-one.

26. The compound according to claim 9, wherein the compound is (1R)-2-(4-ethylbenzyl)-7-hydroxy-l-phenyl-1, 2,3,4-tetrahydro-8H-pyrido[1,2-a]pyrazin-8-one or a phar-maceutically acceptable salt thereof.

27. The compound according to claim 9, wherein the compound is (1R)-2-(4-ethylbenzyl)-7-hydroxy-l-phenyl-1, 2,3,4-tetrahydro-8H-pyrido[1,2-a]pyrazin-8-one.

28. The compound according to claim 9, wherein the compound is 2-[(2-chlorophenyl)methyl]-7-hydroxy-3,4-di-hydro-1H-pyrido[1,2-a]pyrazin-8-one or a pharmaceutically acceptable salt thereof.

29. The compound according to claim 9, wherein the compound is 2-[(2-chlorophenyl)methyl]-7-hydroxy-3,4-di-hydro-1H-pyrido[1,2-a]pyrazin-8-one.

30. The compound according to claim 9, wherein the compound is 2-(4-ethylbenzyl)-7-hydroxy-1-(propan-2-yl)-1,2,3,4-tetrahydro-8H-pyrido[1,2-a]pyrazin-8-one or a phar-maceutically acceptable salt thereof.

31. The compound according to claim 9, wherein the compound is 2-(4-ethylbenzyl)-7-hydroxy-1-(propan-2-yl)-1,2,3,4-tetrahydro-8H-pyrido[1,2-a]pyrazin-8-one.

32. The compound according to claim 9, wherein the compound is 2-(2,6-dimethylbenzyl)-7-hydroxy-l-methyl-1, 2,3,4-tetrahydro-8H-pyrido[1,2-a]pyrazin-8-one or a phar-maceutically acceptable salt thereof.

33. The compound according to claim 9, wherein the compound is 2-(2,6-dimethylbenzyl)-7-hydroxy-l-methyl-1, 2,3,4-tetrahydro-8H-pyrido[1,2-a]pyrazin-8-one.

34. A pharmaceutical composition comprising at least one compound of claim 1 in combination with a pharmaceuti-cally acceptable carrier.

35. The pharmaceutical composition of claim 34, further comprising at least one additional therapeutic agent wherein the additional therapeutic agent is selected from the group consisting of levodopa, carbidopa, benserazide and combi-nations thereof.

36. A method for reducing the number or intensity of one or more symptoms of a psychiatric or neurological disorder for which inhibiting COMT provides a therapeutic effect in a patient in need thereof, the method comprising adminis-tering a pharmaceutical composition of claim 10 to said patient.

37. The method according to claim 36, wherein the psychiatric disorder is selected from ADHD, obsessive-compulsive disorder, alcoholism and other addictions, depression, bipolar disorder, age-associated cognitive symp-toms, impulse control disorders and schizophrenia.

38. The method according to claim 36, wherein the psychiatric disorder is schizophrenia.

39. The method according to claim 36, wherein the neurological disorder is Parkinson's disease.

40. The method according to claim 39, wherein the method further comprises administering at least one additional therapeutic agent selected from the group consisting of levodopa, carbidopa, benserazide and combinations thereof.

41. The method according to claim 36, wherein the patient has a neurological or psychiatric disorder selected from the group consisting of schizophrenia, bipolar disorder, depression, premenstrual syndrome (PMS) and premenstrual dysphoric disorder (PDD), learning disorders, pervasive developmental disorders, autism, tic disorders, anxiety disorders, cognitive disorders associated with dementia, Alzheimer's, Parkinson's, Huntington's disease, spasticity, myoclonus, muscle spasm, tinnitus and hearing impairment and loss.

42. The method according to claim 41, wherein the patient has a cognitive, learning and mental related disorder.

43. The method according to claim 41, wherein the patient has anxiety.

44. The method according to claim 36, wherein the compound is 7-hydroxy-2-(6,7,8,9-tetrahydro-5H-benzo[7]annulen-5-yl)-1,2,3,4-tetrahydro-8H-pyrido[1,2-a]pyrazin-8-one or a pharmaceutically acceptable salt thereof.

45. The method according to claim 36, wherein the compound is 7-hydroxy-2-(6,7,8,9-tetrahydro-5H-benzo[7]annulen-5-yl)-1,2,3,4-tetrahydro-8H-pyrido[1,2- a]pyrazin-8-one.

46. The method according to claim 36, wherein the compound is 2[1-(2,5-dimethylphenyl)ethyl]-7-hydroxy-1,2,3,4-tetrahydro-8H-pyrido[1,2-a]pyrazin-8-one or a pharmaceutically acceptable salt thereof.

47. The method according to claim 36, wherein the compound is 2[1-(2,5-dimethylphenyl)ethyl]-7-hydroxy-1,2,3,4-tetrahydro-8H-pyrido[1,2-a]pyrazin-8-one.

48. The method according to claim 36, wherein the compound is 2-(1,2-diphenylethyl)-7-hydroxy-1,2,3,4-tetrahydro-8H-pyrido[1,2-a]pyrazin-8-one or a pharmaceutically acceptable salt thereof.

49. The method according to claim 36, wherein the compound is 2-(1,2-diphenylethyl)-7-hydroxy-1,2,3,4-tetrahydro-8H-pyrido[1,2-a]pyrazin-8-one.

50. The method according to claim 36, wherein the compound is 2-(4-ethylbenzyl)-7-hydroxy-1,2,3,4-tetrahydro-8H-pyrido[1,2-a]pyrazin-8-one or a pharmaceutically acceptable salt thereof.

51. The method according to claim 36, wherein the compound is 2-(4-ethylbenzyl)-7-hydroxy-1,2,3,4-tetrahydro-8H-pyrido[1,2-a]pyrazin-8-one.

52. The method according to claim 36, wherein the compound is 2-(2,6-dimethylbenzyl)-7-hydroxy-1,2,3,4-tetrahydro-8H-pyrido[1,2-a]pyrazin-8-one or a pharmaceutically acceptable salt thereof.

53. The method according to claim 36, wherein the compound is 2-(2,6-dimethylbenzyl)-7-hydroxy-1,2,3,4-tetrahydro-8H-pyrido[1,2-a]pyrazin-8-one.

54. The method according to claim 36, wherein the compound is 2-(2,5-dimethylbenzyl)-7-hydroxy-1,2,3,4-tetrahydro-8H-pyrido[1,2-a]pyrazin-8-one or a pharmaceutically acceptable salt thereof.

55. The method according to claim 36, wherein the compound is 2-(2,5-dimethylbenzyl)-7-hydroxy-1,2,3,4-tetrahydro-8H-pyrido[1,2-a]pyrazin-8-one.

56. The method according to claim 36, wherein the compound is 7-hydroxy-2-[(2,4-dichlorophenyl)methyl]-1,2,3,4-tetrahydro-8H-pyrido[1,2-a]pyrazin-8-one or a pharmaceutically acceptable salt thereof.

57. The method according to claim 36, wherein the compound is 7-hydroxy-2-[(2,4-dichlorophenyl)methyl]-1,2,3,4-tetrahydro-8H-pyrido[1,2-a]pyrazin-8-one.

58. The method according to claim 36, wherein the compound is 242,6-dichlorobenzyl)-7-hydroxy-l-phenyl-1,2,3,4-tetrahydro-8H-pyrido[1,2-a]pyrazin-8-one or a pharmaceutically acceptable salt thereof.

59. The method according to claim 36, wherein the compound is 242,6-dichlorobenzyl)-7-hydroxy-l-phenyl-1,2,3,4-tetrahydro-8H-pyrido[1,2-a]pyrazin-8-one.

60. The method according to claim 36, wherein the compound is (1R)-2-(4-ethylbenzyl)-7-hydroxy-l-phenyl-1,2,3,4-tetrahydro-8H-pyrido[1,2-a]pyrazin-8-one or a pharmaceutically acceptable salt thereof.

61. The method according to claim 36, wherein the compound is (1R)-2-(4-ethylbenzyl)-7-hydroxy-l-phenyl-1,2,3,4-tetrahydro-8H-pyrido[1,2-a]pyrazin-8-one.

62. The method according to claim 36, wherein the compound is 2-[(2-chlorophenyl)methyl]-7-hydroxy-3,4-dihydro-1H-pyrido[1,2-a]pyrazin-8-one or a pharmaceutically acceptable salt thereof.

63. The method according to claim 36, wherein the compound is 2-[(2-chlorophenyl)methyl]-7-hydroxy-3,4-dihydro-1H-pyrido[1,2-a]pyrazin-8-one.

64. The method according to claim 36, wherein the compound is 2-(4-ethylbenzyl)-7-hydroxy-1-(propan-2-yl)-1,2,3,4-tetrahydro-8H-pyrido[1,2-a]pyrazin-8-one or a pharmaceutically acceptable salt thereof.

65. The method according to claim 36, wherein the compound is 2-(4-ethylbenzyl)-7-hydroxy-1-(propan-2-yl)-1,2,3,4-tetrahydro-8H-pyrido[1,2-a]pyrazin-8-one.

66. The method according to claim 36, wherein the compound is 2-(2,6-dimethylbenzyl)-7-hydroxy-l-methyl-1,2,3,4-tetrahydro-8H-pyrido[1,2-a]pyrazin-8-one or a pharmaceutically acceptable salt thereof.

67. The method according to claim 36, wherein the compound is 2-(2,6-dimethylbenzyl)-7-hydroxy-l-methyl-1,2,3,4-tetrahydro-8H-pyrido[1,2-a]pyrazin-8-one.

68. A method for reducing the number or intensity of one or more symptoms of a condition for which inhibiting COMT provides a therapeutic effect in a patient in need thereof wherein the condition is selected from the following: pain; substance-related disorders and addictive behaviors; obesity or eating disorders associated with excessive food intake and complications associated therewith; and a mood and depressive disorder, the method comprising administering a pharmaceutical composition of claim 10 to said patient.

69. The method according to claim 68, wherein the patient has substance-related disorders and addictive behaviors.

70. The method according to claim 68, wherein the patient has obesity or eating disorders associated with excessive food intake and complications associated therewith.

71. The method according to claim 68, wherein the patient has a mood and depressive disorder.

* * * * *